United States Patent
Noureldin et al.

(10) Patent No.: US 10,436,517 B2
(45) Date of Patent: *Oct. 8, 2019

(54) SYSTEMS FOR RECOVERY AND RE-USE OF WASTE ENERGY IN HYDROCRACKING-BASED CONFIGURATION FOR INTEGRATED CRUDE OIL REFINING AND AROMATICS COMPLEX

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/833,859

(22) Filed: Dec. 6, 2017

(65) Prior Publication Data
US 2018/0094866 A1    Apr. 5, 2018

Related U.S. Application Data

(62) Division of application No. 15/242,115, filed on Aug. 19, 2016, now Pat. No. 9,891,004.
(Continued)

(51) Int. Cl.
*F28D 7/00* (2006.01)
*C01B 3/24* (2006.01)
(Continued)

(52) U.S. Cl.
CPC .......... *F28D 7/0083* (2013.01); *B01D 3/007* (2013.01); *B01D 3/32* (2013.01); *B01D 51/10* (2013.01);
(Continued)

(58) Field of Classification Search
CPC ......... F28D 7/00; F28D 7/0083; C10G 33/06; C10G 35/04; C10G 65/12; C10L 3/10; C07C 7/08
See application file for complete search history.

(56) References Cited

U.S. PATENT DOCUMENTS

| 3,995,428 A | 12/1976 | Roberts |
| 4,109,469 A | 8/1978 | Carson |

(Continued)

FOREIGN PATENT DOCUMENTS

| CN | 1844325 | 10/2006 |
| CN | 101424453 | 5/2009 |

(Continued)

OTHER PUBLICATIONS

Feng Xu, D. Yogi Goswami and Sunil S. Bhagwat, "A combined power/cooling cycle," Energy, 25 (2000), 233-246.
(Continued)

*Primary Examiner* — Brian A McCaig
(74) *Attorney, Agent, or Firm* — Fish & Richardson P.C.

(57) ABSTRACT

Configurations and related processing schemes of specific direct or indirect inter-plants integration for energy consumption reduction synthesized for grassroots medium grade crude oil semi-conversion refineries to increase energy efficiency from specific portions of low grade waste heat sources are described. Configurations and related processing schemes of specific direct or indirect inter-plants integration for energy consumption reduction for integrated medium grade crude oil semi-conversion refineries and aromatics complex for increasing energy efficiency from specific portions of low grade waste sources are also described.

17 Claims, 137 Drawing Sheets

Related U.S. Application Data

(60) Provisional application No. 62/209,217, filed on Aug. 24, 2015, provisional application No. 62/209,147, filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| *C01B 3/34* | (2006.01) | |
| *F01K 23/06* | (2006.01) | |
| *F01K 25/08* | (2006.01) | |
| *B01D 53/047* | (2006.01) | |
| *B01D 53/86* | (2006.01) | |
| *C10G 45/44* | (2006.01) | |
| *C10G 69/00* | (2006.01) | |
| *C10G 45/02* | (2006.01) | |
| *C10G 35/04* | (2006.01) | |
| *C10L 3/10* | (2006.01) | |
| *C07C 7/08* | (2006.01) | |
| *C10G 65/12* | (2006.01) | |
| *C10G 33/06* | (2006.01) | |
| *B01D 3/00* | (2006.01) | |
| *B01D 3/32* | (2006.01) | |
| *B01D 51/10* | (2006.01) | |
| *B01D 53/14* | (2006.01) | |
| *B01D 53/18* | (2006.01) | |
| *B01D 53/34* | (2006.01) | |
| *B01D 53/48* | (2006.01) | |
| *B01D 53/96* | (2006.01) | |
| *C02F 1/58* | (2006.01) | |
| *C10G 47/00* | (2006.01) | |
| *F28F 9/26* | (2006.01) | |
| *C10G 65/00* | (2006.01) | |
| *F01D 17/14* | (2006.01) | |
| *F01K 3/18* | (2006.01) | |
| *F01K 13/02* | (2006.01) | |
| *H02K 7/18* | (2006.01) | |
| *F01K 25/06* | (2006.01) | |
| *F01K 27/02* | (2006.01) | |
| *F01K 13/00* | (2006.01) | |
| *C10G 45/00* | (2006.01) | |
| *C10K 3/04* | (2006.01) | |
| *F01K 27/00* | (2006.01) | |
| *C02F 101/10* | (2006.01) | |
| *C02F 101/16* | (2006.01) | |
| *C02F 103/18* | (2006.01) | |
| *C02F 103/36* | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C01B 3/34* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0227* (2013.01); *C01B 2203/0233* (2013.01); *C01B 2203/0283* (2013.01); *C01B 2203/043* (2013.01); *C01B 2203/127* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11); *Y02P 30/10* (2015.11)

(56) References Cited

U.S. PATENT DOCUMENTS

| | | |
|---|---|---|
| 4,291,232 A | 9/1981 | Cardone |
| 4,471,619 A | 9/1984 | Nolley, Jr. |
| 4,512,155 A | 4/1985 | Sheinbaum |
| 4,792,390 A | 12/1988 | Staggs |
| 4,962,238 A | 10/1990 | Wolfe |
| 5,007,240 A | 4/1991 | Ishida |
| 5,164,070 A | 11/1992 | Munro |
| 5,240,476 A | 8/1993 | Hegarty |
| 5,497,624 A | 3/1996 | Amir |
| 6,733,636 B1 | 5/2004 | Heins |
| 8,046,999 B2 | 11/2011 | Doty |
| 9,328,634 B2 | 5/2016 | Ikegami |
| 9,562,201 B2 | 2/2017 | Noureldin |
| 9,851,153 B2 | 12/2017 | Noureldin |
| 2002/0023538 A1 | 2/2002 | Agarwal |
| 2003/0092952 A1 | 5/2003 | Netzer |
| 2003/0132138 A1 | 7/2003 | Mehra |
| 2004/0186332 A1 | 9/2004 | Kong |
| 2006/0010872 A1 | 1/2006 | Singh |
| 2008/0128134 A1 | 6/2008 | Mudunuri |
| 2008/0174115 A1 | 7/2008 | Lambirth |
| 2008/0257413 A1 | 10/2008 | Noureldin et al. |
| 2008/0289588 A1 | 11/2008 | Wees et al. |
| 2008/0314726 A1 | 12/2008 | Choros |
| 2009/0000299 A1 | 1/2009 | Ast |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2011/0016863 A1 | 1/2011 | Ernst |
| 2011/0072819 A1 | 3/2011 | Silva |
| 2011/0072820 A1 | 3/2011 | Finkenrath |
| 2011/0083437 A1 | 4/2011 | Ast |
| 2011/0158858 A1 | 6/2011 | Alves |
| 2012/0031096 A1 | 2/2012 | Acikgoz et al. |
| 2012/0047889 A1 | 3/2012 | Acikgoz et al. |
| 2012/0048718 A1 | 3/2012 | Werba |
| 2012/0085096 A1 | 4/2012 | Penton et al. |
| 2012/0131921 A1 | 5/2012 | Held |
| 2012/0279728 A1 | 11/2012 | Northrop |
| 2012/0279900 A1 | 11/2012 | Noureldin et al. |
| 2012/0285169 A1 | 11/2012 | Freund |
| 2012/0298552 A1 | 11/2012 | Koseoglu |
| 2013/0104546 A1 | 5/2013 | Goswami |
| 2013/0145763 A1 | 6/2013 | Mirmobin et al. |
| 2013/0165534 A1 | 6/2013 | McComish |
| 2013/0213040 A1 | 8/2013 | Goswami |
| 2013/0231909 A1 | 9/2013 | Noureldin |

(56) References Cited

U.S. PATENT DOCUMENTS

| | | | |
|---|---|---|---|
| 2013/0238154 | A1 | 9/2013 | Noureldin |
| 2013/0334060 | A1 | 12/2013 | Koseoglu et al. |
| 2014/0090405 | A1 | 4/2014 | Held et al. |
| 2014/0142364 | A1 | 5/2014 | Io |
| 2014/0260311 | A1 | 9/2014 | Berlowitz |
| 2015/0377079 | A1 | 12/2015 | Noureldin |
| 2016/0045841 | A1 | 2/2016 | Kaplan |
| 2017/0058206 | A1 | 3/2017 | Noureldin et al. |
| 2017/0082373 | A1 | 3/2017 | Noureldin et al. |

FOREIGN PATENT DOCUMENTS

| | | |
|---|---|---|
| CN | 104560082 | 4/2015 |
| DE | 3731978 | 3/1988 |
| EP | 292391 | 11/1988 |
| EP | 949318 | 10/1999 |
| EP | 2516326 | 10/2012 |
| FR | 2990990 | 11/2013 |
| SU | 295317 | 10/1977 |
| WO | 97/21786 | 6/1997 |
| WO | 2004102082 | 11/2004 |
| WO | 2011090553 | 7/2011 |
| WO | 2012048132 | 4/2012 |
| WO | 2013055864 | 4/2013 |
| WO | 2014205163 | 12/2014 |

OTHER PUBLICATIONS

D. Zheng, B. Chen, Y. Qi and H. Jin, "Thermodynamic analysis of a novel absorption power/cooling combined cycle," Applied Energy, 83 (2006), 311-323.

Meng Liu, and Na Zhang, "Proposal and analysis of a novel ammonia-water cycle for power and refrigeration cogeneration," Energy, 32 (2007), 961-970.

J.Wang, Y. Dai and L. Gao, "Parametric analysis and optimization for a combined power and refrigeration cycle," Applied Energy, 85 (2008), 1071-1085.

R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.

D. Ayou, J. C. Bruno, R. Saravanan and A. Coronas, "An Overview of Combined Absorption Power and Cooling Cycles," Renewable sustainable energy reviews, 21 (2013), 728-748.

J. Hua, Y. Chen, Y. Wang and A.P. Roskilly, "Thermodynamic analysis of ammonia-water power/chilling cogeneration cycle with low grade waste heat," Applied thermal engineering , 64 (2014), 483-490.

Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.

Stecco, "Kalina Cycles: Some Possible Applications and Comments," Proceedings of the American Power Conference, XP000609703, Jan. 1, 1993, vol. 1, pp. 196-201.

Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.

Sadrameli et al., "Optimum Operating Conditions for a Combined Power and Cooling Thermodynamic Cycle," Science Direct, Applied Energy, vol. 84, No. 3, Nov. 10, 2006, pp. 254-265.

Vidal, "Analysis of a Combined Power and Refrigeration Cycle by the Exergy Method," Science Direct, Energy 31, Dec. 1, 2006, pp. 3401-3414.

Schaschke, "A Dictionary of Chemical Engineering: Tatoray Process," Oxford, 2014, p. 371.

Marcilly, "Acido-Basic Catalysis: Applications to refining and Petrochemistry," IFP Publications, 2005, pp. 512-513.

Gary, "Petroleum Refining Technology and Economics: Figure 1.1 Refinery Flow Diagram," CRC Press, 5th ed., 2007, p. 3.

PCT International Search Report and Written Opinion of the International Searching Authority, PCT/US2016/027417, dated Jul. 6, 2016, 11 pages.

PCT International Search Report and Written Opinion of the International Searching Authority, PCT/US2016/027797, dated Oct. 19, 2016, 12 pages.

PCT International Search Report and Written Opinion of the International Searching Authority, PCT/US2016/027794, dated Oct. 19, 2016, 13 pages.

PCT International Search Report and Written Opinion of the International Searching Authority, PCT/US2016/030063, dated Oct. 19, 2016, 13 pages.

PCT International Search Report and Written Opinion of the International Searching Authority, PCT/US2016/030156, dated Oct. 19, 2016, 12 pages.

PCT International Search Report and Written Opinion of the International Searching Authority, PCT/US2016/048074, dated Nov. 9, 2016, 12 pages.

PCT International Search Report and Written Opinion of the International Searching Authority, PCT/US2016/048042, dated Nov. 9, 2016, 12 pages.

PCT International Search Report and Written Opinion of the International Searching Authority, PCT/US2016/048067, dated Nov. 15, 2016, 11 pages.

PCT International Search Report and Written Opinion of the International Searching Authority, PCT/US2016/048066, dated Nov. 15, 2016, 11 pages.

PCT International Search Report and Written Opinion of the International Searching Authority, PCT/US2016/048078, dated Nov. 15, 2016, 12 pages.

PCT International Search Report and Written Opinion of the International Searching Authority, PCT/US2016/048076, dated Nov. 15, 2016, 12 pages.

PCT International Search Report and Written Opinion of the International Searching Authority, PCT/US2016/048207, dated Nov. 21, 2016, 12 pages.

PCT International Search Report and Written Opinion of the International Searching Authority, PCT/US2016/048219, dated Nov. 21, 2016, 13 pages.

PCT International Search Report and Written Opinion of the International Searching Authority, PCT/US2016/048229, dated Nov. 21, 2016, 13 pages.

PCT International Search Report and Written Opinion of the International Searching Authority, PCT/US2016/048236, dated Nov. 21, 2016, 13 pages.

PCT International Search Report and Written Opinion of the International Searching Authority, PCT/US2016/027413, dated Nov. 22, 2016, 11 pages.

PCT International Search Report and Written Opinion of the International Searching Authority, PCT/US2016/048063, dated Nov. 23, 2016, 11 pages.

PCT International Search Report and Written Opinion of the International Searching Authority, PCT/US2016/048071, dated Nov. 23, 2016, 11 pages.

PCT International Search Report and Written Opinion of the International Searching Authority, PCT/US2016/048210, dated Dec. 22, 2016, 11 pages.

PCT International Search Report and Written Opinion of the International Searching Authority, PCT/US2016/048224, dated Dec. 22, 2016, 11 pages.

PCT International Search Report and Written Opinion of the International Searching Authority, PCT/US2016/048209, dated Dec. 22, 2016, 11 pages.

PCT International Search Report and Written Opinion of the International Searching Authority, PCT/US2016/048237, dated Dec. 22, 2016, 11 pages.

PCT International Search Report and Written Opinion of the International Searching Authority, PCT/US2016/048223, dated Dec. 22, 2016, 11 pages.

PCT International Search Report and Written Opinion of the International Searching Authority, PCT/US2016/048212, dated Dec. 22, 2016, 11 pages.

(56) References Cited

OTHER PUBLICATIONS

Communication Pursuant to Article 94(3) EPC issued in European Application No. 16758058.8 dated Dec. 11, 2018, 4 pages.
International Preliminary Report on Patentability in International Application No. PCT/US2016/048042, dated Mar. 8, 2018, 8 pages.
International Preliminary Report on Patentability in International Application No. PCT/US2016/048076, dated Mar. 8, 2018, 8 pages.
International Preliminary Report on Patentability in International Application No. PCT/US2016/048066, dated Mar. 8, 2018, 8 pages.
International Preliminary Report on Patentability in International Application No. PCT/US2016/048067, dated Mar. 8, 2018, 8 pages.
International Preliminary Report on Patentability in International Application No. PCT/US2016/048078, dated Mar. 8, 2018, 8 pages.
International Preliminary Report on Patentability in International Application No. PCT/US2016/048063, dated Mar. 8, 2018, 8 pages.
International Preliminary Report on Patentability in International Application No. PCT/US2016/048071, dated Mar. 8, 2018, 8 pages.
Gulf Cooperation Council Examination Report issued in GCC Application No. GC 2016-31904 dated Nov. 13, 2018, 3 pages.
Gulf Cooperation Council Examination Report issued in GCC Application No. GC 2016-31907 dated Nov. 13, 2018, 3 pages.
Gulf Cooperation Council Examination Report issued in GCC Application No. GC 2016-31906 dated Nov. 13, 2018, 3 pages.
Gulf Cooperation Council Examination Report issued in GCC Application No. GC 2016-31908 dated Nov. 13, 2018, 3 pages.
Gulf Cooperation Council Examination Report issued in GCC Application No. GC 2016-31901 dated Nov. 13, 2018, 3 pages.
Gulf Cooperation Council Examination Report issued in GCC Application No. GC 2016-31905 dated Nov. 13, 2018, 3 pages.
Gulf Cooperation Council Examination Report issued in GCC Application No. GC 2016-31902 dated Nov. 13, 2018, 3 pages.
Gulf Cooperation Council Examination Report issued in GCC Application No. GC 2016-31903 dated Nov. 13, 2018, 3 pages.
Communication Pursuant to Article 94(3) EPC issued in European Application No. 16758061.2 dated Dec. 18, 2018, 4 pages.

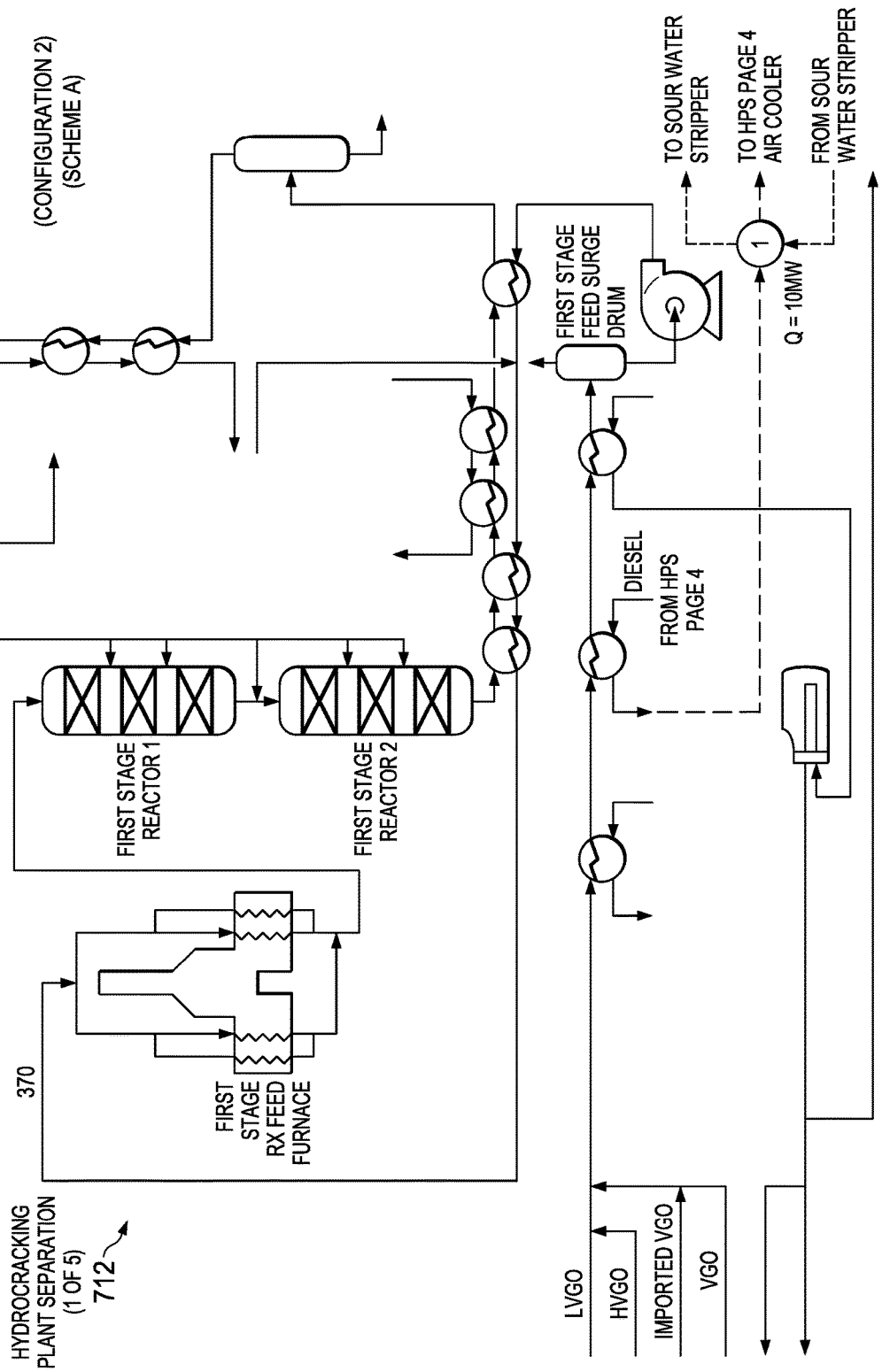

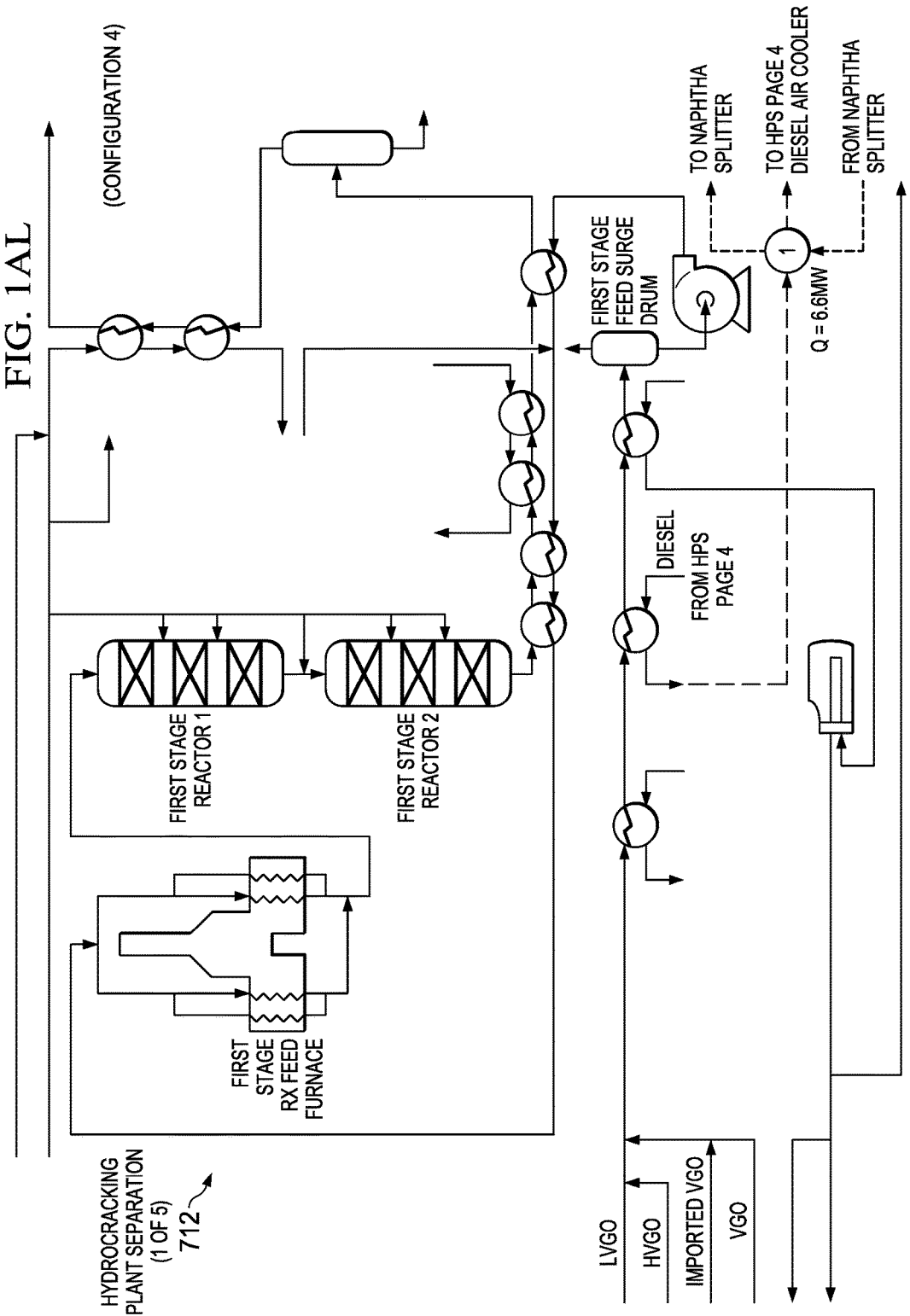
FIG. 1AL (CONFIGURATION 4)

FIG. 1CK (CONFIGURATION 9)

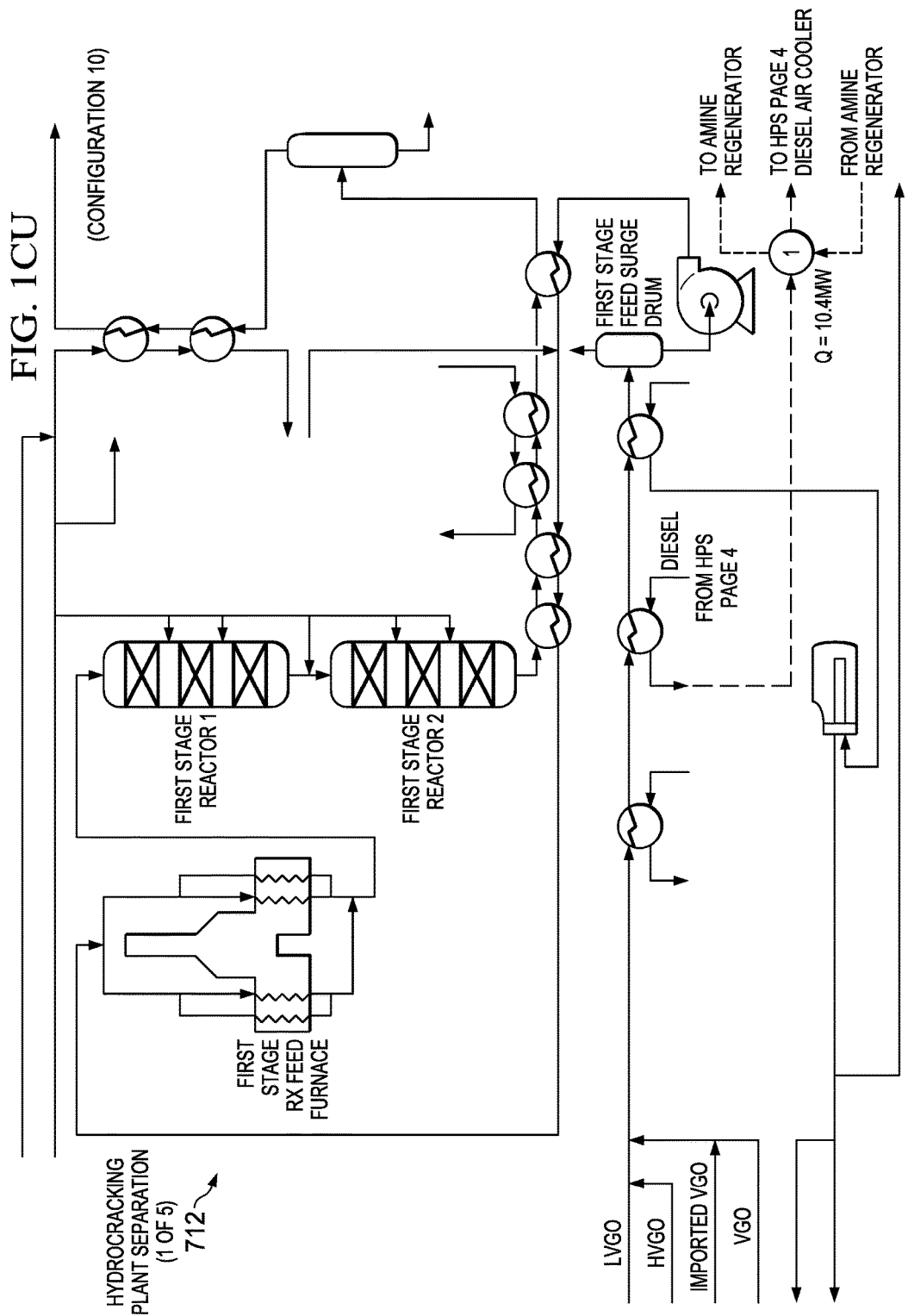
FIG. 1CU (CONFIGURATION 10)

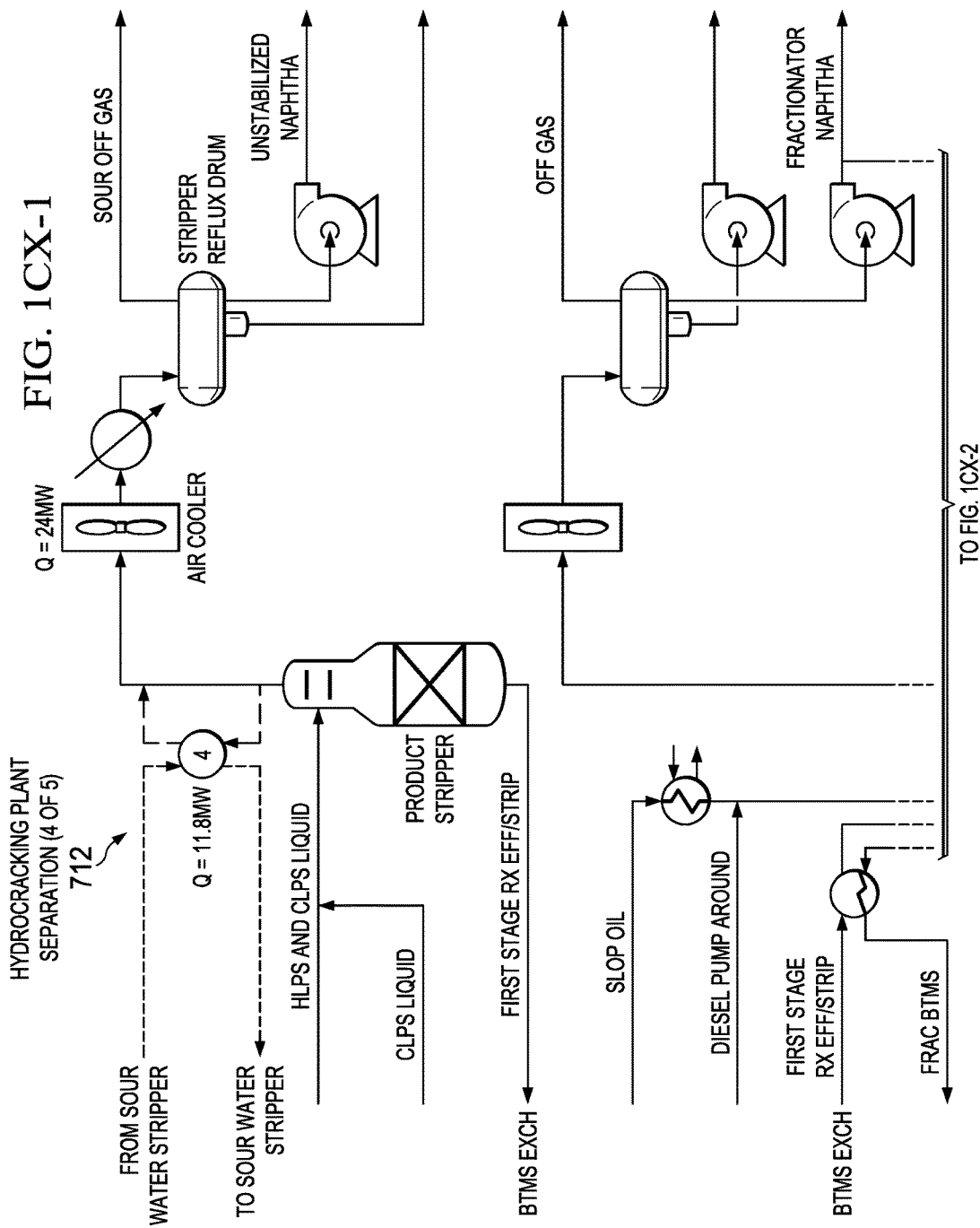

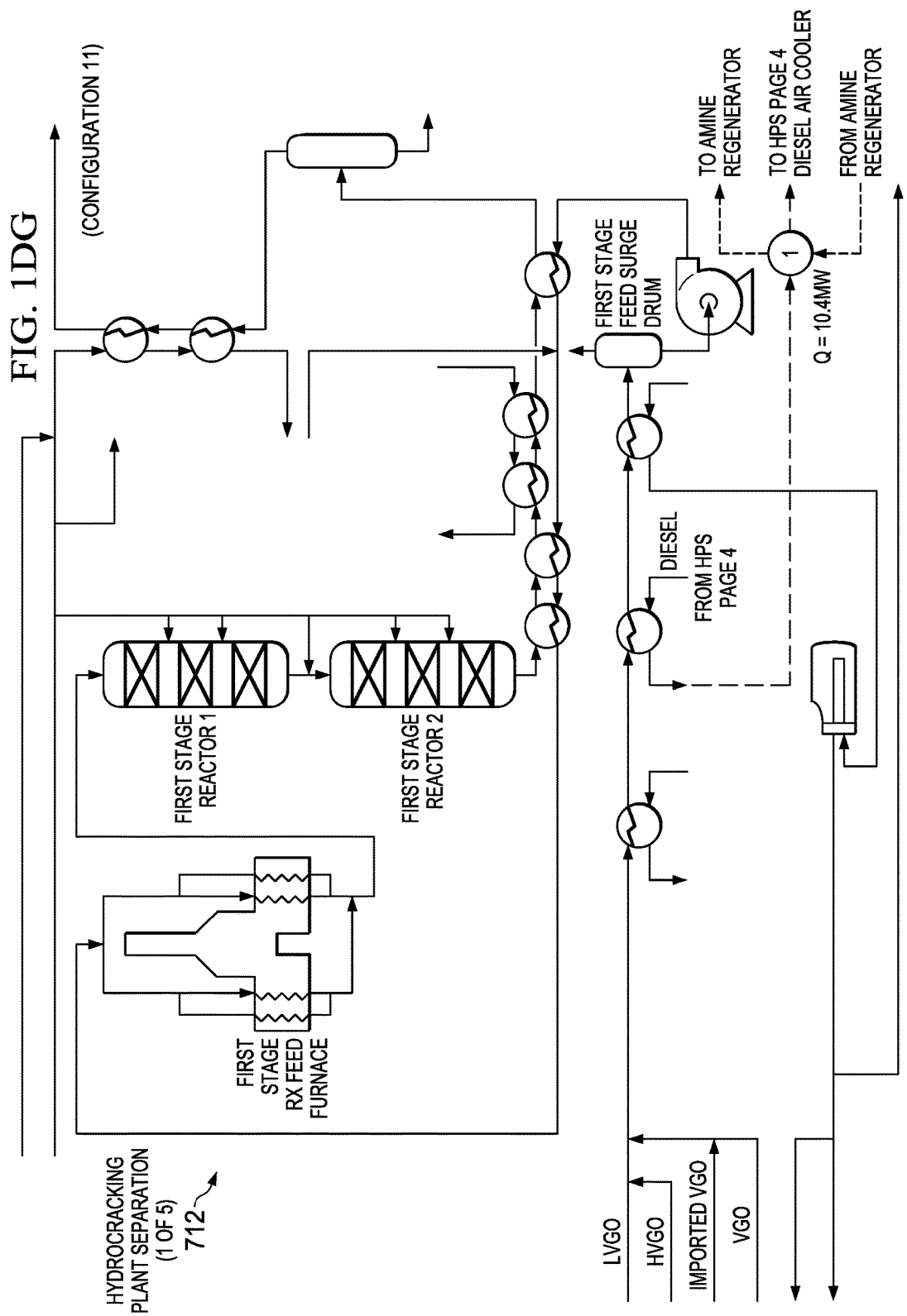
FIG. 1DG (CONFIGURATION 11)

US 10,436,517 B2

SYSTEMS FOR RECOVERY AND RE-USE OF WASTE ENERGY IN HYDROCRACKING-BASED CONFIGURATION FOR INTEGRATED CRUDE OIL REFINING AND AROMATICS COMPLEX

CROSS-REFERENCE TO RELATED APPLICATIONS

This application is a divisional application of and claims the benefit of priority to U.S. patent application Ser. No. 15/242,115, filed on Aug. 19, 2016, which claims priority under 35 U.S.C. § 119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to specific direct or indirect inter-plants integration for energy consumption reduction from waste energy in industrial facilities.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 1O-1AC illustrate a second set of configurations and related scheme details for thermally integrating different refining plants in the crude oil refining facility.

FIGS. 1AD-1AK illustrate a third set configurations and related scheme details for thermally integrating different refining plants in the crude oil refining facility.

FIGS. 1AL-1AT illustrate a fourth set of configurations and related scheme details for thermally integrating different refining plants in the crude oil refining facility.

FIGS. 1AU-1BB illustrate a fifth set of configurations and related scheme details for thermally integrating different refining plants in the crude oil refining facility.

FIGS. 1BR-1BZ illustrate a seventh set of configurations and related scheme details for thermally integrating different refining plants in the crude oil refining facility.

FIGS. 1CK-1CT illustrate a ninth set of configurations and related scheme details for thermally integrating different refining plants in the crude oil refining facility.

FIGS. 1CU-1DF illustrate a tenth set of configurations and related scheme details for thermally integrating different refining plants in the crude oil refining facility.

DETAILED DESCRIPTION

Figure 1A:
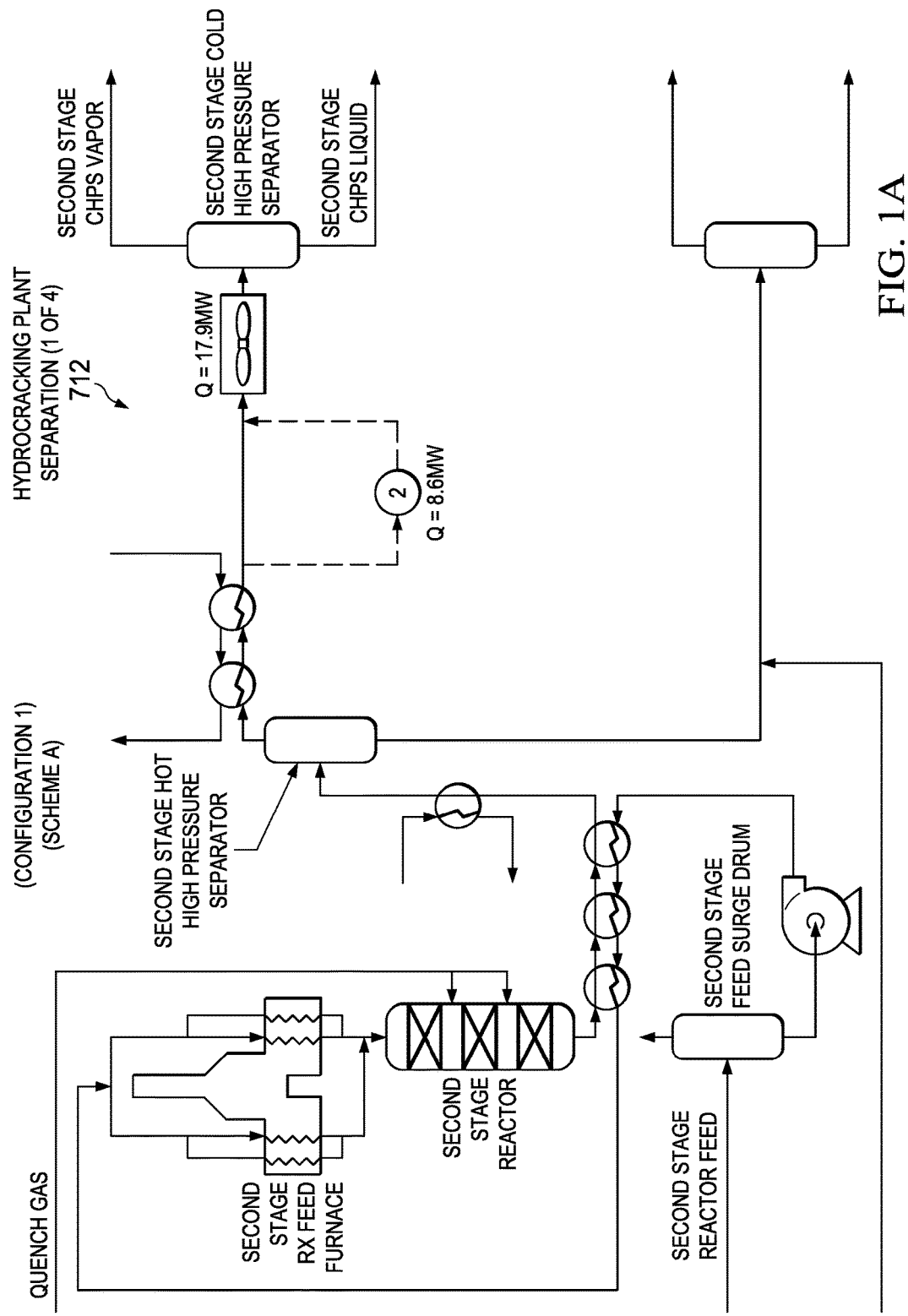
FIGS. 1A-1N illustrate a first set of configurations and related scheme details for thermally integrating different refining plants in the crude oil refining facility.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM British Thermal Units per hour (Btu/hr) can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydrotreating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3° C. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used in an acid gas absorber and regenerator to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatic content or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromatic feedstock is converted into lighter products under a wide range of high pressures and high temperatures in the presence of hydrogen and special catalysts. When the feedstock has a high paraffinic content, hydrogen prevents the formation of polycyclic aromatic compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Recovery Plant

Sulfur recovery facilities in refineries operate to regulate the discharge of sulfur compounds to the atmosphere to meet environmental regulations. In a sulfur recovery plant, combustion products that include sulfur can be processed, for example, by heating, cooling with condensers, using sulfur conversion catalyst, and by other processing techniques. One technique is to use amines to extract the sulfur and other acid gas compounds.

9. Naphtha Hydrotreating Plant and Continuous Catalytic Reformer Plants

A Naphtha Hydrotreater (NHT) produces 101 Research Octane Number (RON) reformate, with a maximum 4.0 psi (pounds per square inch) Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, that is, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes new energy efficient hydrocracking-based configurations and related specific processing schemes for integrated medium grade semi-conversion crude oil refining and aromatics complex.

In some implementations, a semi-conversion medium grade crude oil refining facility includes an aromatics complex and a hydrocracking plant. This disclosure describes a waste heat recovery and reuse network for such a refining facility. As described later, waste heat can be recovered from multiple plants in the crude oil refining facility including a hydrocracking plant. Such a refinery typically consumes several hundred megawatts of energy in heating utilities. Implementing the configurations described here can not only reduce energy consumption but also reduce energy-based greenhouse gas (GHG) emissions. In particular, this disclosure describes a method implemented in a crude oil refining facility to heat multiple first streams in multiple first plants of a crude oil refining facility using multiple second streams in multiple second plants in the crude oil refining facility. Several configurations of process schemes for doing so are described later with reference to the following figures.

Configuration 1

Figure 1B:
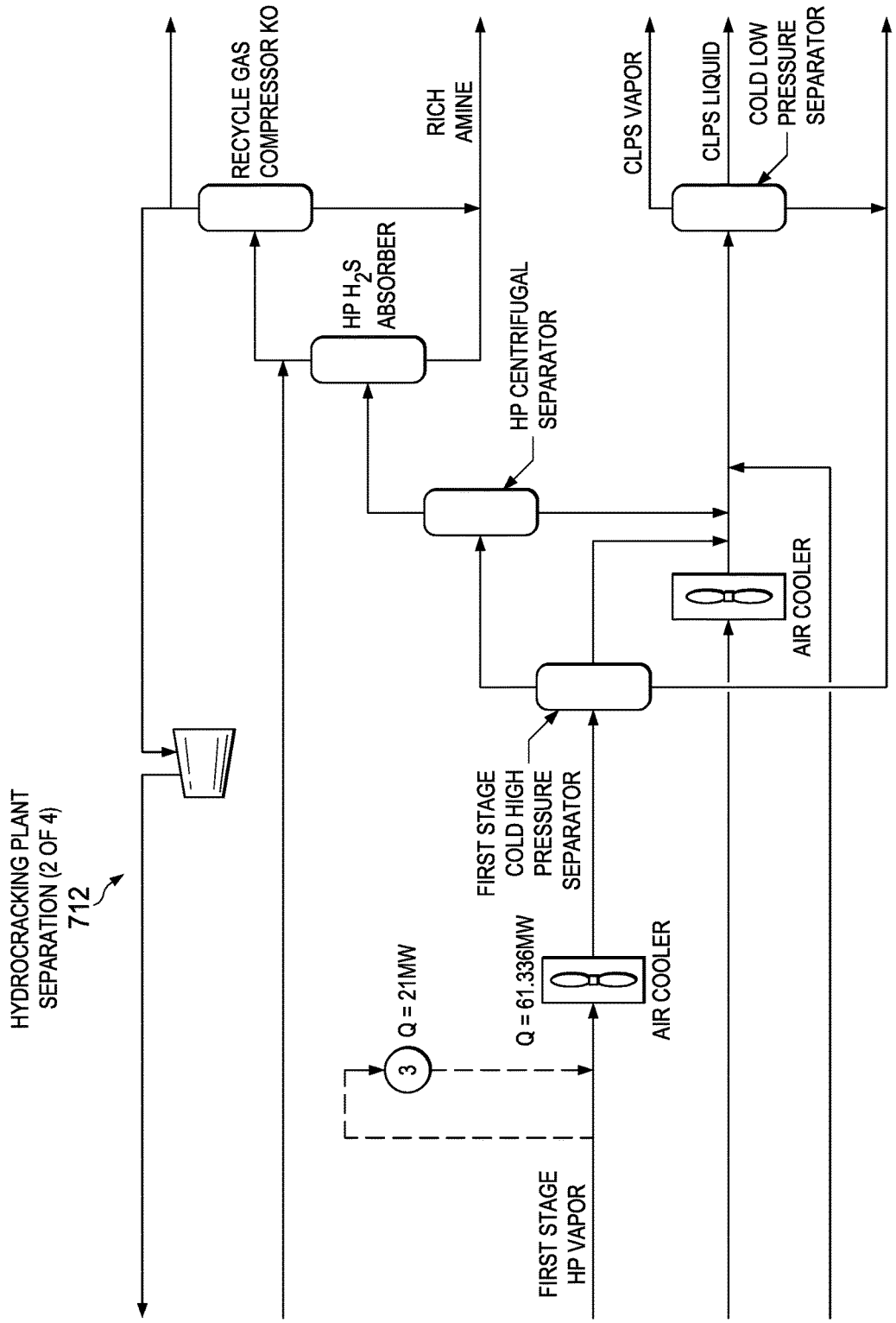
FIGS. 1BC-1BQ illustrate a sixth set of configurations and related scheme details for thermally integrating different refining plants in the crude oil refining facility.
Figures 1, 1C:
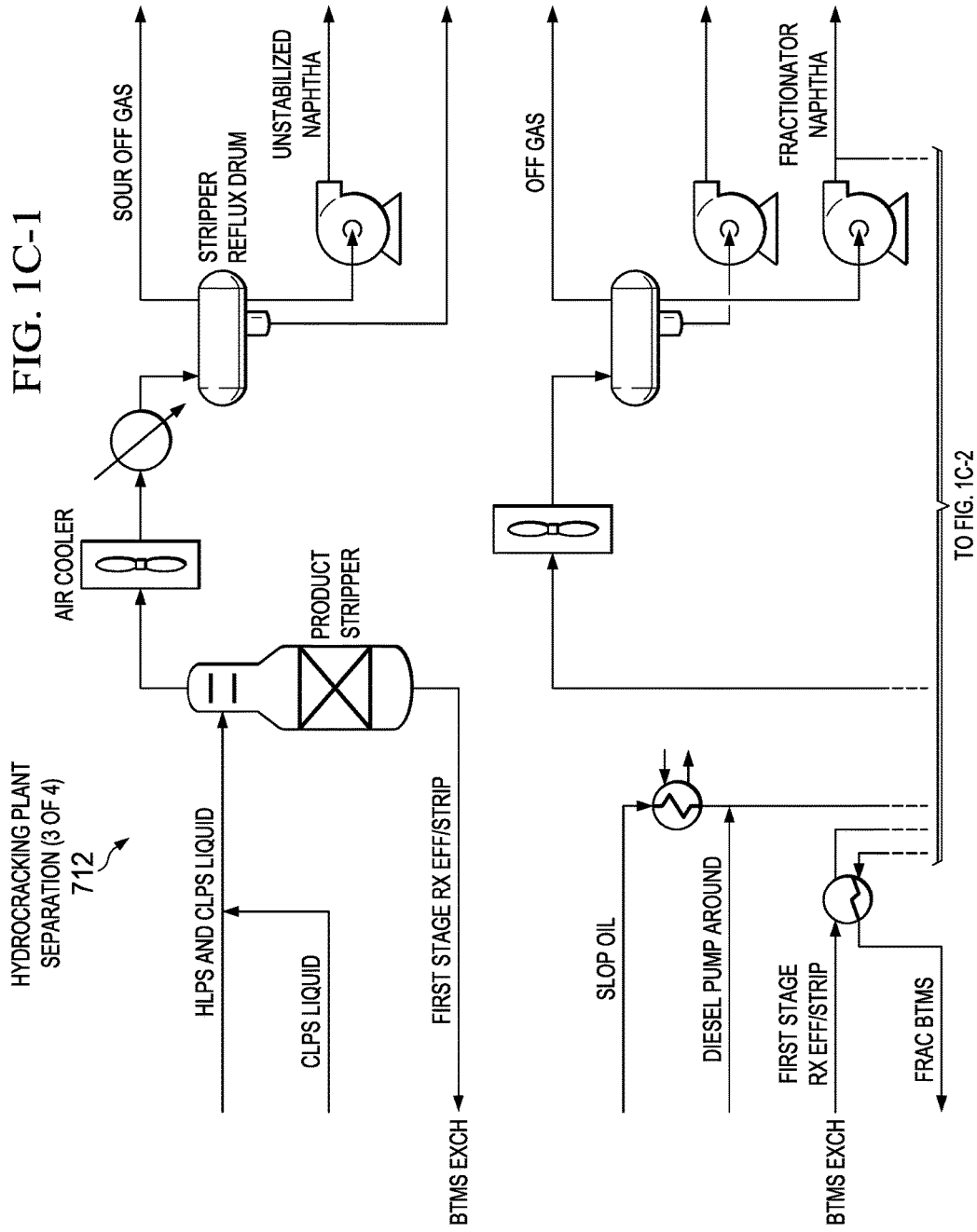
FIGS. 1CA-1CJ illustrate an eighth set of configurations and related scheme details for thermally integrating different refining plants in the crude oil refining facility.
Figures 1, 1C, 2:
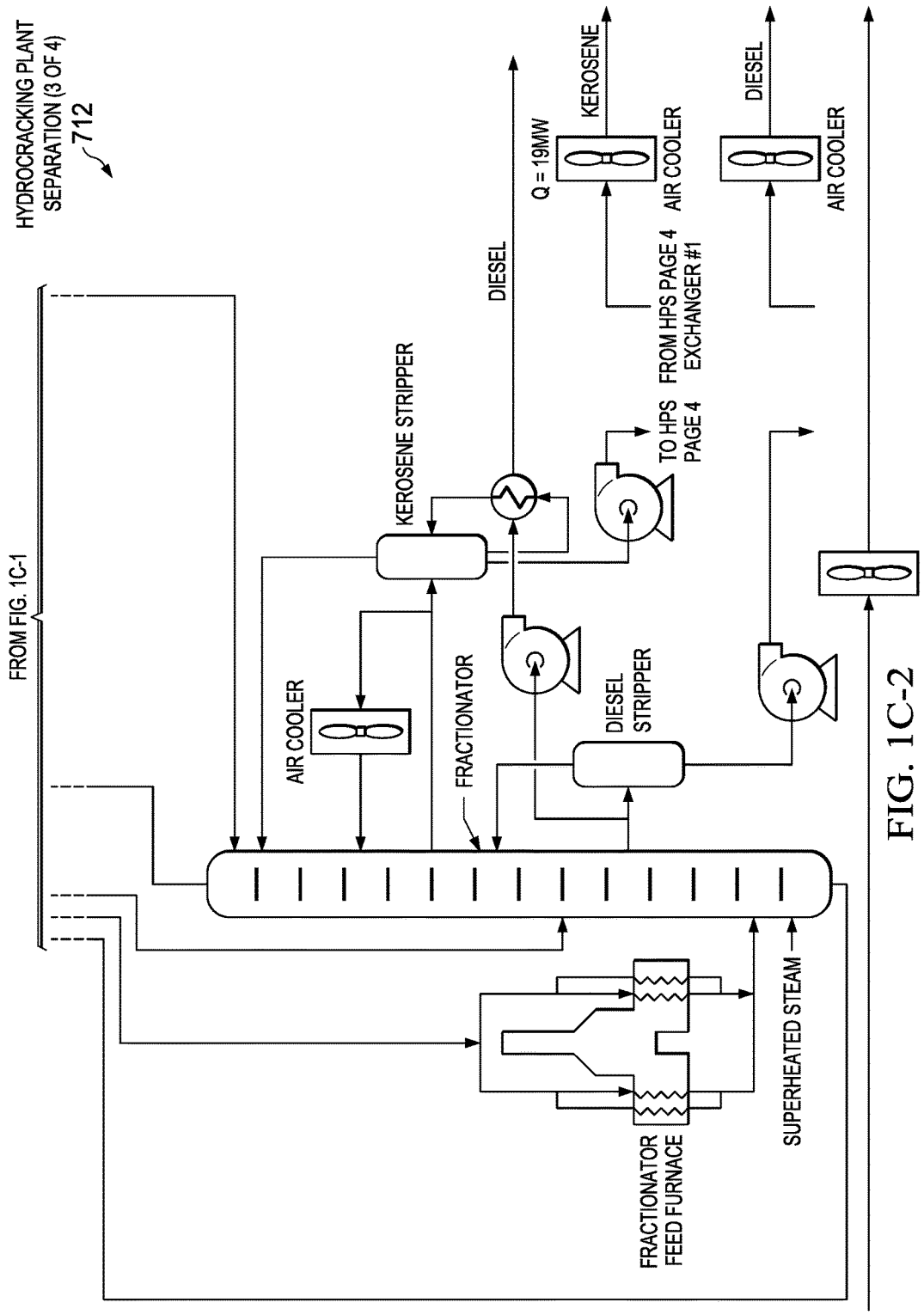
Figure 1D:
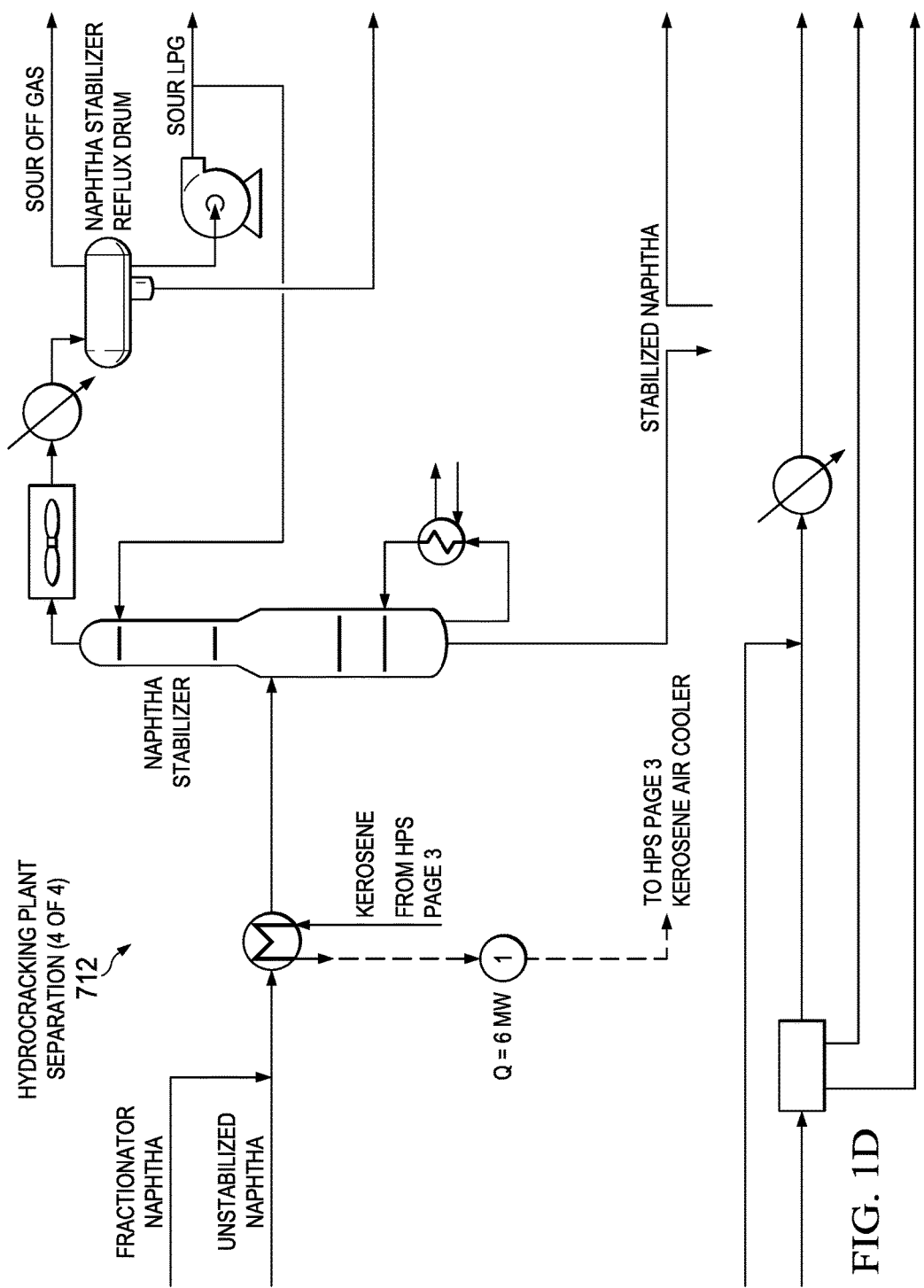
FIGS. 1DG-1DS illustrate an eleventh set of configurations and related scheme details for thermally integrating different refining plants in the crude oil refining facility.
Figure 1E:
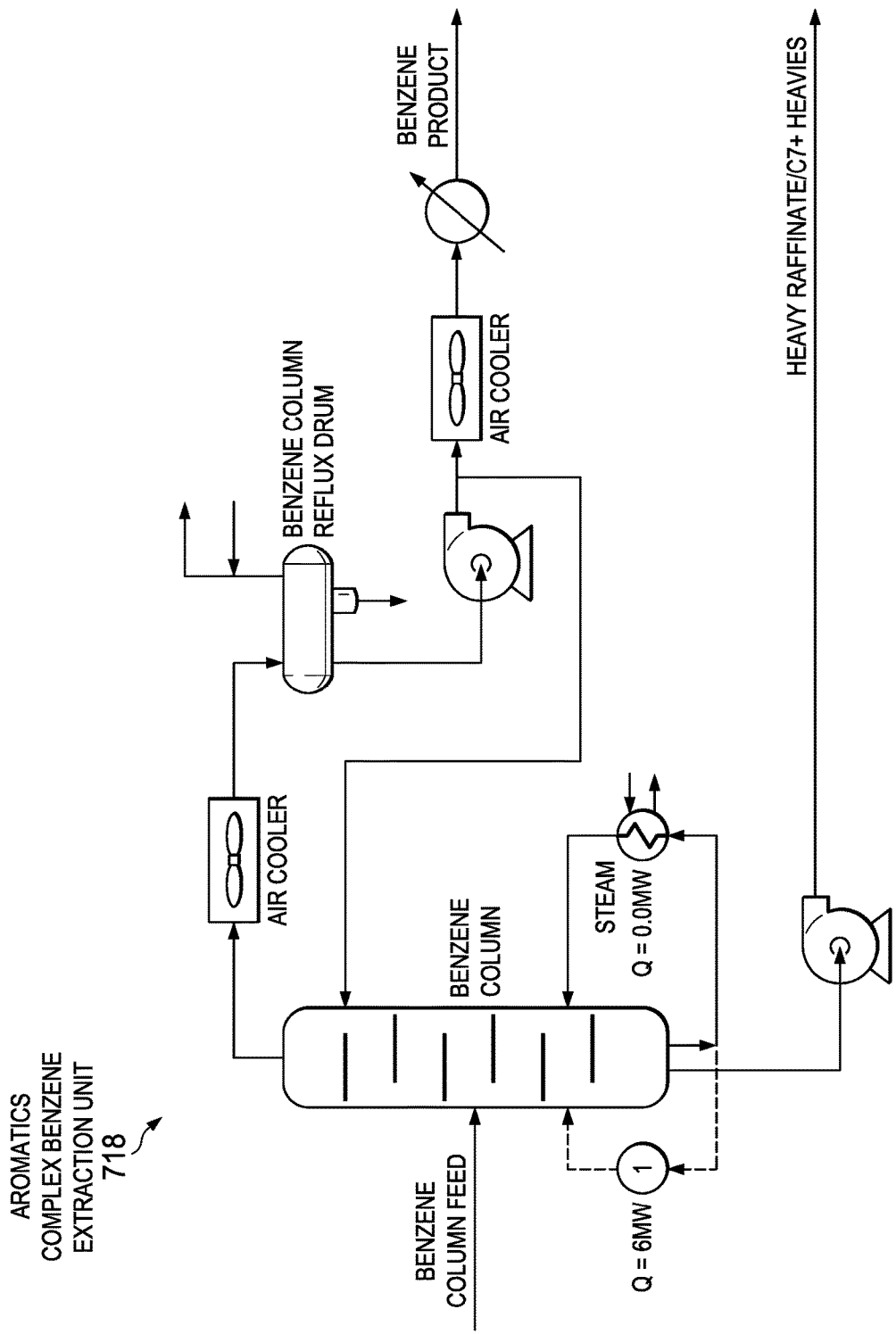
Figure 1F:
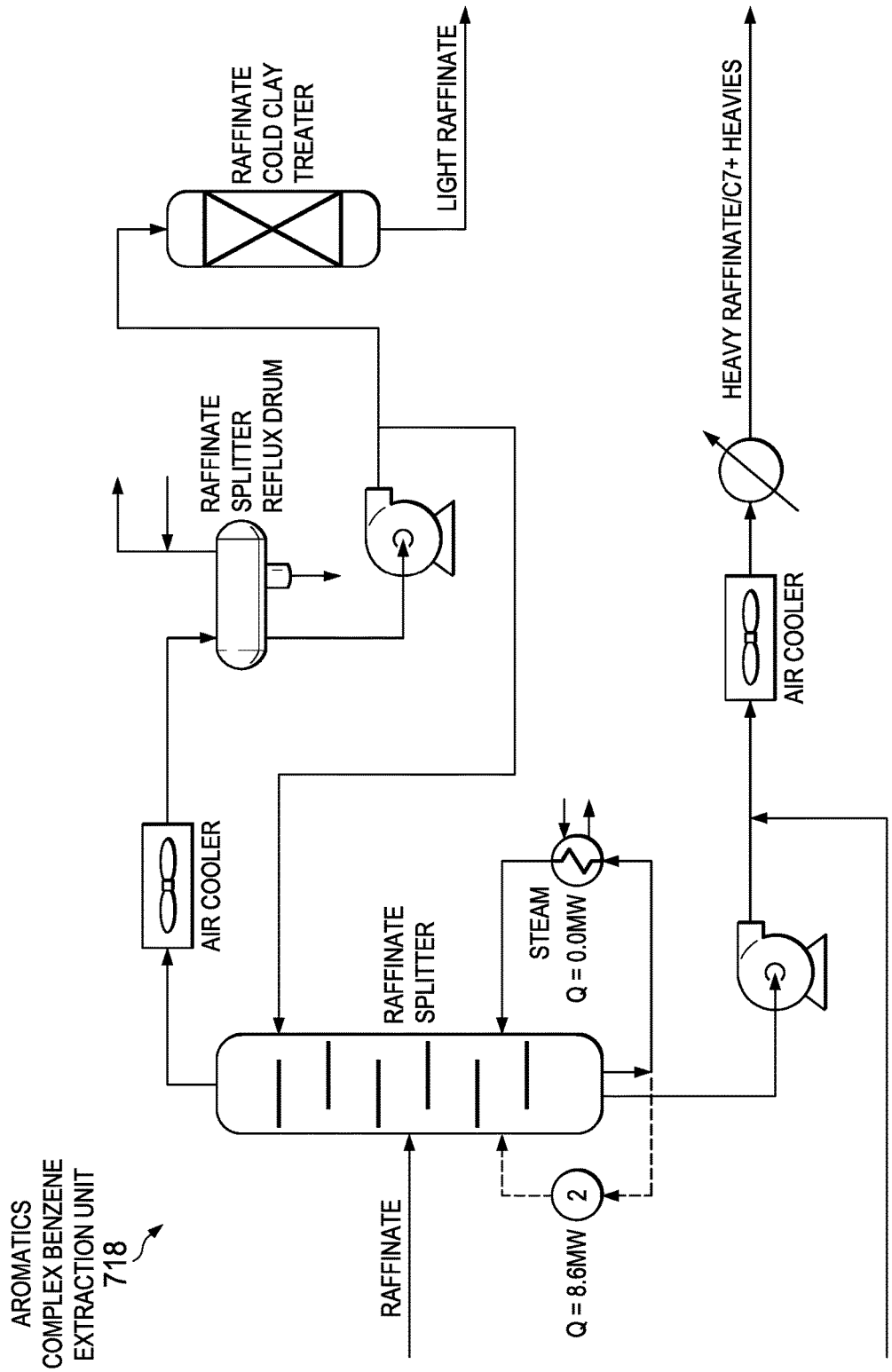
Figure 1G:
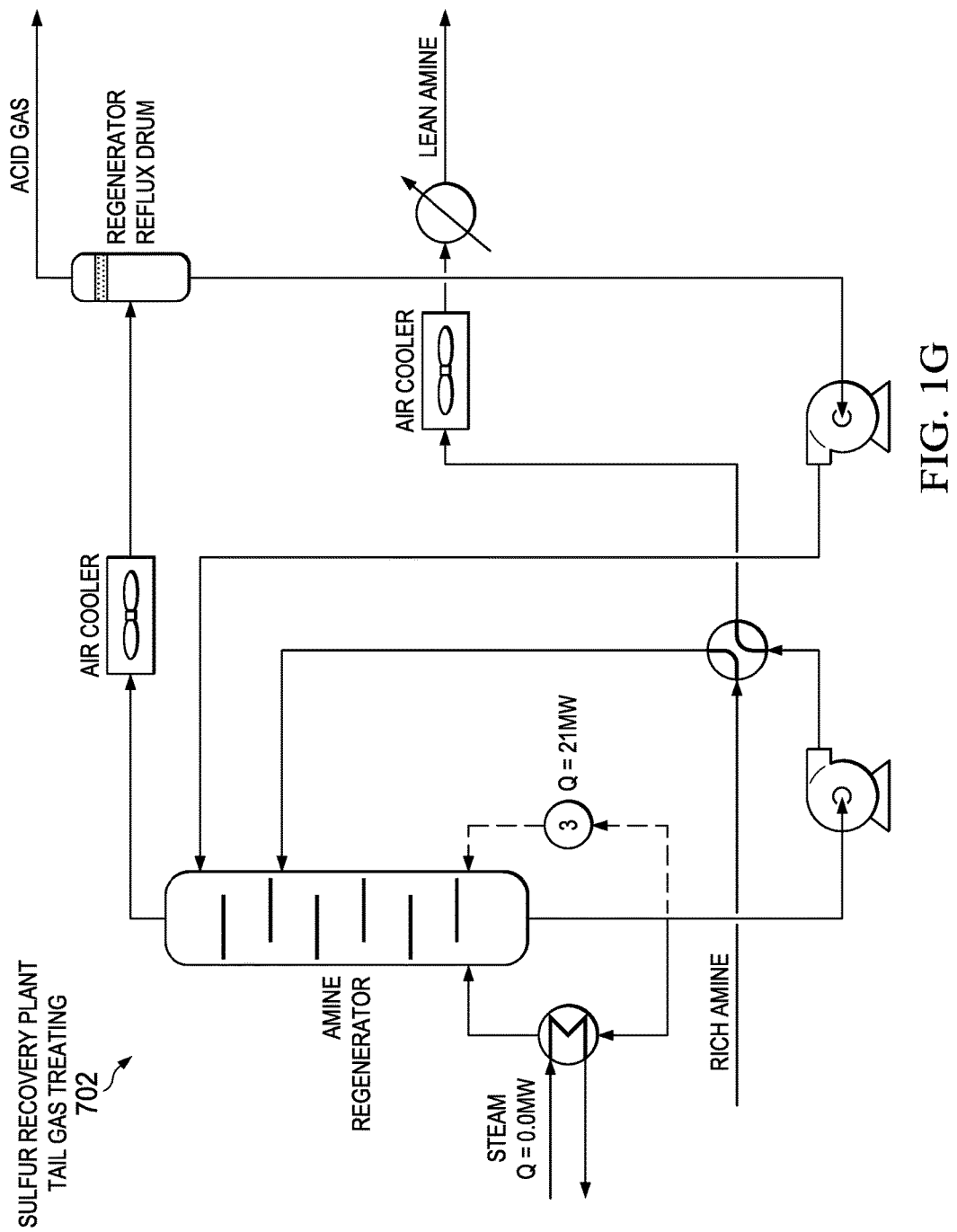
Figure 1H:
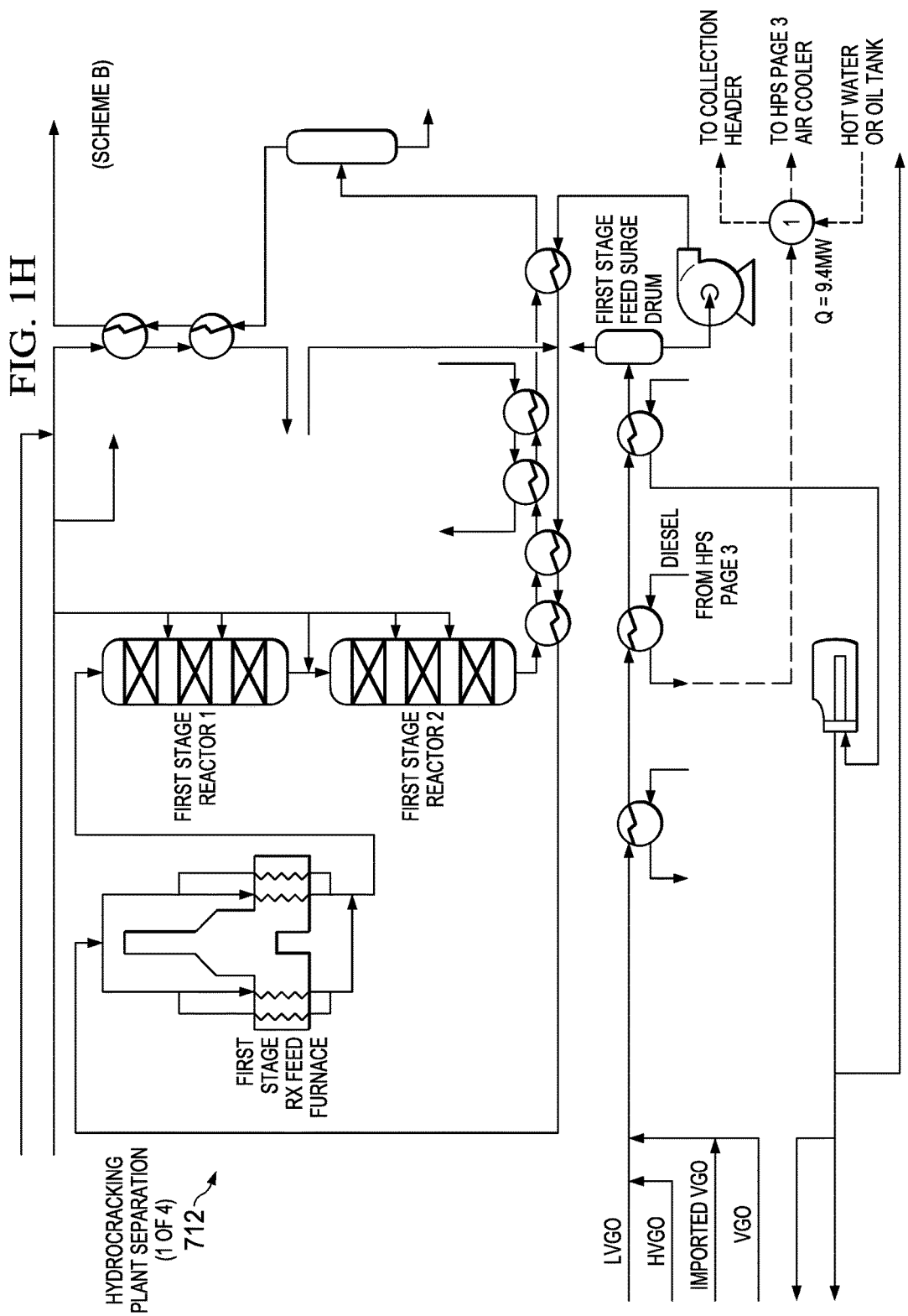
Figure 1I:
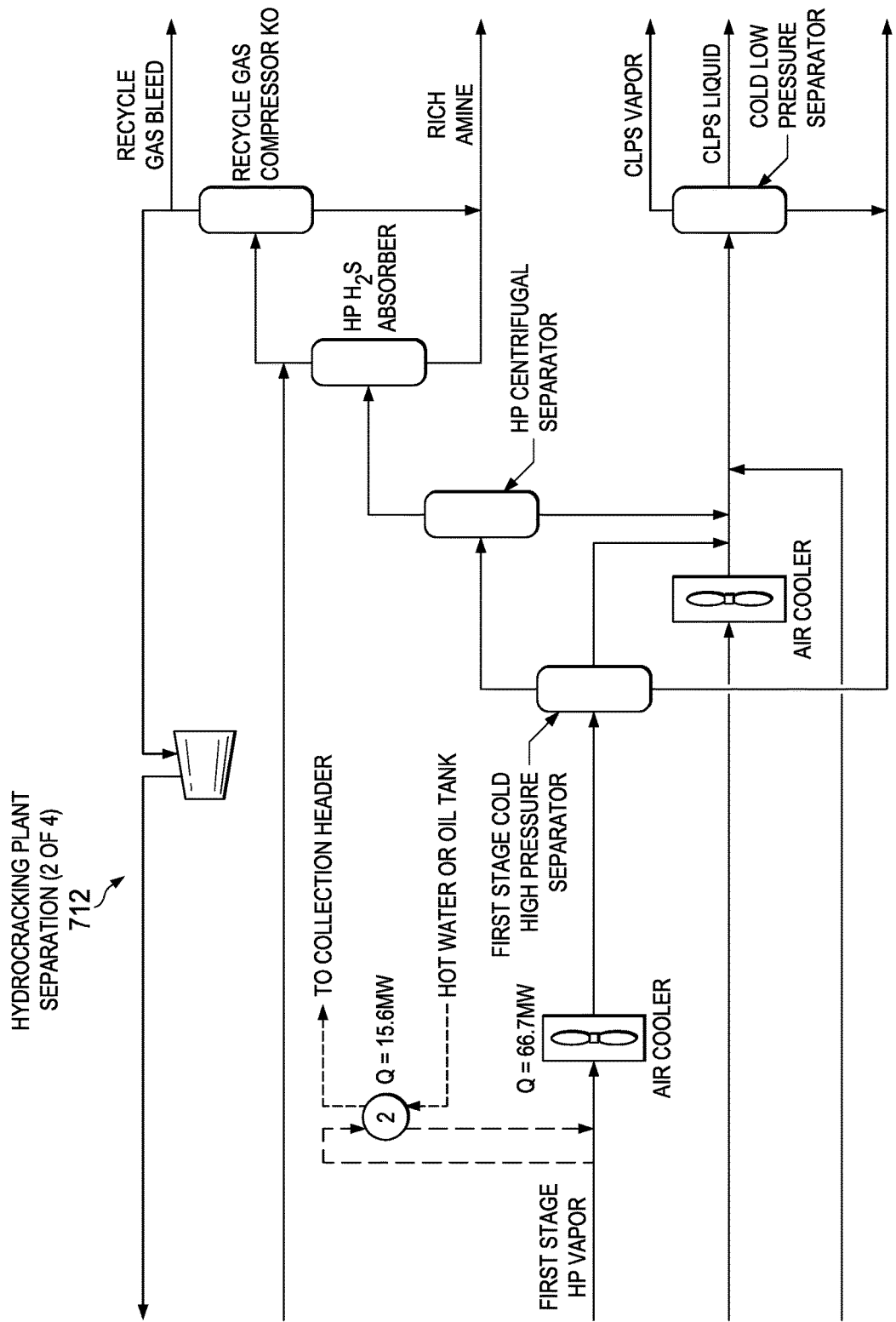
Figures 1, 1J:
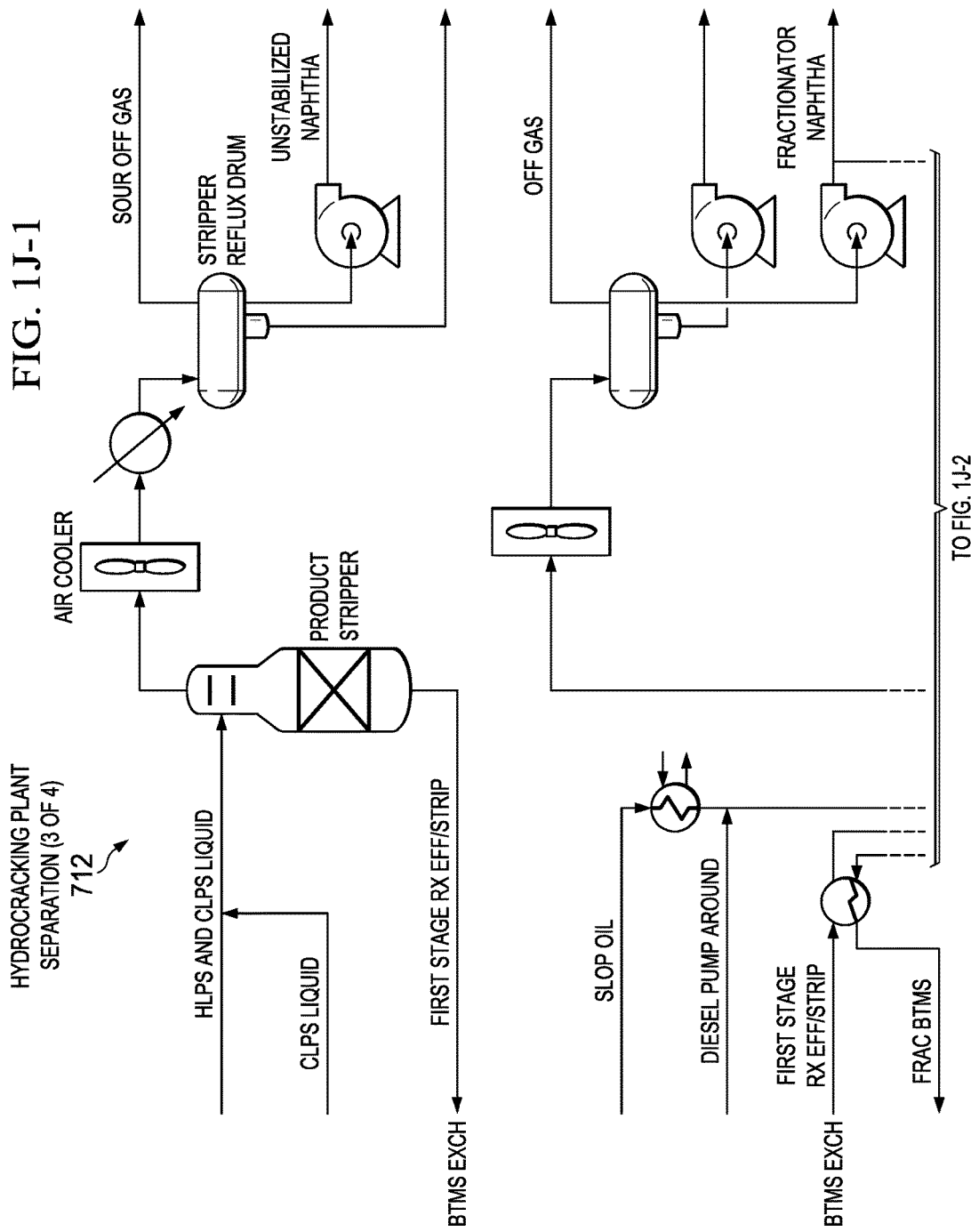
Figures 1, 1J, 2:
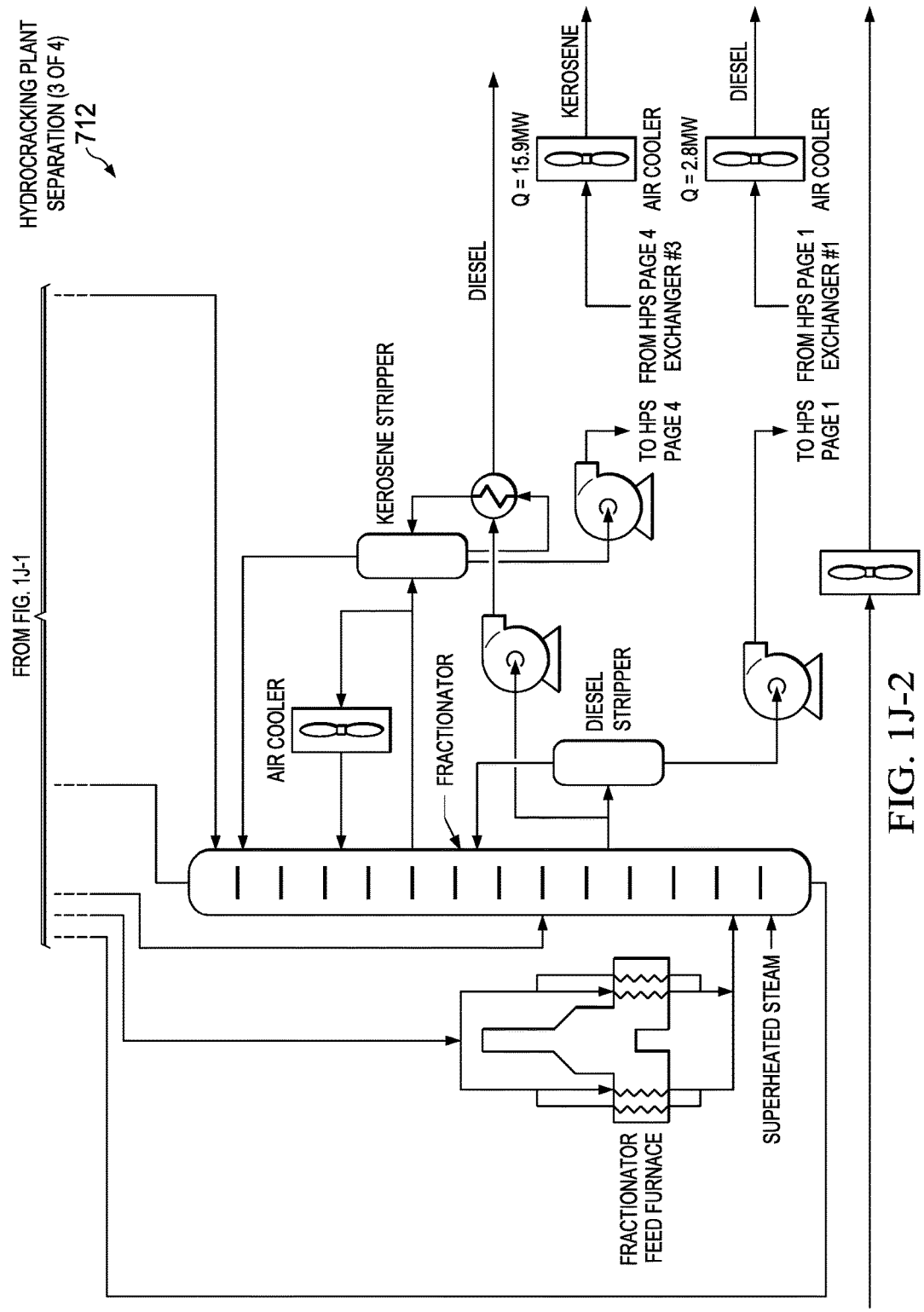
Figure 1K:
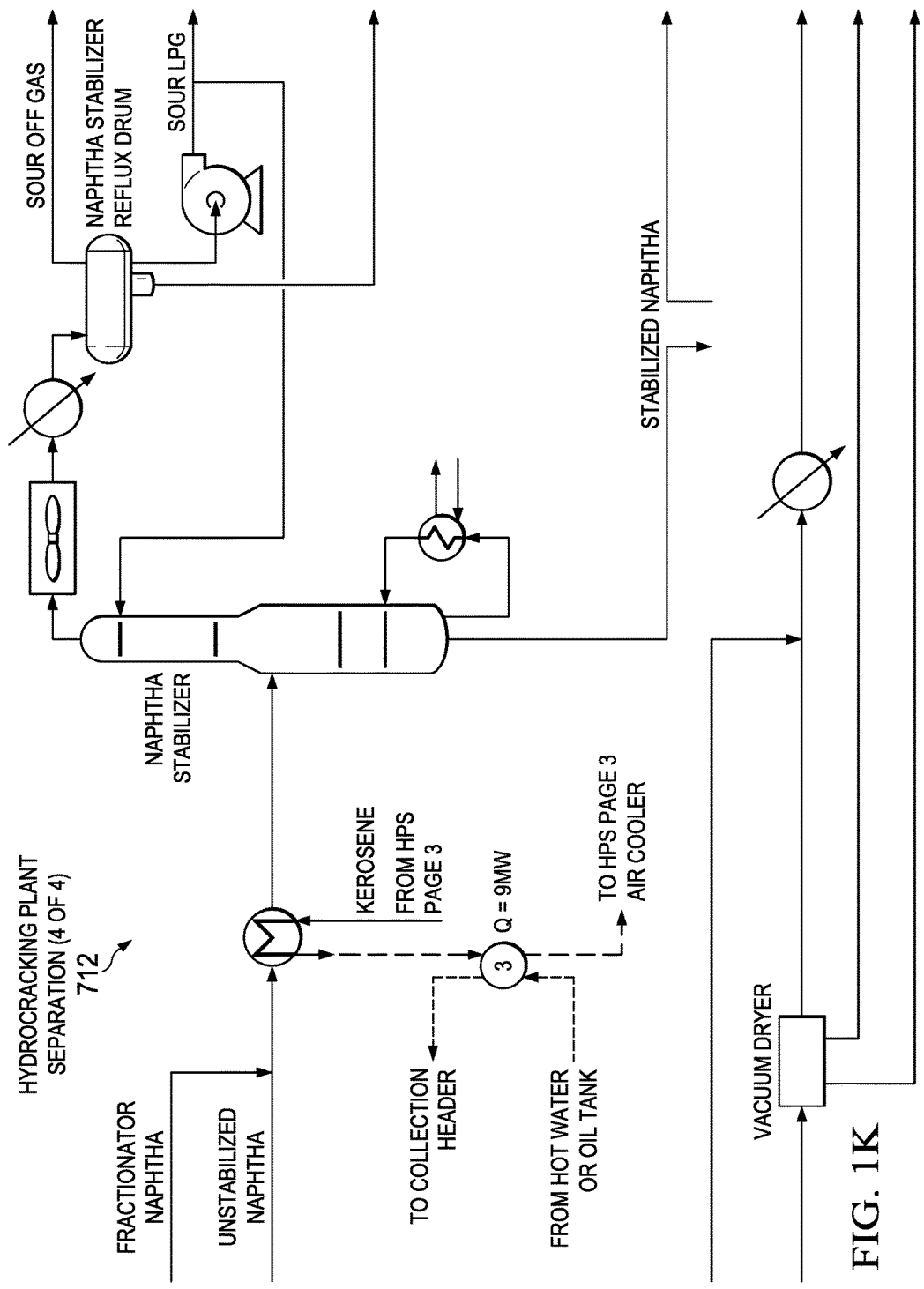
Figure 1L:
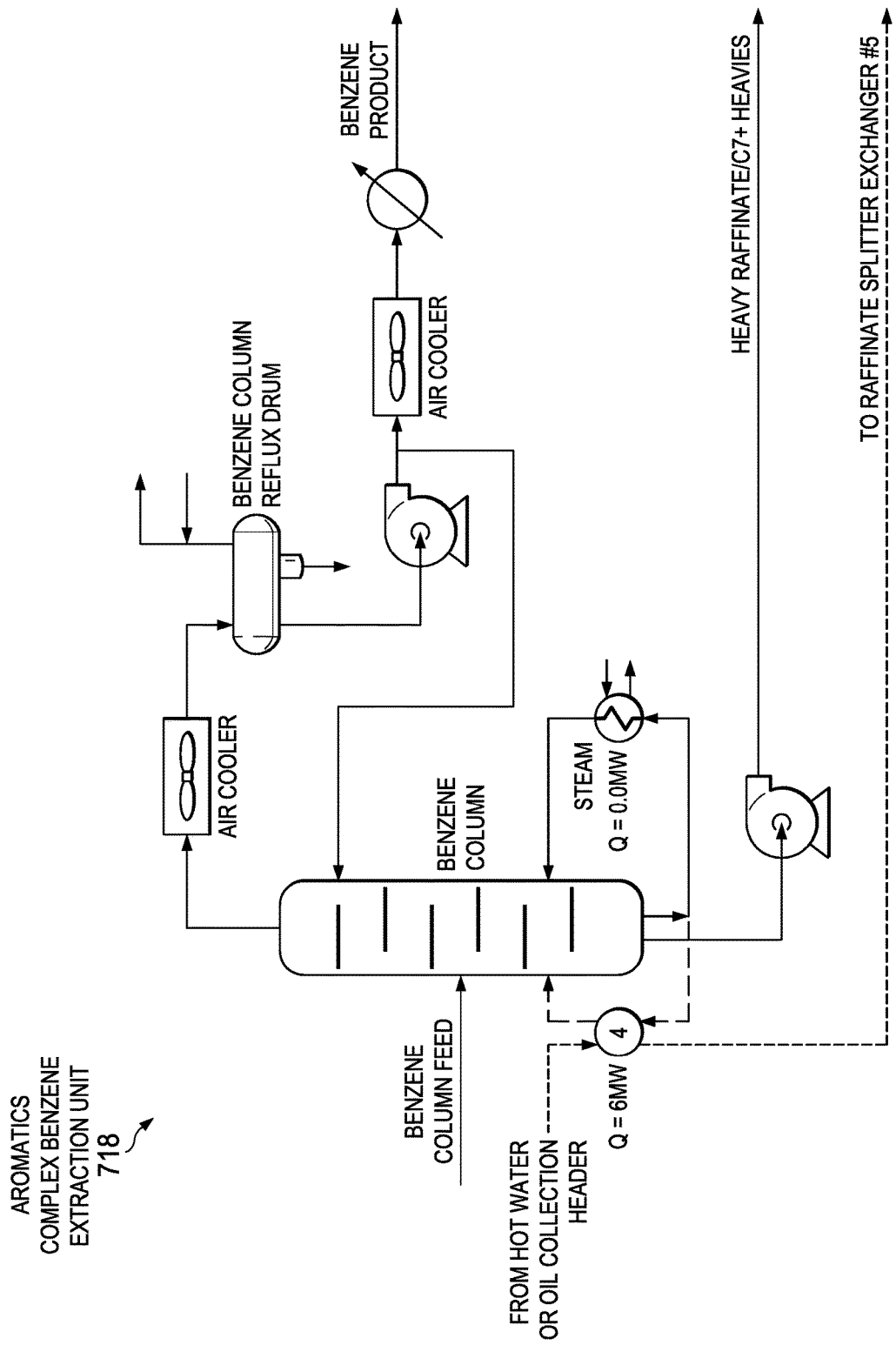
Figure 1M:
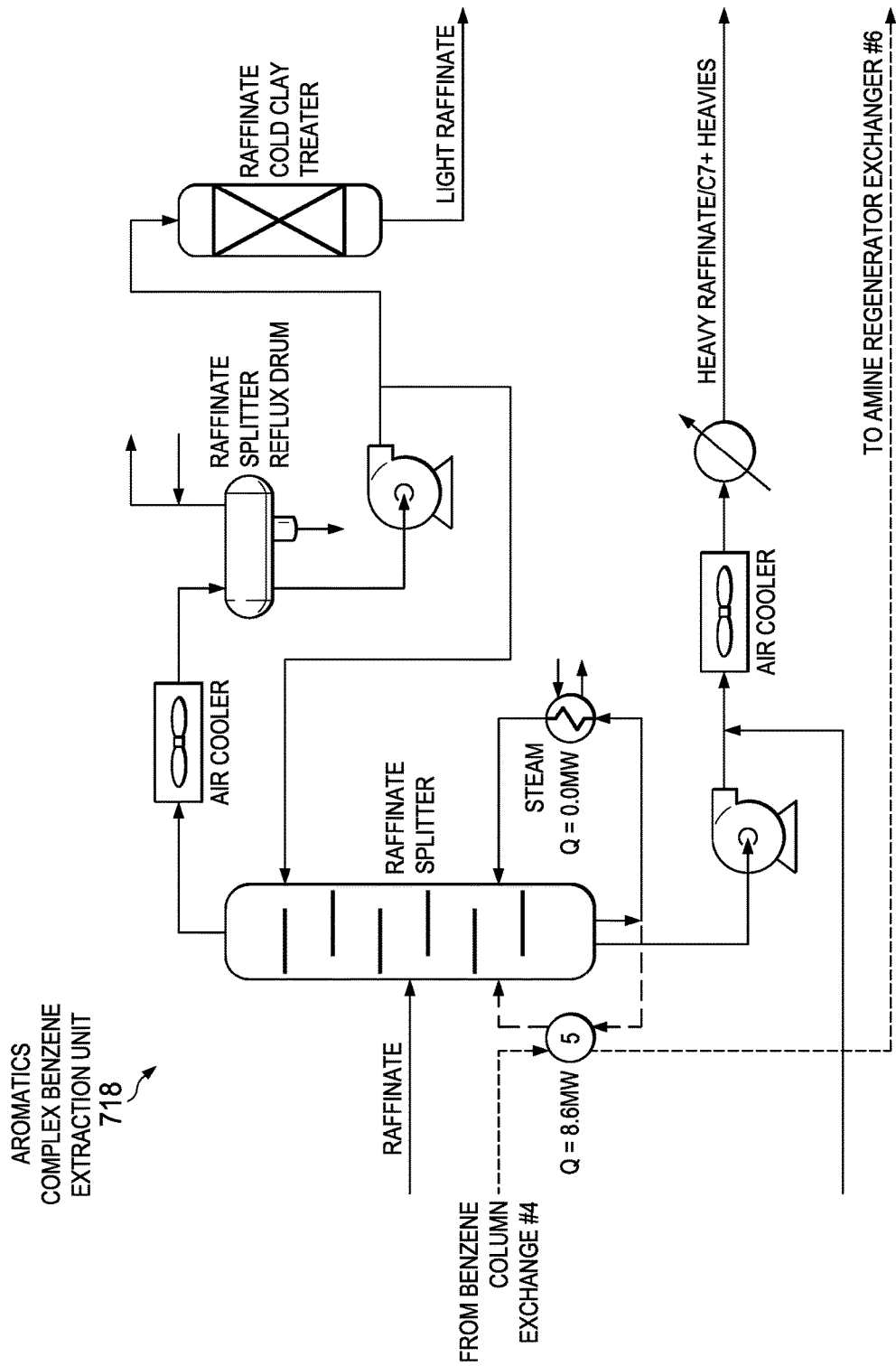
Figure 1N:
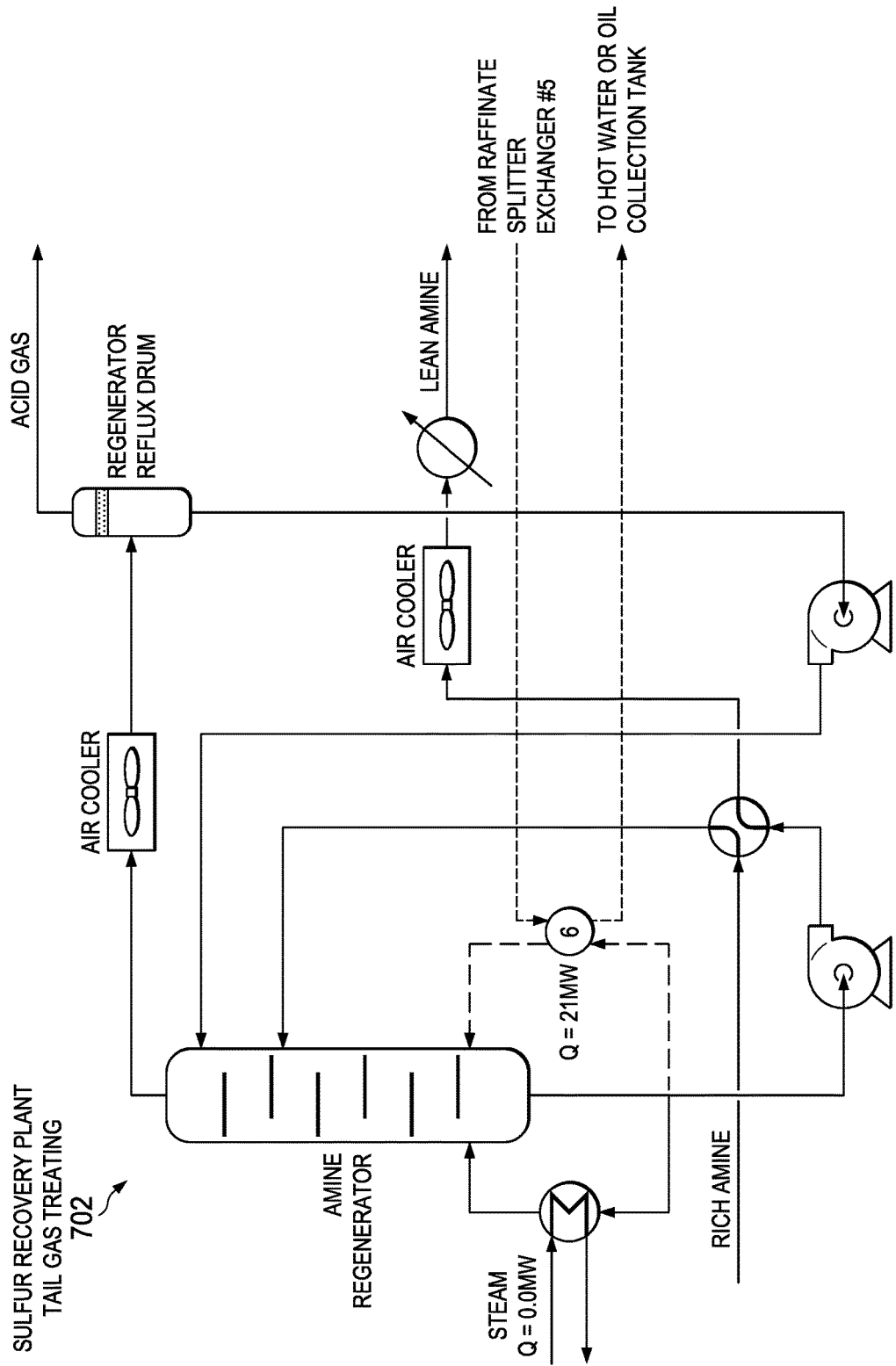

FIGS. 1A-1N illustrate configurations and related scheme details for thermally integrating different refining plants in the crude oil refining facility. The thermal integration described in these configurations and illustrated in FIGS. 1A-1N can reduce the crude oil refining facility's energy consumption (for example, heating and cooling utilities). For example, a reduction in energy consumption by about 36 MW, for example, 35.2 MW, can translate to at least about 6%, for example, 5.4%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 1—Scheme A

In some implementations, multiple first streams in the multiple first plants can be directly heated using multiple second streams in a second plant. In some implementations, the multiple first plants can include a sulfur recovery plant and an aromatics plant sub-unit including an aromatics complex benzene extraction unit. The second plant can include a hydrocracking plant.

FIGS. 1A-1D show a hydrocracking plant 712 in a crude oil refinery facility. As shown in FIG. 1A, a second stage reaction section feed to a second stage cold high pressure separator can directly heat a raffinate splitter bottoms stream in a second heat exchanger with a thermal duty that can range between about 5 MW and 15 MW (for example, 8.6 MW). The transfer of heat directly to another process streams captures heat that would have otherwise been discharged to the environment. The second stage reaction section feed to a second stage cold high pressure separator is returned to the hydrocracking plant 712 for further processing.

FIG. 1F shows an aromatics complex benzene extraction unit 718 in a crude oil refinery facility. The heated raffinate splitter bottoms stream can be flowed to the benzene extraction plant 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

As shown in FIG. 1B, a first stage reaction section feed to a first stage cold high pressure separator in the hydrocracking plant 712 can directly heat an amine regenerator bottoms stream in a third heat exchanger with a thermal duty that can range between about 15 MW and 25 MW (for example, 21 MW). The transfer of heat directly to another process streams captures heat that would have otherwise been discharged to the environment. The first stage reaction section feed to a first stage cold high pressure separator is returned to the hydrocracking plant 712 for further processing.

FIG. 1G shows a sulfur recovery plant 702 in a crude oil refinery facility. The heated amine regenerator bottom stream can then be flowed to the sulfur recovery plant 702. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

As shown in FIG. 1D, a kerosene product stream in the hydrocracking plant 712 can directly heat a benzene column bottoms stream in in a first heat exchanger with a thermal duty that can range between about 1 MW and 10 MW (for example, 6 MW). The transfer of heat directly to another process streams captures heat that would have otherwise been discharged to the environment. The kerosene product stream is returned to the hydrocracking plant 712 for further processing.

FIG. 1E also shows an aromatics complex benzene extraction unit 718. The heated benzene column bottoms stream can be flowed to the benzene extraction plant 718 in the aromatics complex. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

Such recovery and reuse of waste heat directly from the hydrocracking plant can result in decreasing or eliminating the heat energy to heat the sulfur recovery plant, the aromatics complex or a combinations of them such as by about 36 MW.

Configuration 1—Scheme B

In some implementations, the multiple first streams in the crude oil refining facility such as those present in the multiple first plants, such as the aromatic complex sub-units such as the benzene extraction unit and the sulfur recovery plant, can be indirectly heated using the multiple second streams in a second plant, such as one or more hydrocracking plant, as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712. The buffer fluid can be flowed into the plant as a single stream and split into multiple streams or it can be flowed into the plant as multiple streams.

FIGS. 1H-1K shows a hydrocracking plant 712 in a crude oil refining facility. Specifically, FIG. 1H shows a first buffer fluid stream can be heated using a diesel product stream in a first heat exchanger with a thermal duty that can range between about 5 MW and 15 MW (for example, 9.4 MW). As shown in FIG. 1I, a second buffer fluid stream can be heated using a first stage reaction section feed to a first stage cold high pressure separator in a second heat exchanger with a thermal duty that can range between about 10 MW and 20 MW (for example, 15.6 MW). As shown in 1K, a third buffer fluid stream can be heated using a kerosene product stream in a third heat exchanger with a thermal duty that can range between about 5 MW and 15 MW (for example, 9 MW). The diesel product stream, first stage reaction section feed to a first stage cold high pressure separator and the kerosene product stream are each returned to the hydrocracking plant 712 for further processing. In all instances, the buffer fluid absorbs heat that would have otherwise been discharged to the environment.

The first, second, and third heated buffer fluid streams are combined into a combined heated buffer fluid in a collection header. In this manner, the first, second and third heat exchangers are parallel to one another relative to the flow of the buffer fluid.

The combined heated buffer fluid from the collection header (or in some embodiments, a heated or insulated buffer fluid tank or storage unit that can hold heated collected buffer fluid for a period before use) can be flowed to the sulfur recovery plant 702 or aromatics complex benzene extraction unit 718 or combination thereof.

In an instance, the combined heated buffer fluid is flowed to the benzene extraction unit 718. FIG. 1L shows an aromatics complex benzene extraction unit 718 in a crude oil refining facility. The benzene column bottoms stream is heated using the combined heated buffer fluid stream in a fourth heat exchanger with a thermal duty that can range between about 1 MW and 10 MW (for example, 6 MW). The fourth heat exchanger is coupled to, in series with and is downstream of the set of the first, second and third heat exchangers relative to the buffer fluid flow. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1M also shows the aromatics complex benzene extraction unit 718. A raffinate splitter bottoms stream can be heated using the combined heated buffer fluid branch in a fifth heat exchanger with a thermal duty that can range between about 5 MW and 15 MW (for example, 8.6 MW). The fifth heat exchanger is coupled to, in series with and is downstream of the set of the first, second and third heat exchangers relative to the buffer fluid flow. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

The combined heated buffer fluid is flowed to the sulfur recovery plant 702. FIG. 1N shows the sulfur recovery plant 702 in a crude oil refining facility. An amine regenerator bottoms stream is heated using the combined heated buffer fluid in a sixth heat exchanger with a thermal duty that can range between about 15 MW and 25 MW (for example, 21 MW). The sixth heat exchanger is coupled to, in series with and is downstream of the set of the first, second and third heat exchangers relative to the buffer fluid flow. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

The combined heated buffer fluid stream exiting the sixth heat exchanger is flowed to the collection header or the buffer fluid tank for reuse. In this manner, the fourth, fifth, and sixth heat exchangers are coupled to and are in series with each other relative to the flow of buffer fluid.

In some implementations, the heated buffer fluid can be flowed in series through the different plants. For example, the heated buffer fluid can be flowed first to the sulfur recovery plant and then to the benzene extraction unit. In another implementation, within the benzene extraction unit the heated buffer fluid stream may flow through the heat exchangers in a different order as presented. The heated buffer fluid exiting the sixth heat exchanger can be flowed to a buffer fluid tank. The buffer fluid from the buffer fluid tank can then be flowed to the different plants to restart the waste heat recovery and reuse cycle.

Such recovery and reuse of waste heat indirectly from the hydrocracking plant can result in decreasing or eliminating the heat energy for heating the sulfur recovery plant, the aromatics complex or combinations of them such as by about 36 MW.

Configuration 2

FIGS. 1O-1AC illustrate configurations and related scheme details for thermally integrating different refining plants in the crude oil refining facility. The thermal integration described in these configurations and illustrated in FIGS. 1O-1AC can reduce the crude oil refining facility's energy consumption (for example, heating and cooling utilities). For example, a reduction in energy consumption by about 41 MW, for example, 40.6 MW, can translate to at least about 7%, for example, 7.2%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 2—Scheme A

In some implementations, multiple first streams in the multiple first plants can be directly heated using multiple second streams in a second plant. In some implementations, the multiple first plants can include a sour water stripper plant and an aromatics plant sub-unit including an aromatic complex benzene extraction unit. The second plant can include a hydrocracking plant.

Figure 1P:
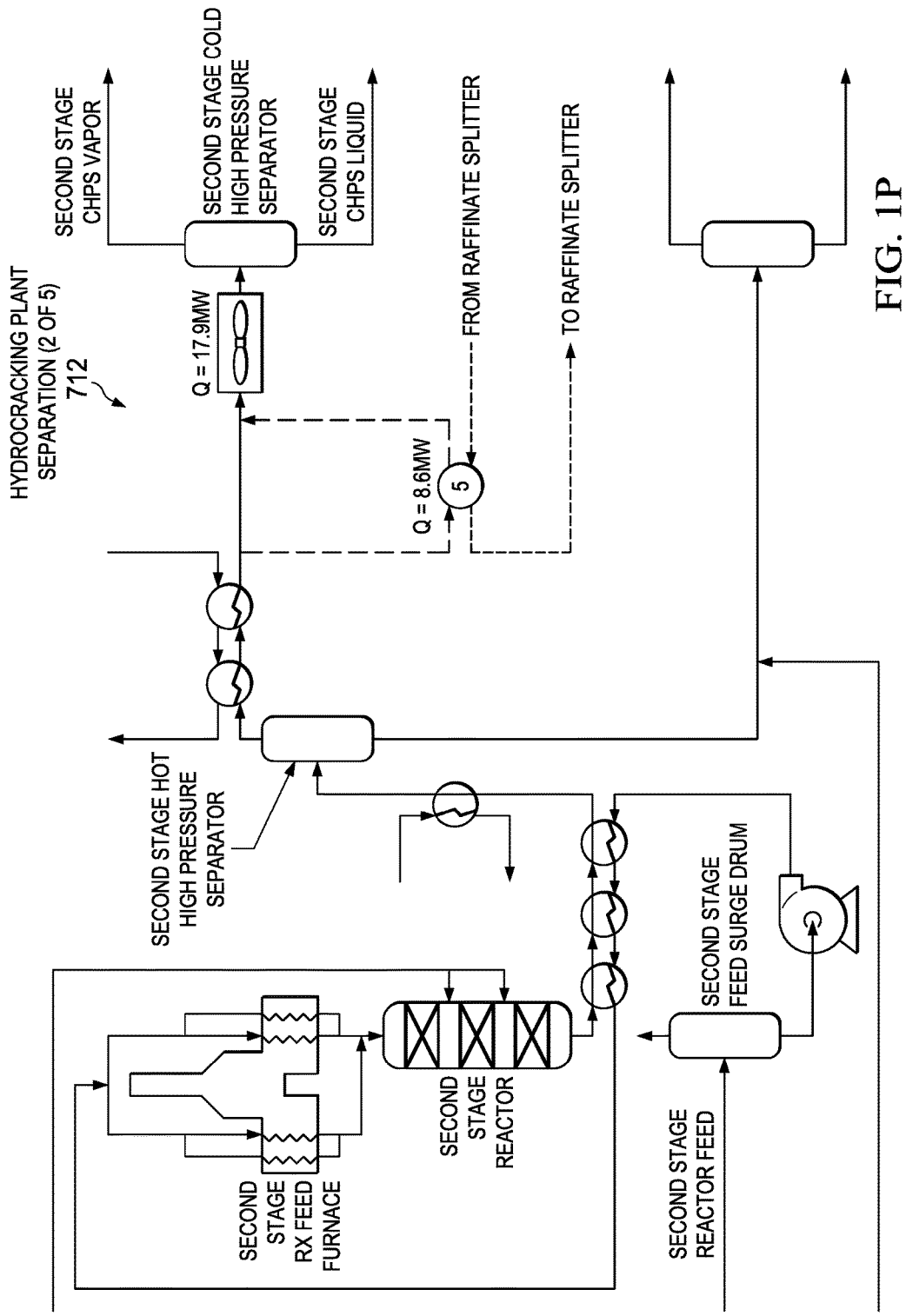
Figure 1Q:
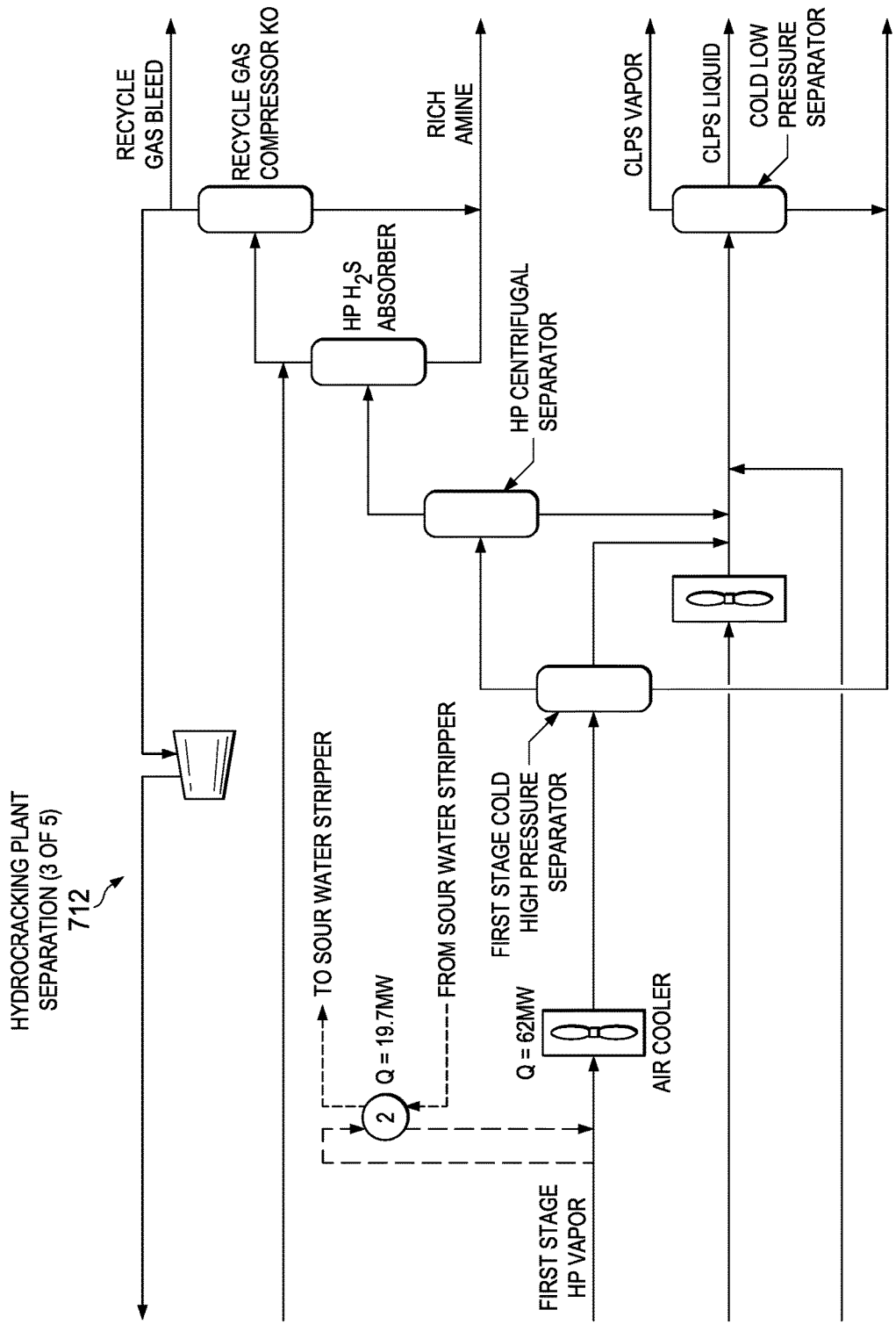
Figures 1, 1R:
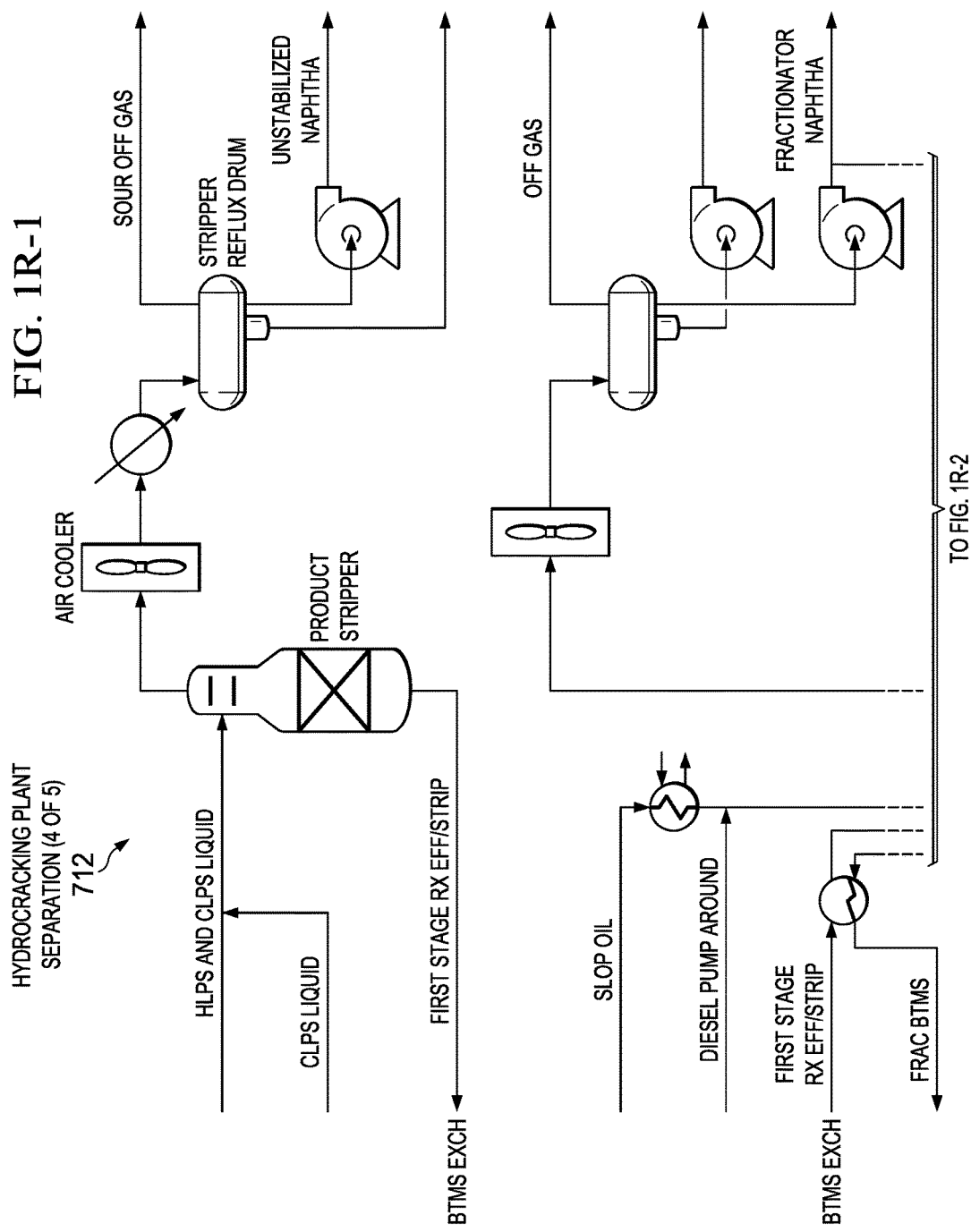
Figures 1, 1R, 2:
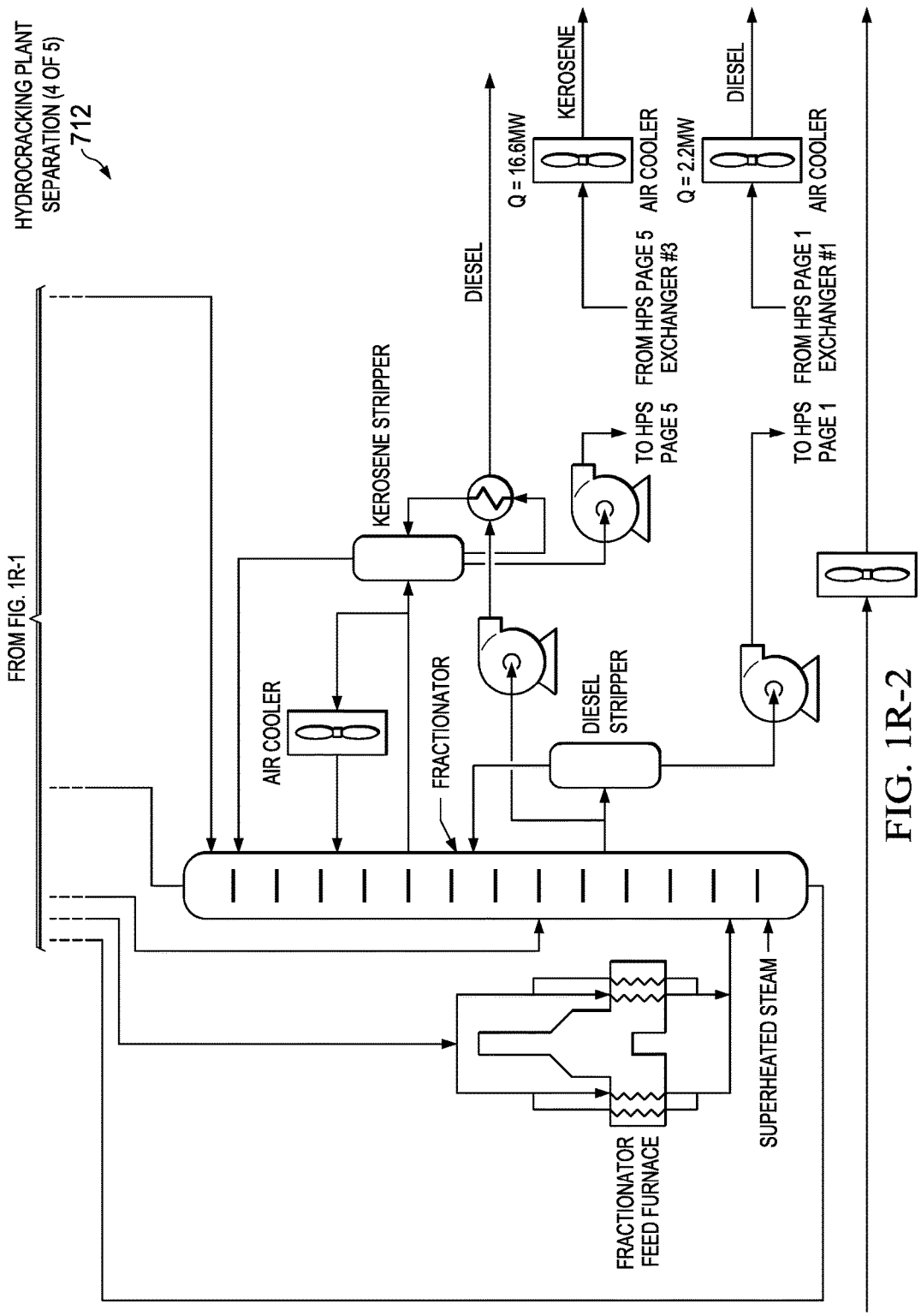
Figure 1S:
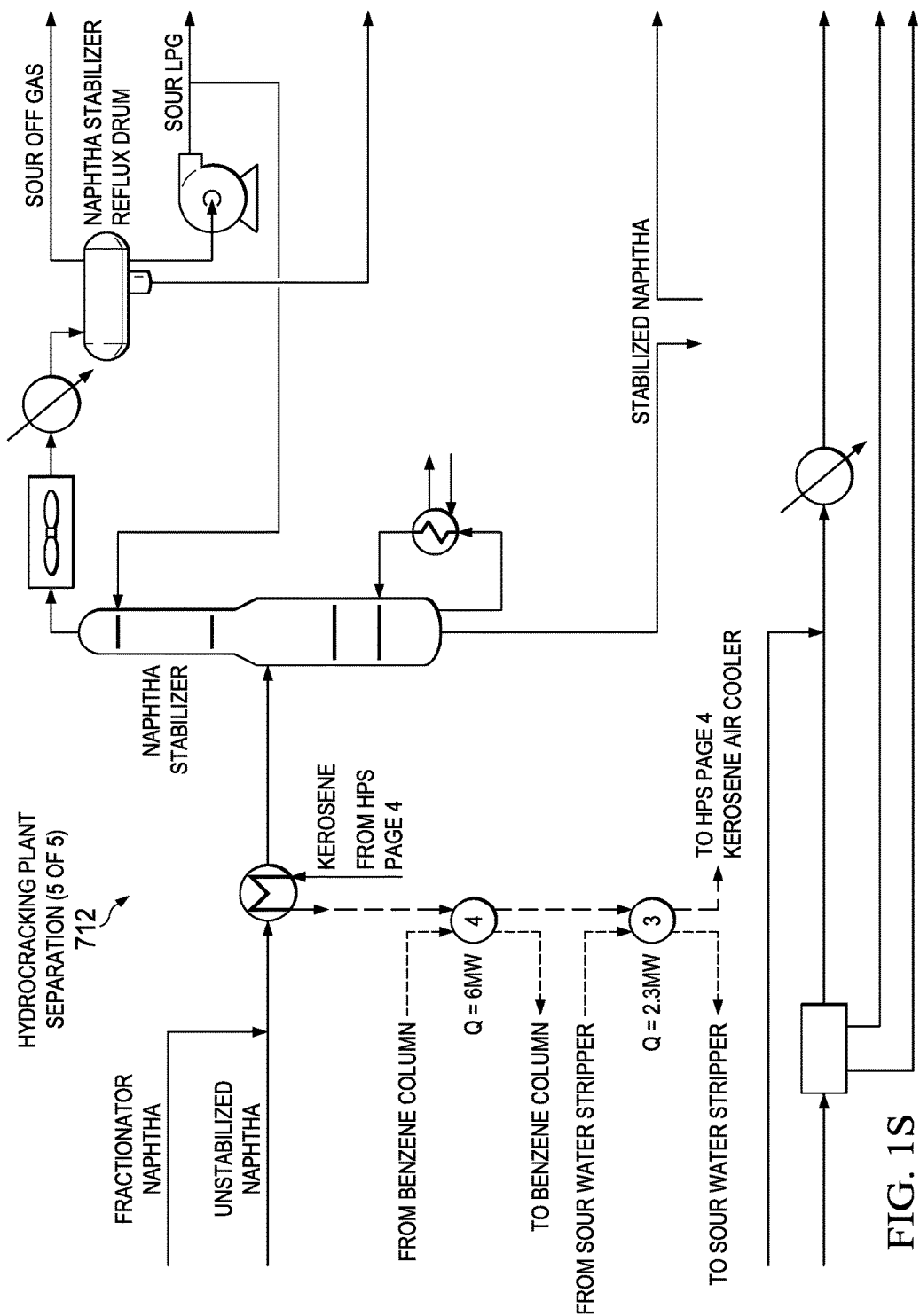
Figure 1T:
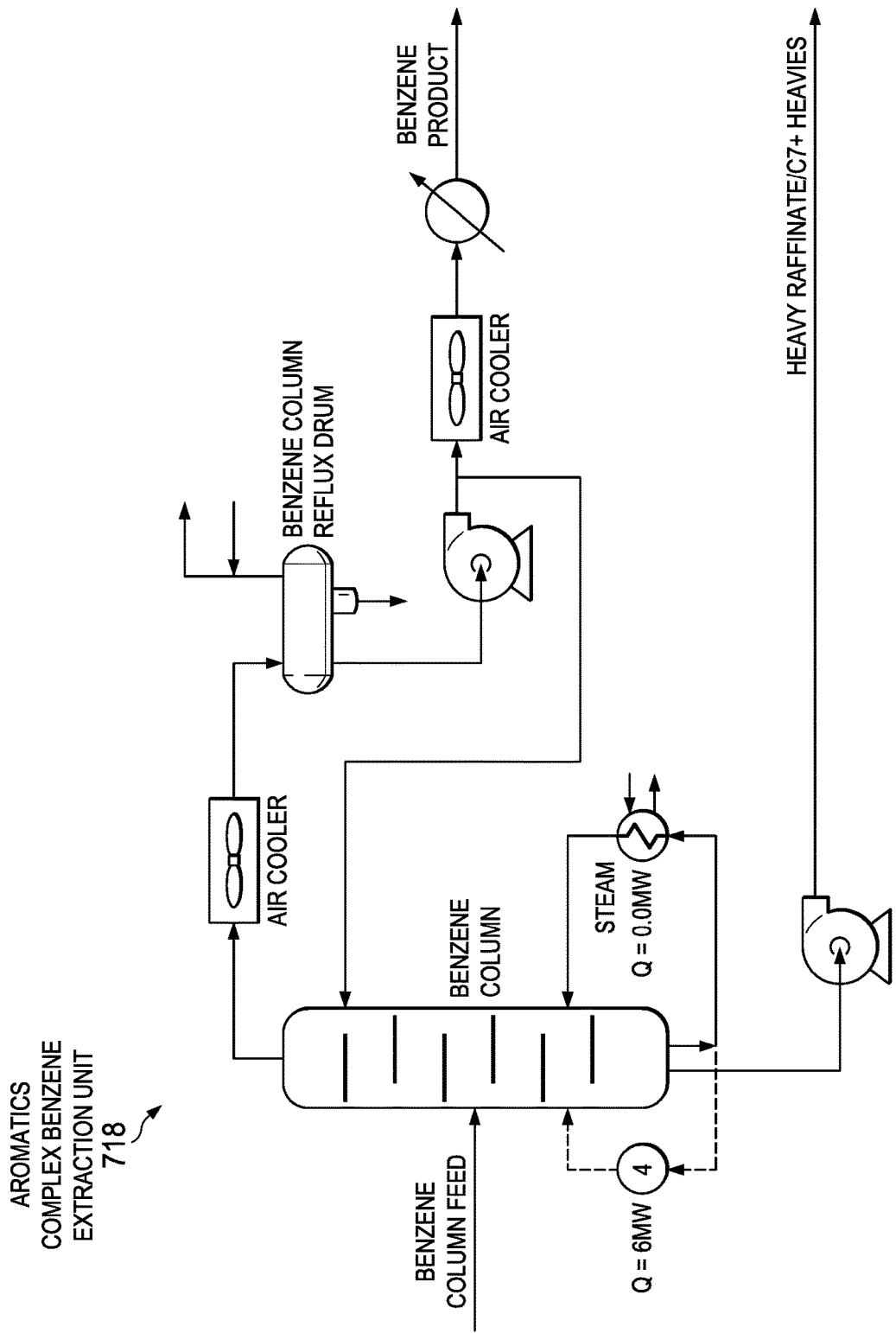
Figure 1U:
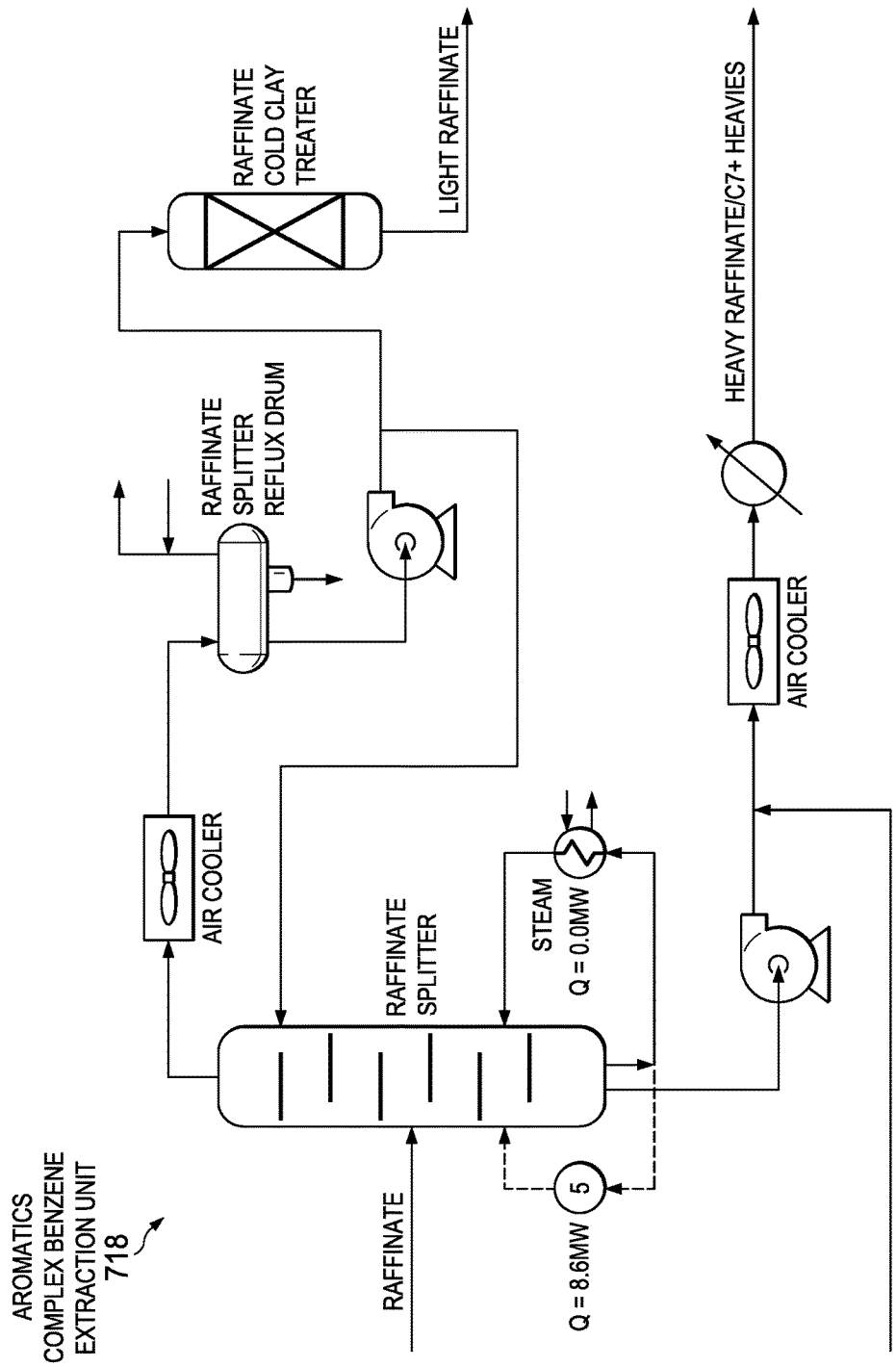
Figure 1V:
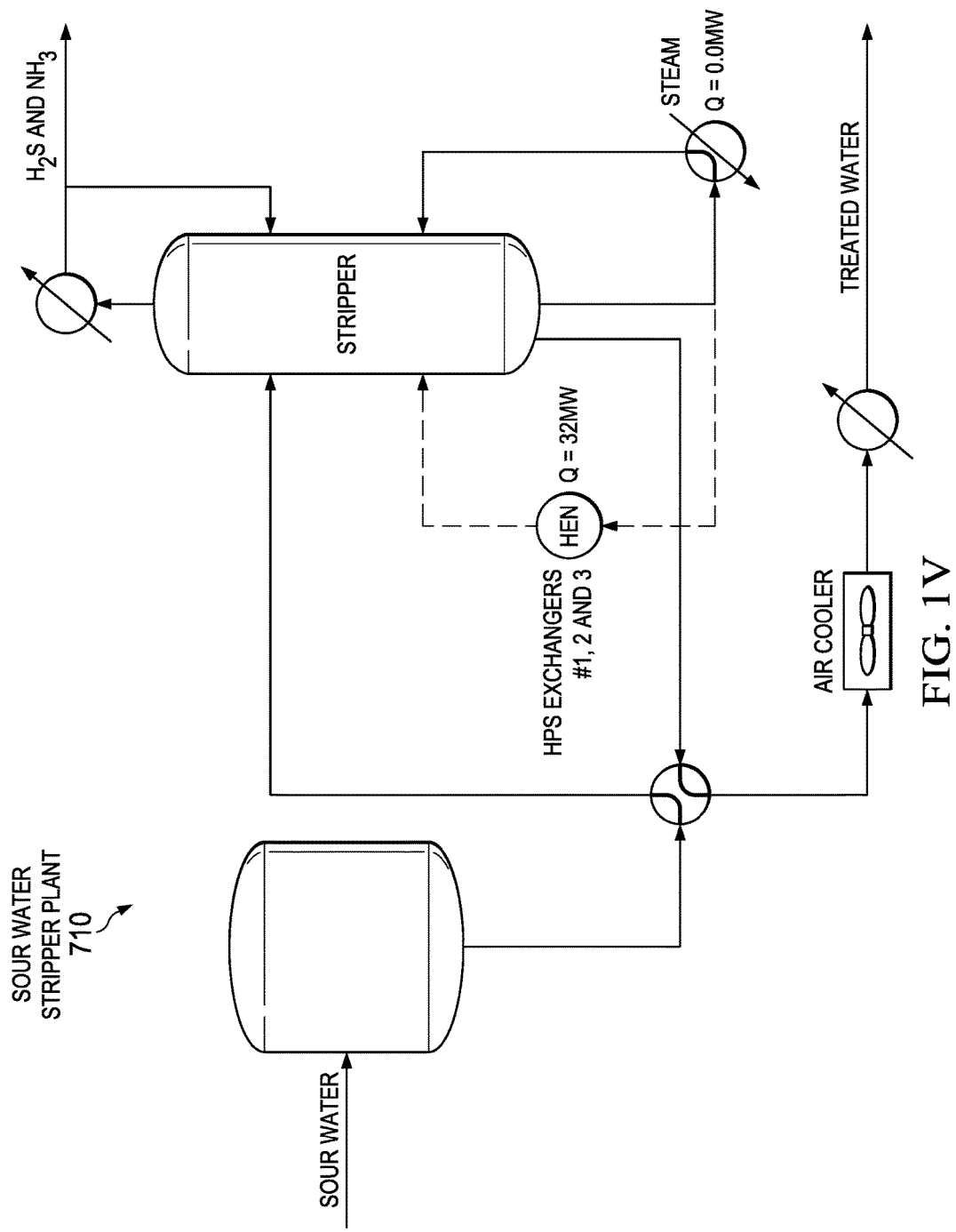
Figure 1W:
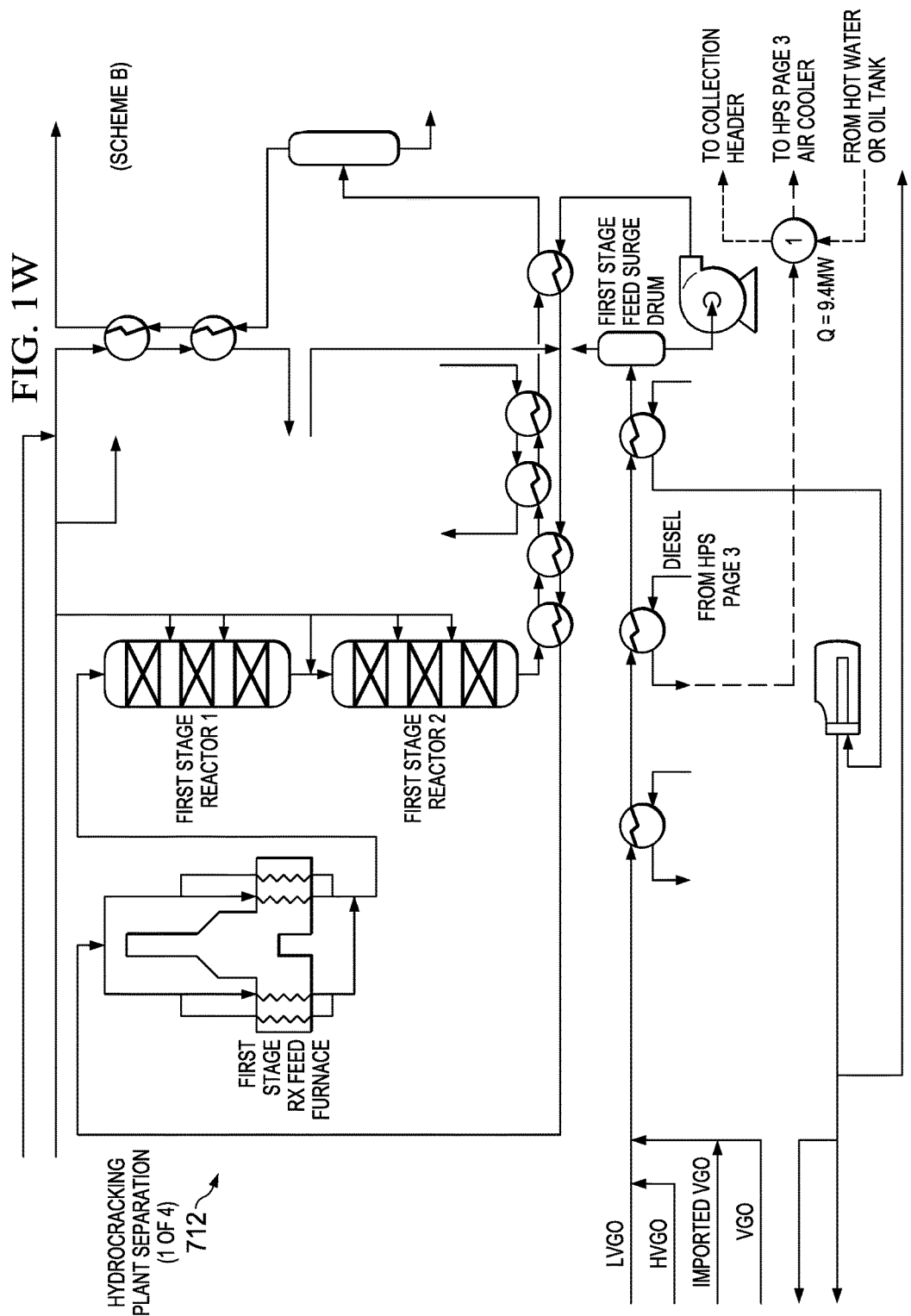

FIG. 1V shows a sour water stripper plant 710 in a crude oil refinery facility. The sour water stripper bottoms stream can be flowed in the plant as a single stream and split into multiple streams or it can be flowed into the plant as multiple streams to facilitate heat recovery.

FIGS. 1O-1S show a hydrocracking plant 712 in a crude oil refinery facility. As shown in FIG. 1O, a diesel product stream can directly heat a first sour water stripper bottoms stream in a first heat exchanger with a thermal duty that can range between about 5 MW and 15 MW (for example, 10 MW). The transfer of heat directly to another process streams captures heat that would have otherwise been discharged to the environment. The diesel product stream is returned to the hydrocracking plant 712 for further processing.

As shown in FIG. 1P, a second stage reaction section feed to a second stage cold high pressure separator can directly heat a raffinate splitter bottom stream in a fifth heat exchanger with a thermal duty that can range between about 5 MW and 15 MW (for example, 8.6 MW). The transfer of heat directly to another process streams captures heat that would have otherwise been discharged to the environment. The second stage reaction section feed to the second stage cold high pressure separator is returned to the hydrocracking plant 712 for further processing.

As shown in FIG. 1Q, a first stage reaction feed stream to first stage cold high pressure separator can directly heat a second sour water stripper bottoms stream in a second heat exchanger with a thermal duty that can range between about 15 MW and 25 MW (for example, 19.7 MW). The transfer of heat directly to another process streams captures heat that would have otherwise been discharged to the environment. The first stage reaction feed stream to the first stage cold high pressure separator is returned to the hydrocracking plant 712 for further processing.

As shown in FIG. 1S, a kerosene product stream can directly heat a third sour water stripper bottoms stream in a third heat exchanger having a thermal duty that can range between about 1 MW and 10 MW (for example, 2.3 MW). The transfer of heat directly to another process streams captures heat that would have otherwise been discharged to the environment.

The kerosene product stream can also directly heat a benzene column bottoms stream in a fourth heat exchanger having a thermal duty that can range between about 1 MW and 10 MW (for example, 6 MW). The transfer of heat directly to another process streams captures heat that would have otherwise been discharged to the environment. The kerosene product stream is returned to the hydrocracking plant 712 for further processing.

As shown in FIG. 1S, the third heat exchanger is coupled to, in series with and is downstream of the fourth heat exchanger relative to the flow of kerosene product stream. In some implementations, the kerosene product stream can be flowed in series through the different plants. For example, the kerosene product stream is flowed first through the sour water stripper heat exchanger and then through the aromatics complex heat exchanger. As shown in FIG. 1V, the three heated sour water stripper bottoms streams are recombined and flowed to the sour water stripper plant 710. In this manner, the first heat exchanger, the second heat exchanger, and the third heat exchanger can be coupled to each other in parallel relative to the flow of sour water stripper bottoms. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1T shows an aromatics complex benzene extraction unit 718 in a crude oil refining facility. The heated benzene column bottoms stream can be flowed to the benzene extraction plant 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1U also shows an aromatics complex benzene extraction unit 718. The heated raffinate splitter column bottoms stream can be flowed to the benzene extraction plant 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Such recovery and reuse of waste heat directly from the hydrocracking plant can result in decreasing or eliminating the heat energy to heat the aromatics complex, the sour water stripper plant or a combination of them such as by about 41 MW.

Configuration 2—Scheme B

In some implementations, the multiple first streams in the crude oil refining facility such as those present in the multiple first plants, such as in the aromatic complex sub-units such as the benzene extraction unit and the sour water stripper plant, can be indirectly heated using the multiple second streams in a second plant, such as one or more hydrocracking plant, as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712. The buffer fluid can be flowed into the plant as a single stream and split into multiple streams or it can be flowed into the plant as multiple streams.

Figure 1X:
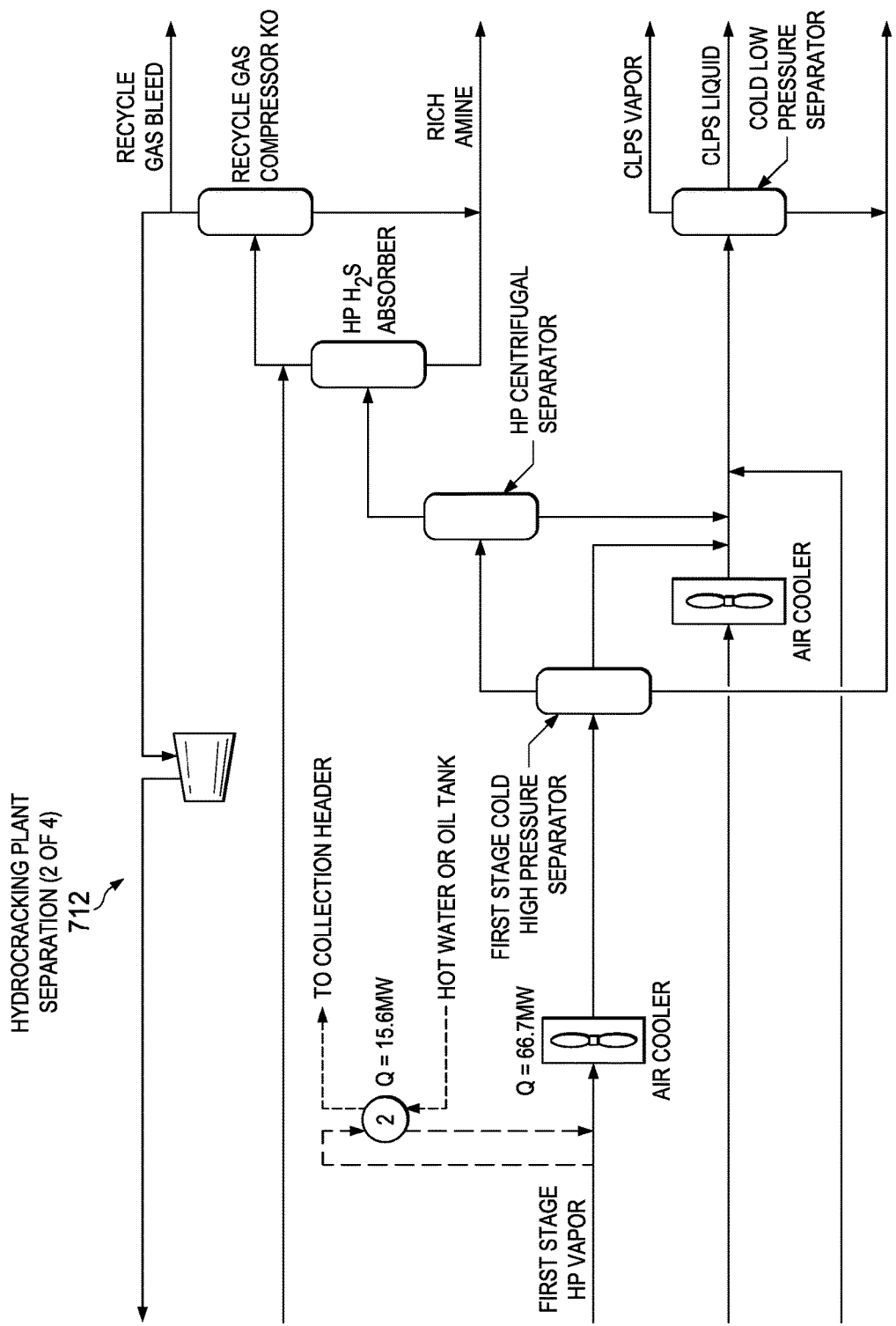
Figures 1, 1Y:
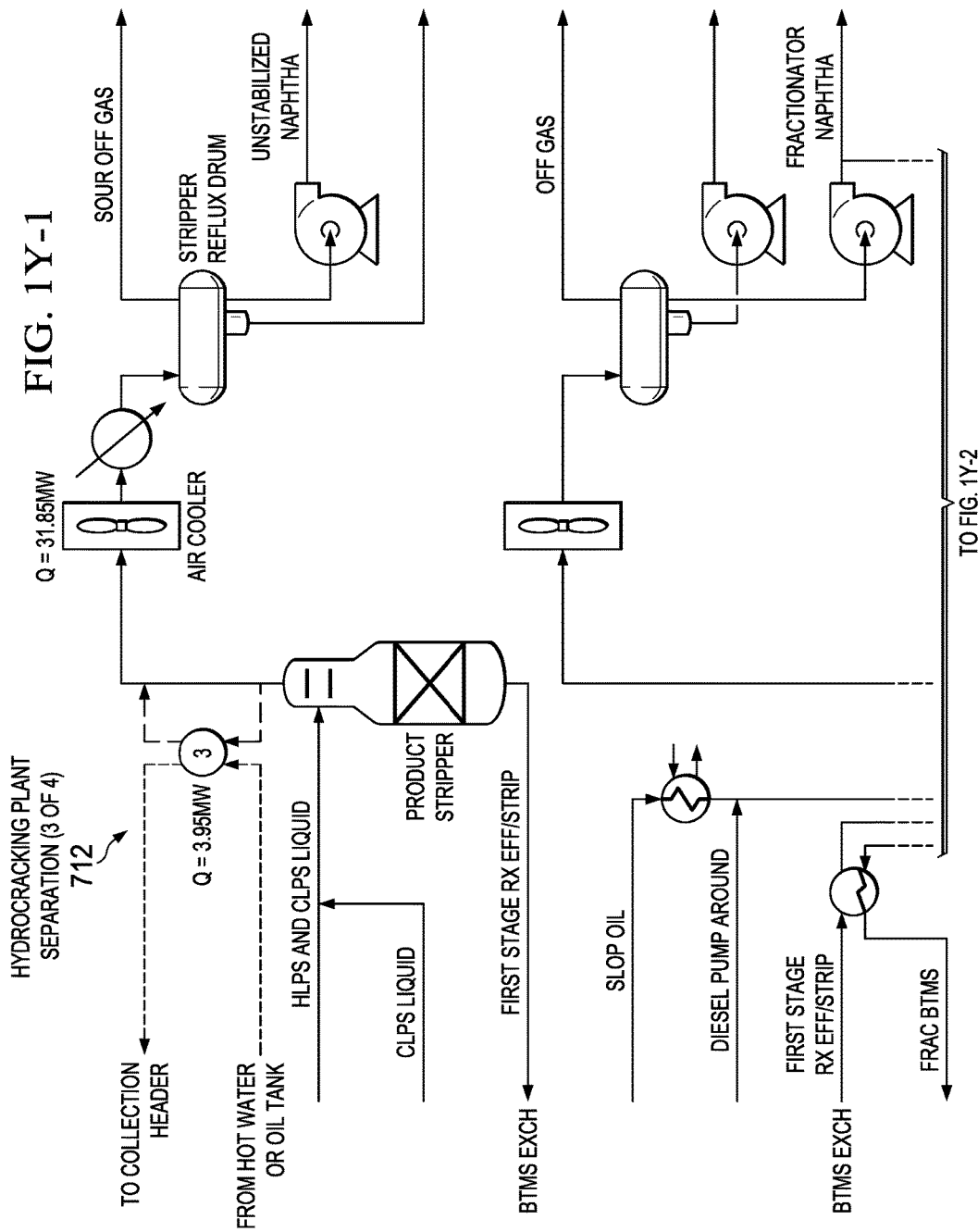
Figures 1, 1Y, 2:
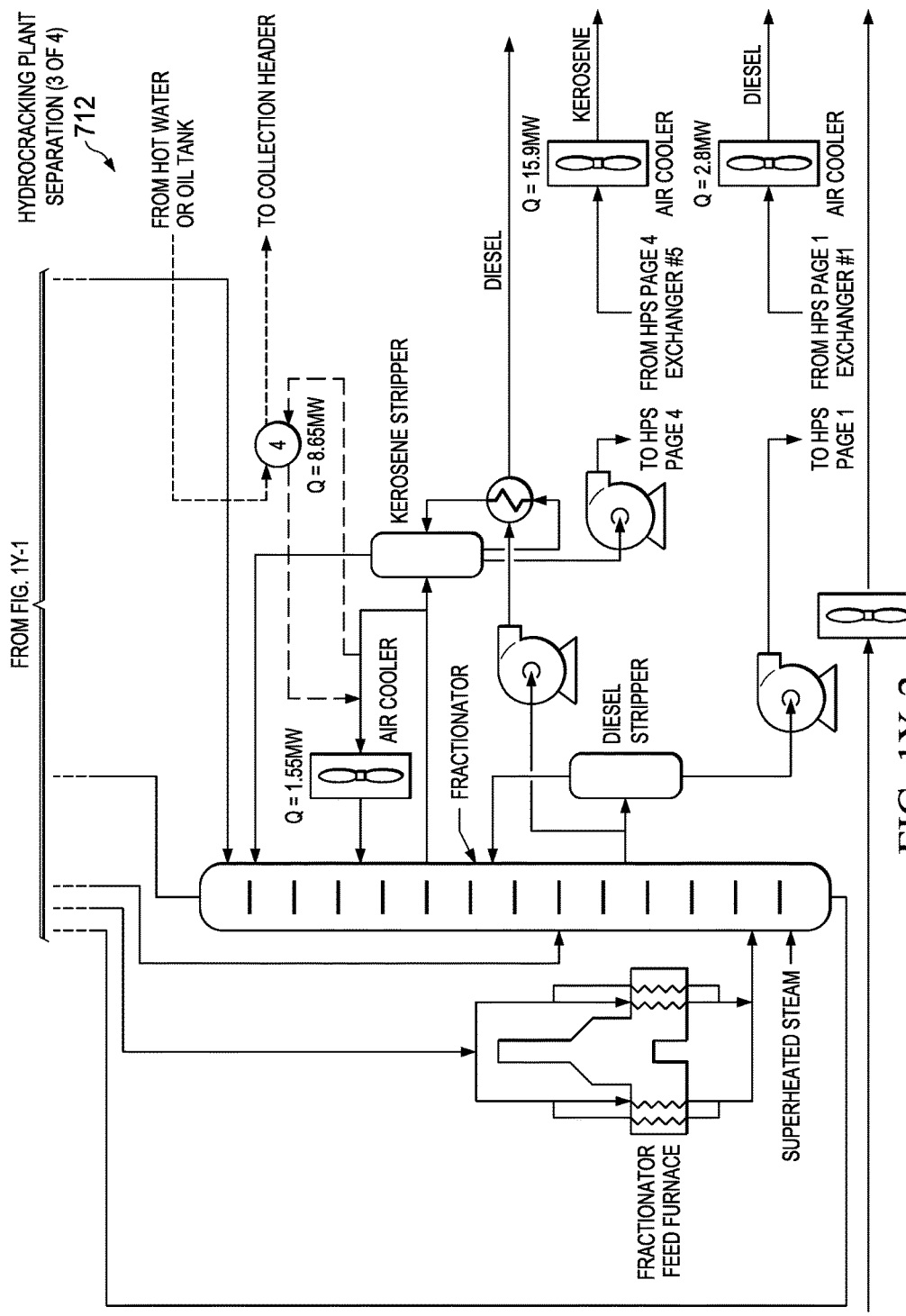
Figure 1Z:
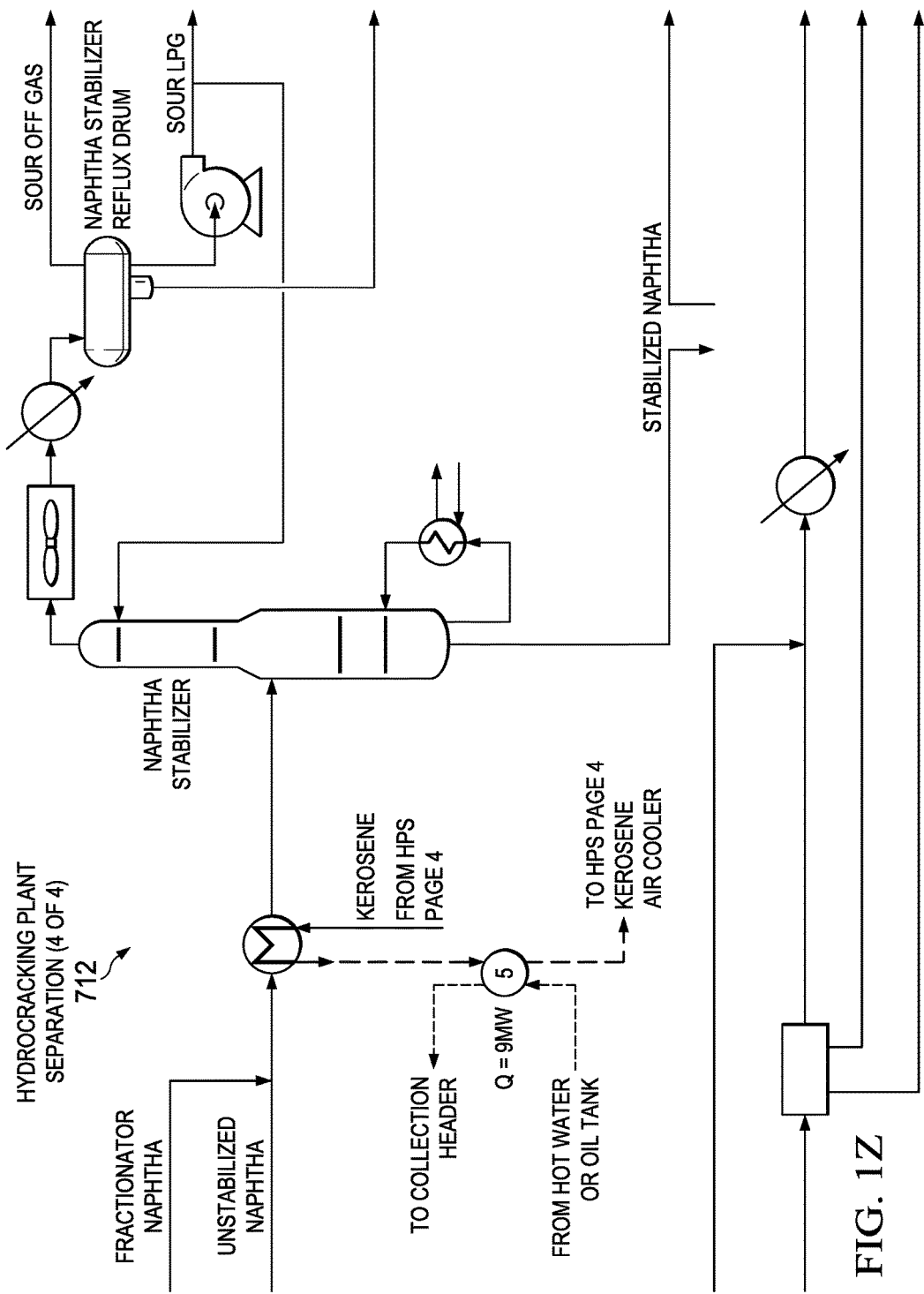
Figure 1A:
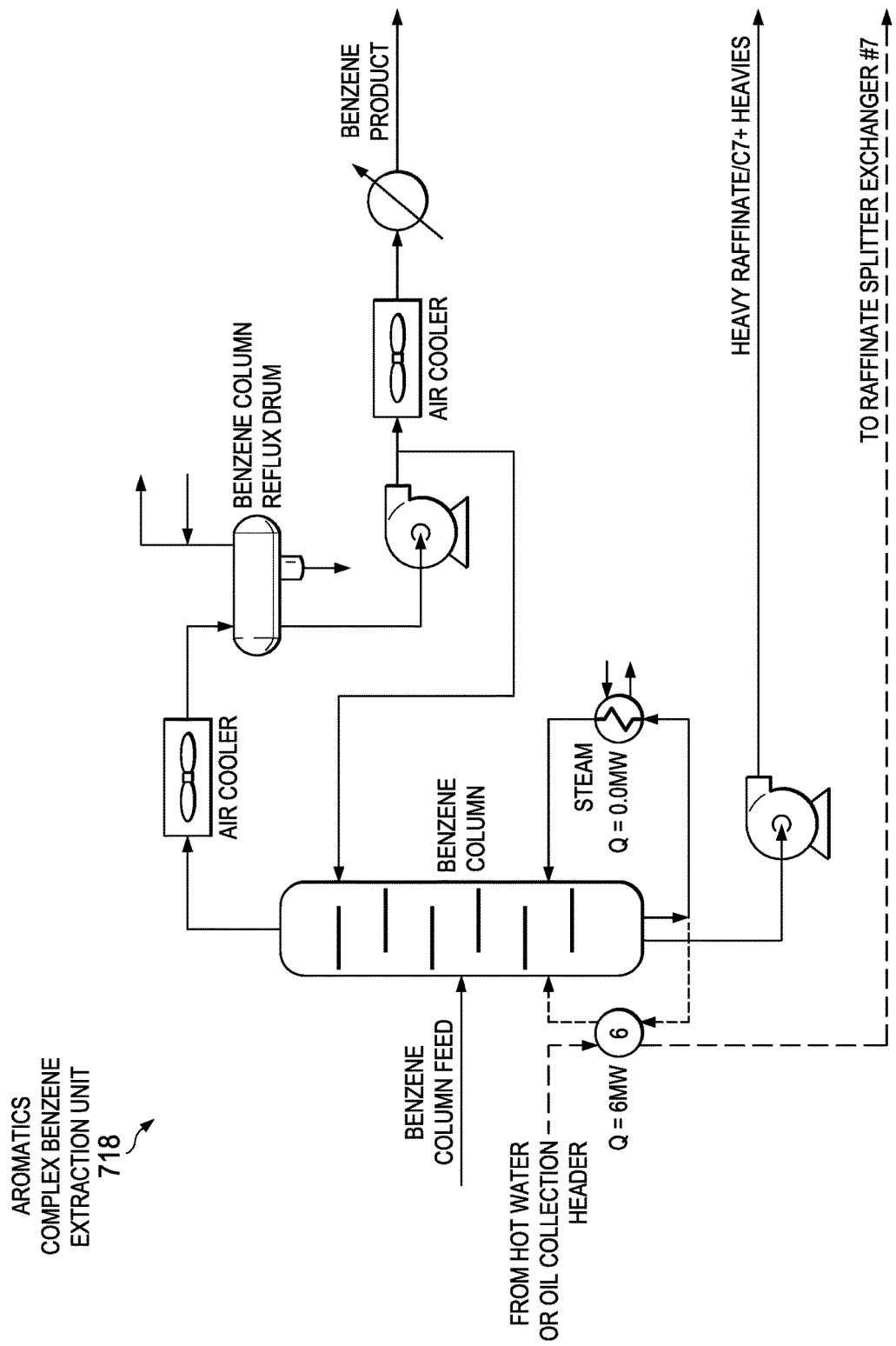
Figure 1A:
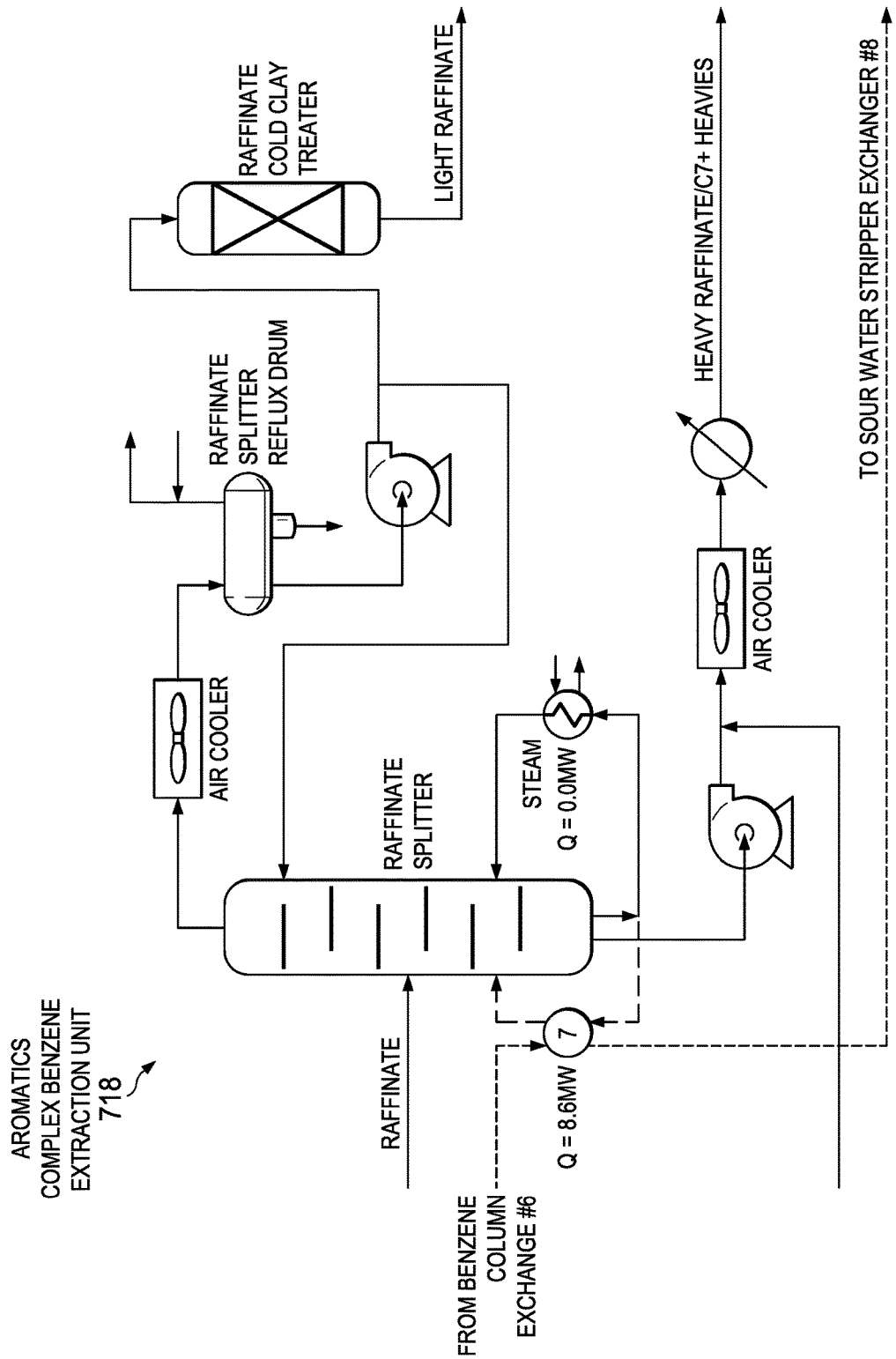
Figure 1A:
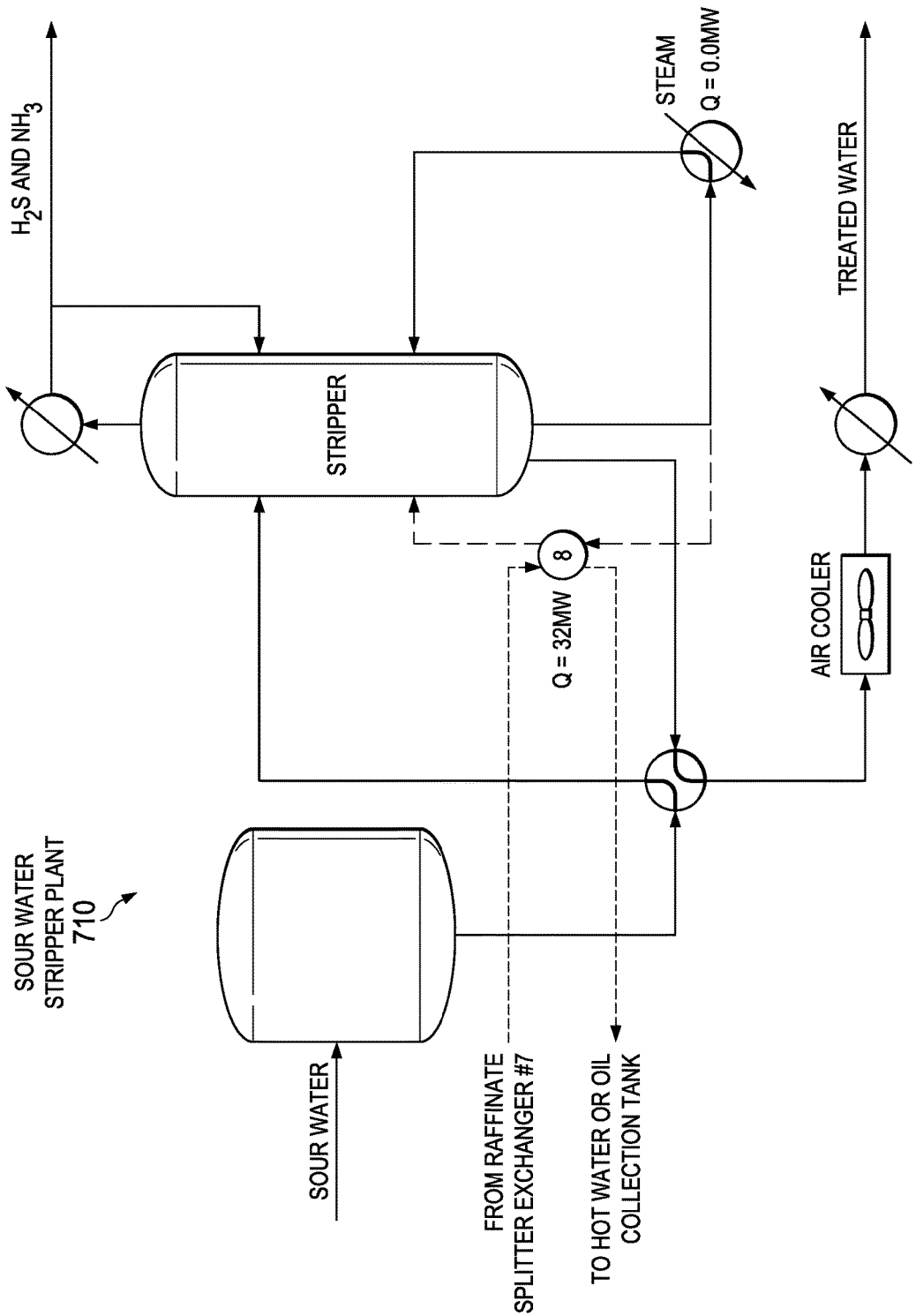
Figure 1A:
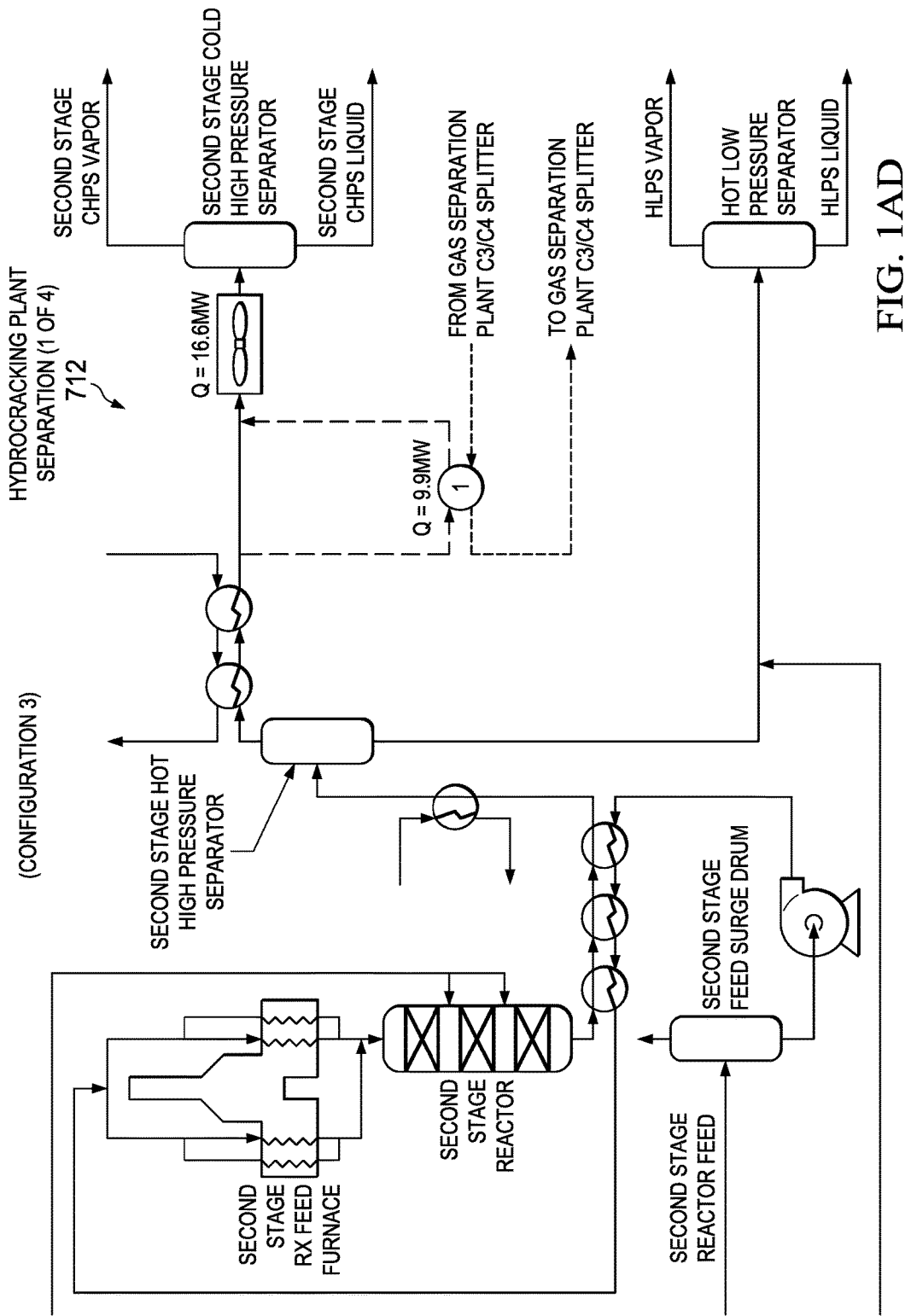
Figure 1A:
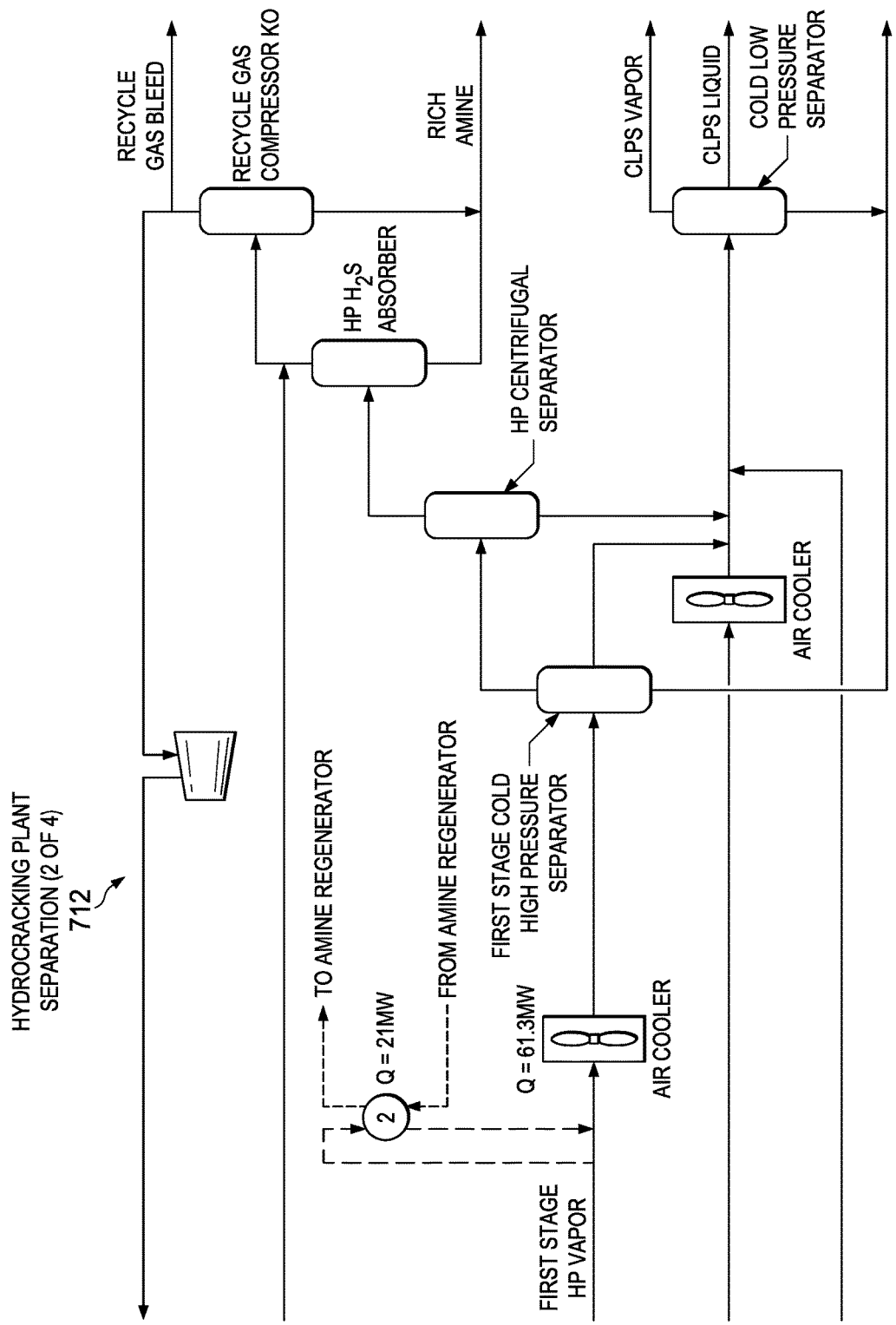
Figure 1A:
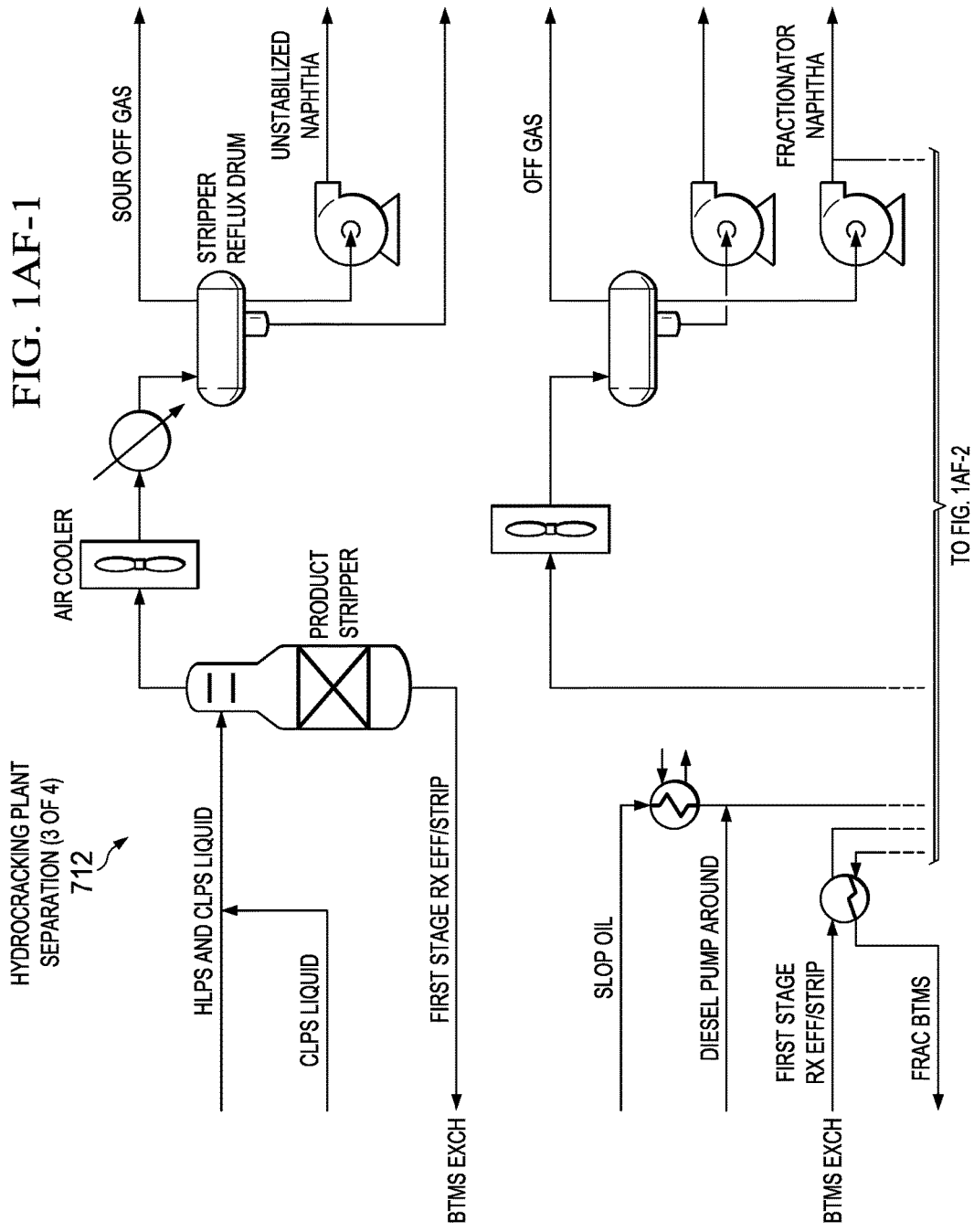
Figure 1A:
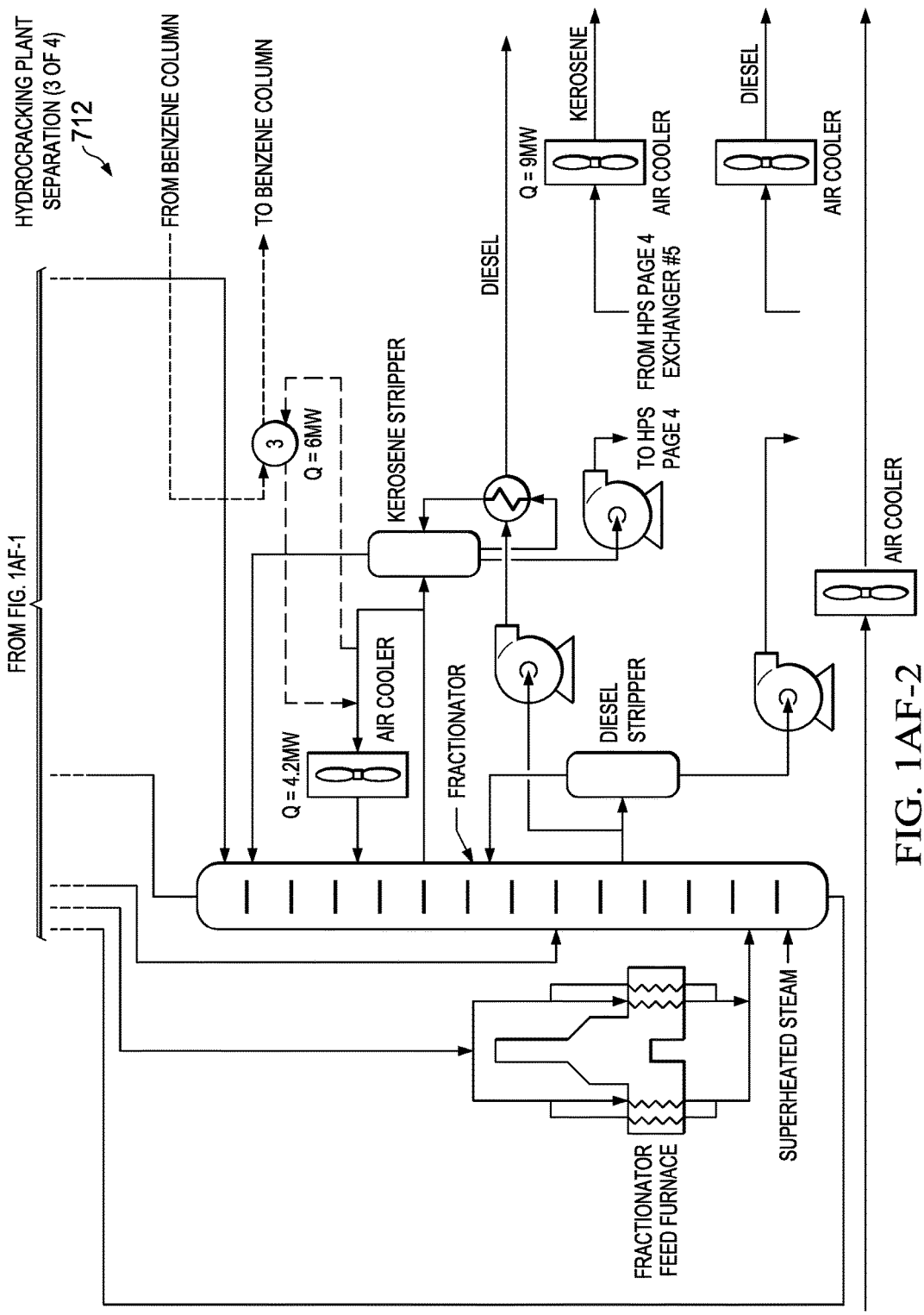
Figure 1A:
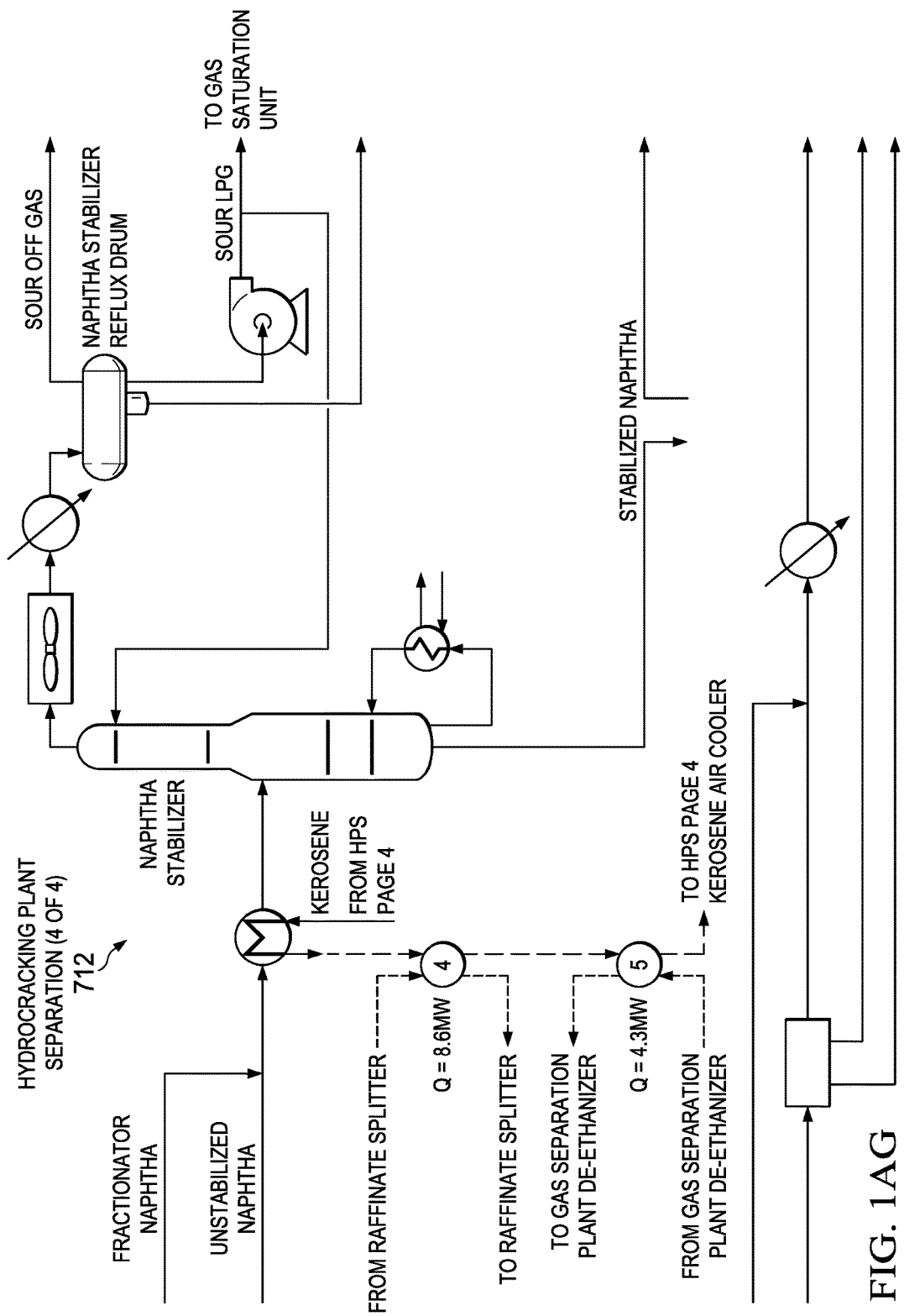
Figure 1A:
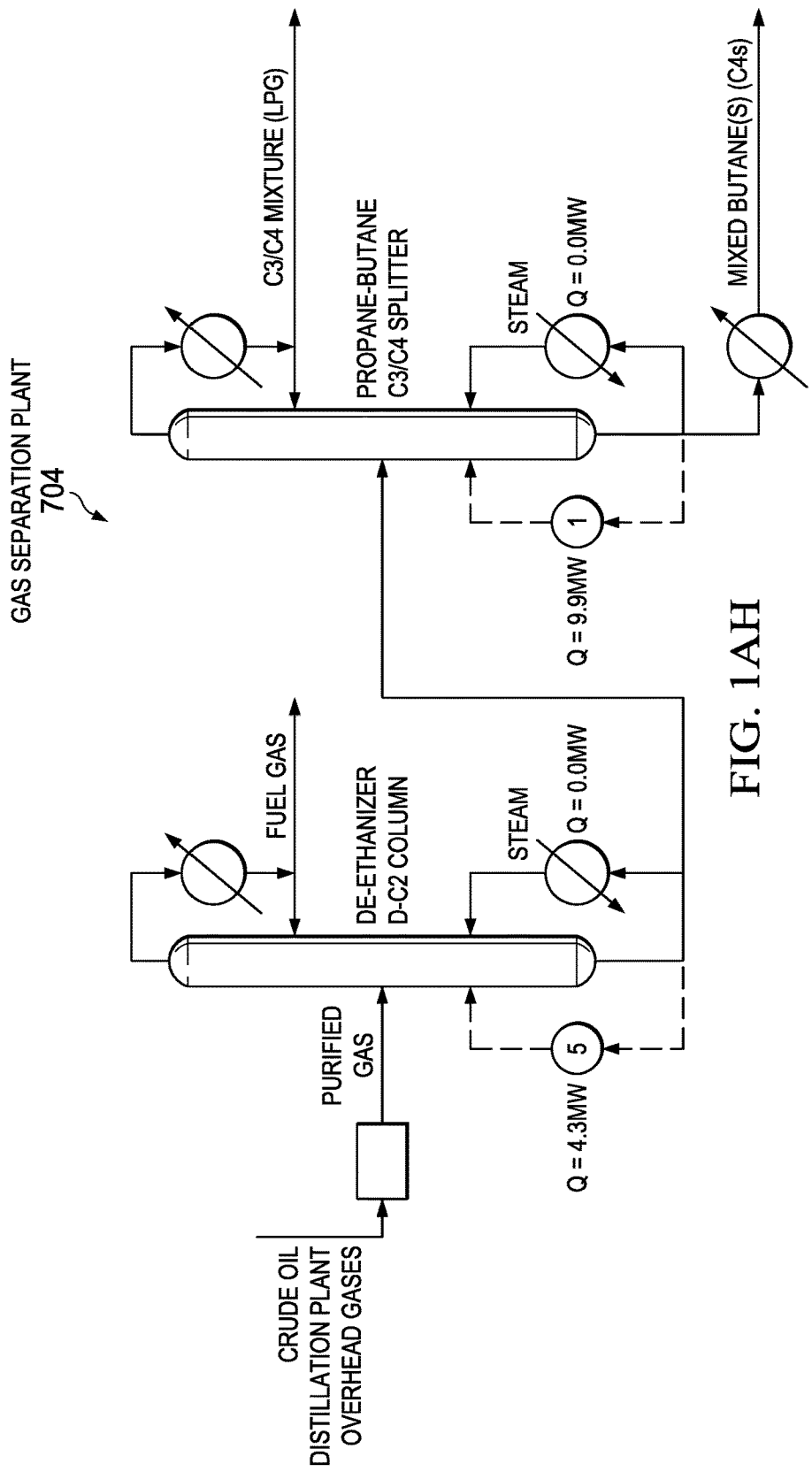
Figure 1A:
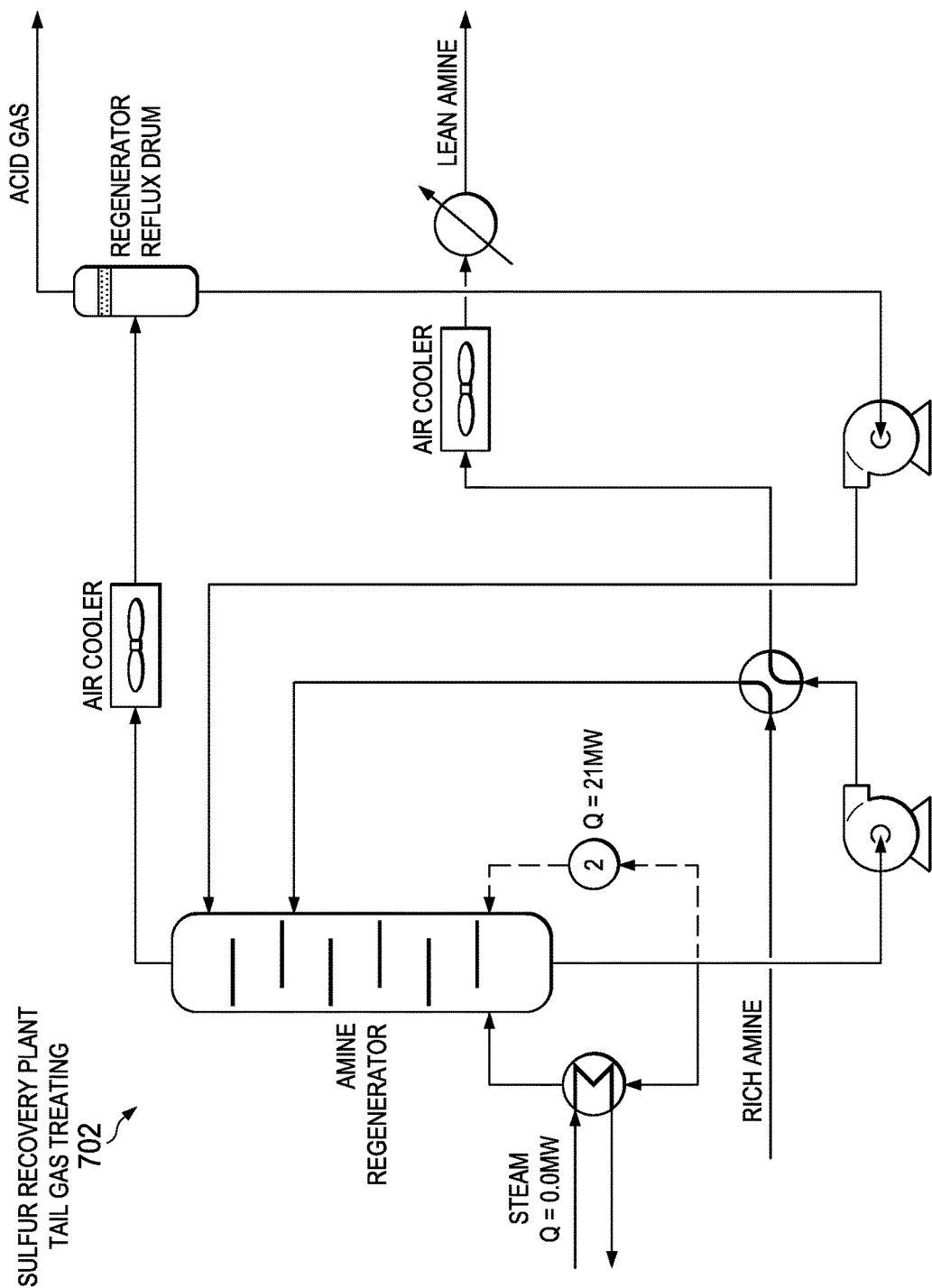
Figure 1A:
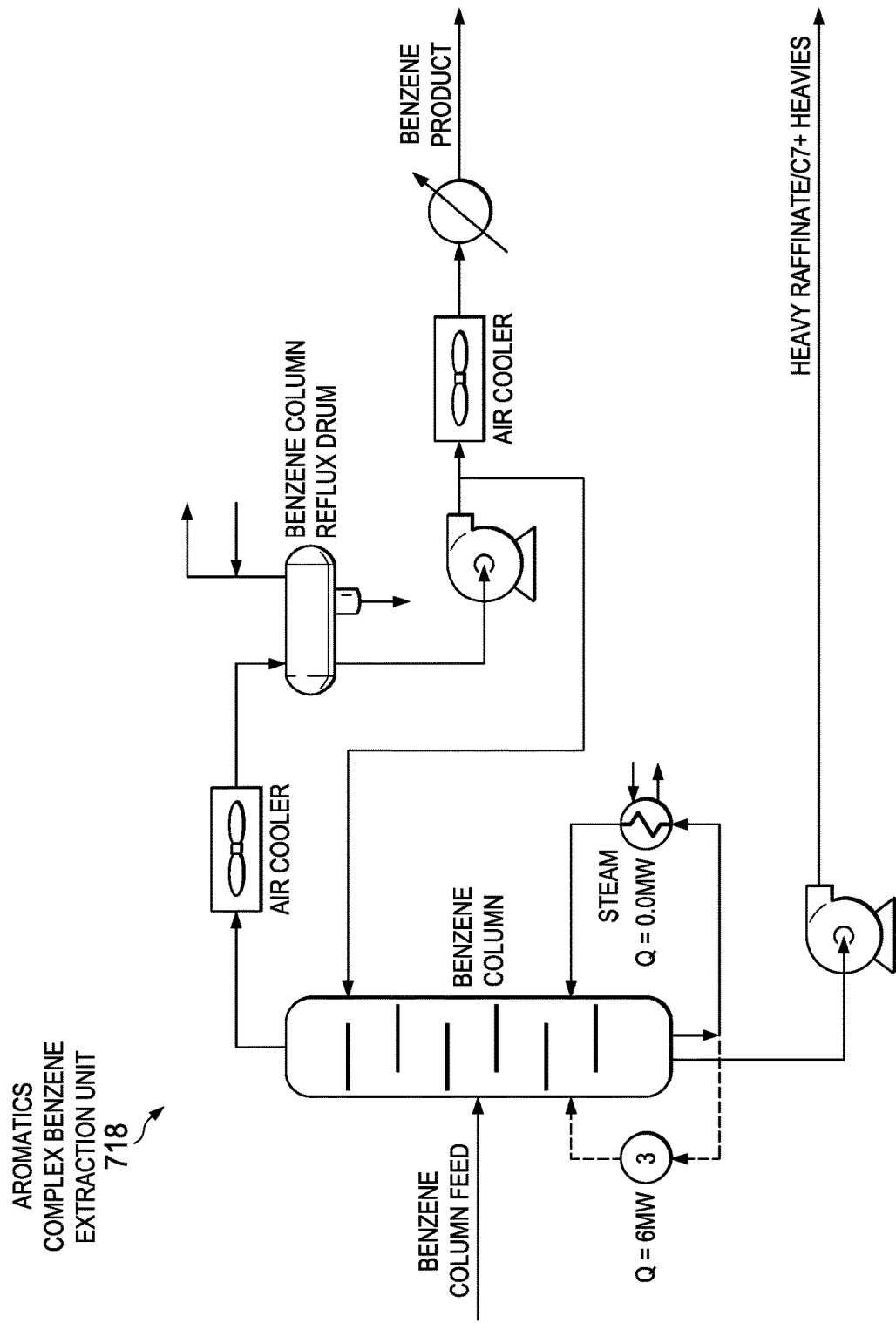
Figure 1A:
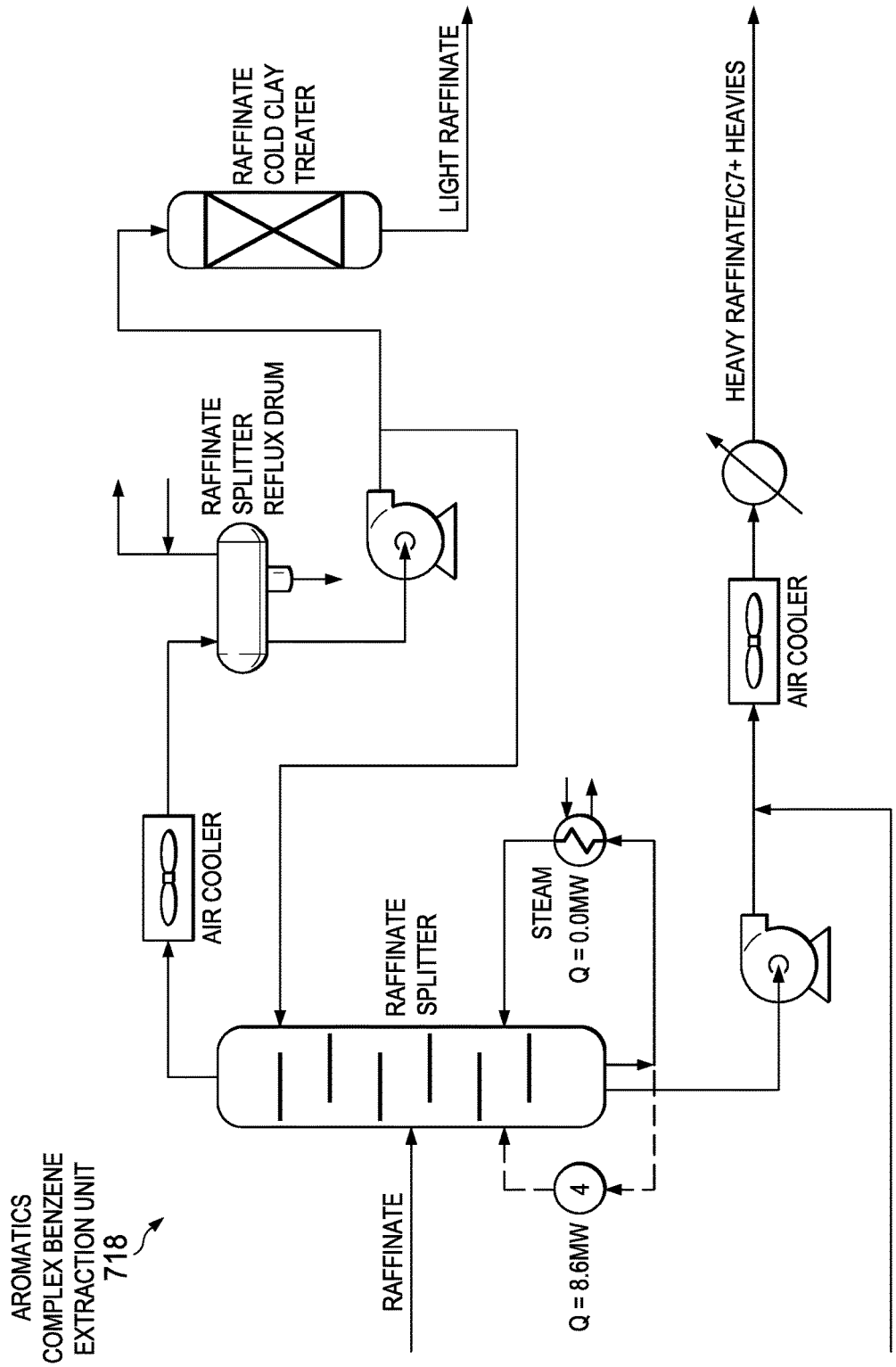
Figure 1A:
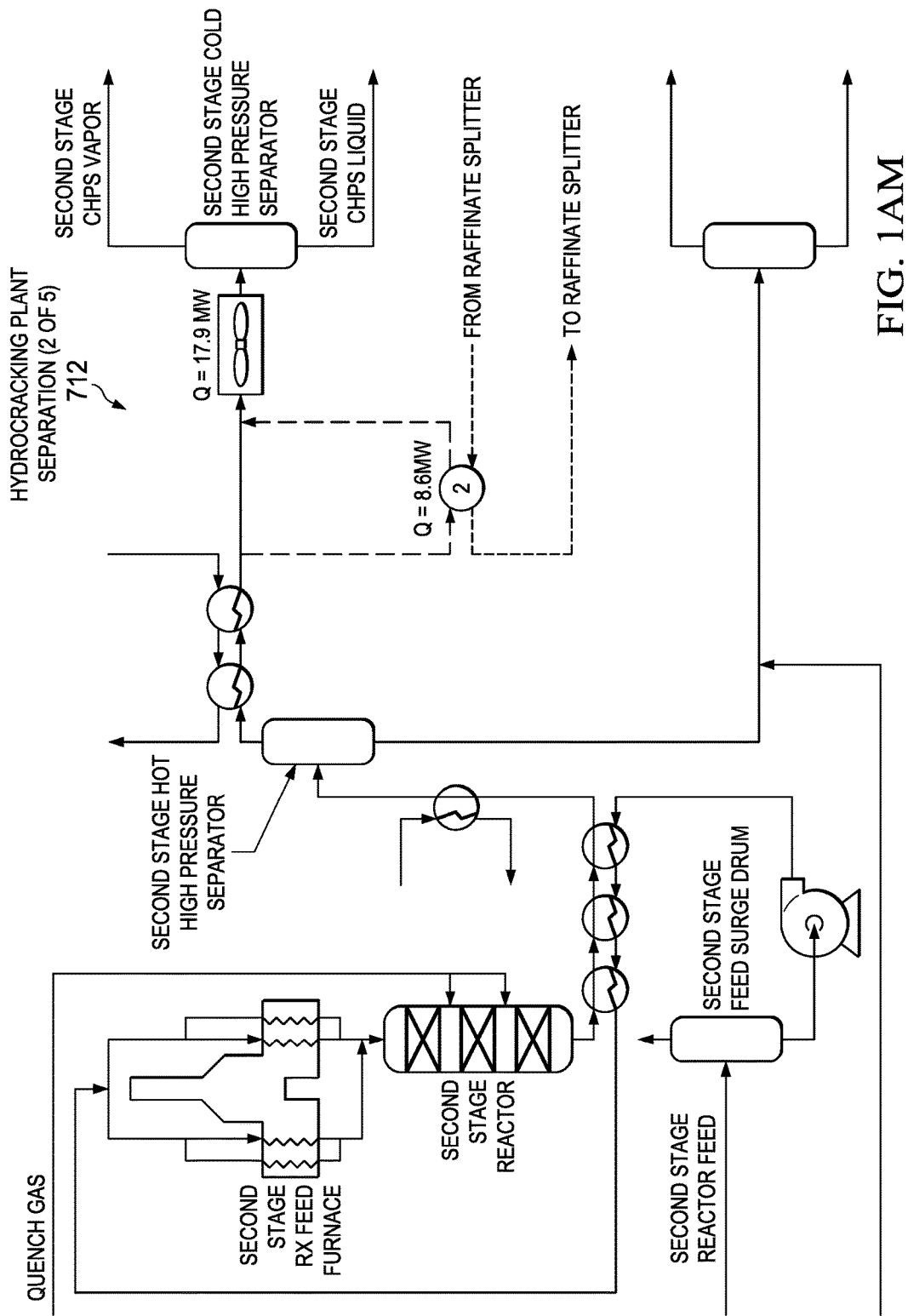
Figure 1A:
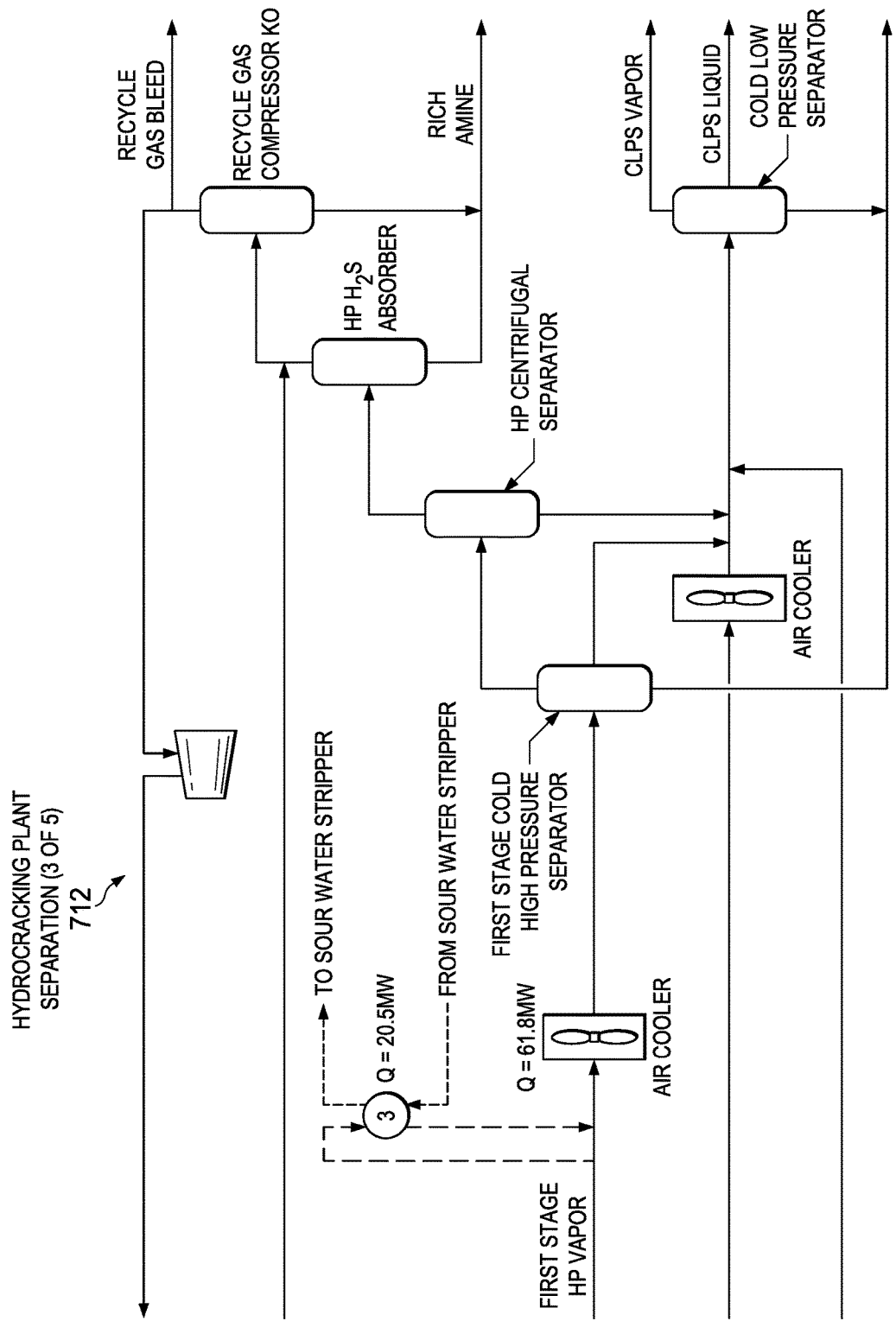
Figure 1A:
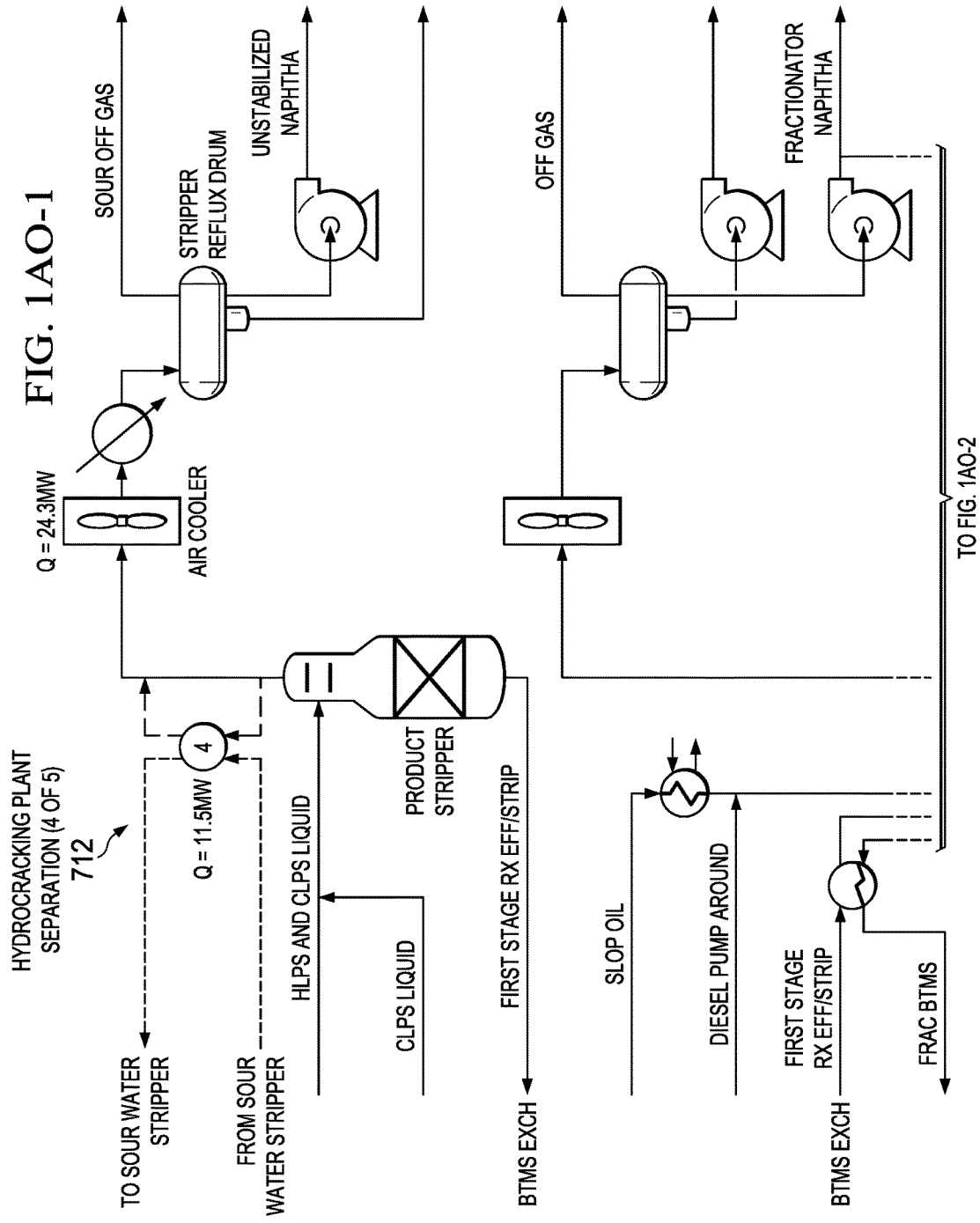
Figure 1A:
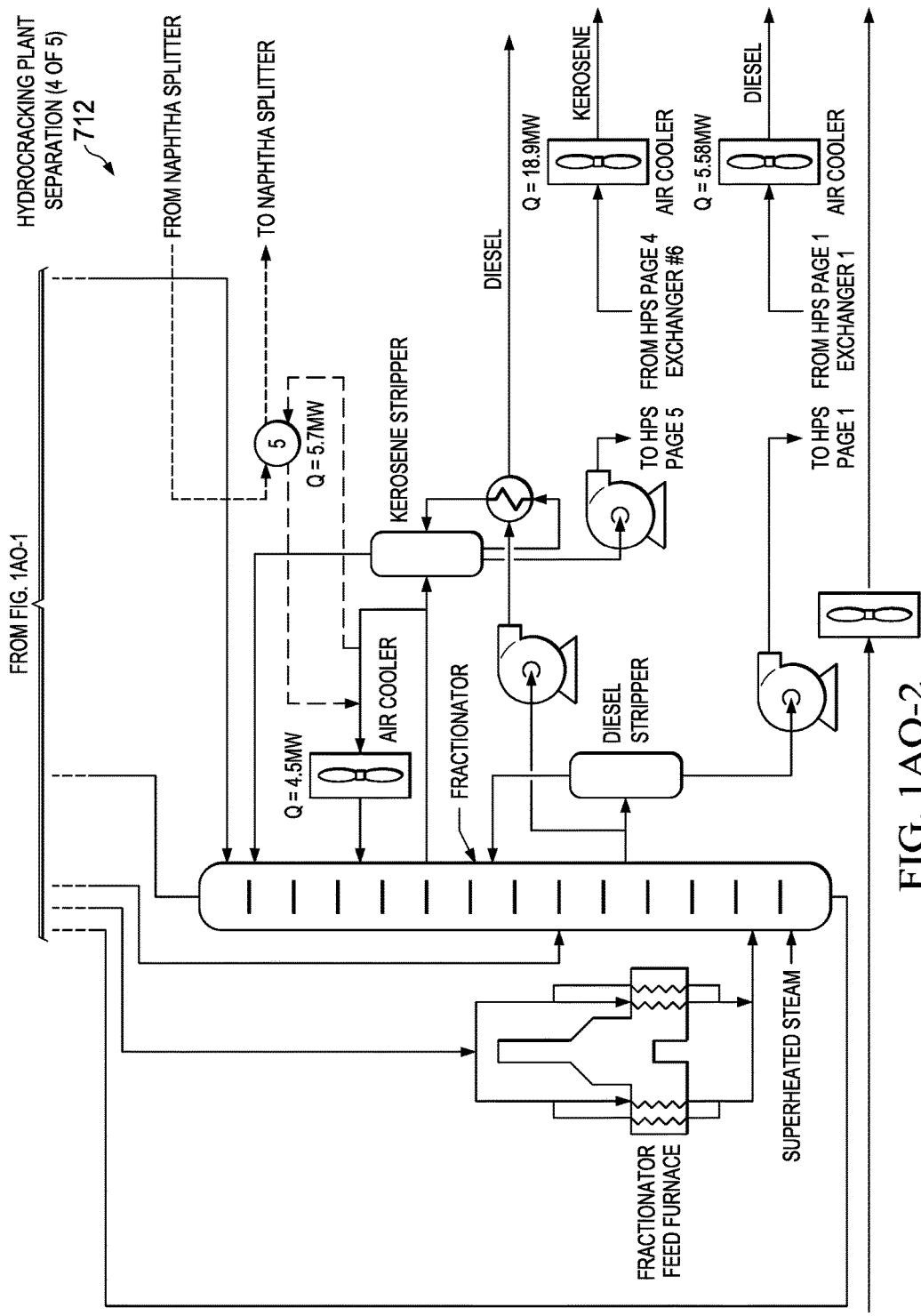
Figure 1A:
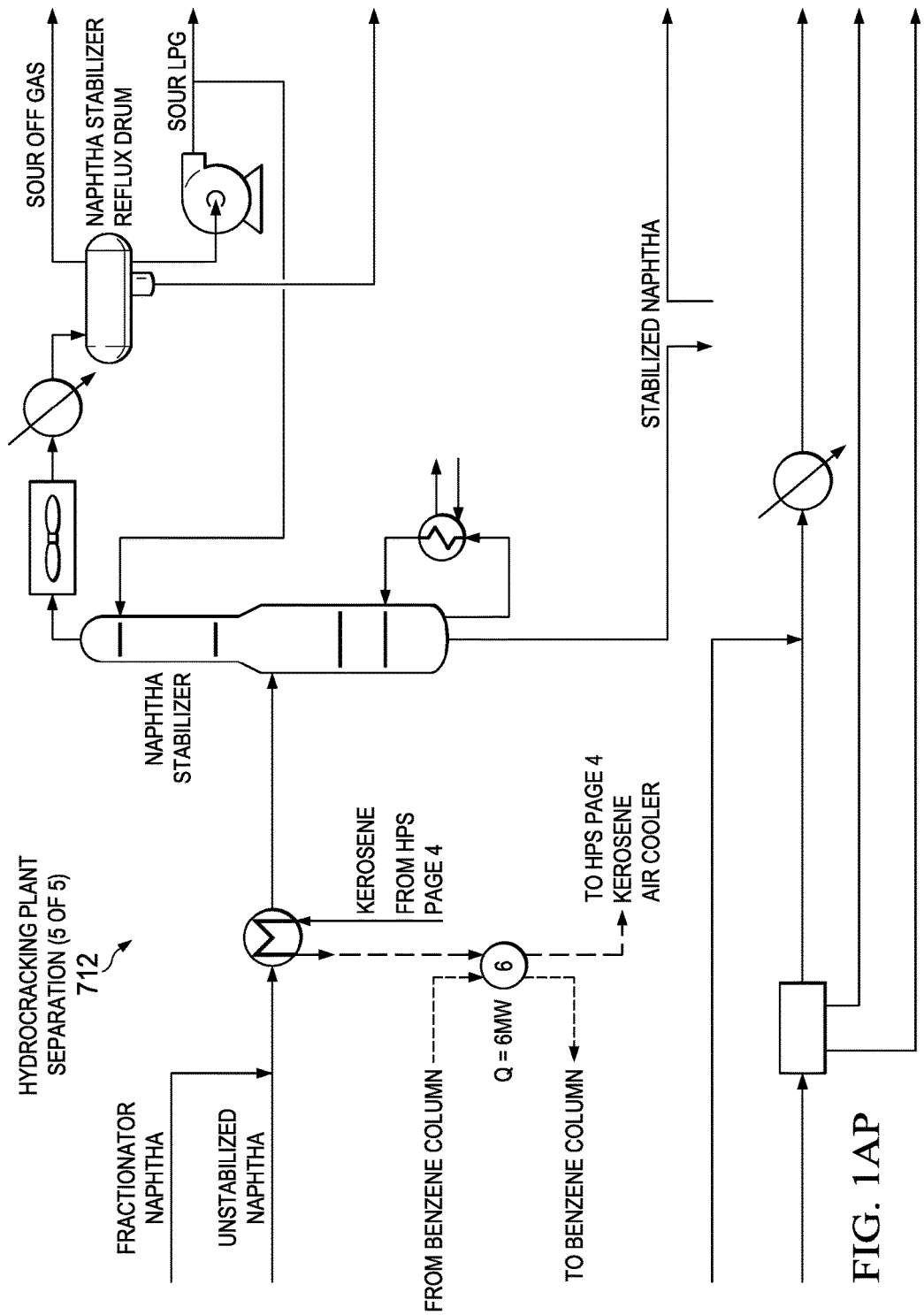
Figure 1A:
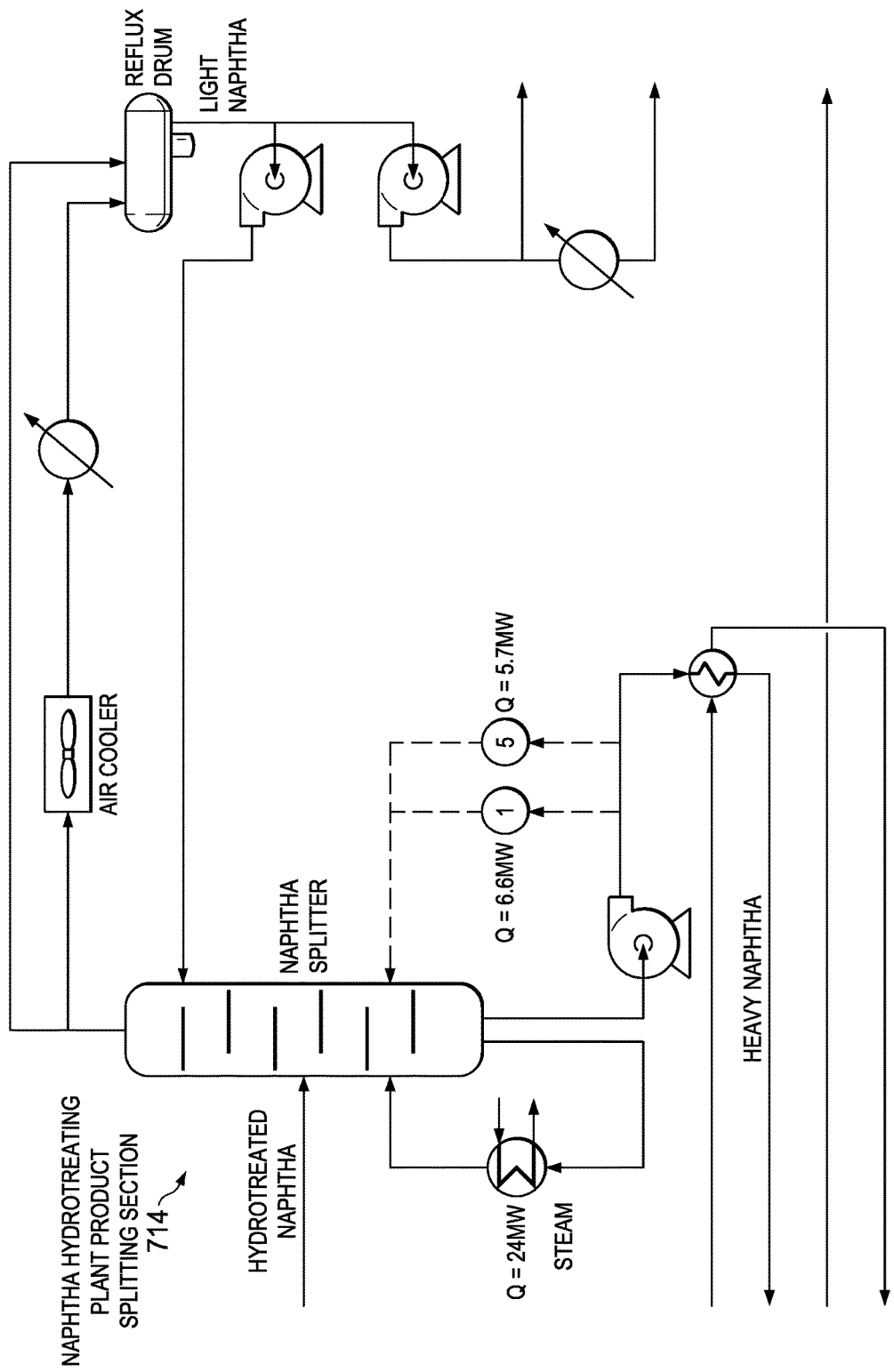
Figure 1A:
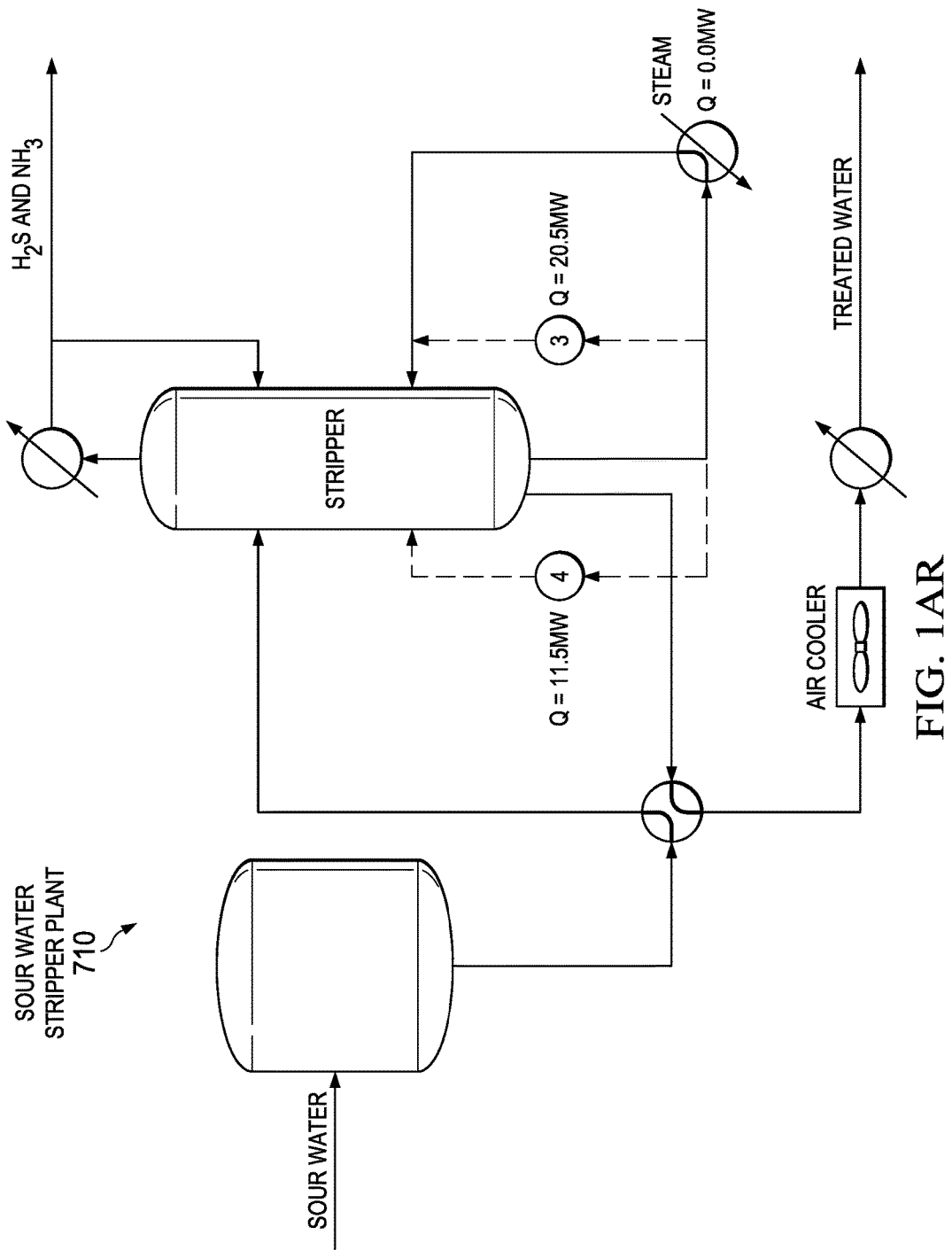
Figure 1A:
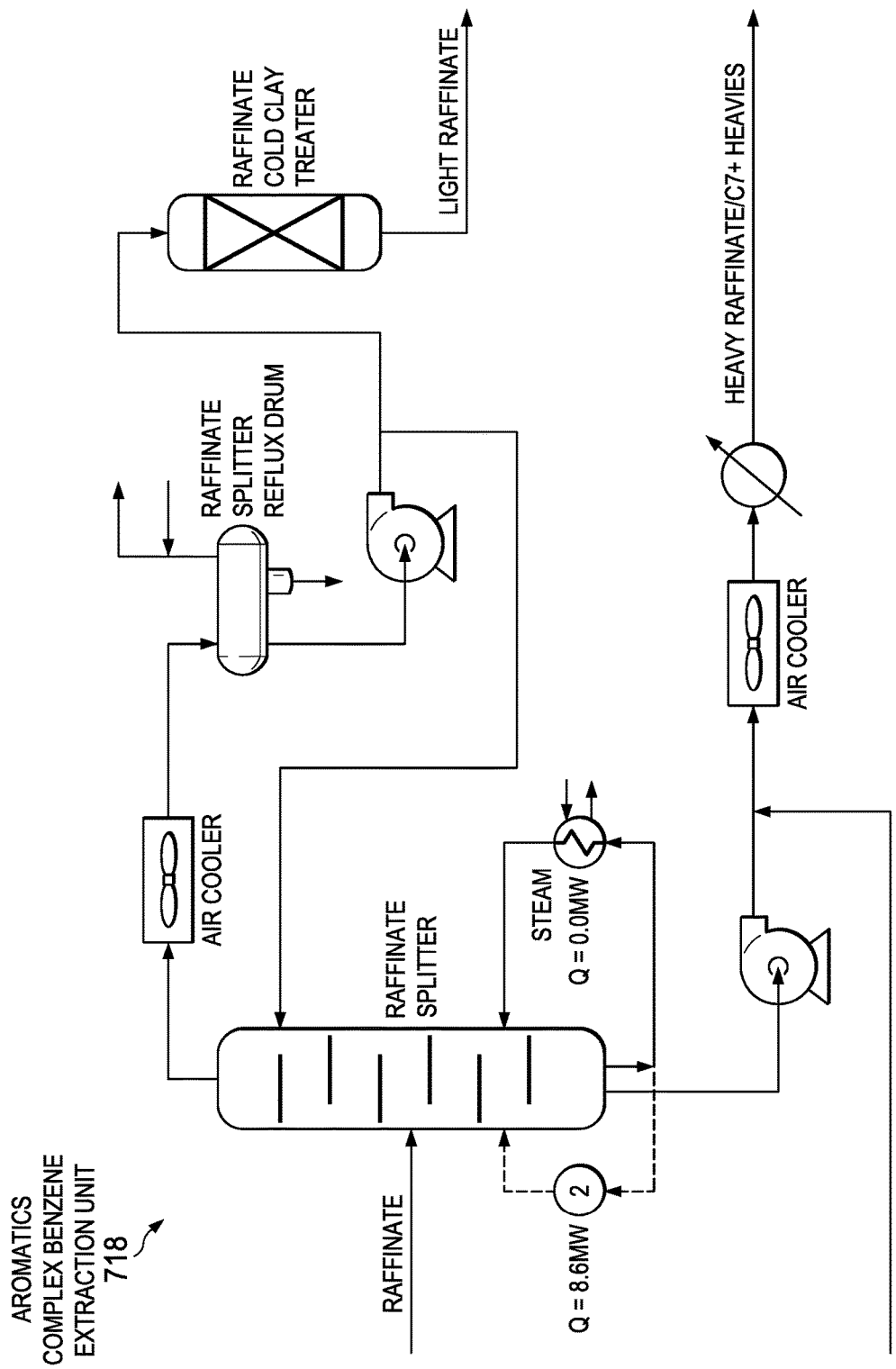
Figure 1A:
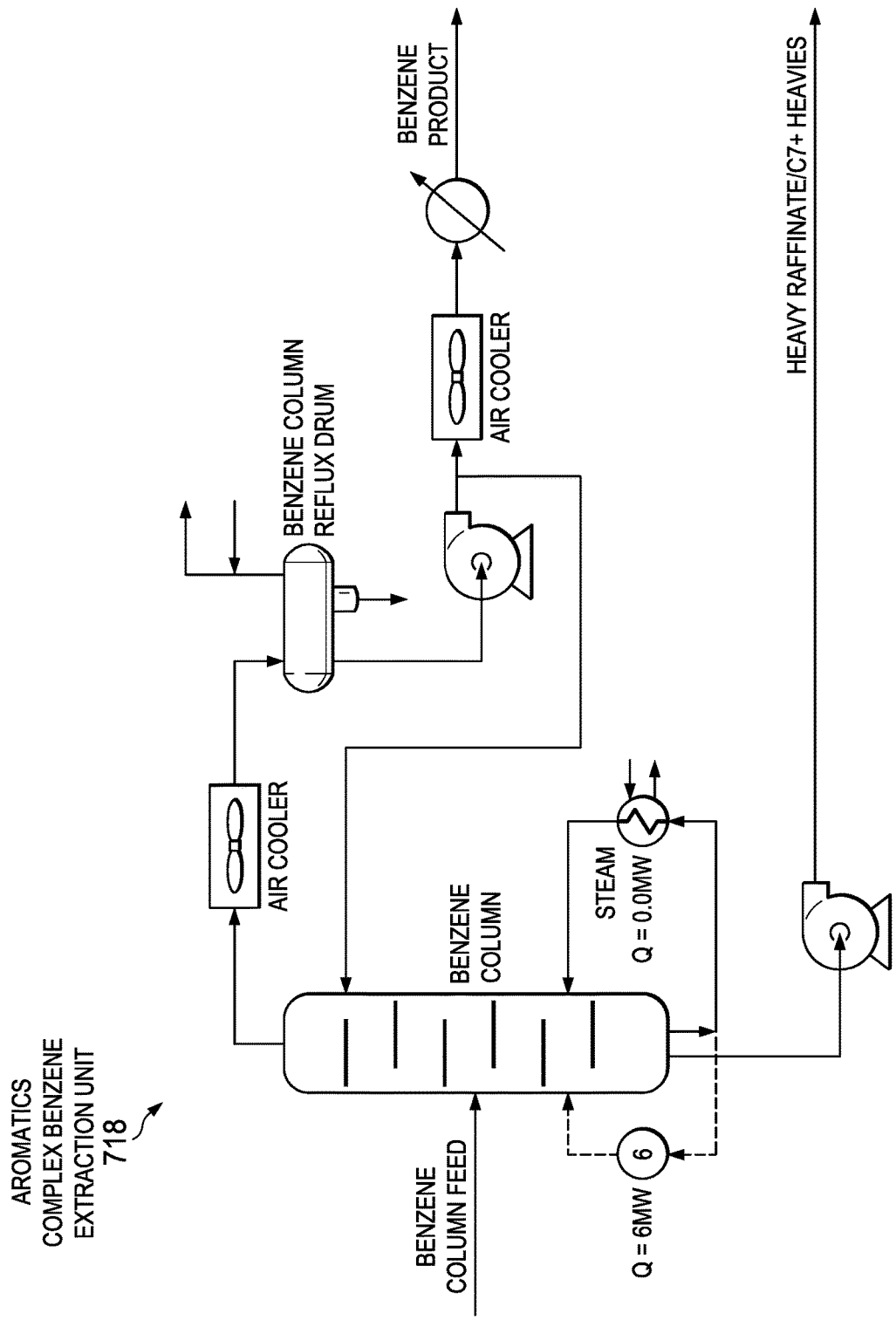
Figure 1A:
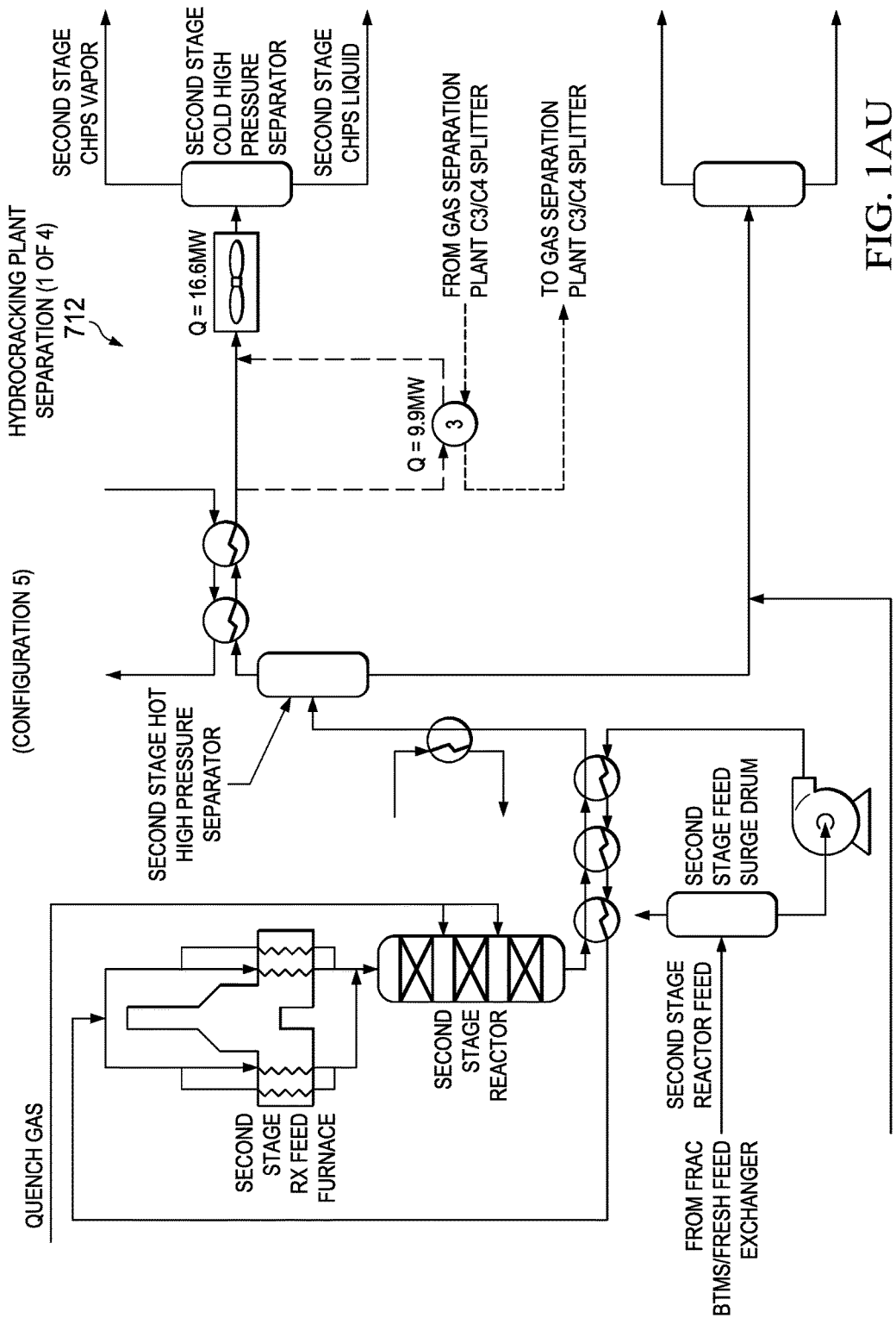
Figure 1A:
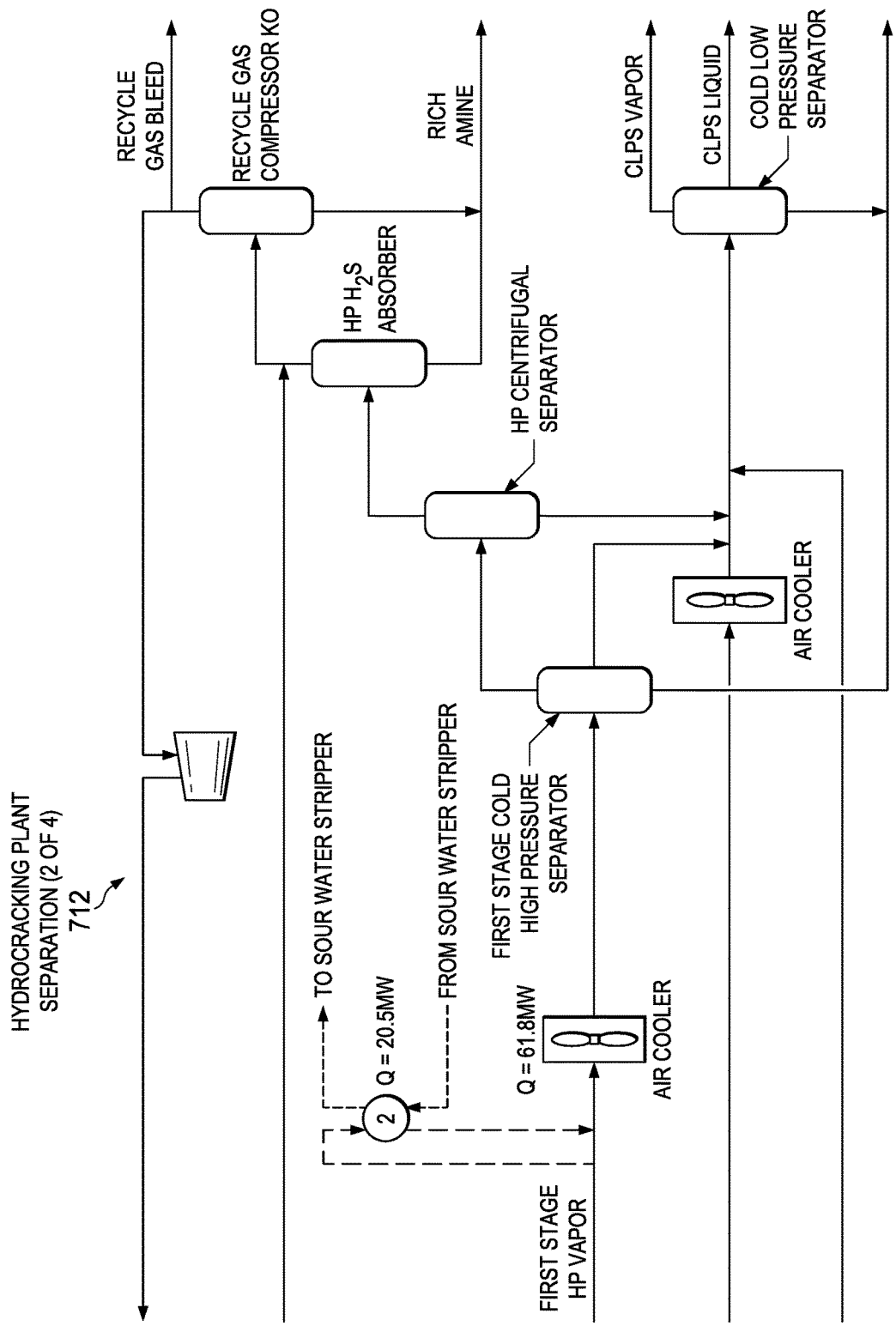
Figure 1A:
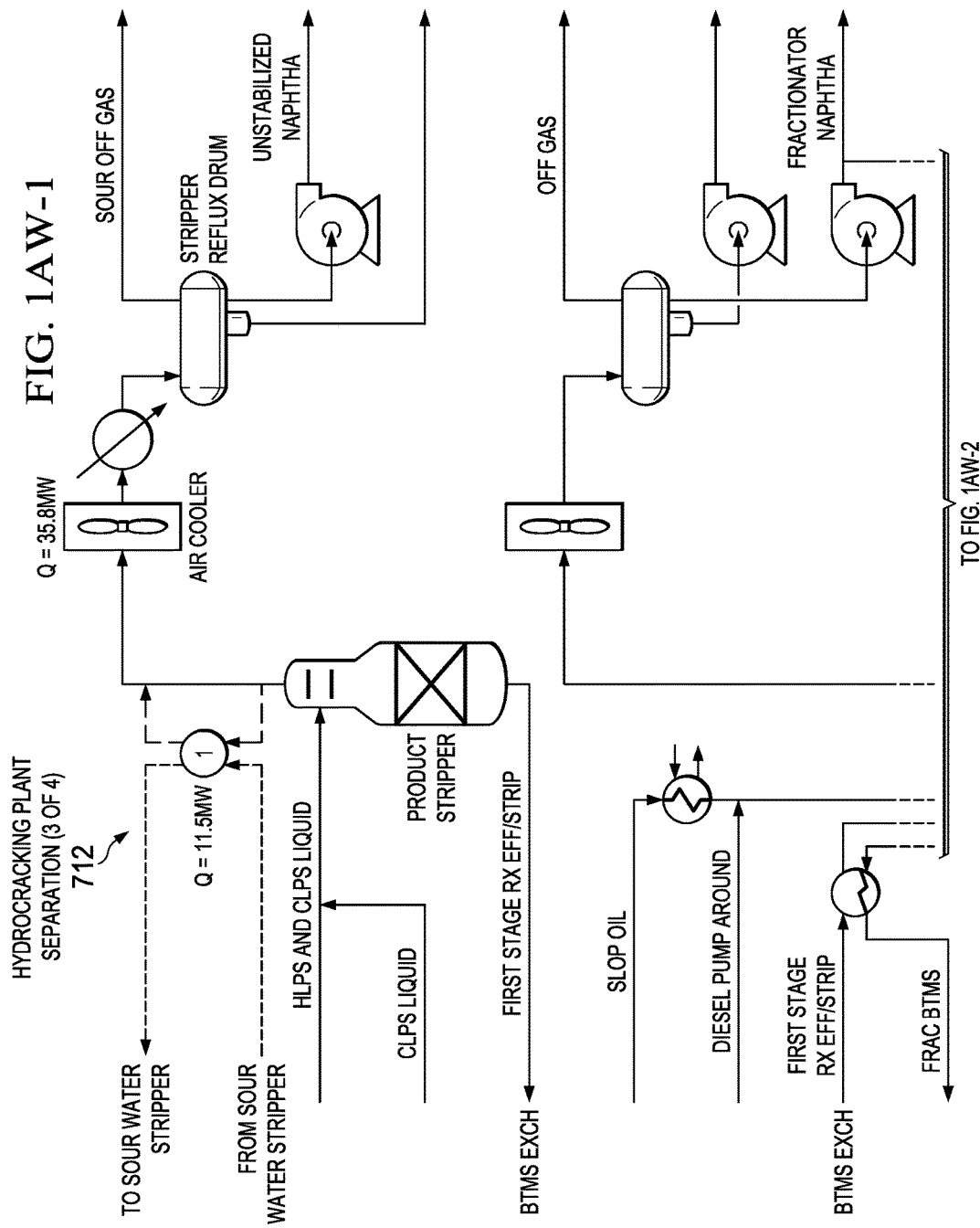
Figure 1A:
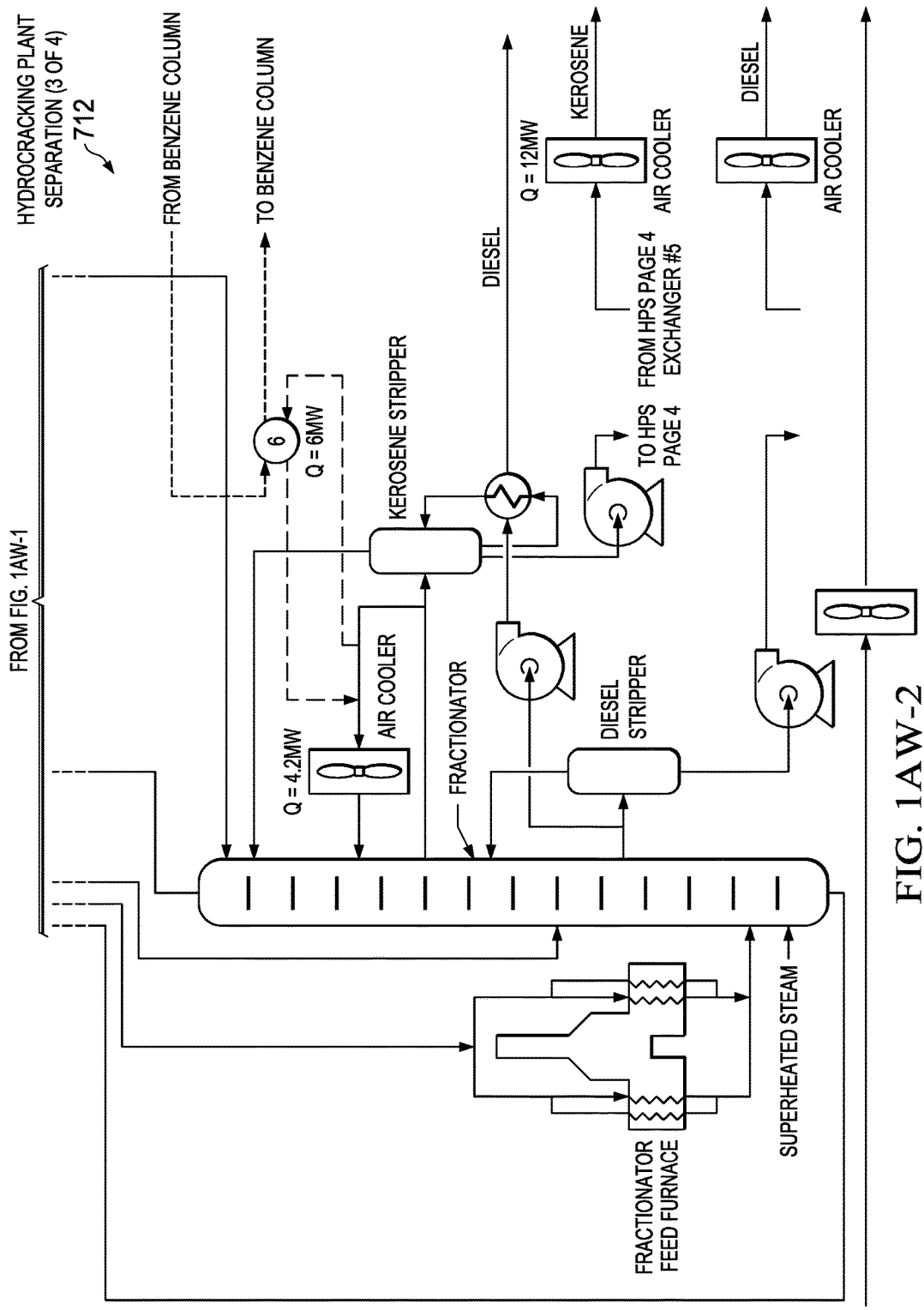
Figure 1A:
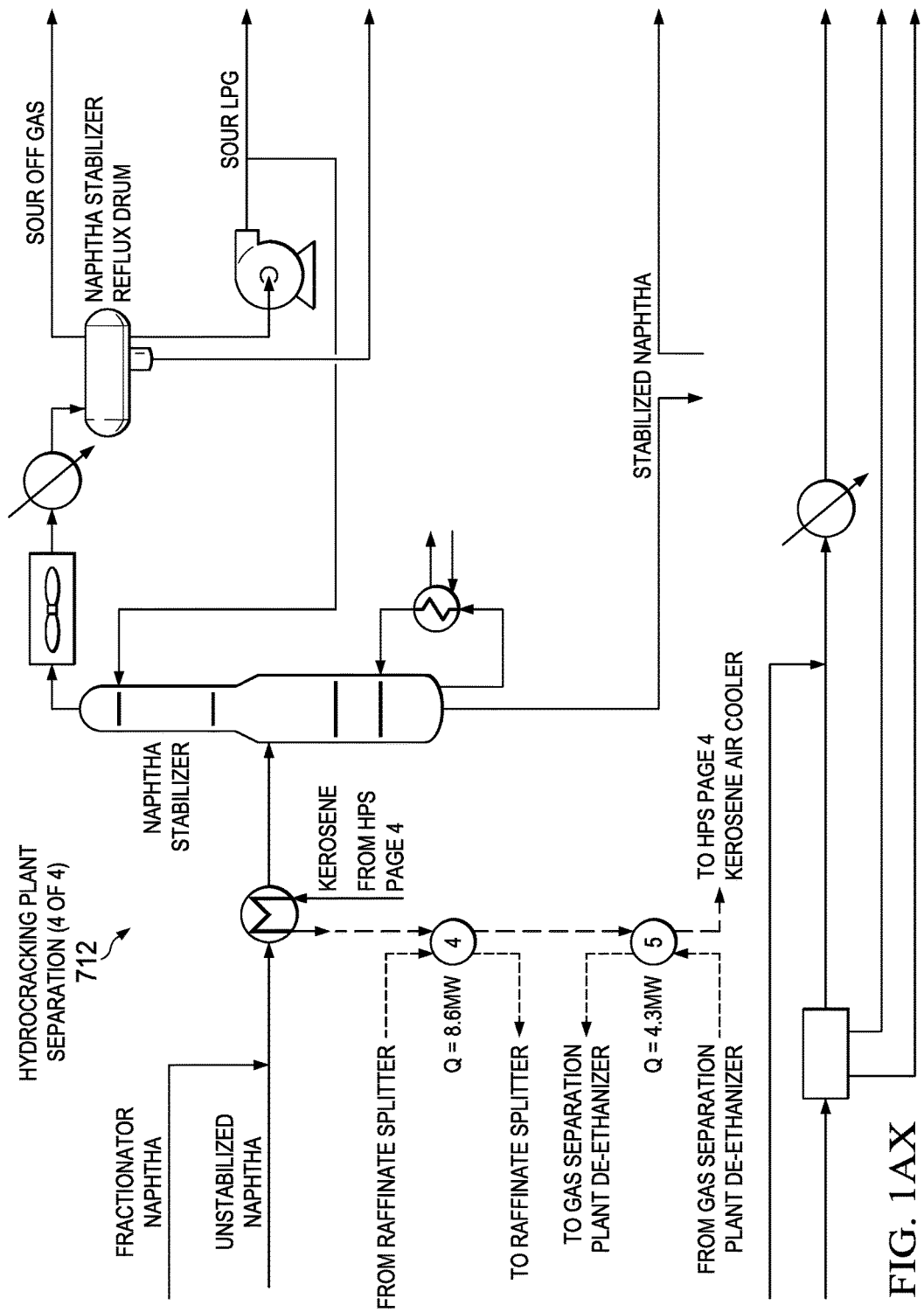
Figure 1A:
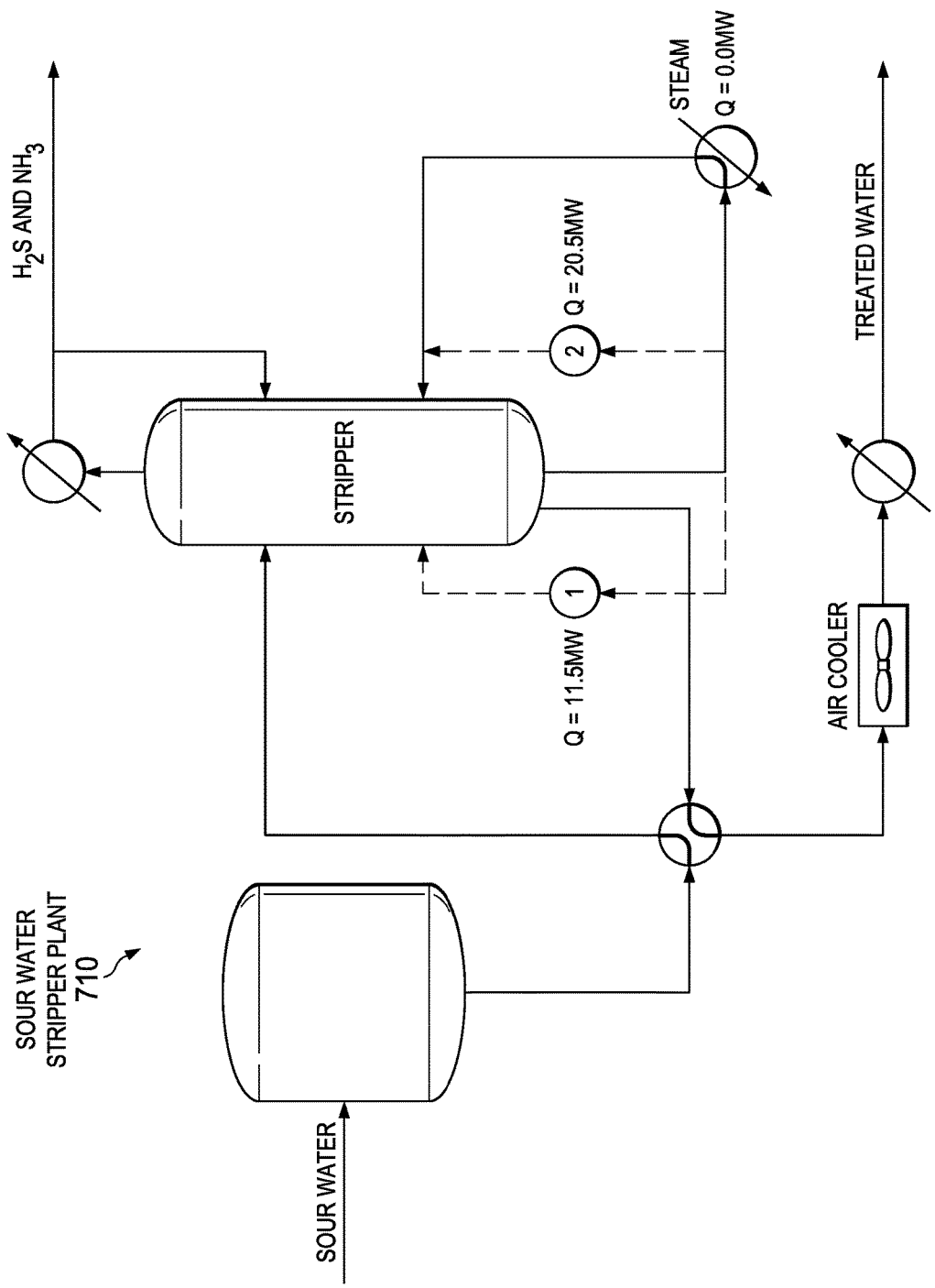
Figure 1A:
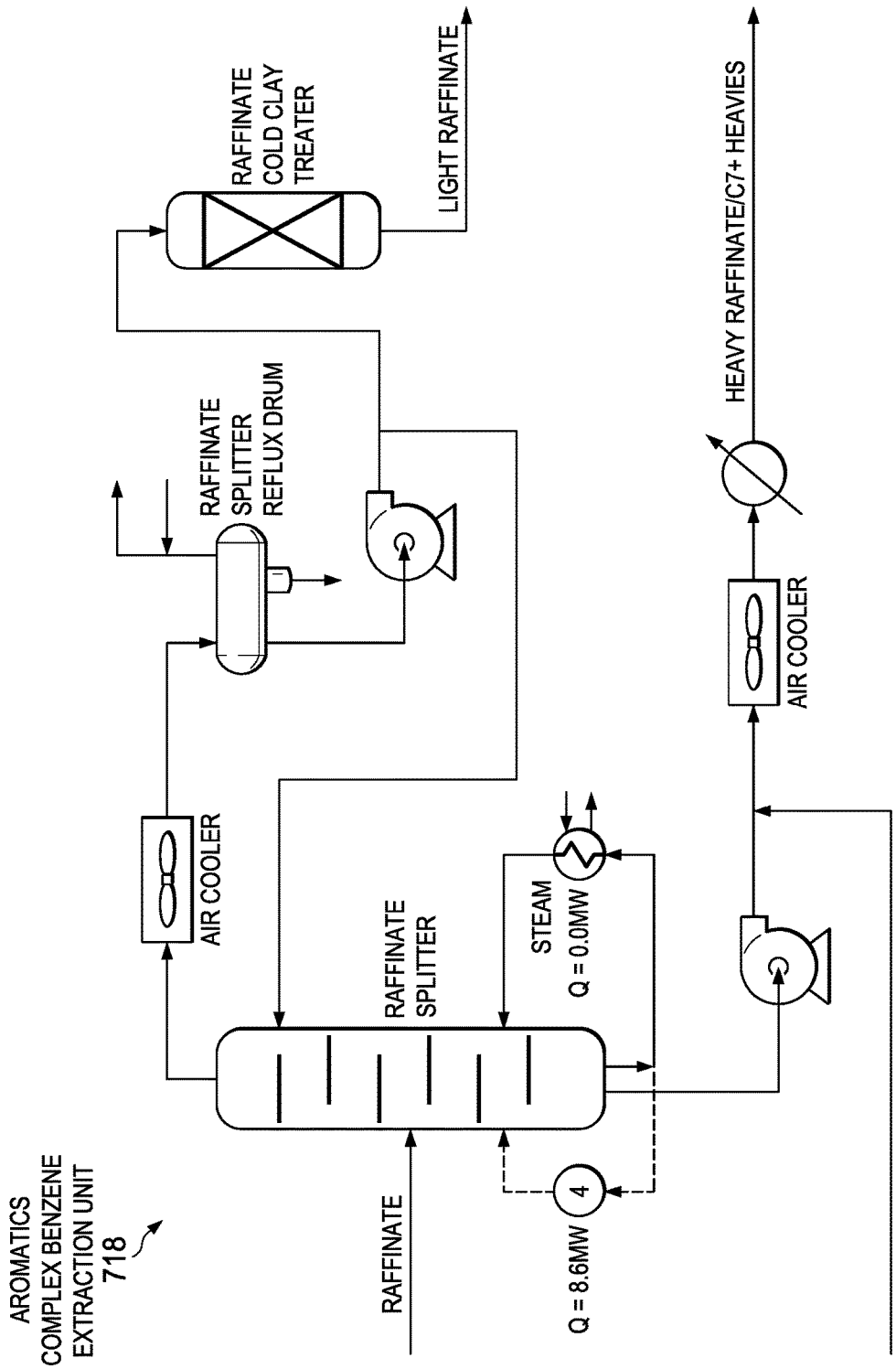
Figure 1B:
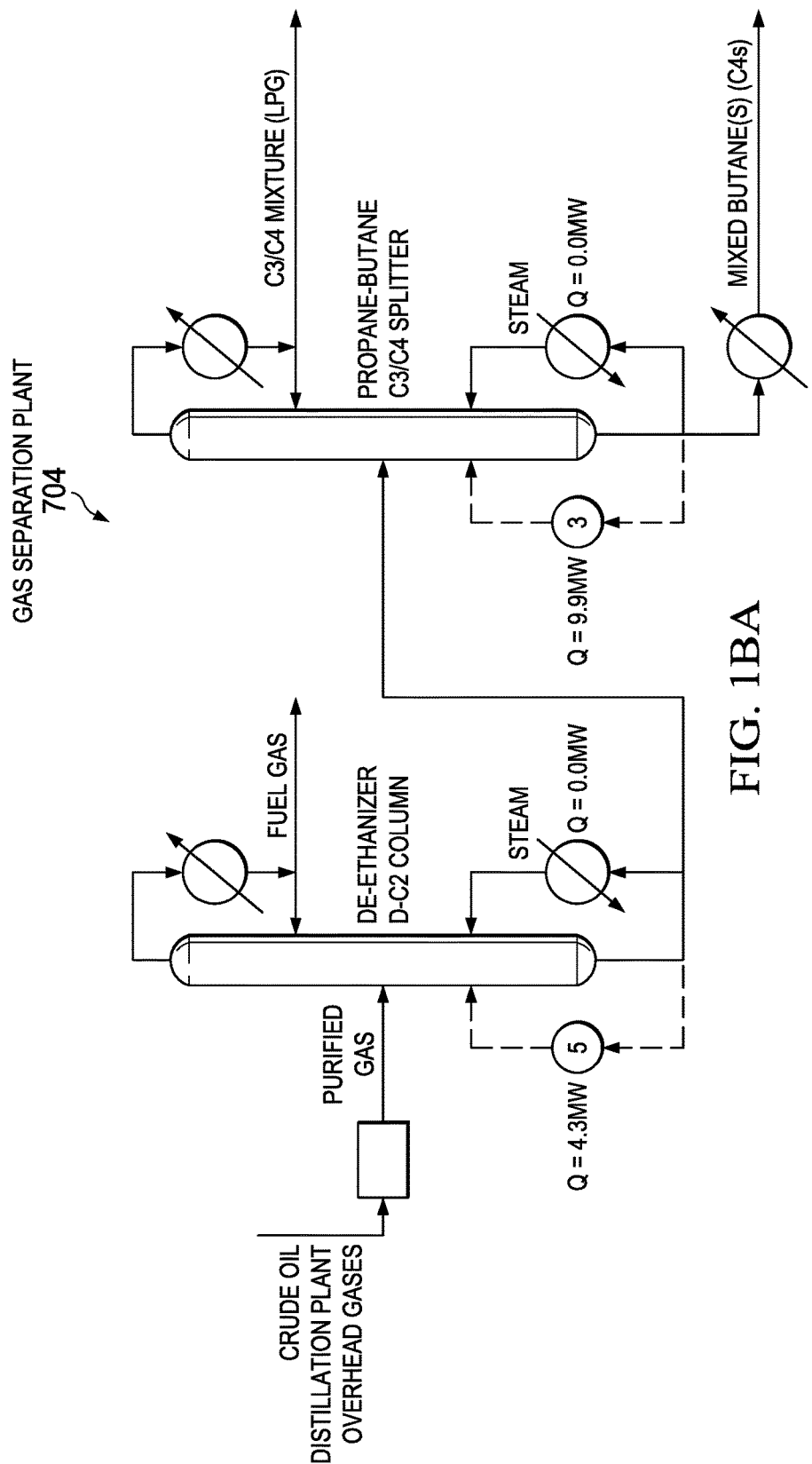
Figure 1B:
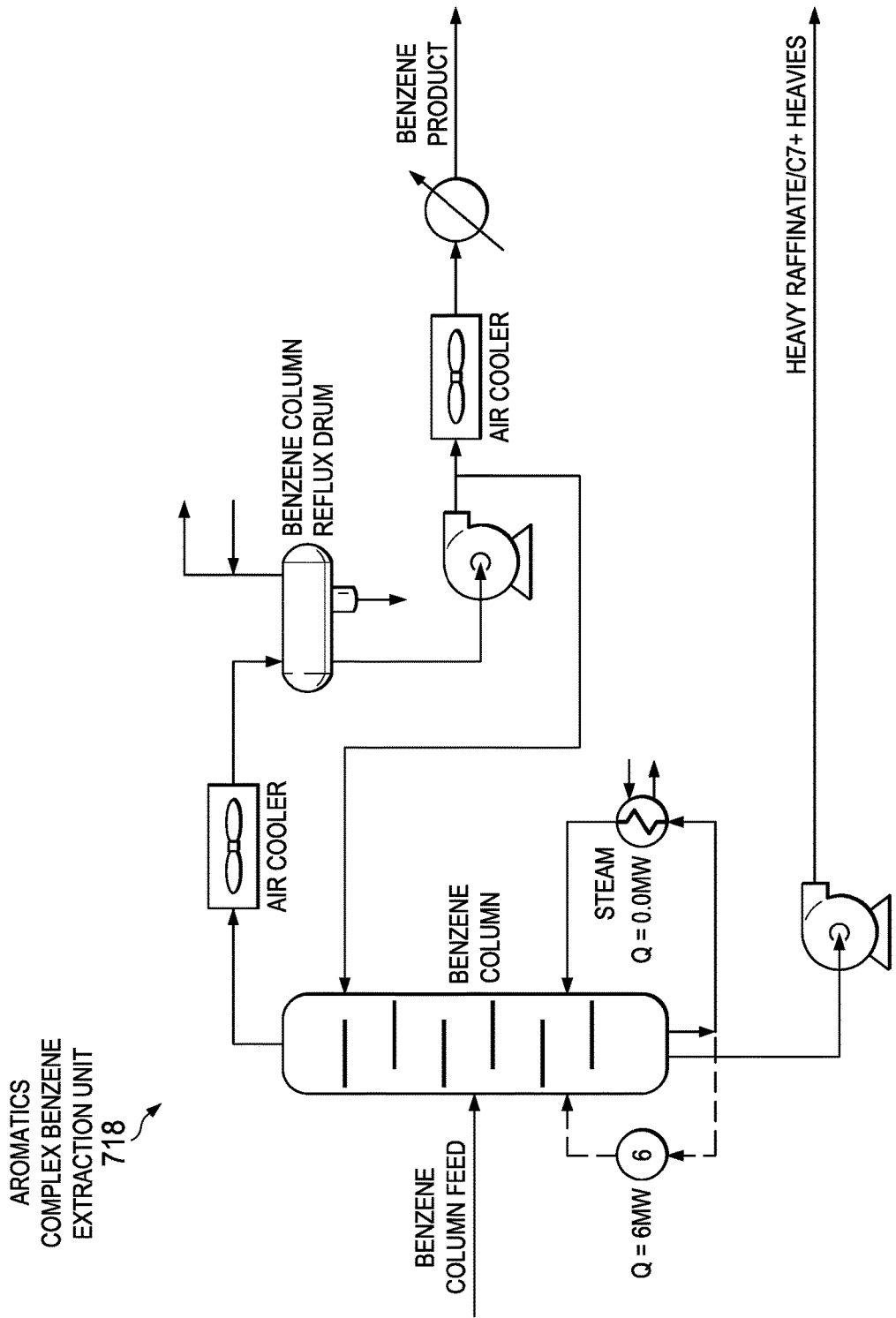
Figure 1B:
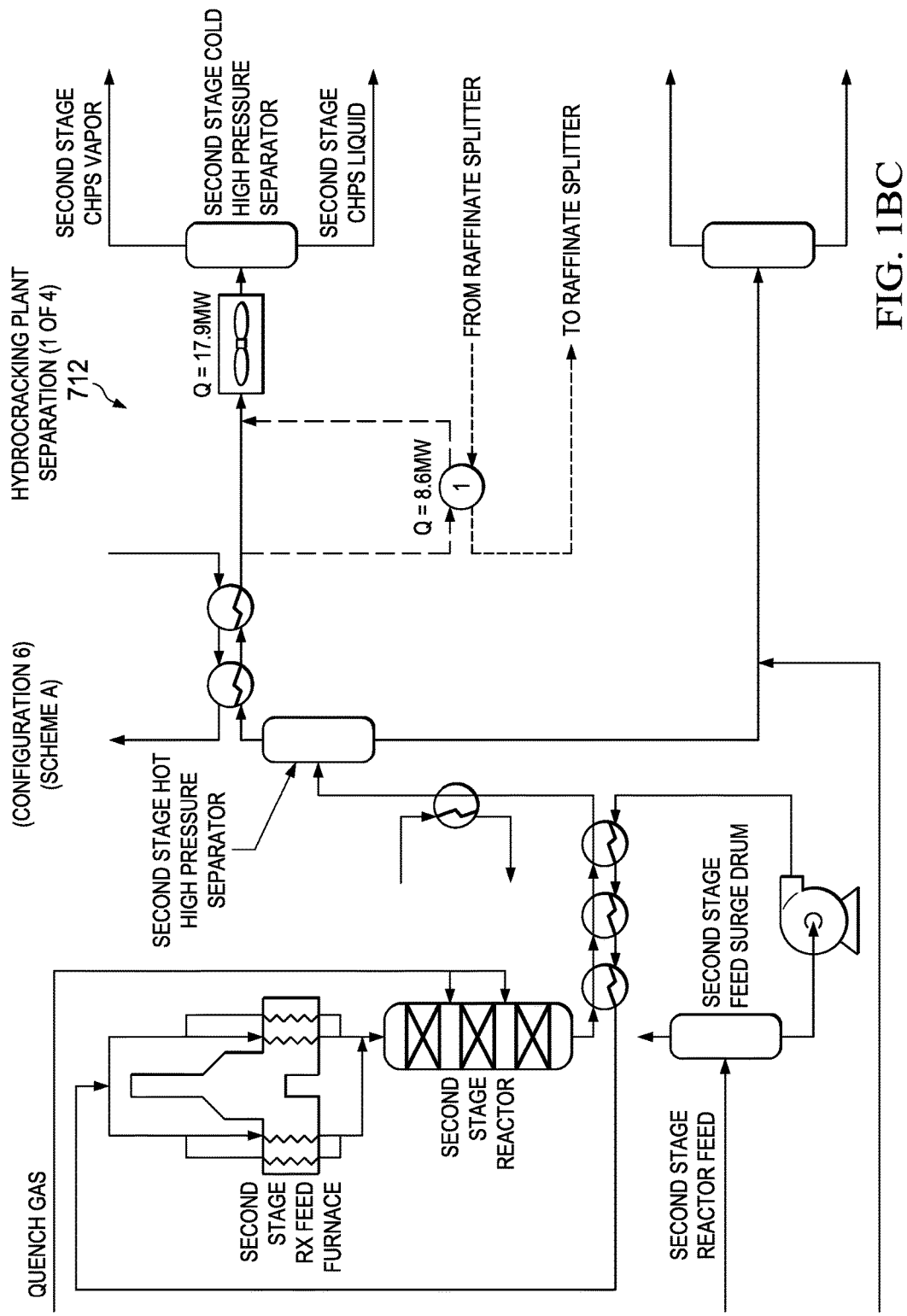
Figure 1B:
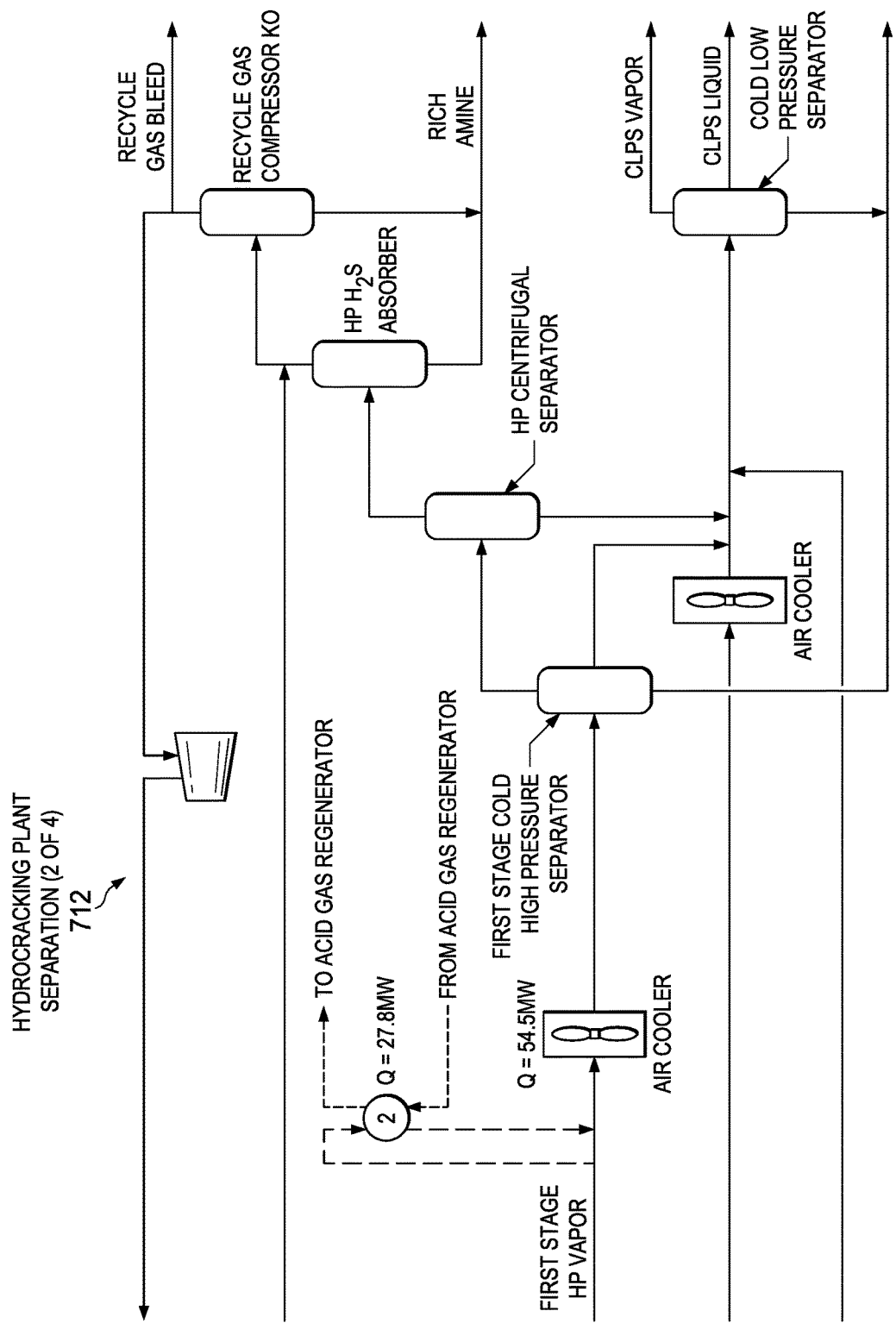
Figure 1B:
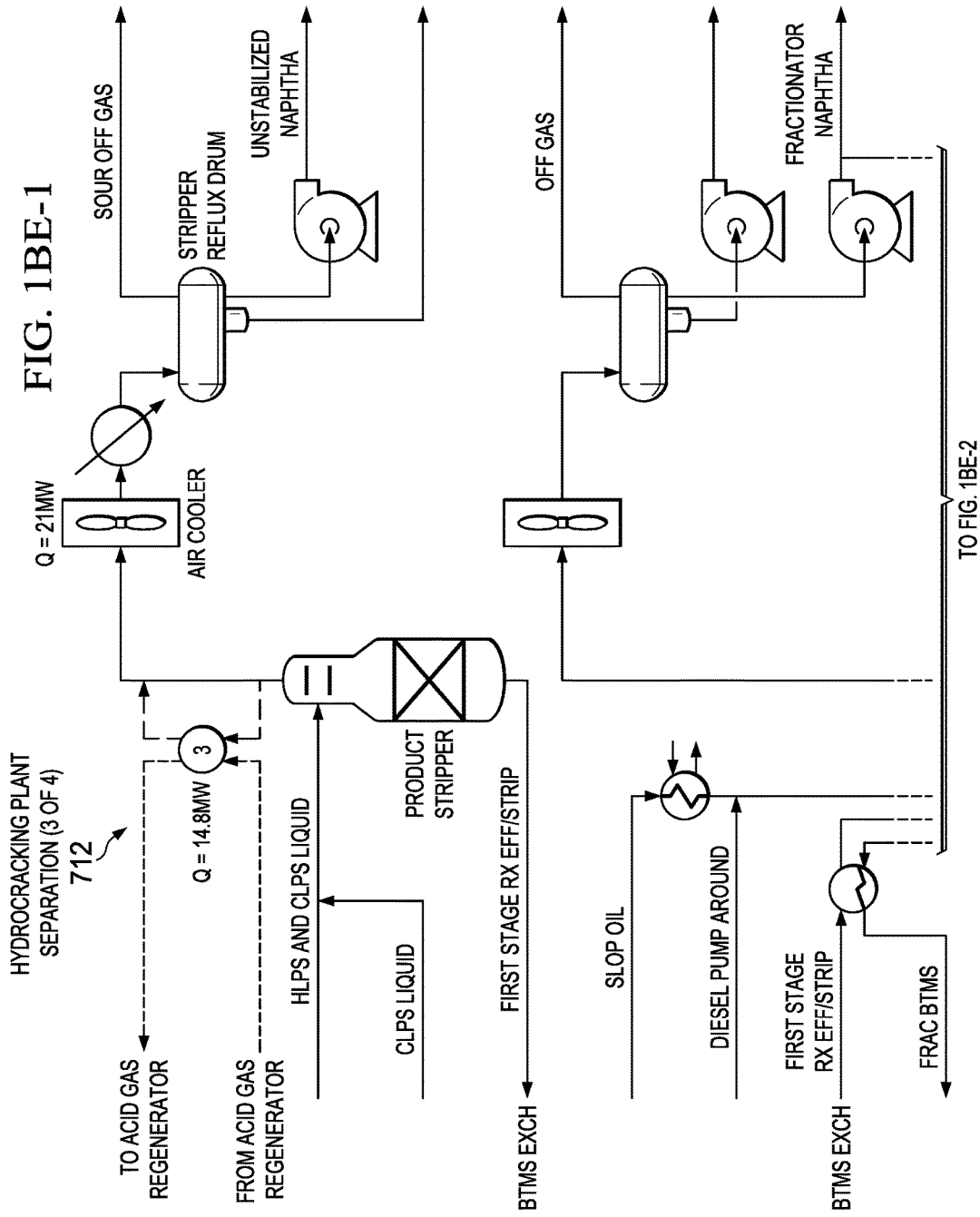
Figure 1B:
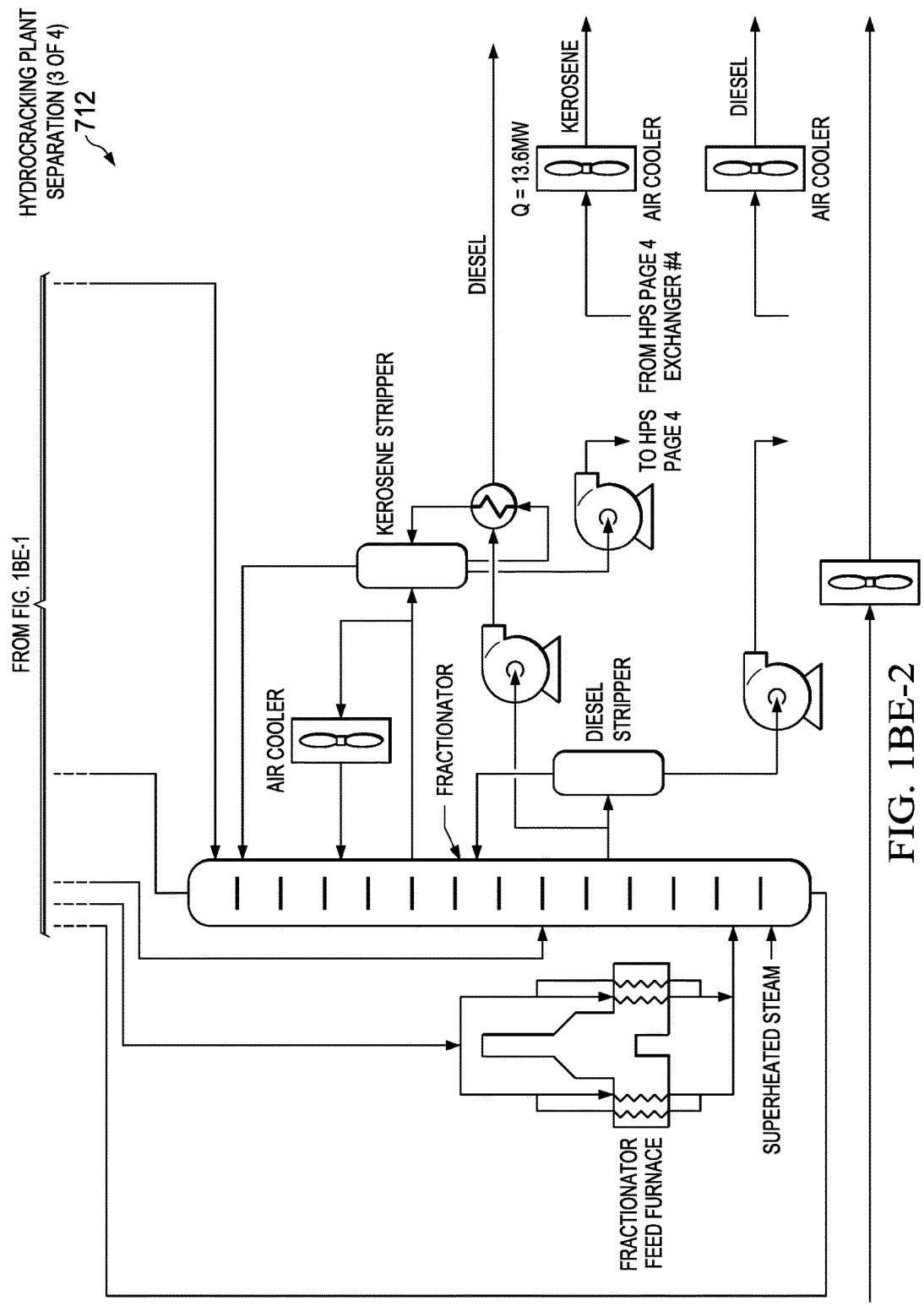
Figure 1B:
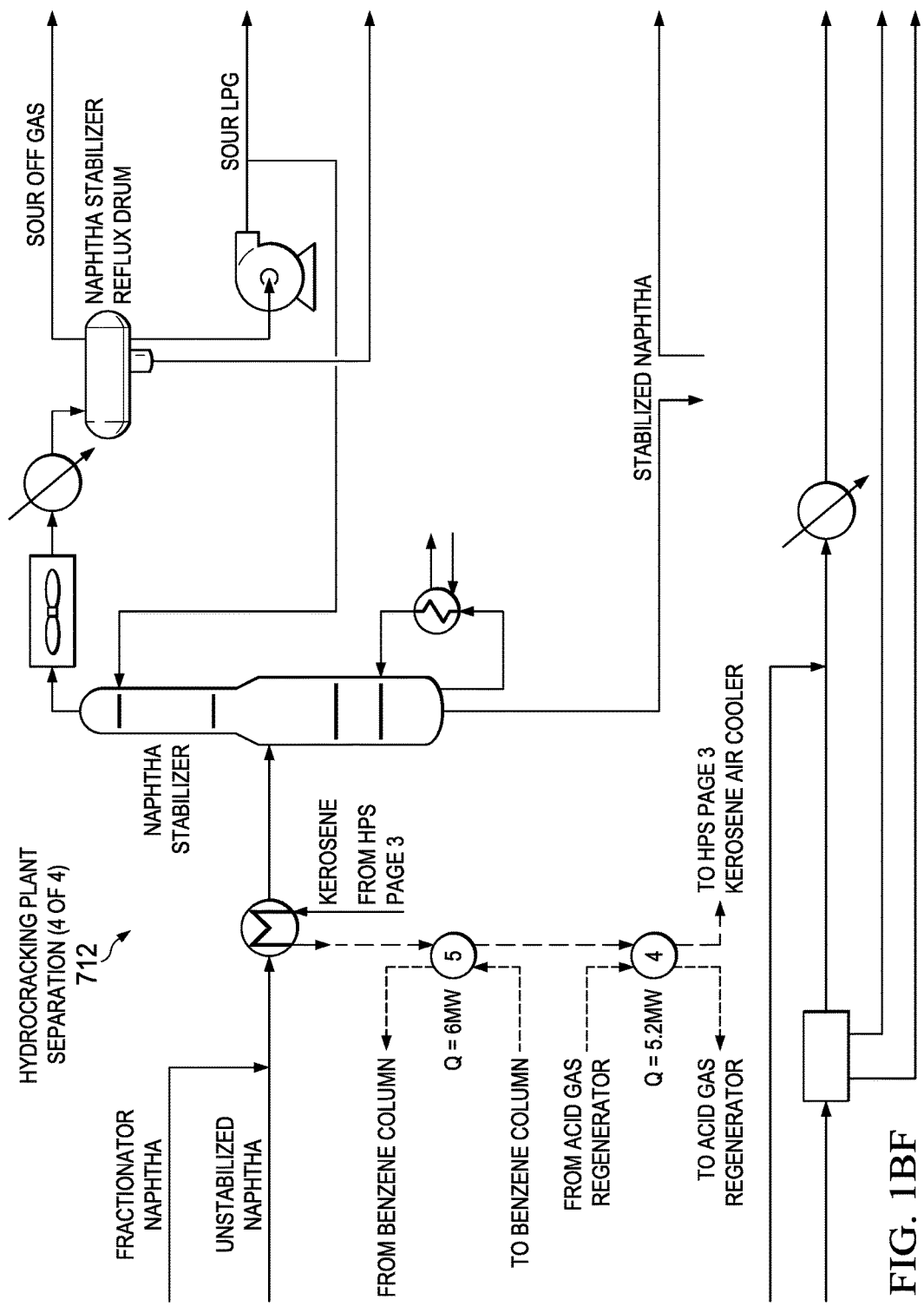
Figure 1B:
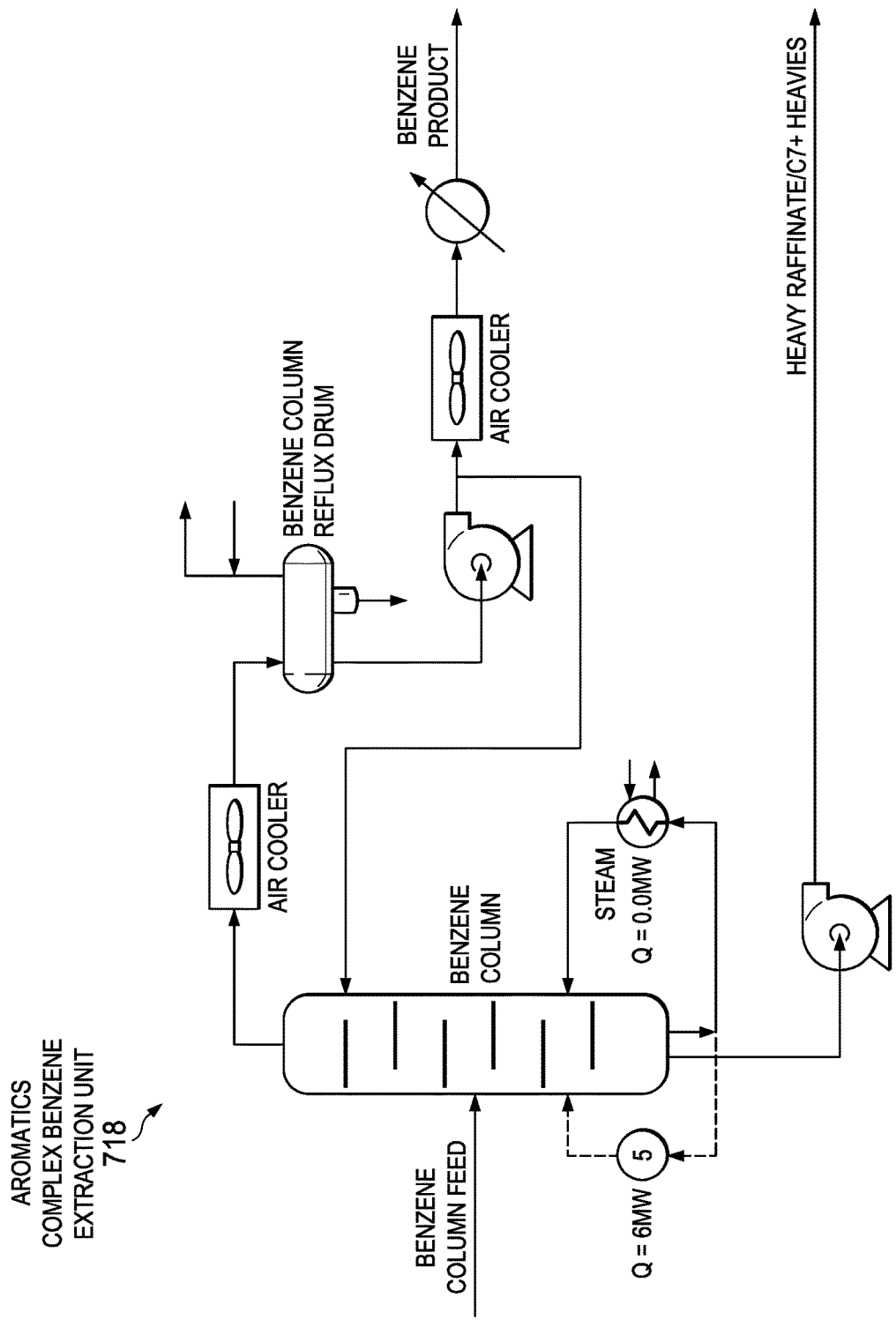
Figure 1B:
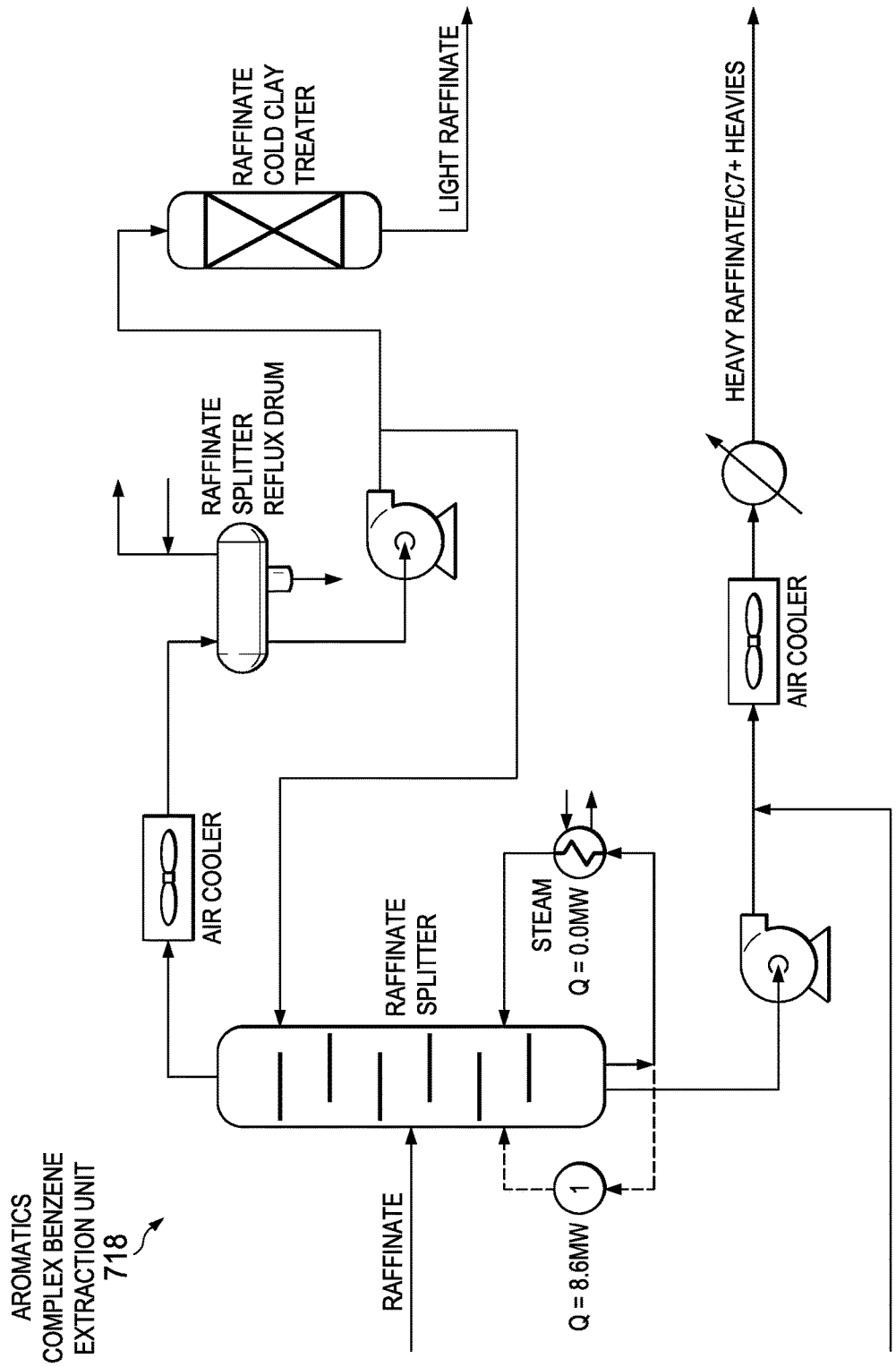
Figure 1B:
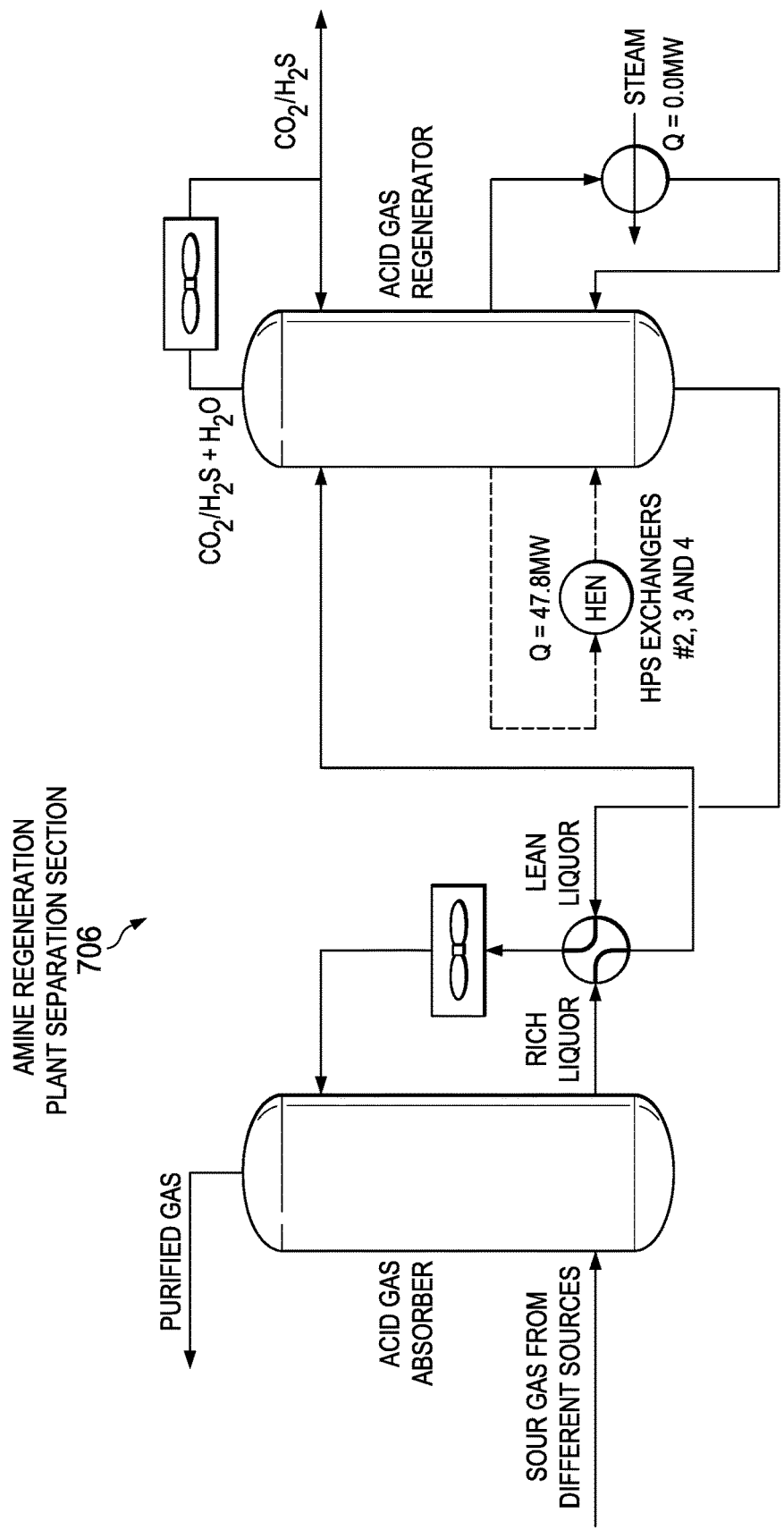
Figure 1B:
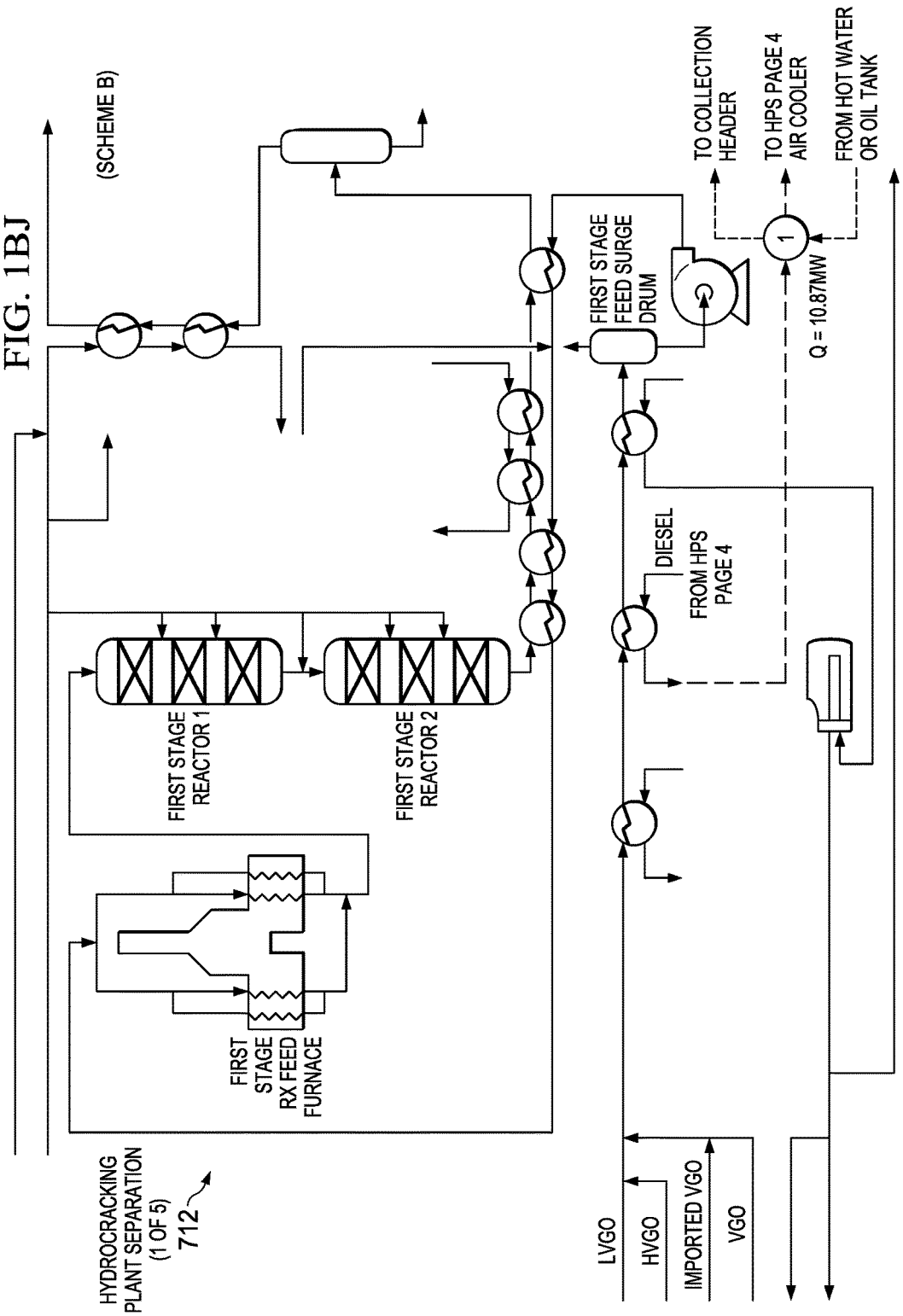
Figure 1B:
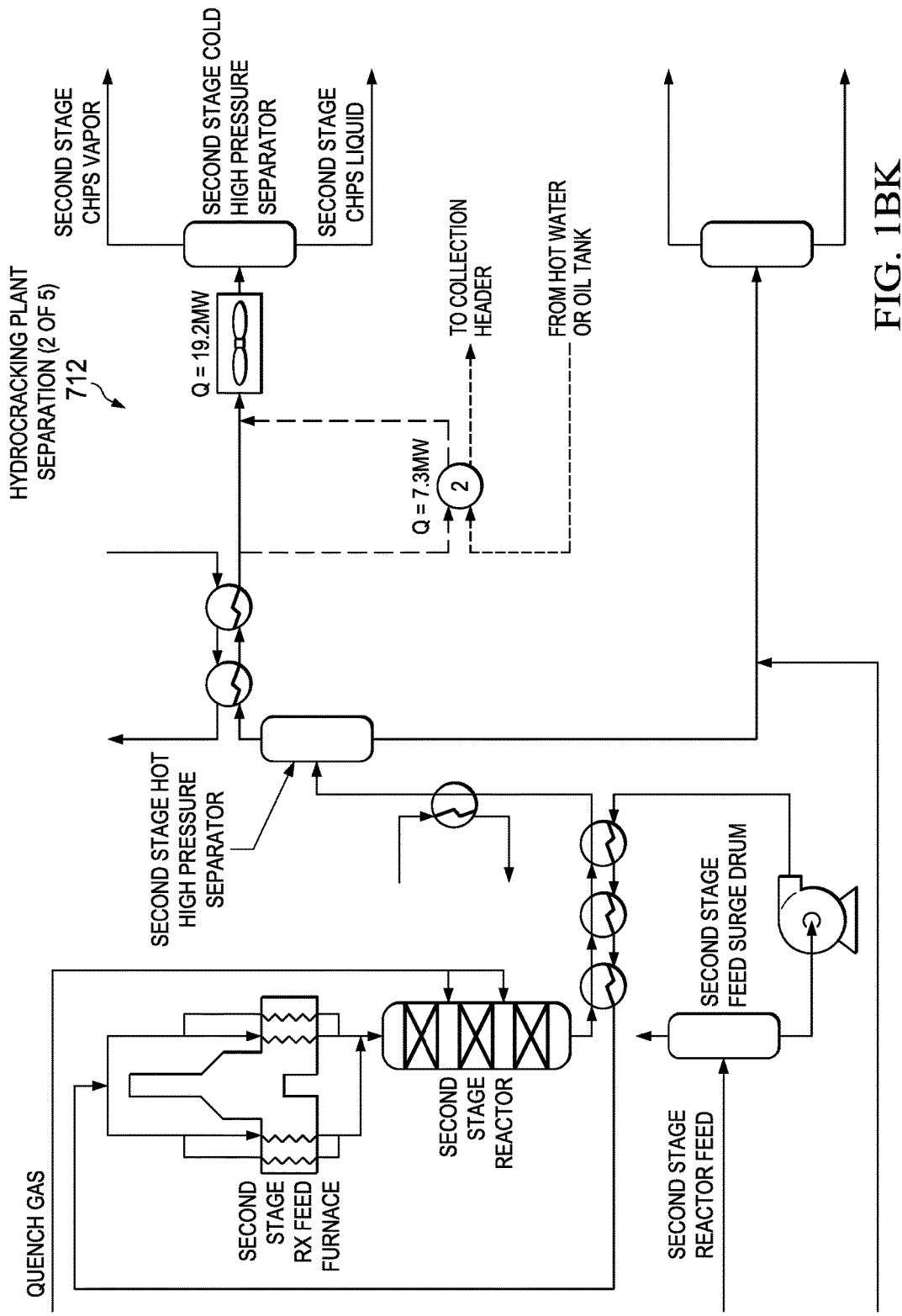
Figure 1B:
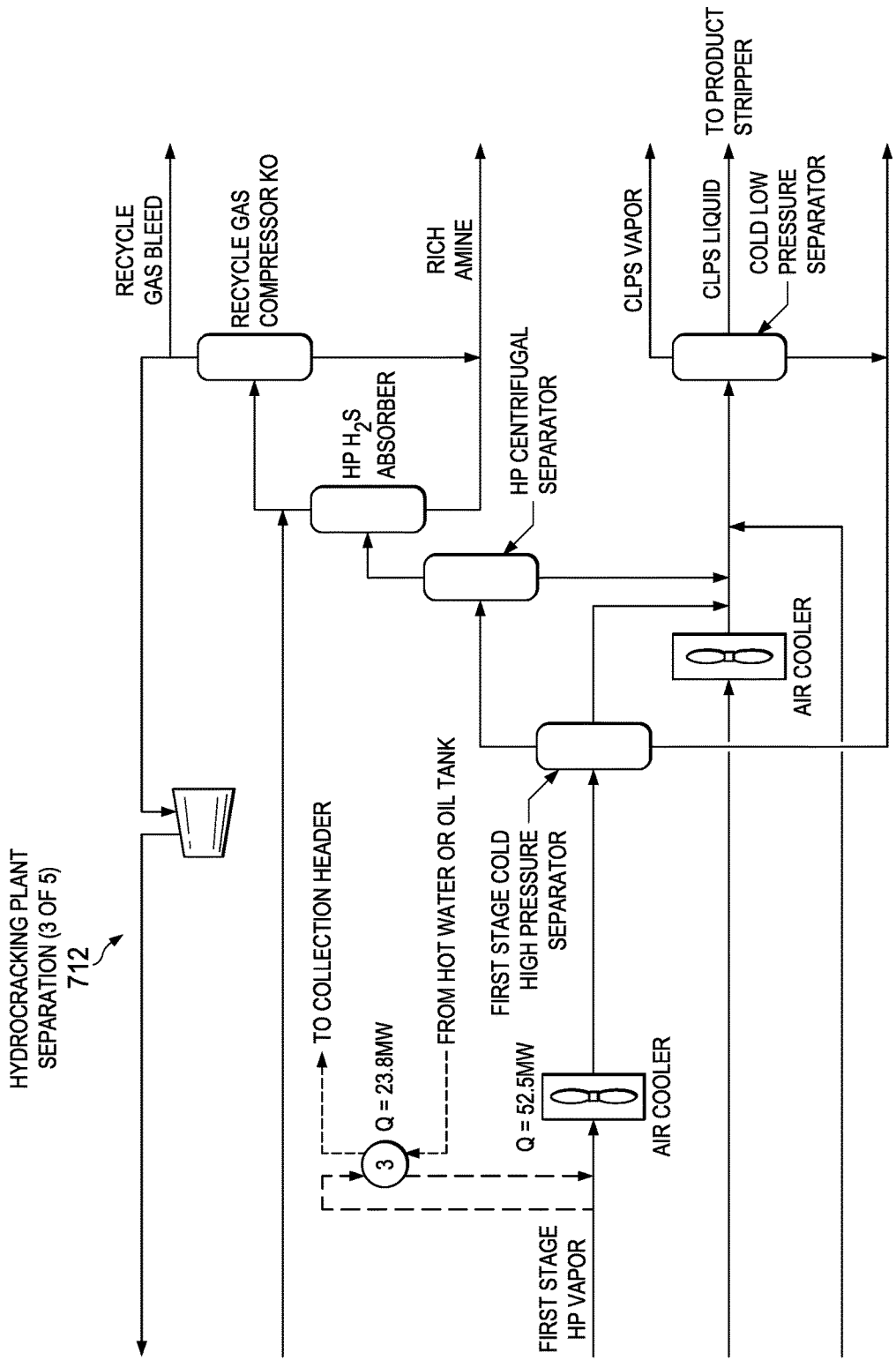
Figure 1B:
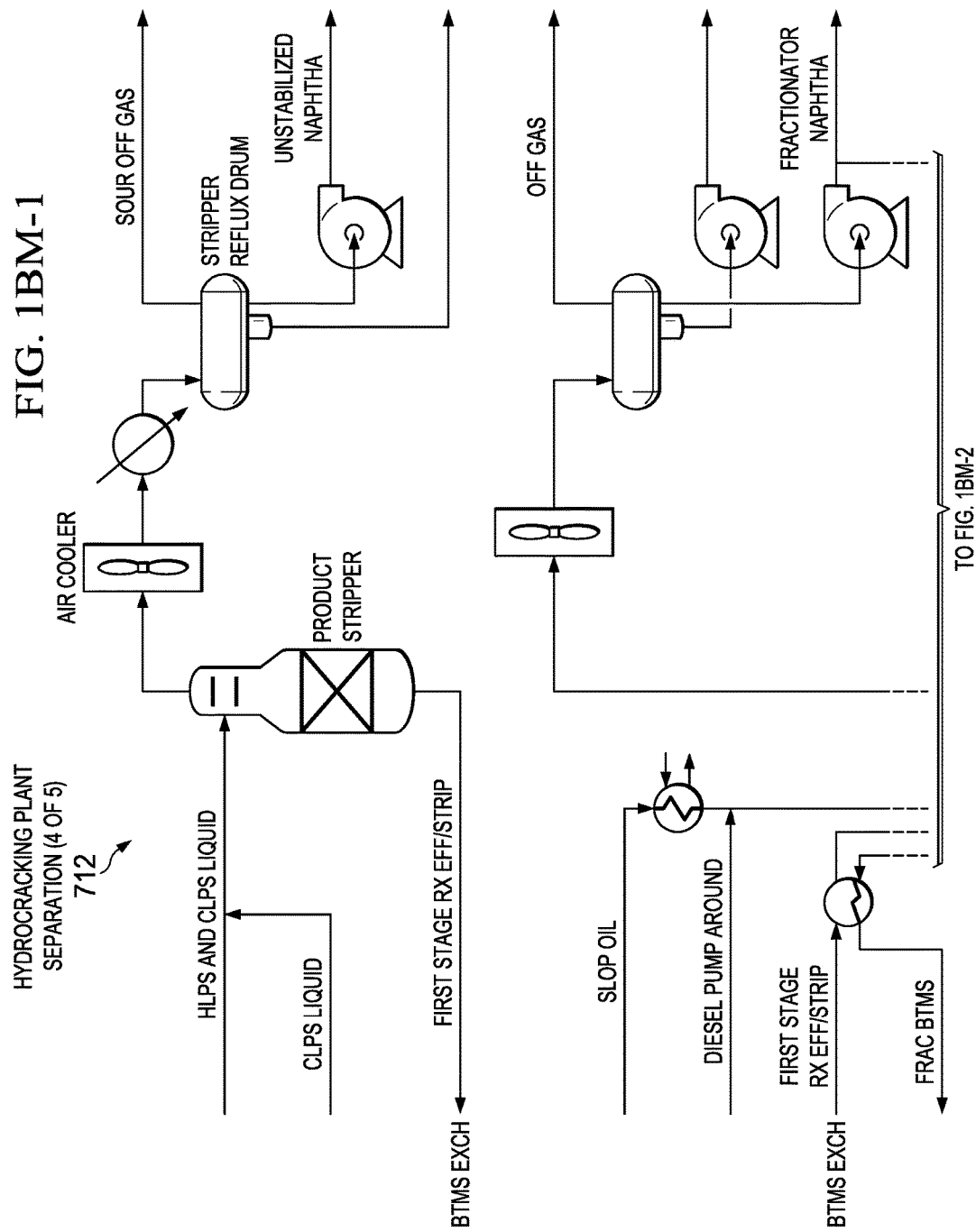
Figure 1B:
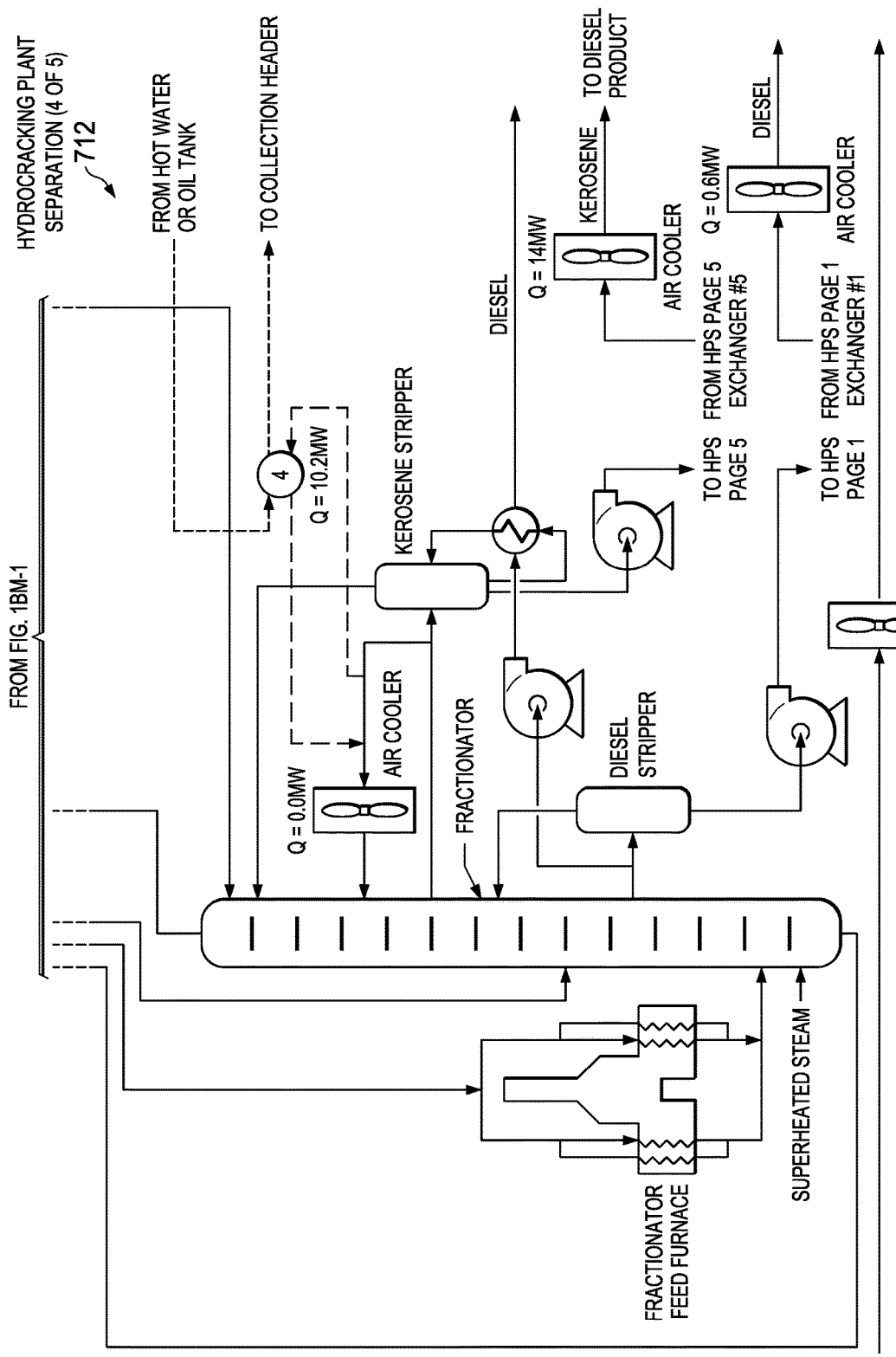
Figure 1B:
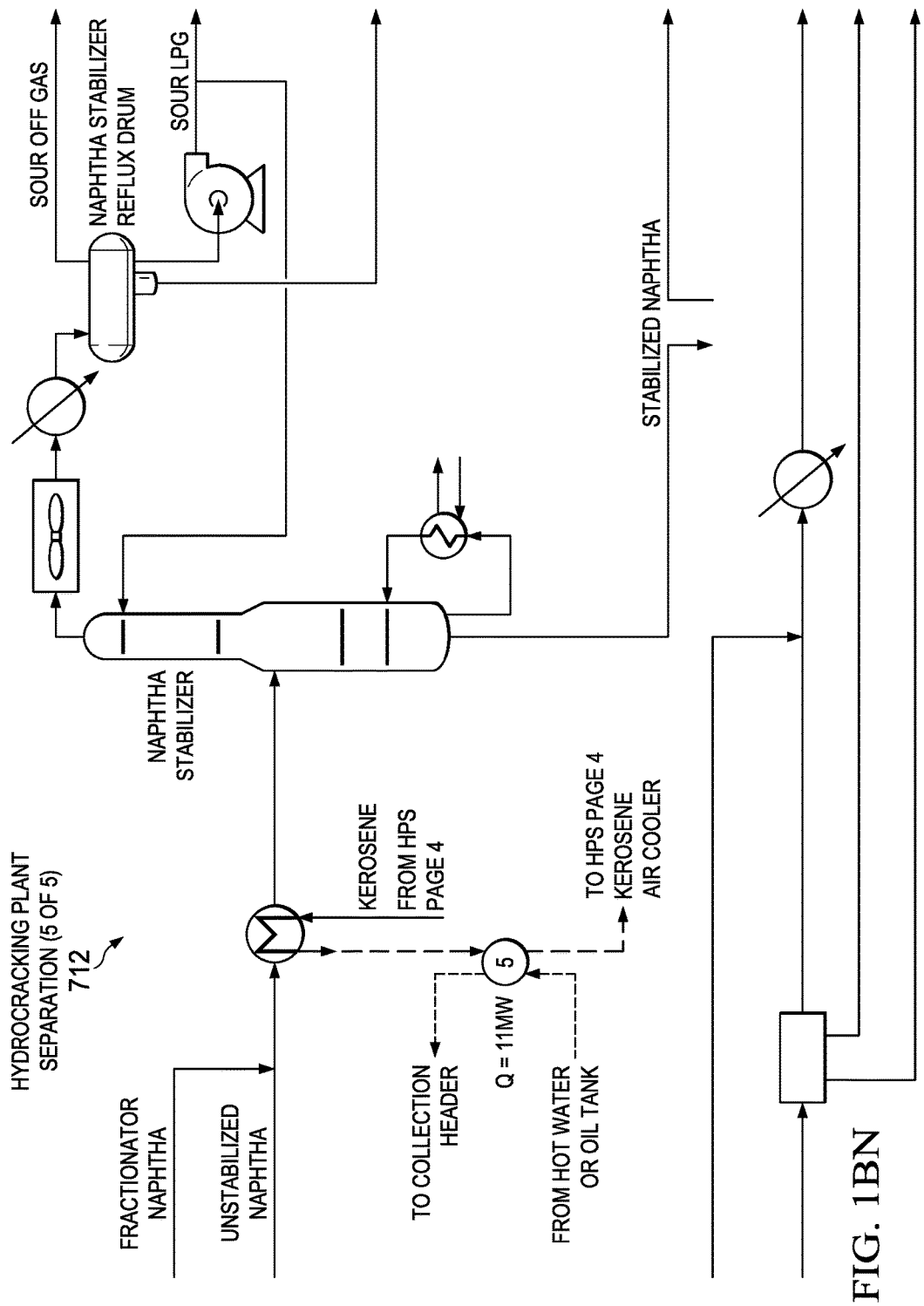
Figure 1B:
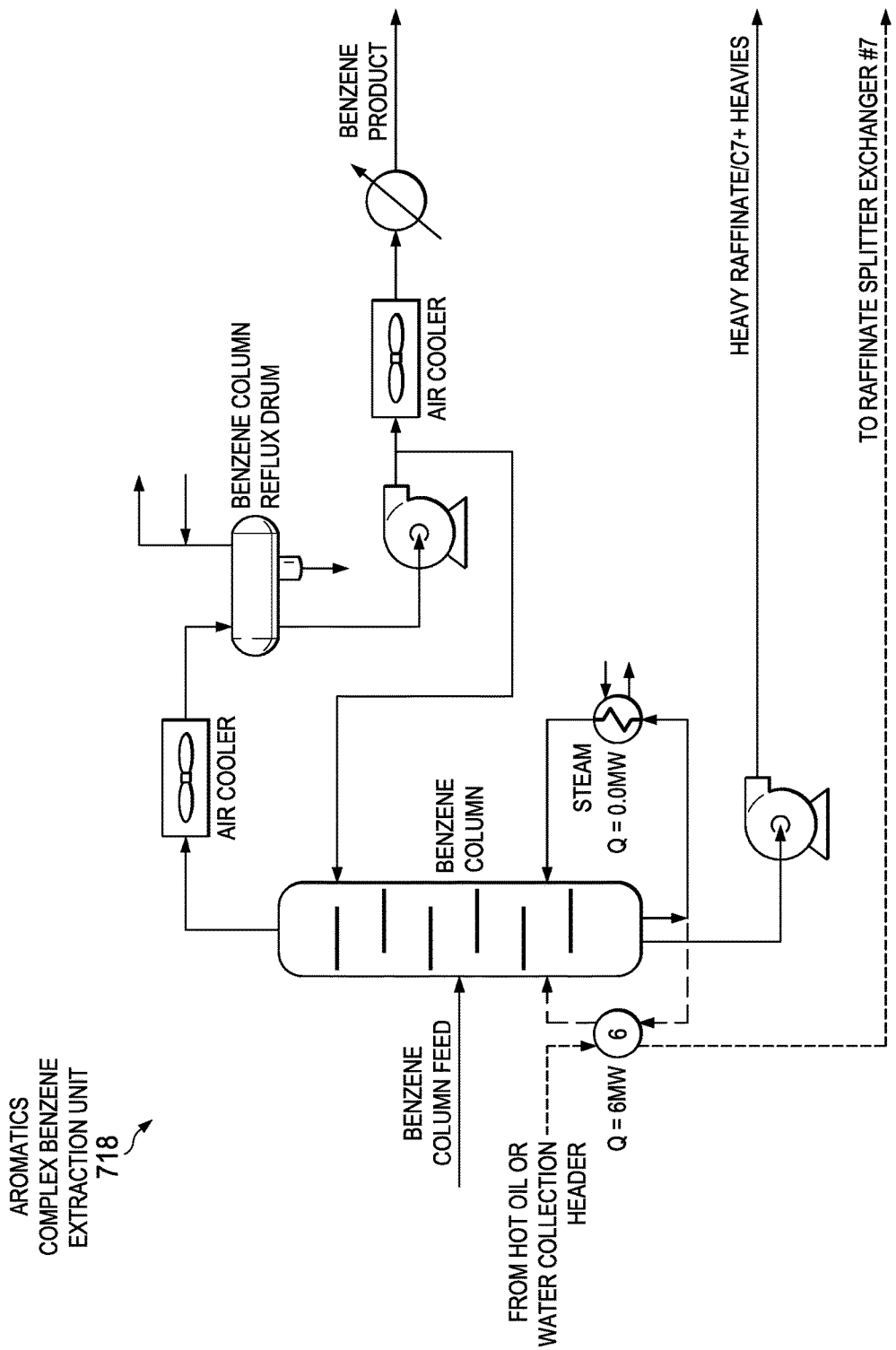
Figure 1B:
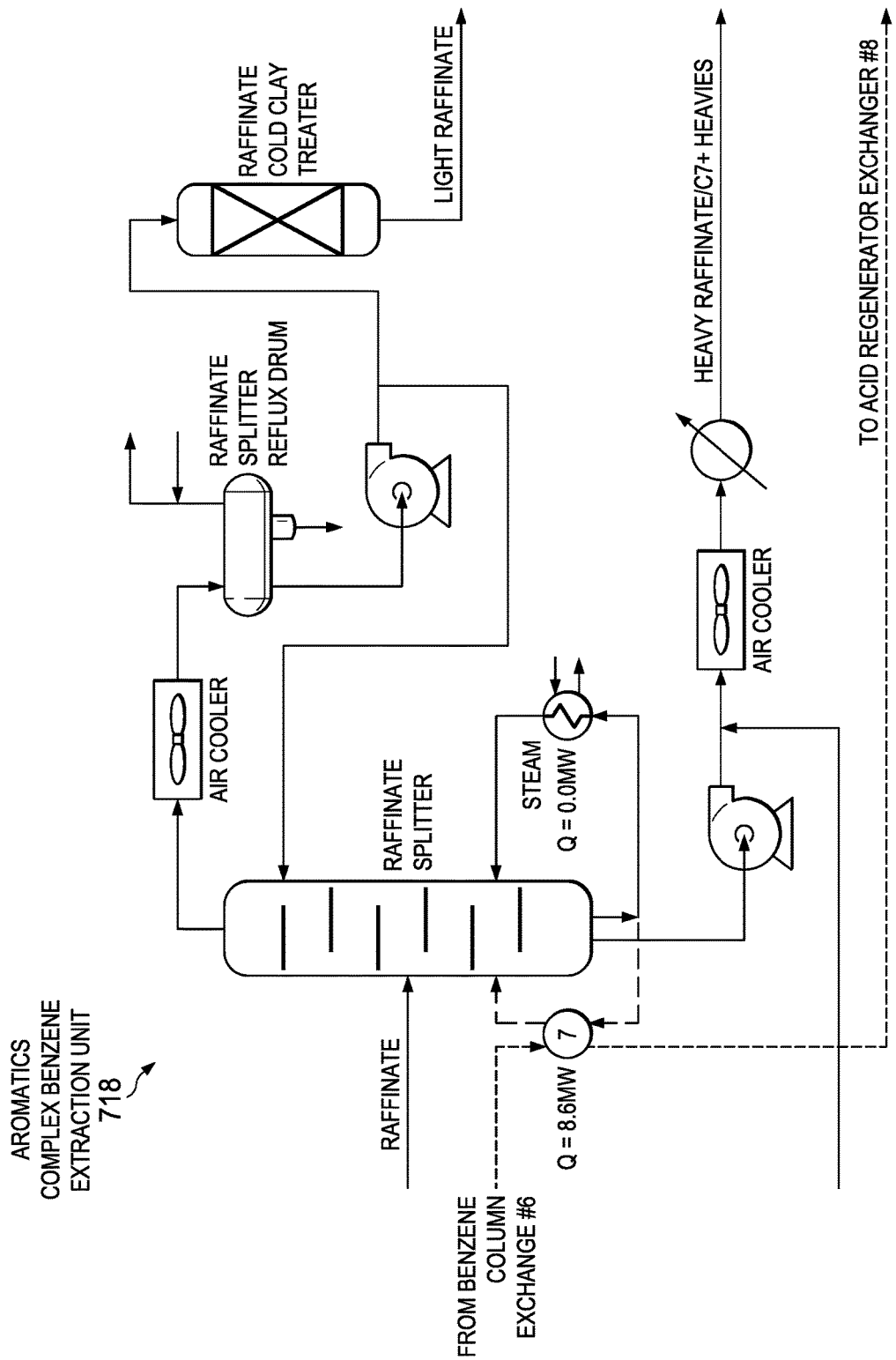
Figure 1B:
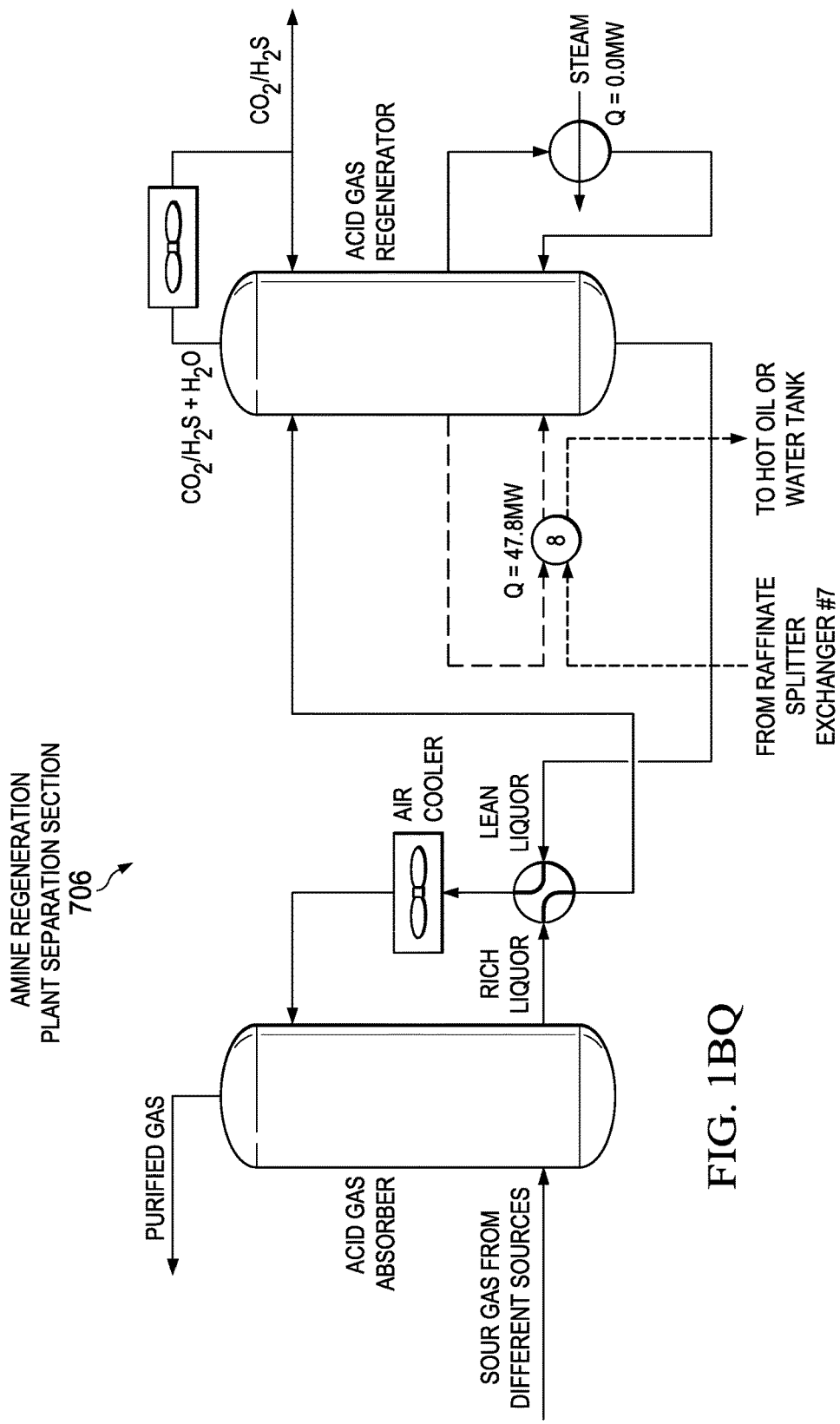
Figure 1B:
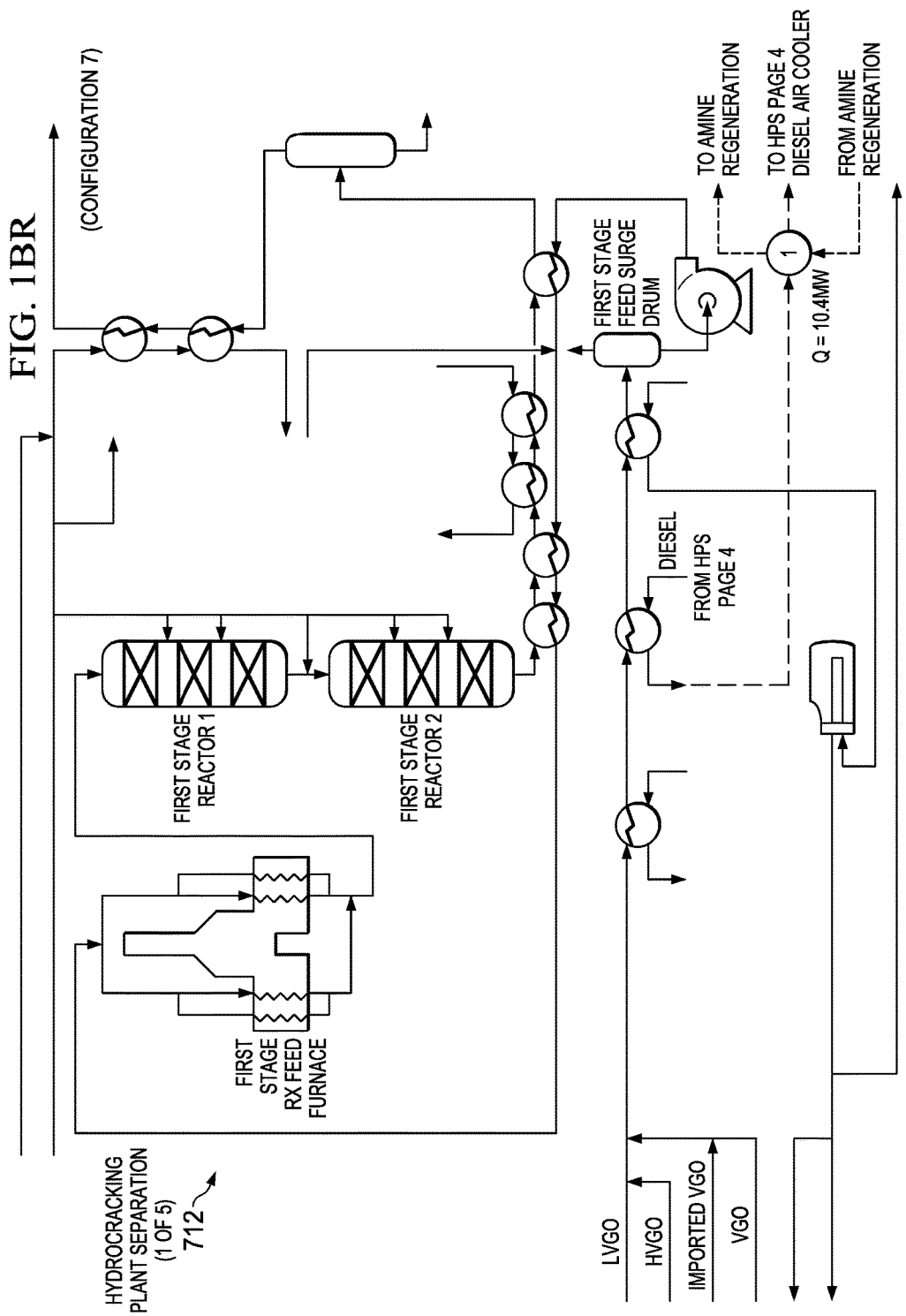
Figure 1B:
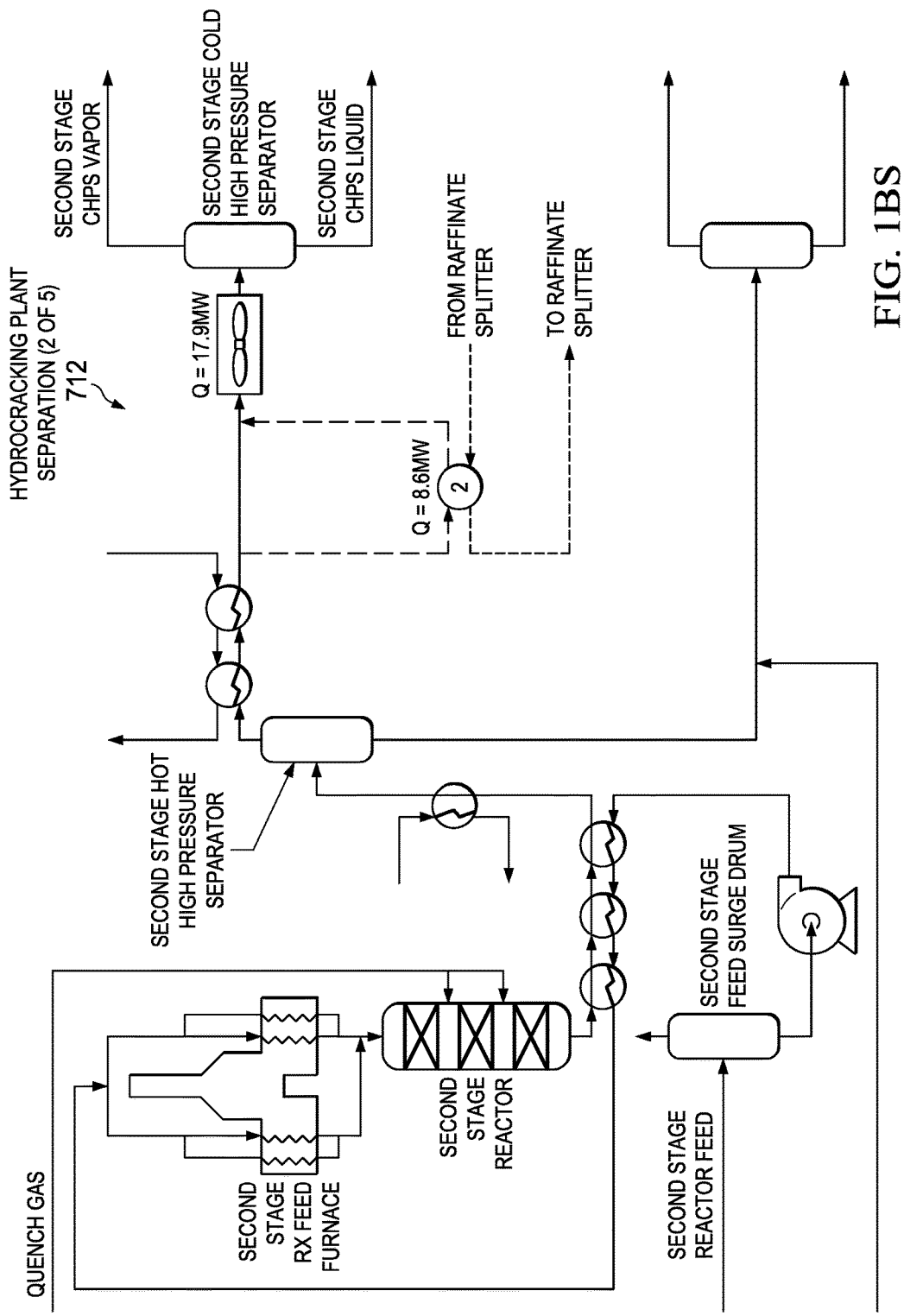
Figure 1B:
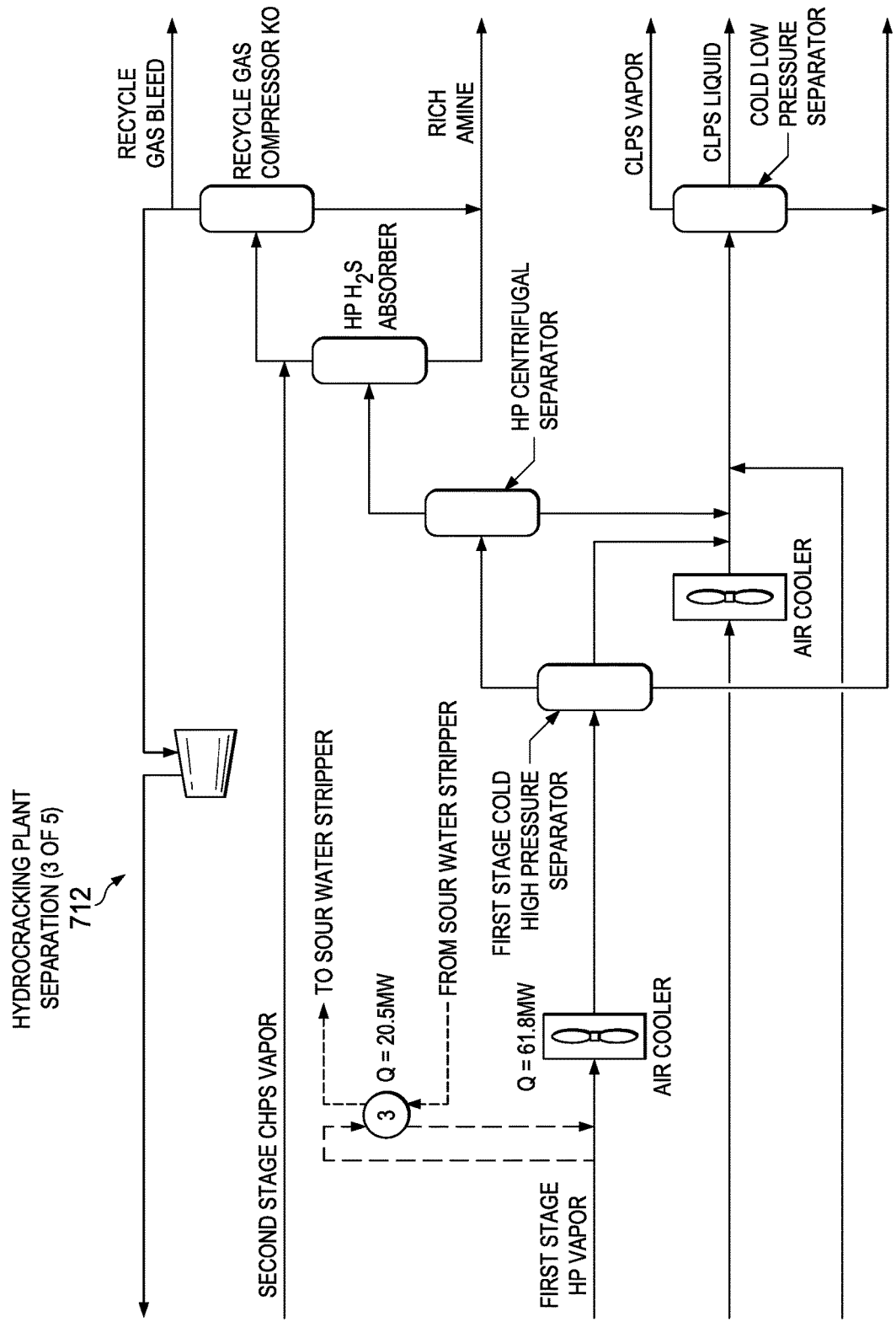
Figure 1B:
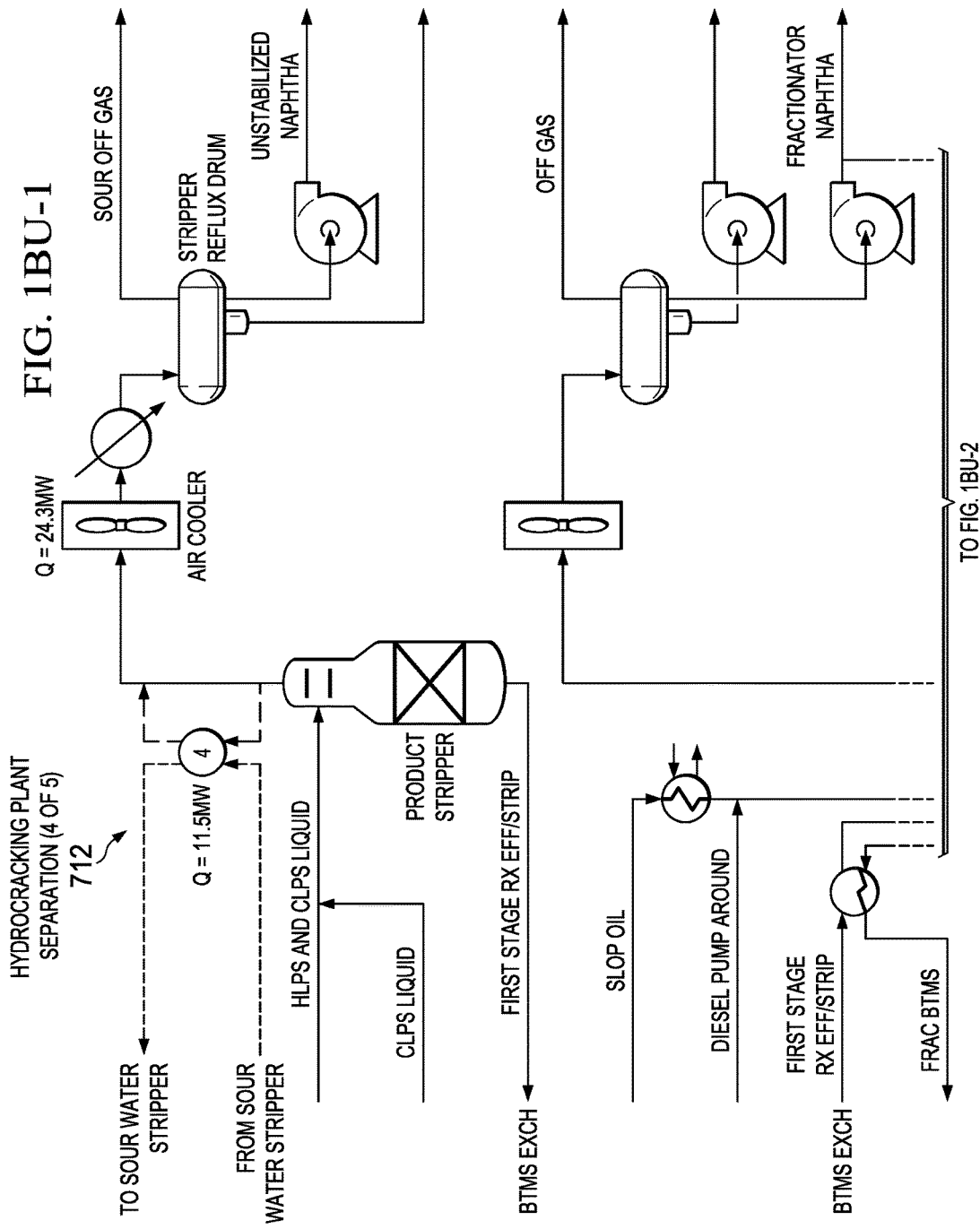
Figure 1B:
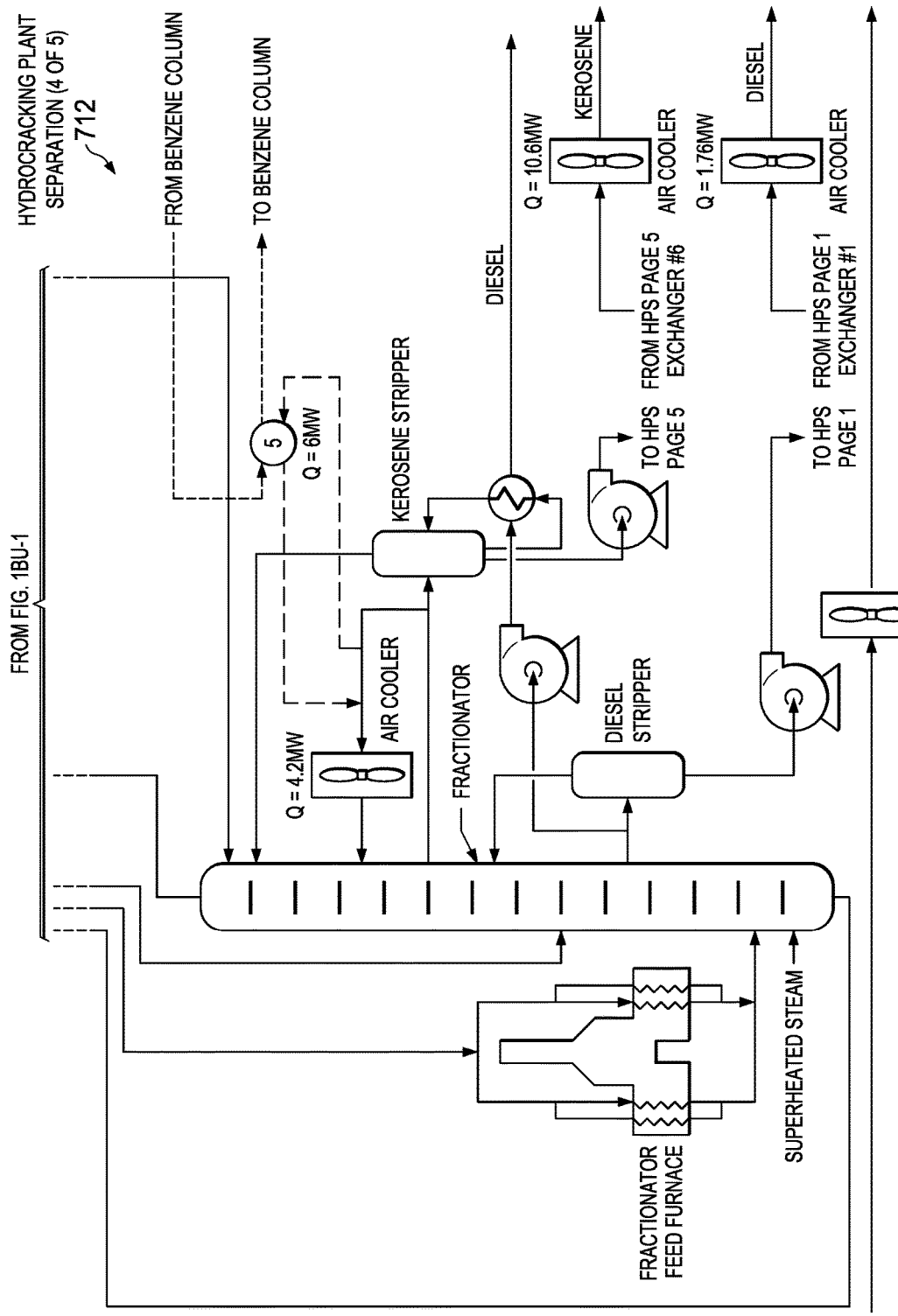
Figure 1B:
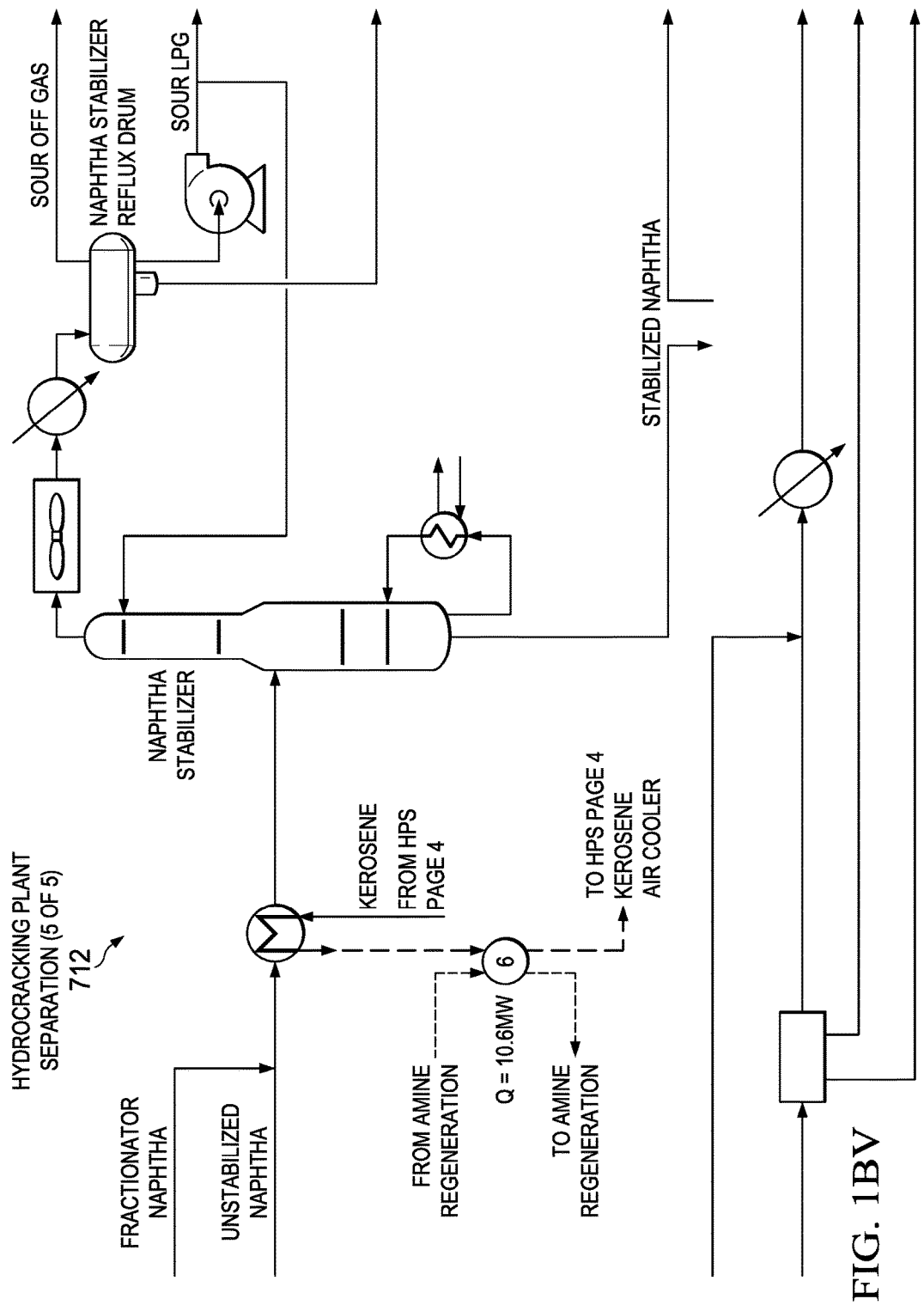
Figure 1B:
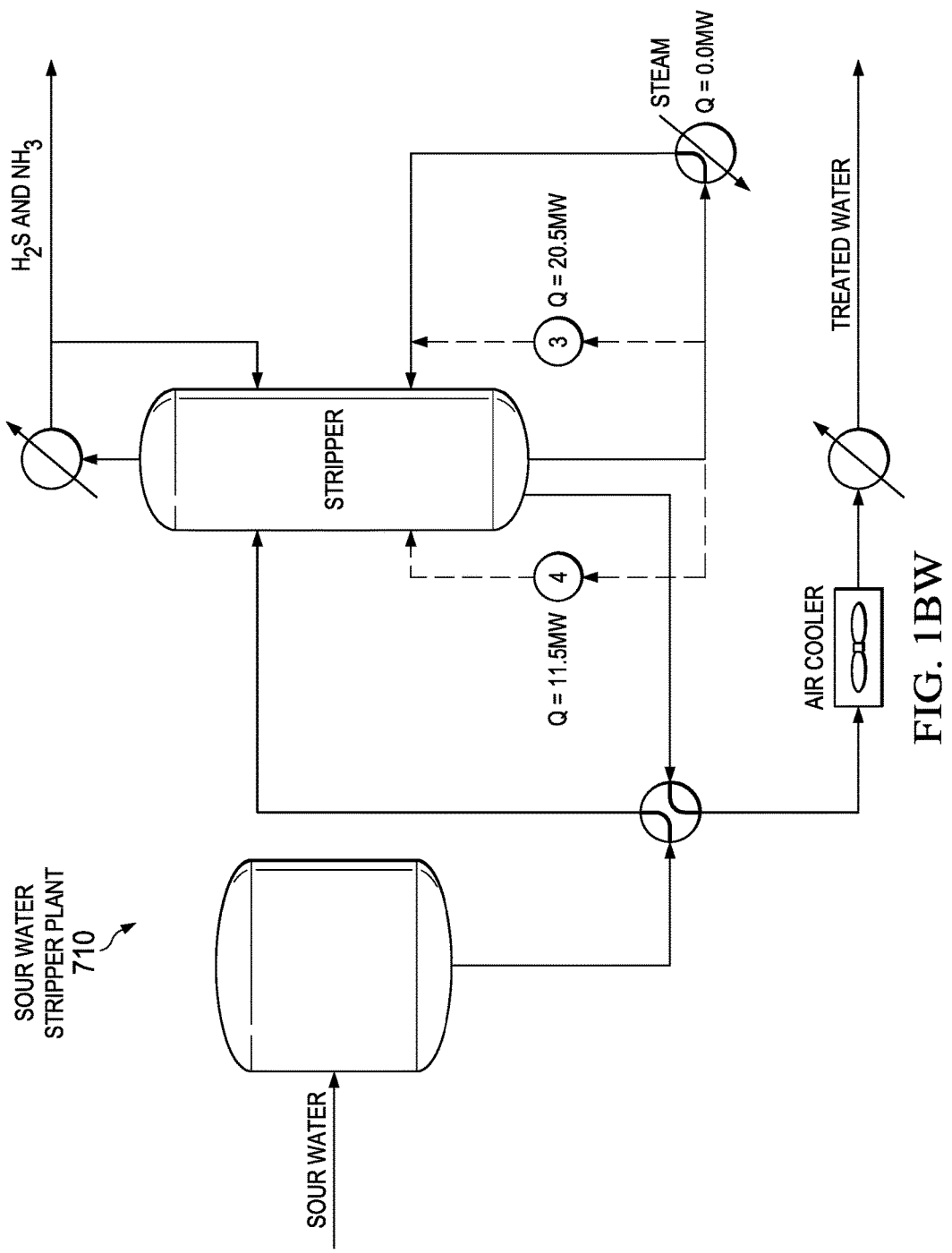
Figure 1B:
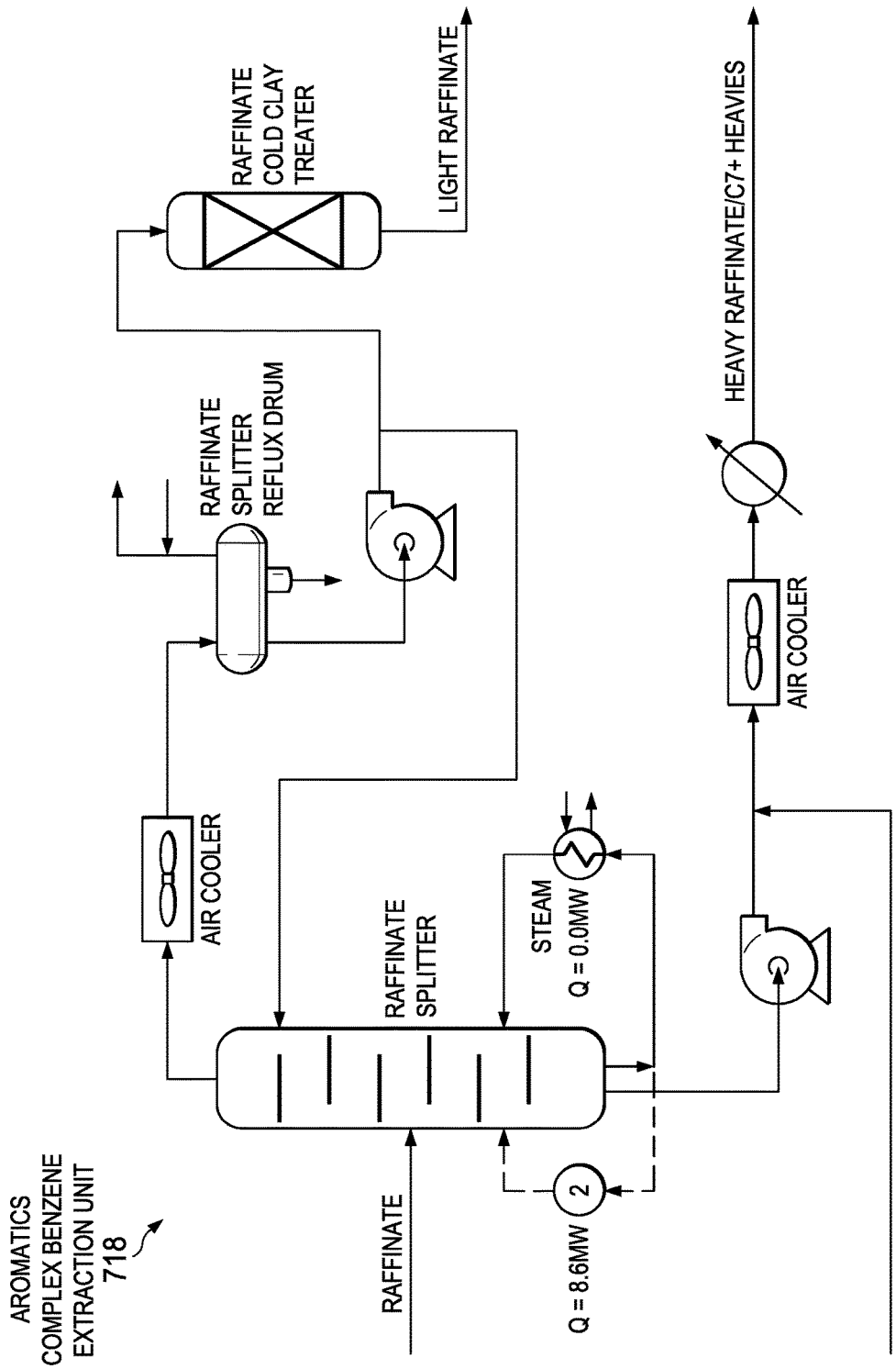
Figure 1B:
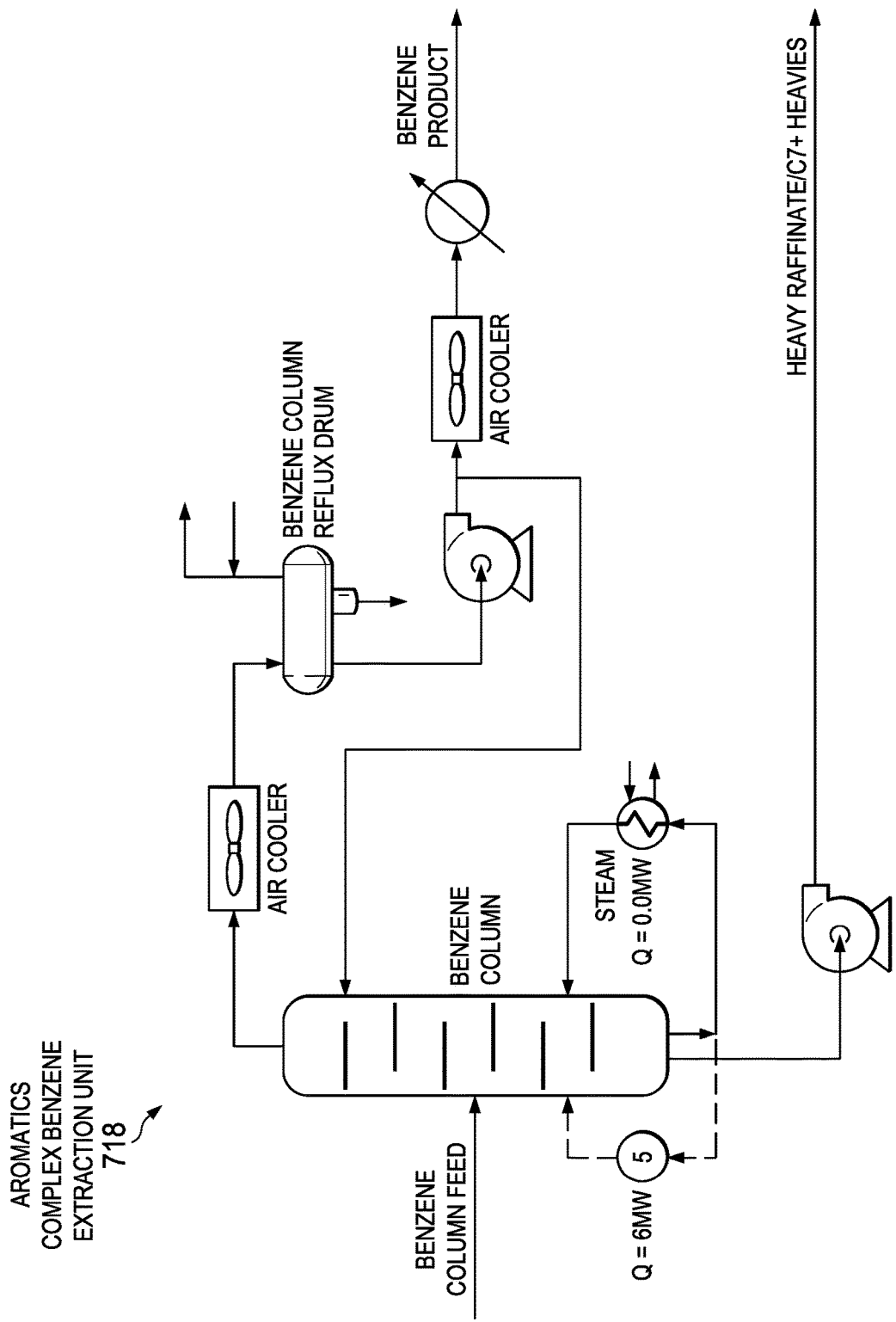
Figure 1B:
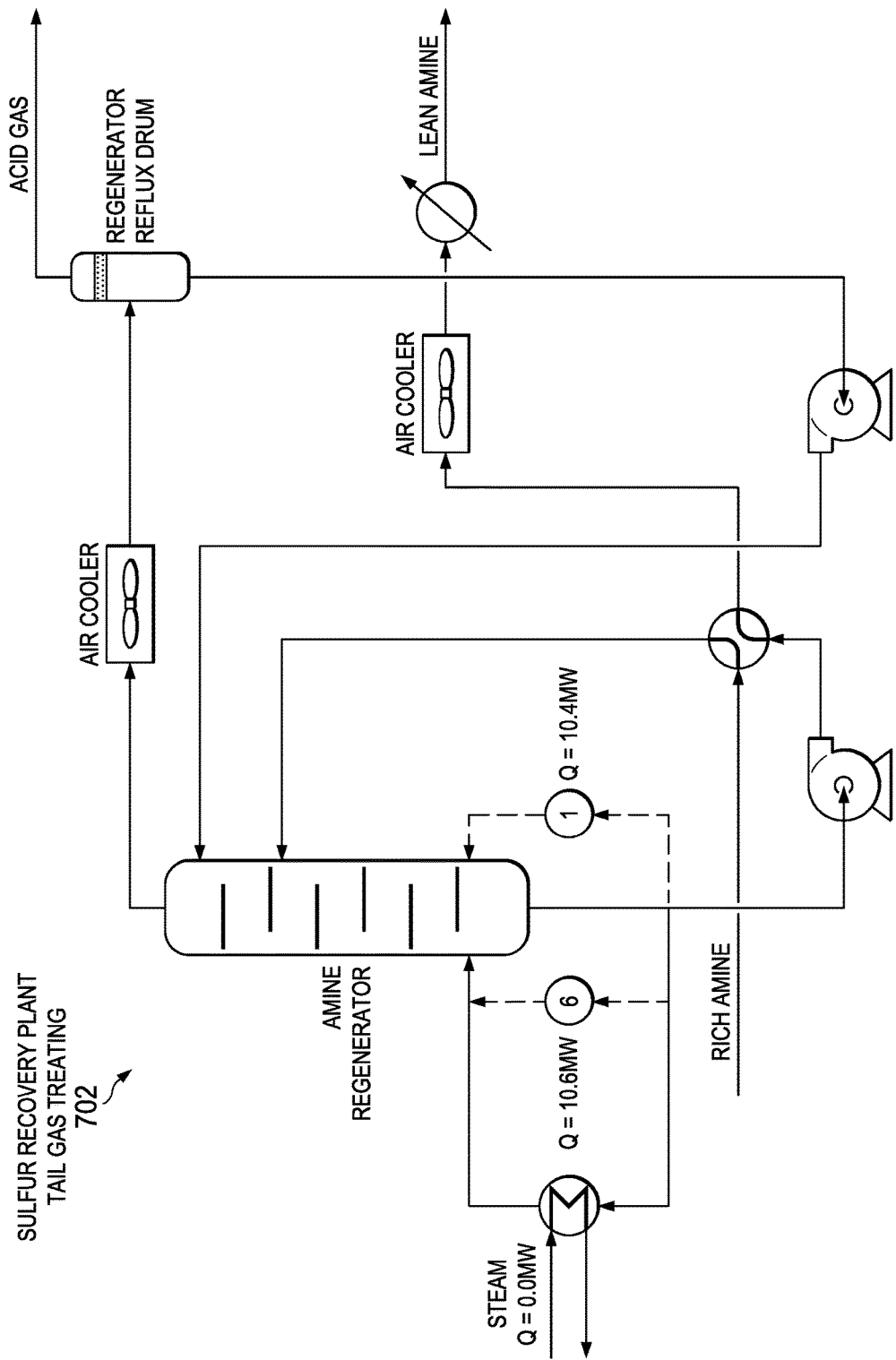
Figure 1C:
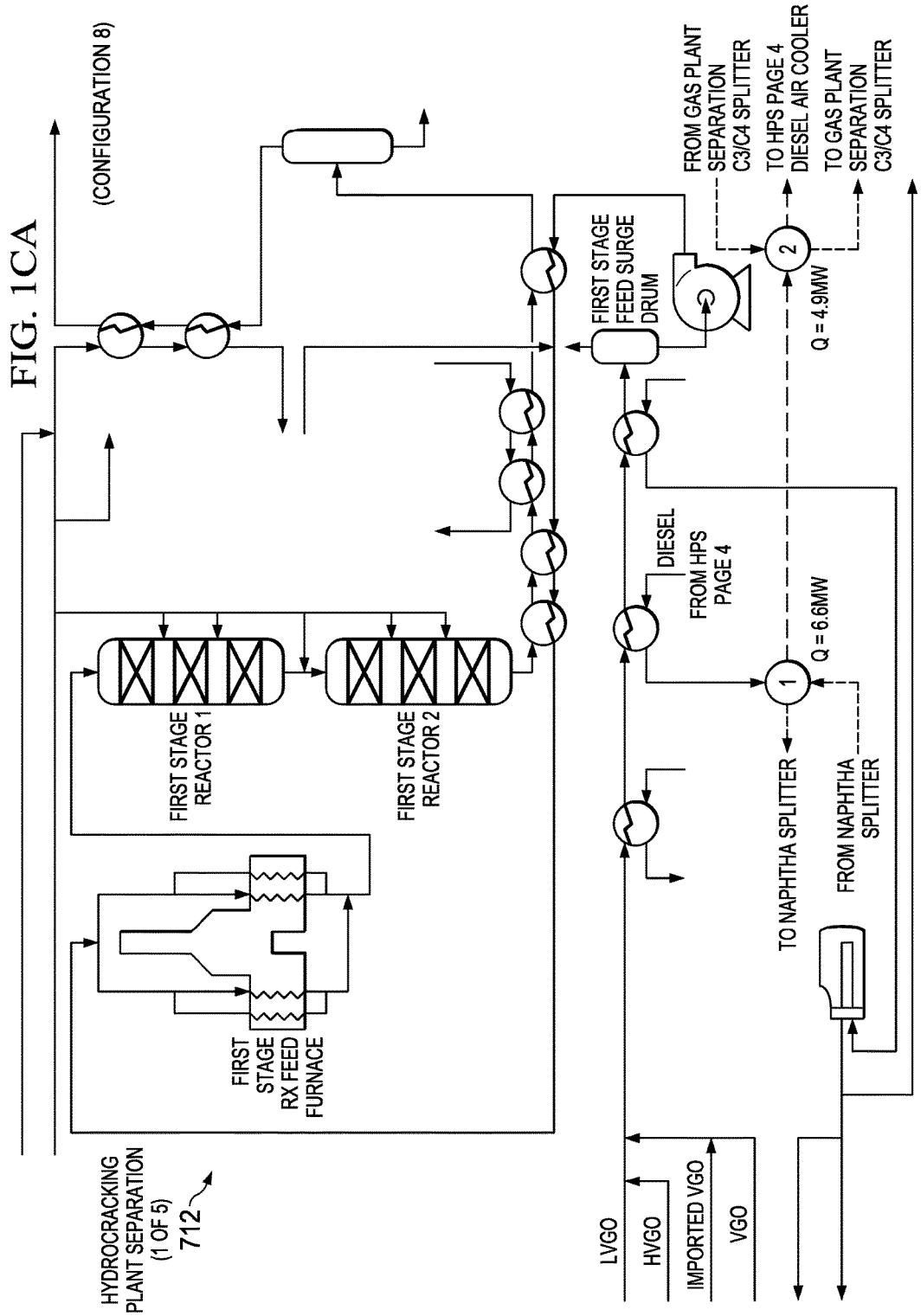
Figure 1C:
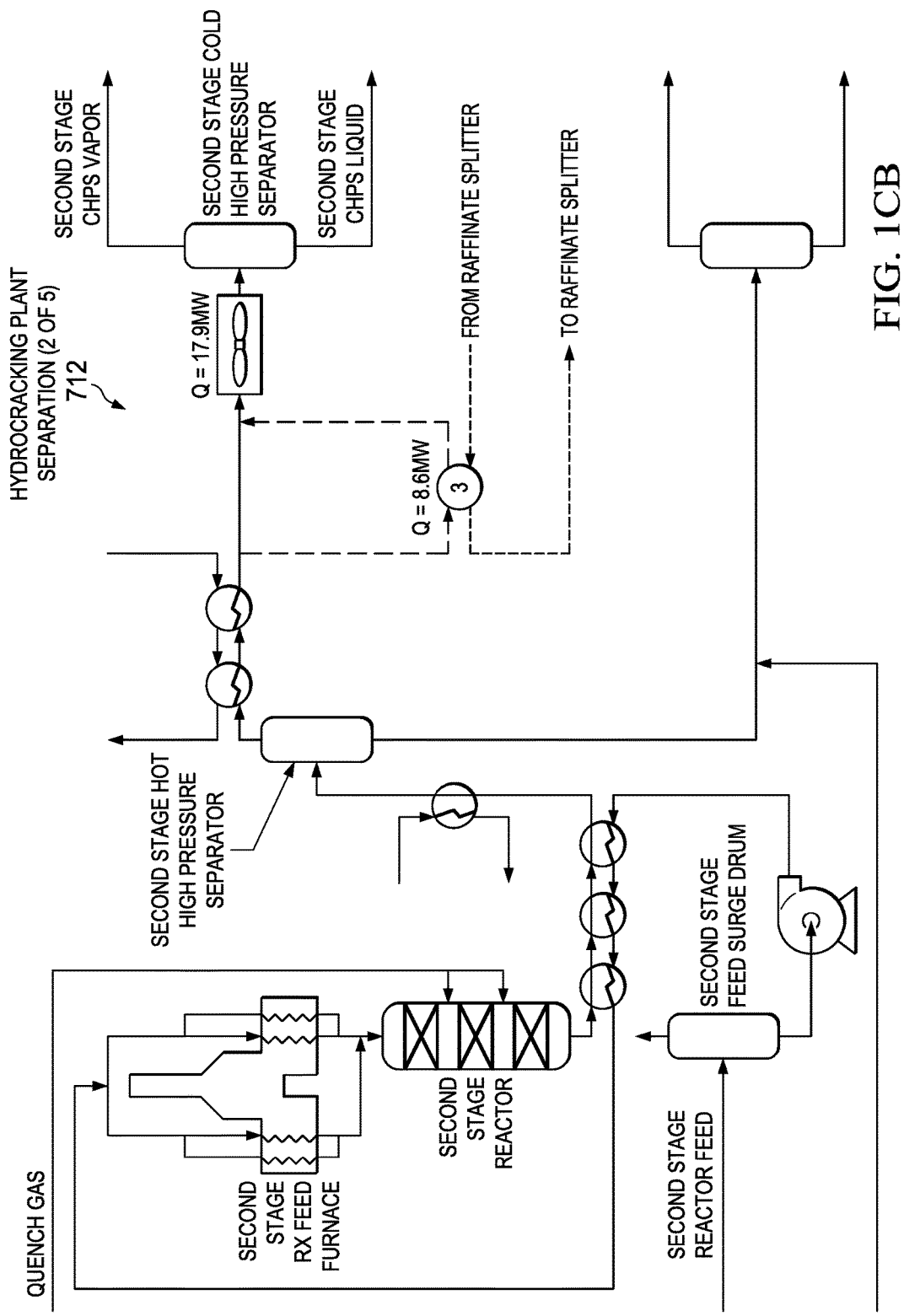
Figure 1C:
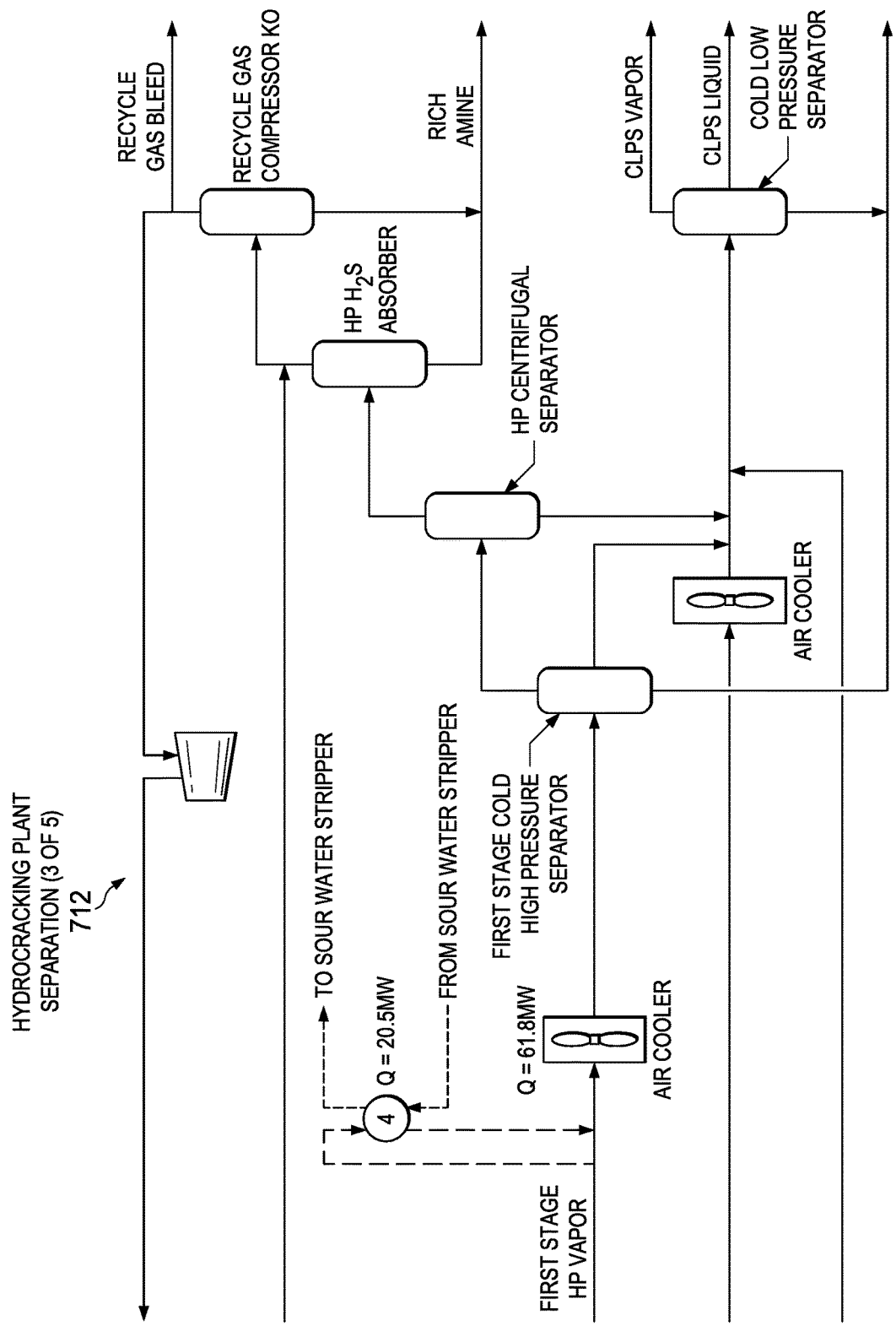
Figure 1C:
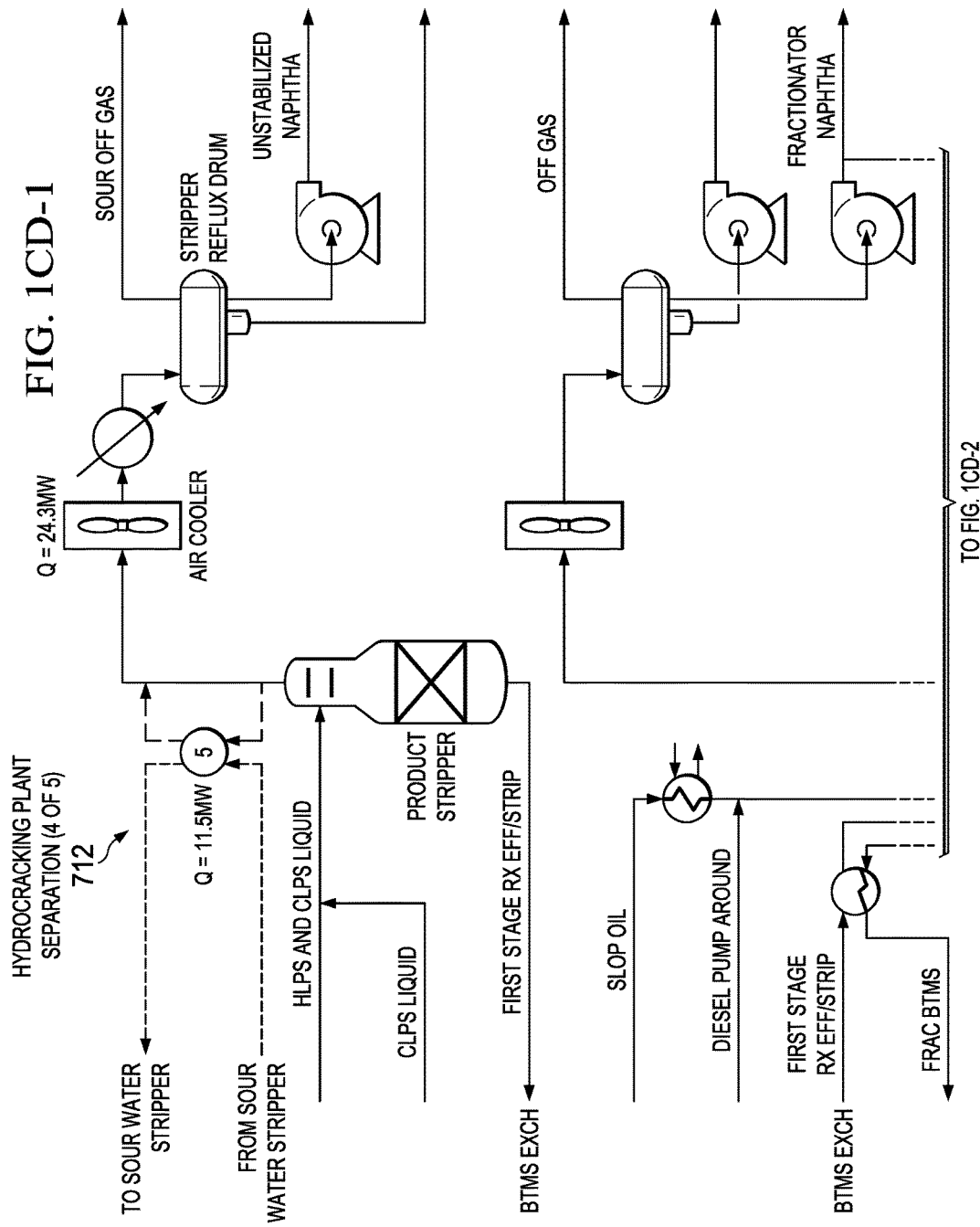
Figure 1C:
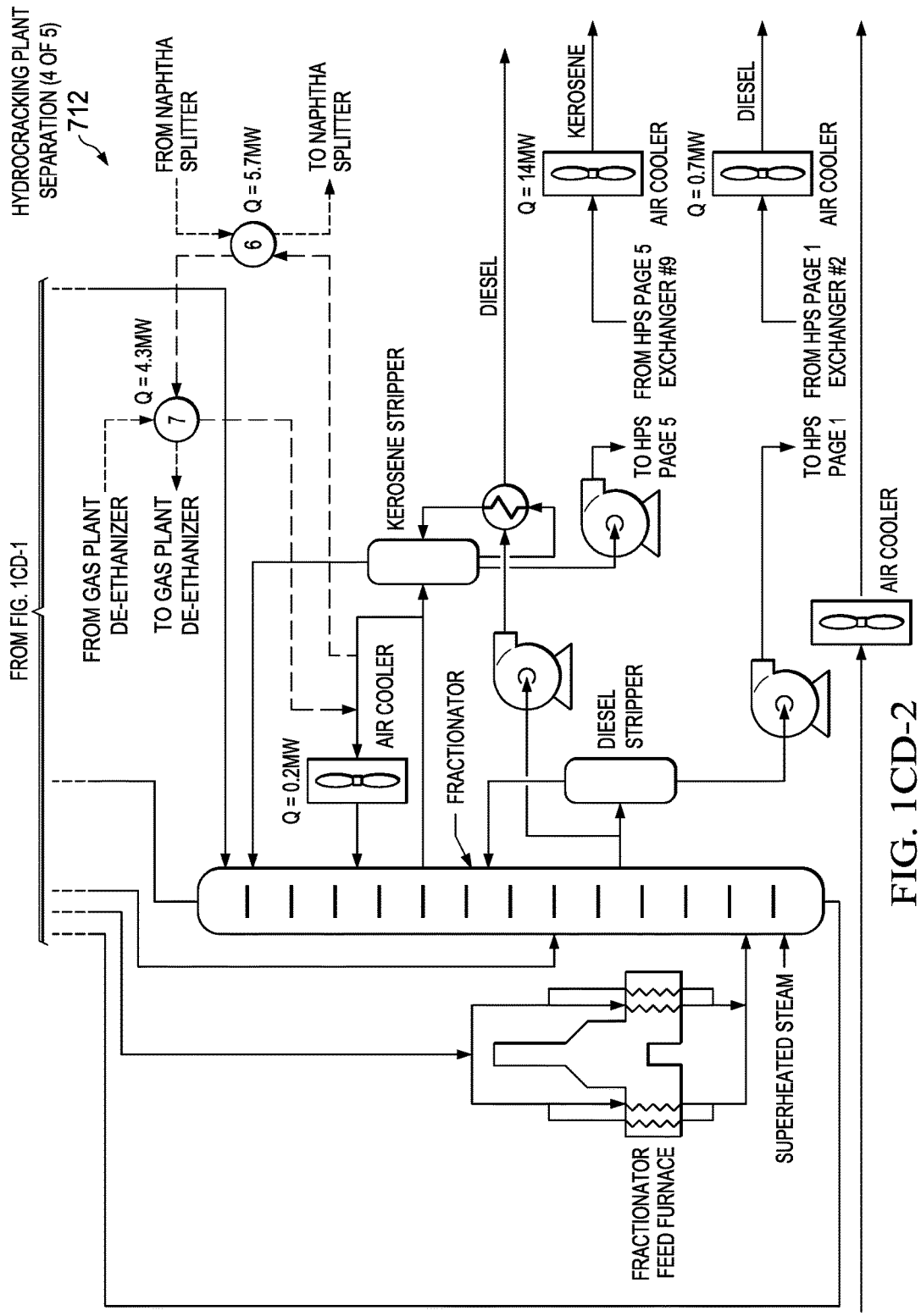
Figure 1C:
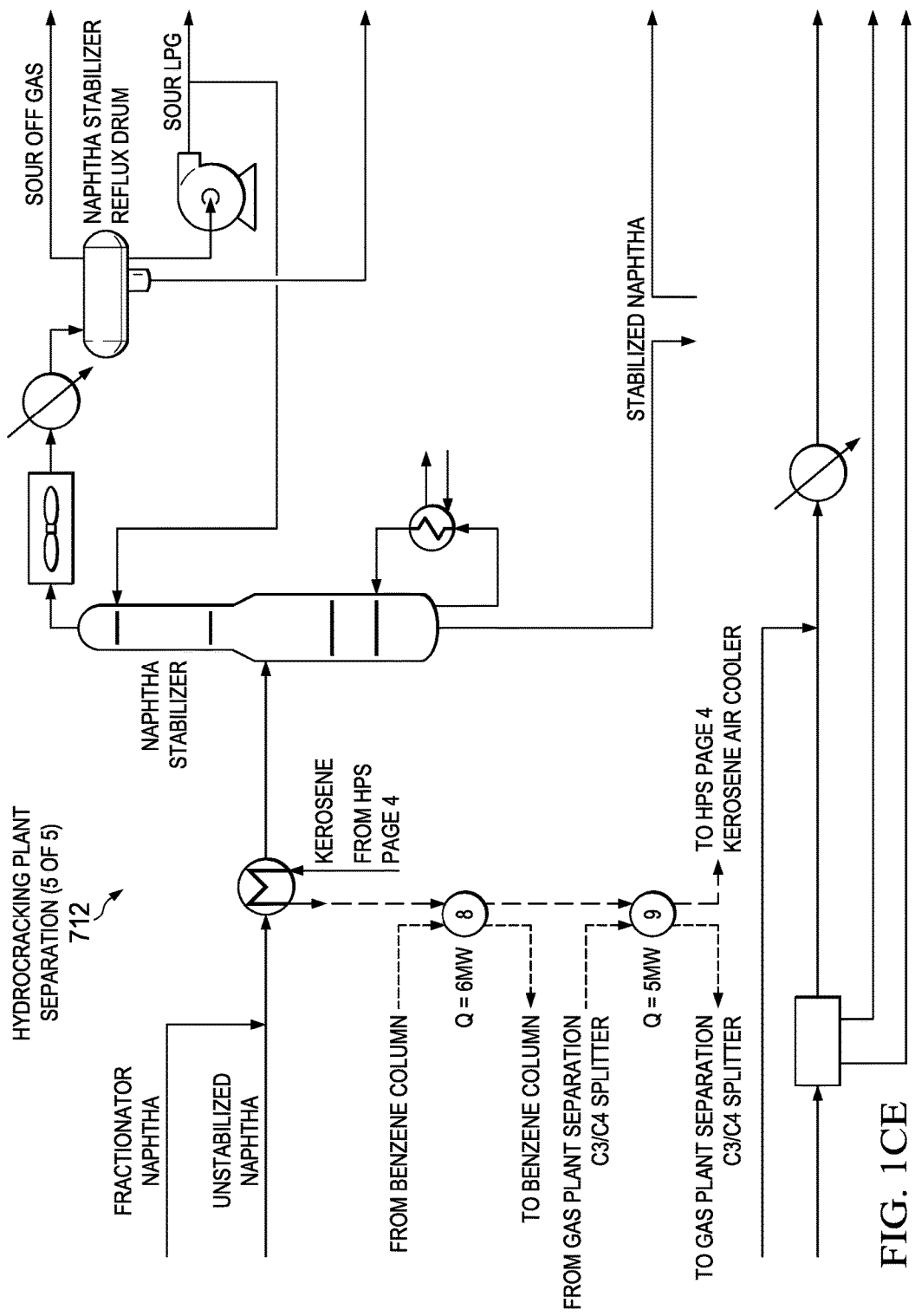
Figure 1C:
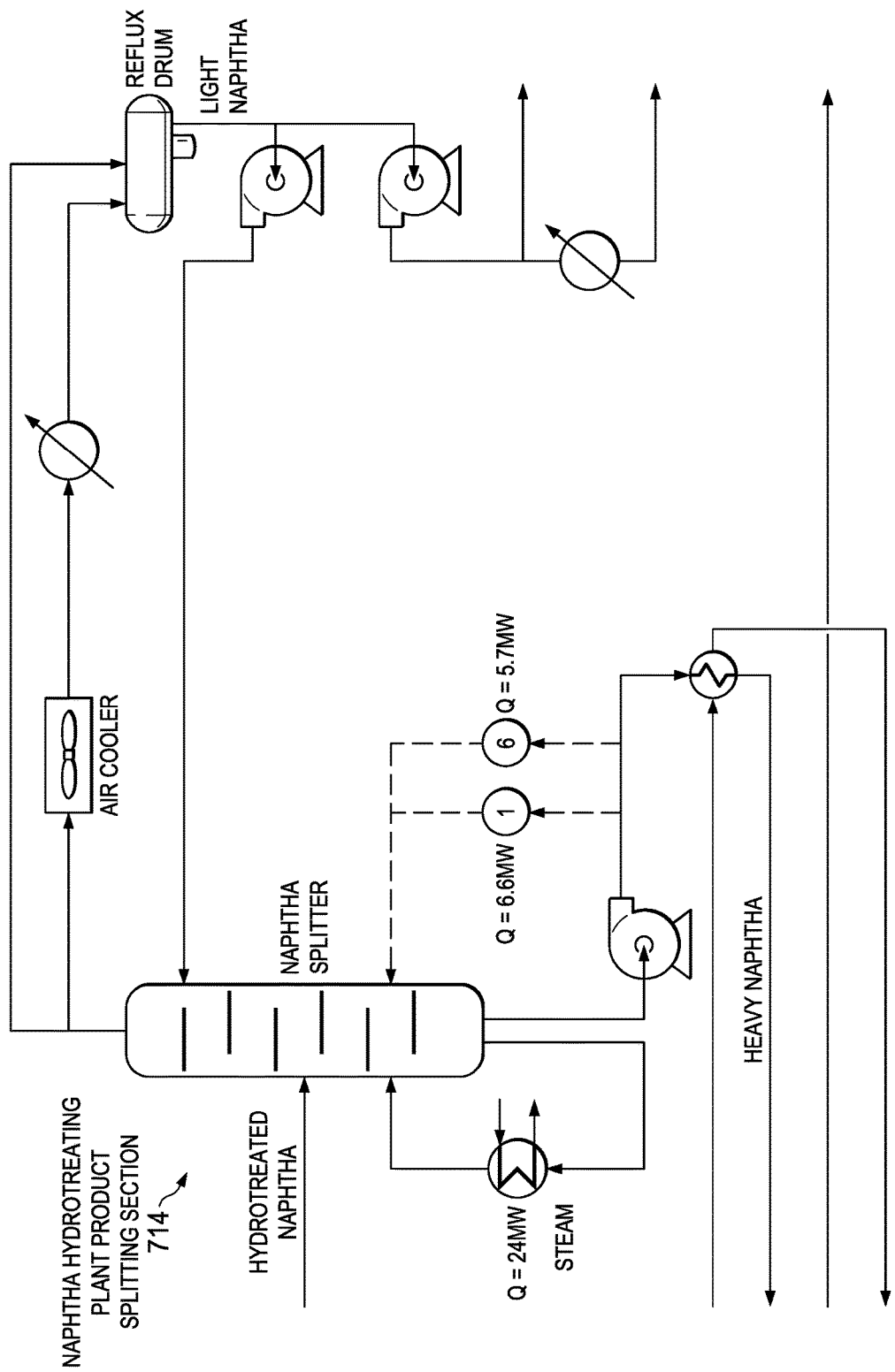
Figure 1C:
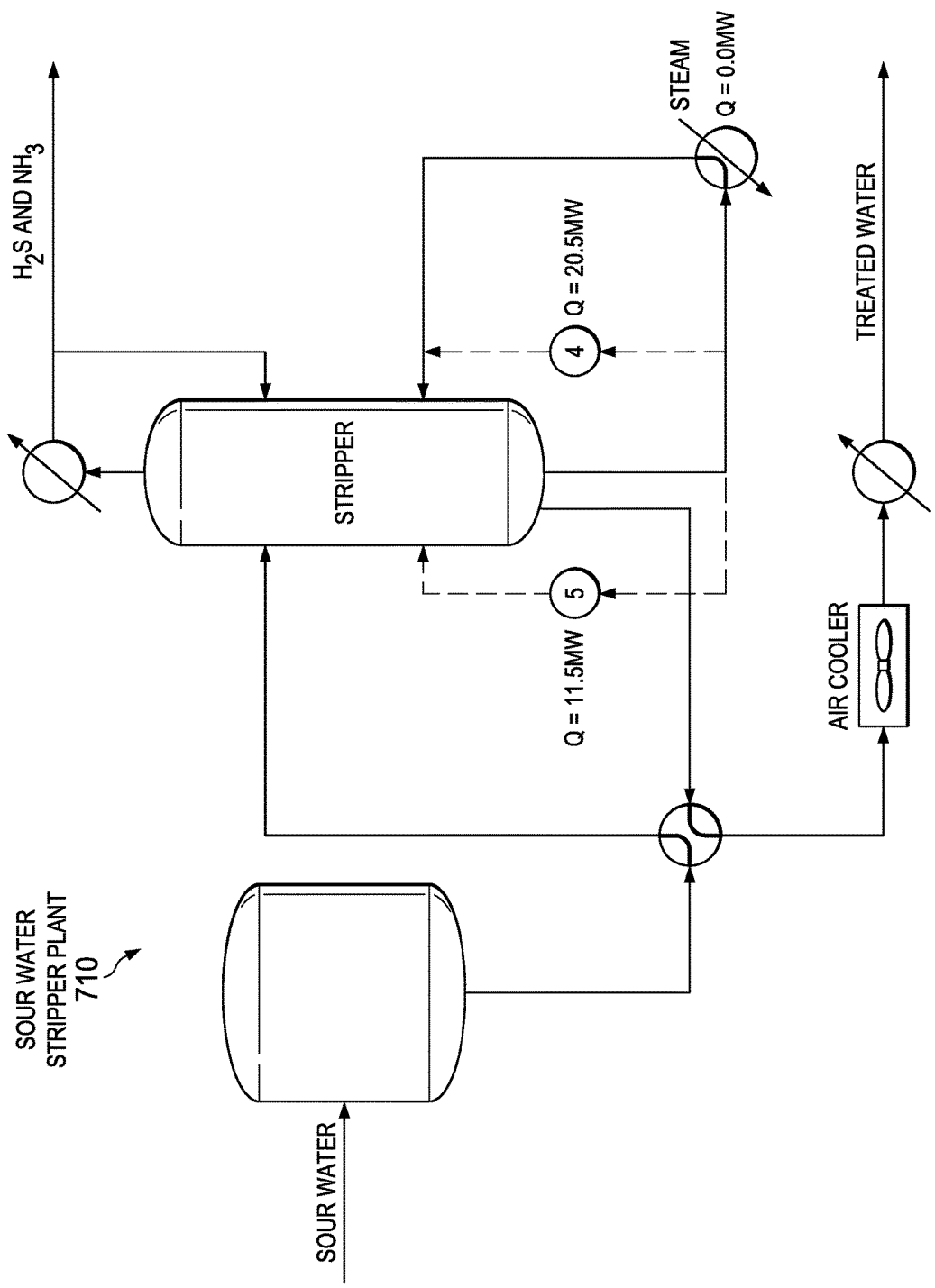
Figure 1C:
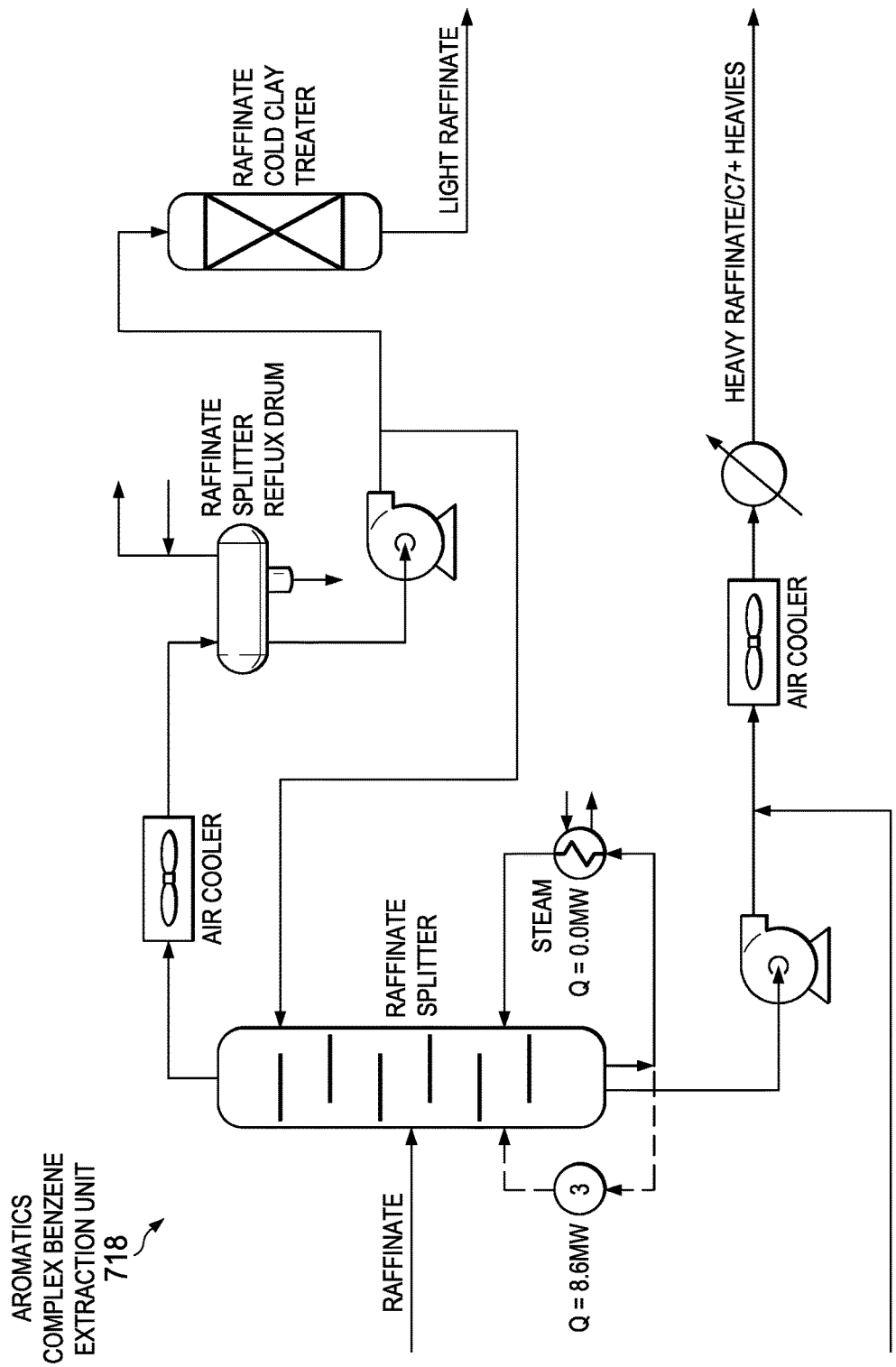
Figure 1C:
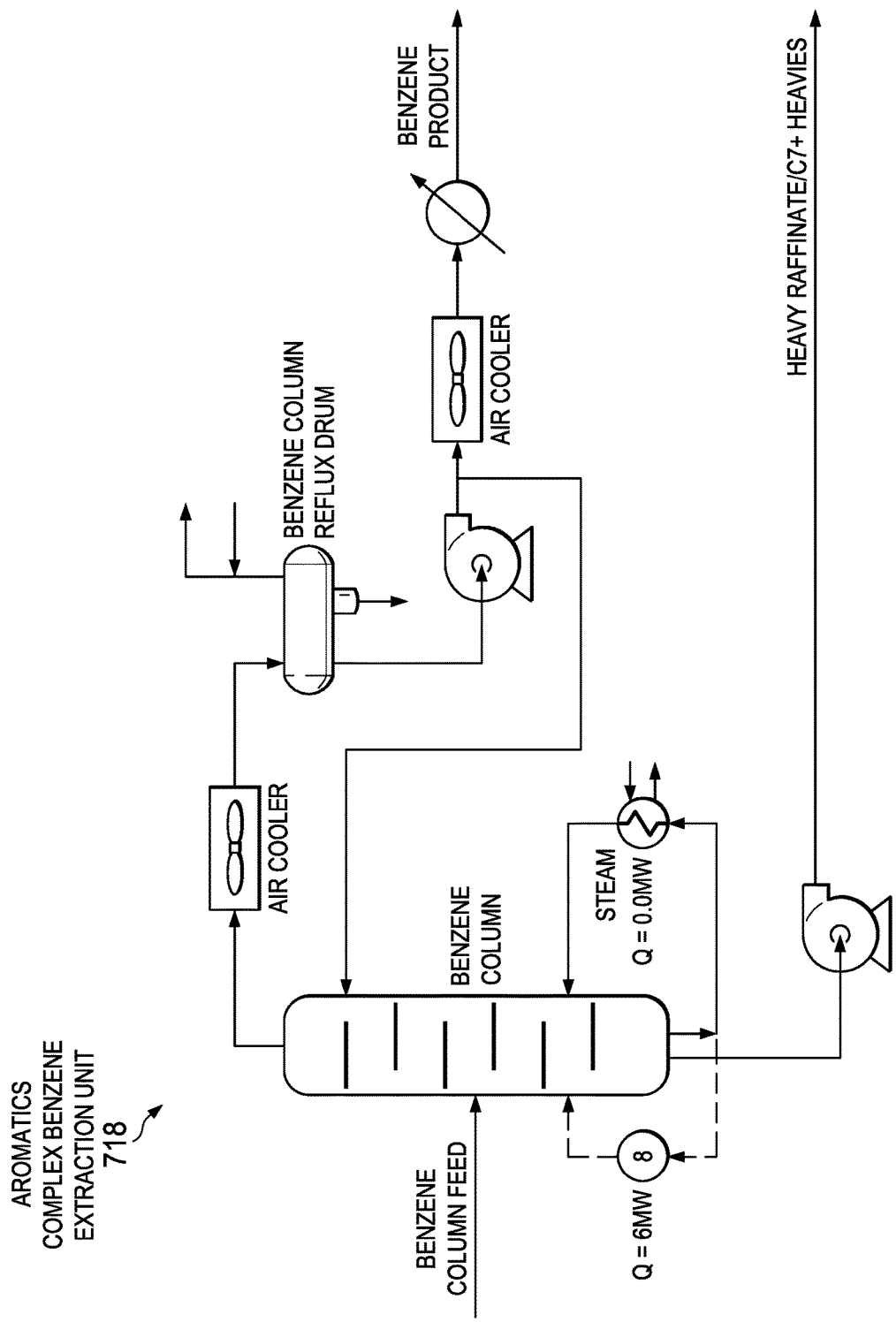
Figure 1C:
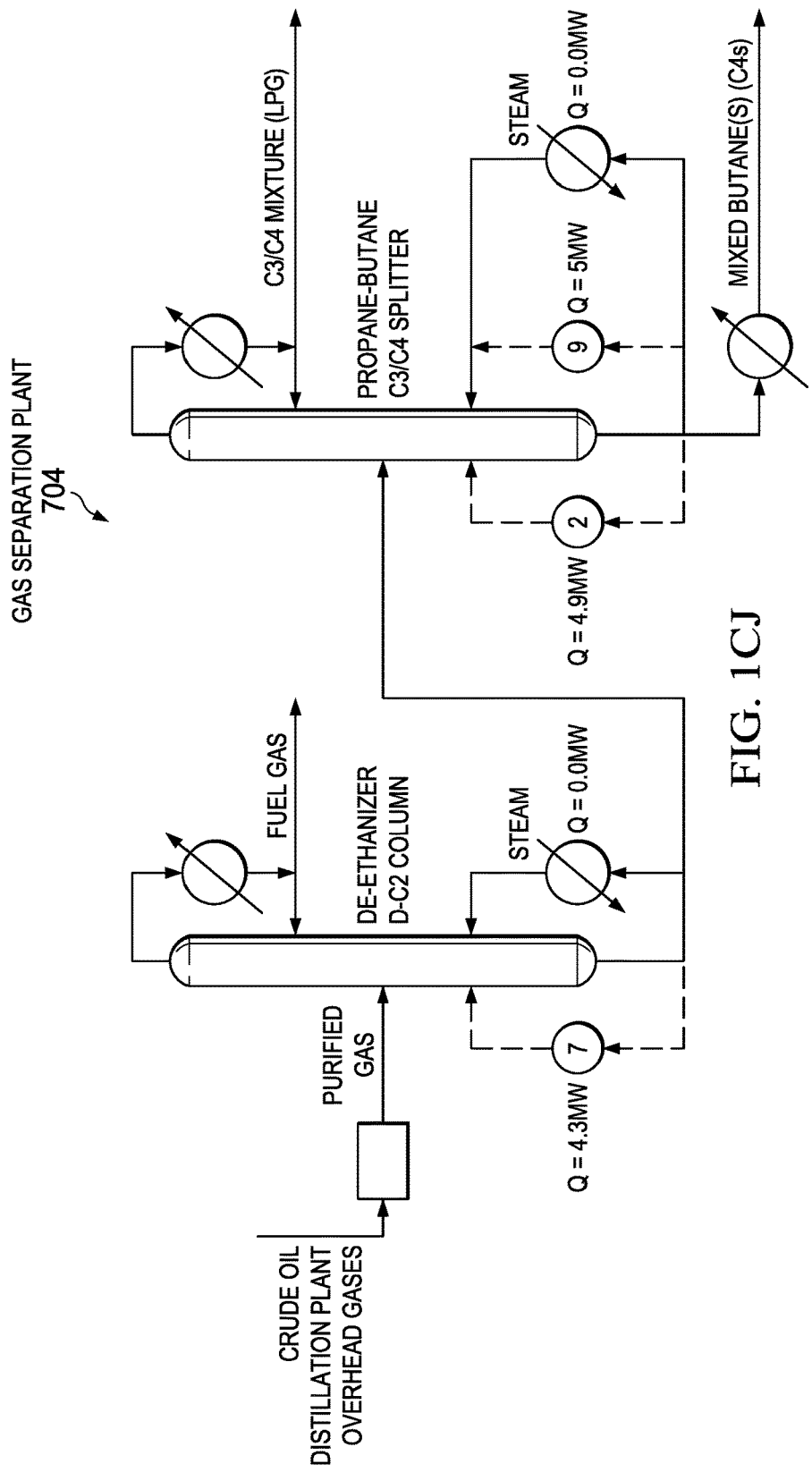
Figure 1C:
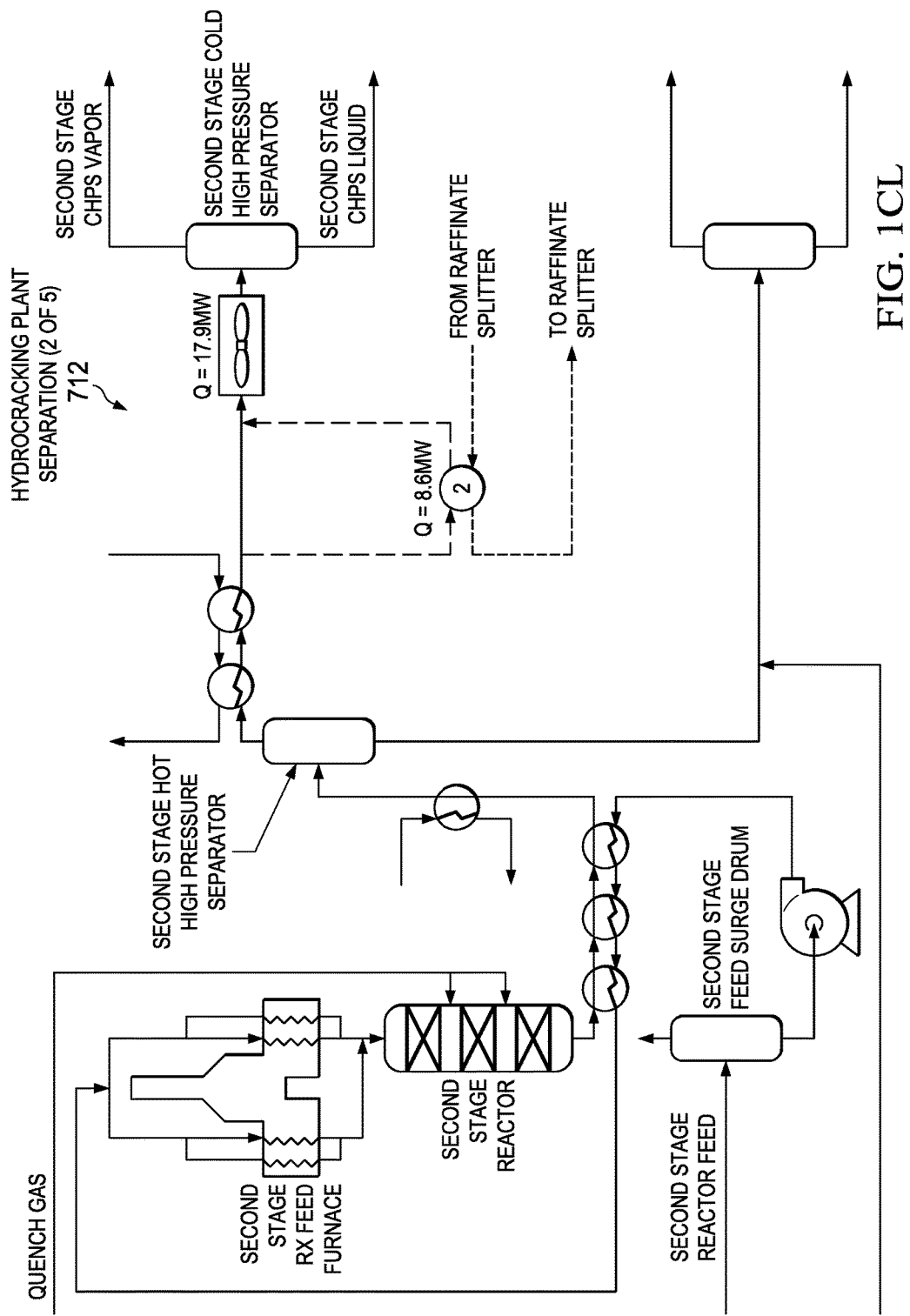
Figure 1C:
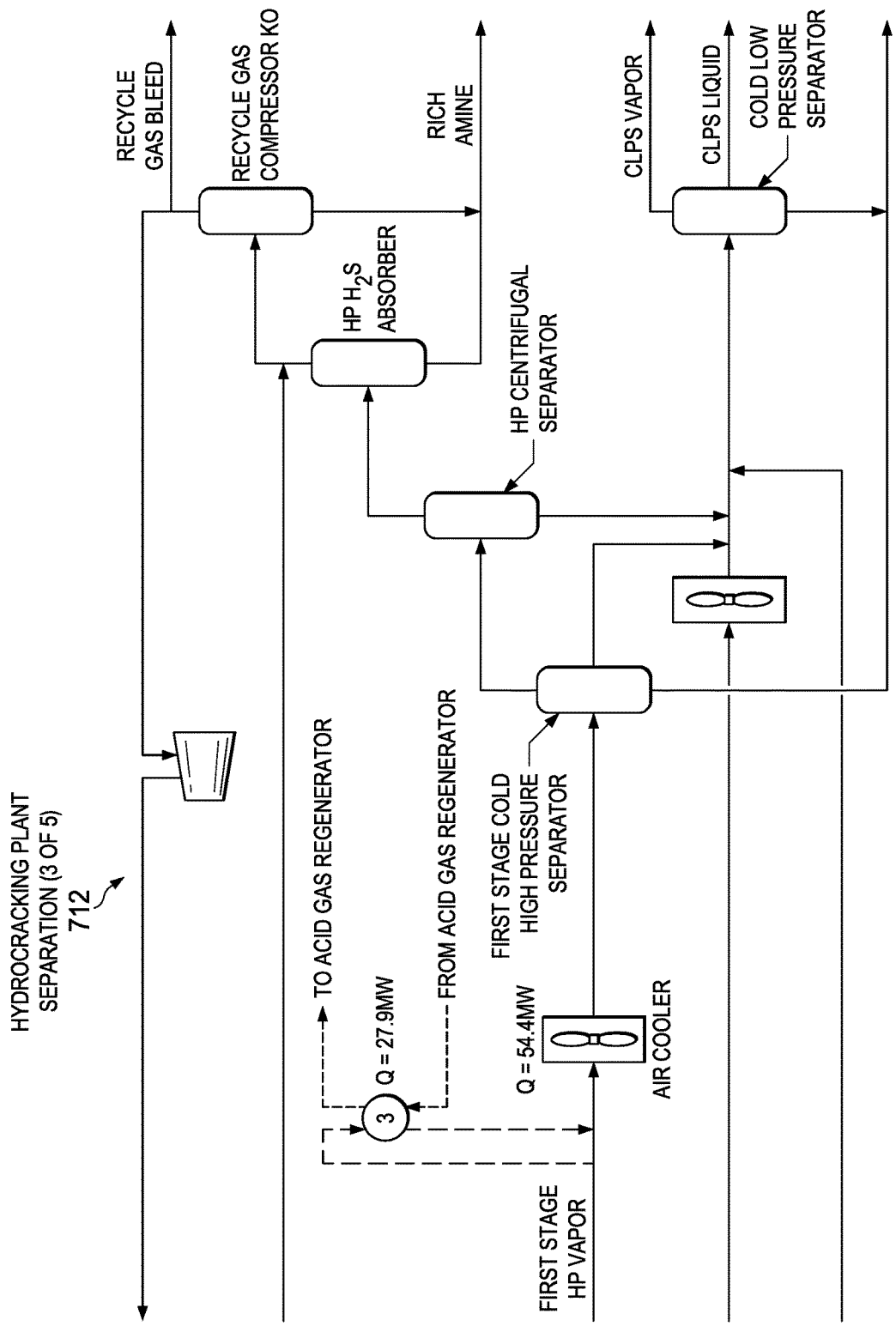
Figure 1C:
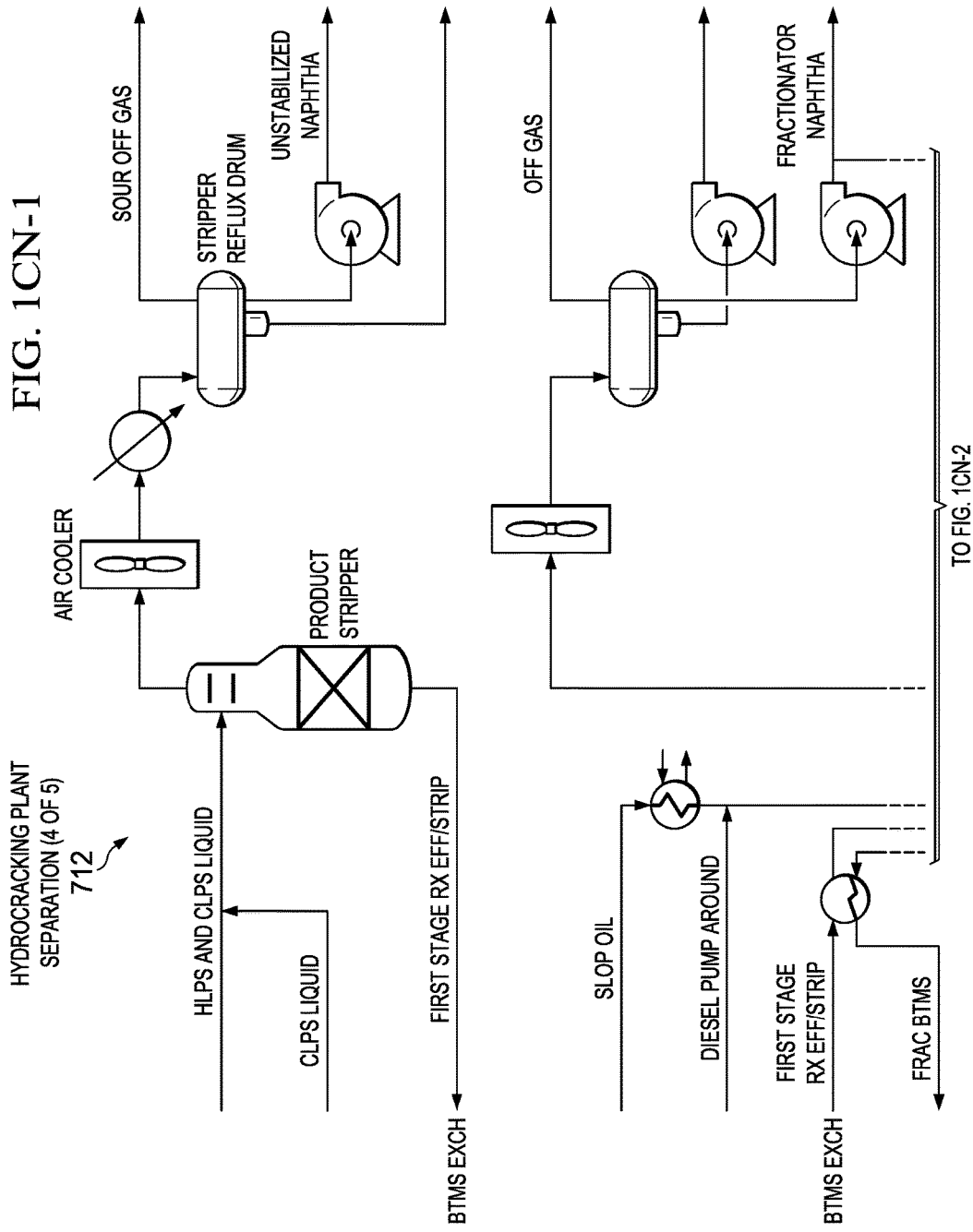
Figure 1C:
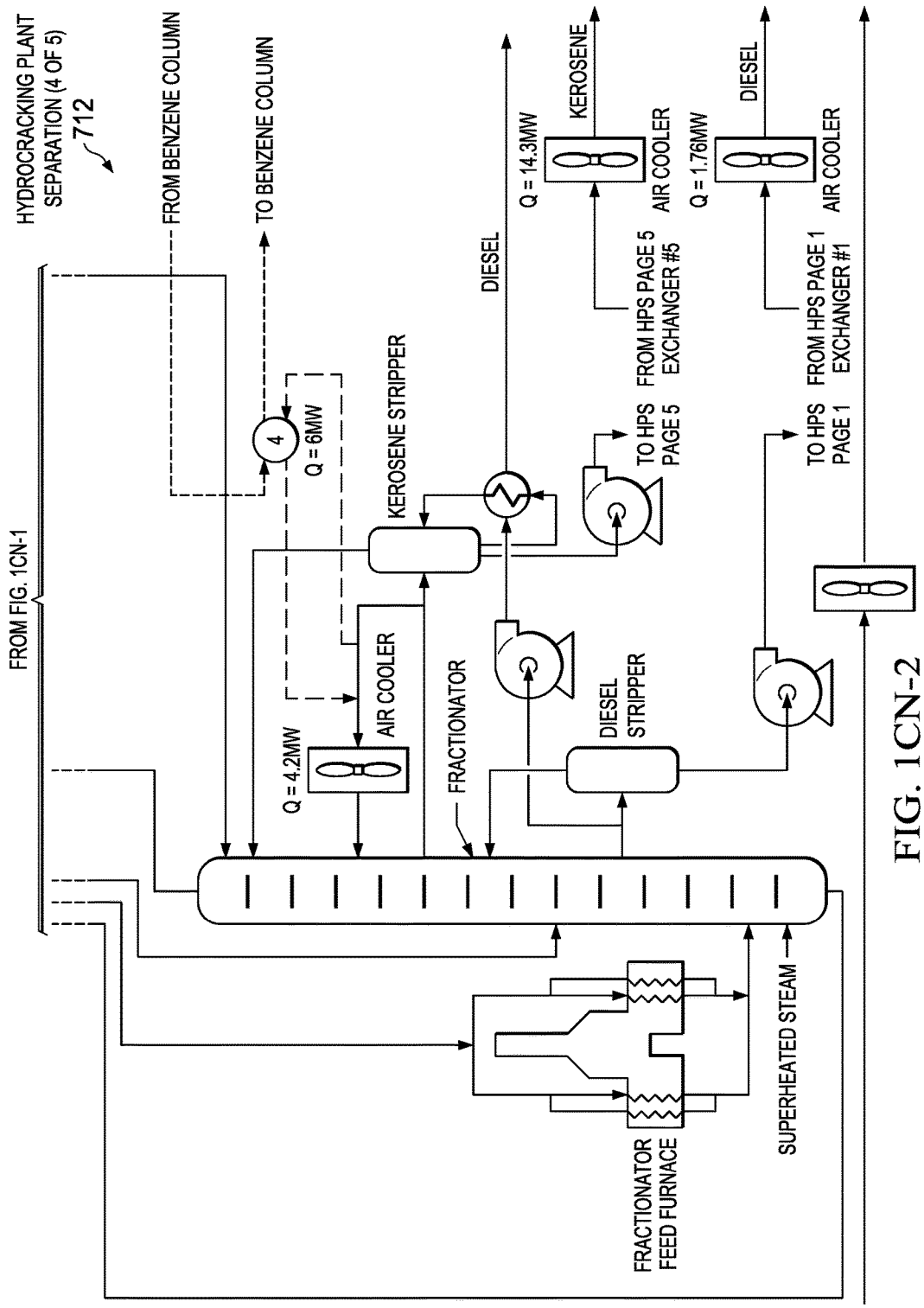
Figure 1C:
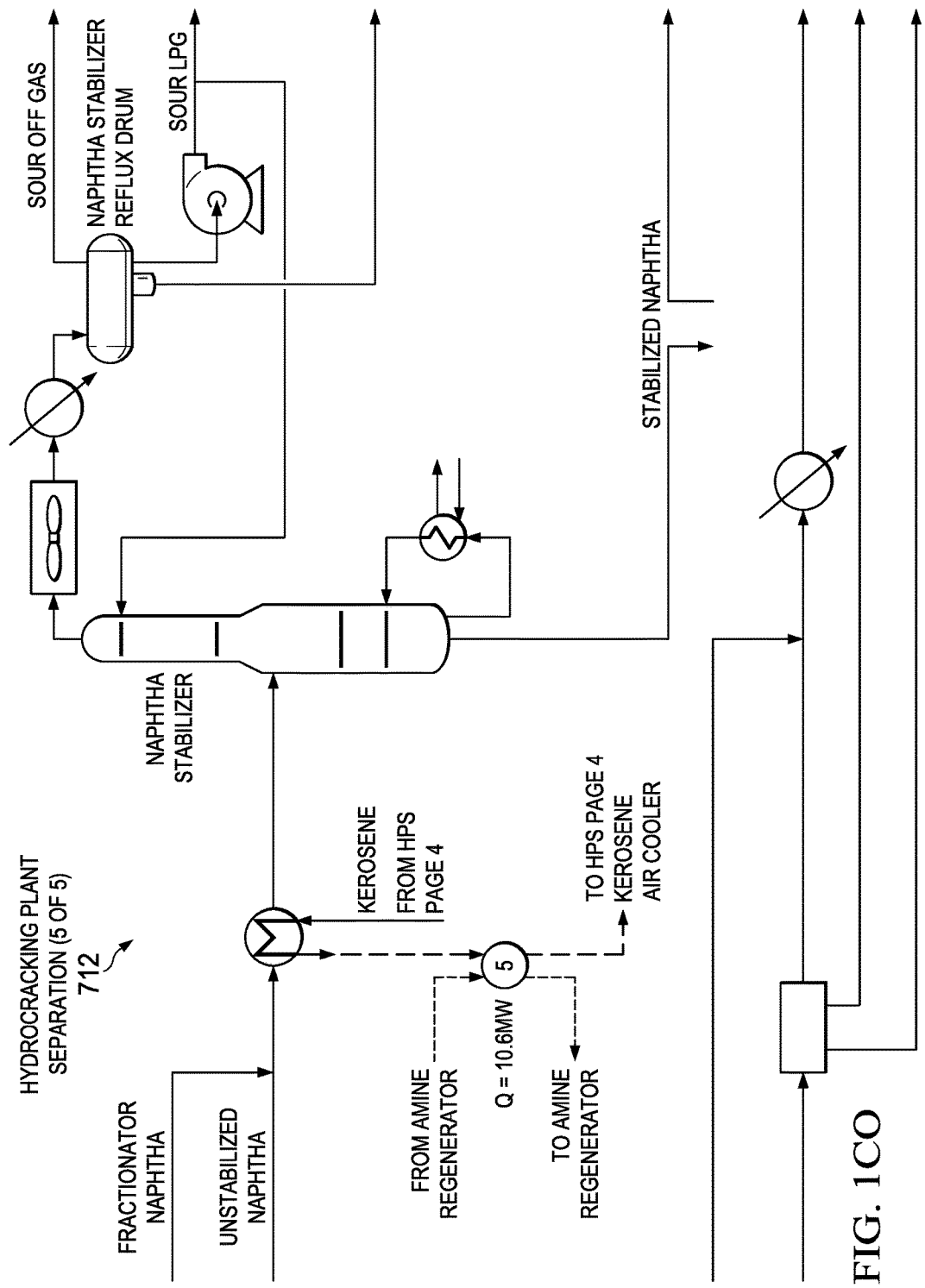
Figure 1C:
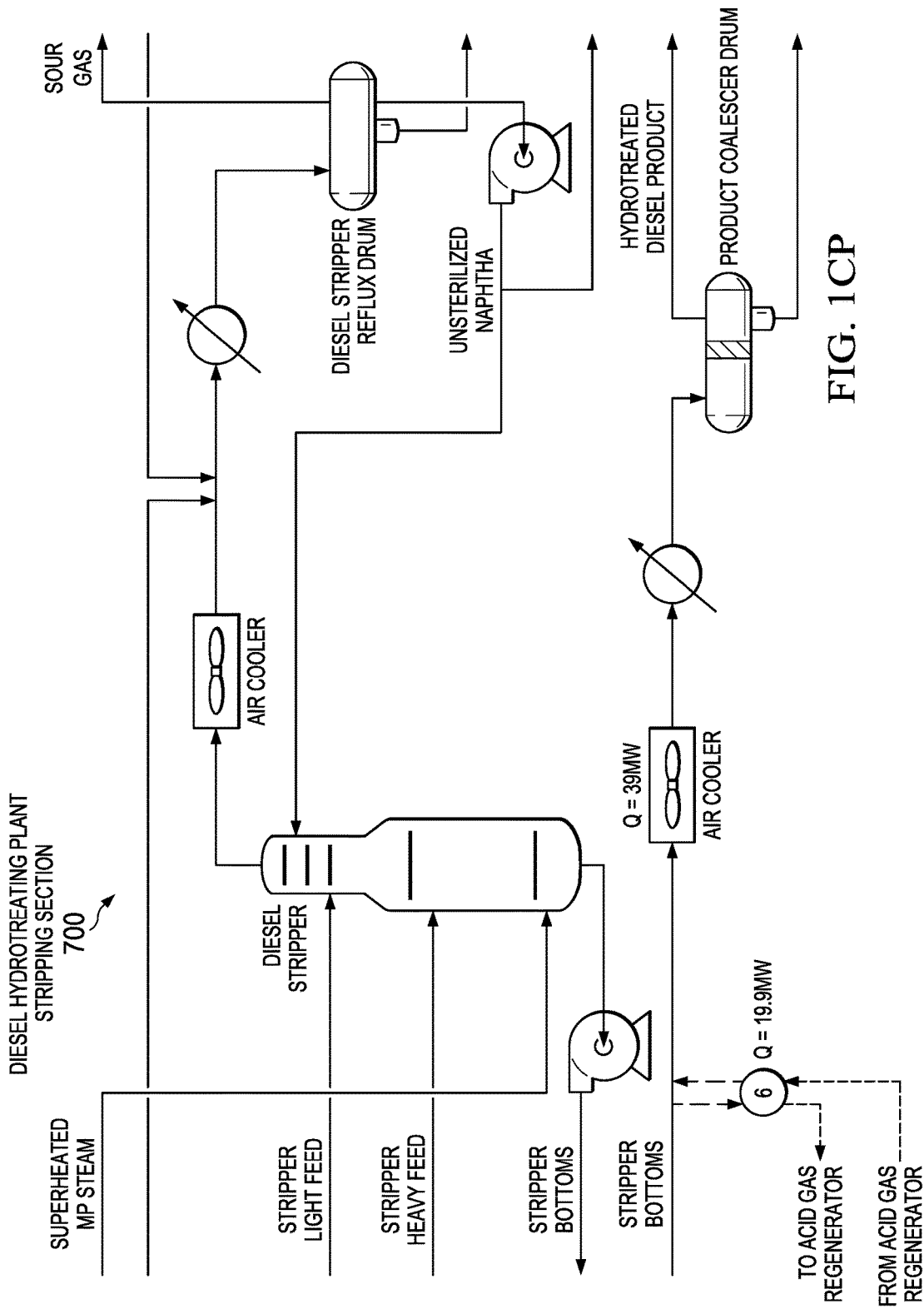
Figure 1C:
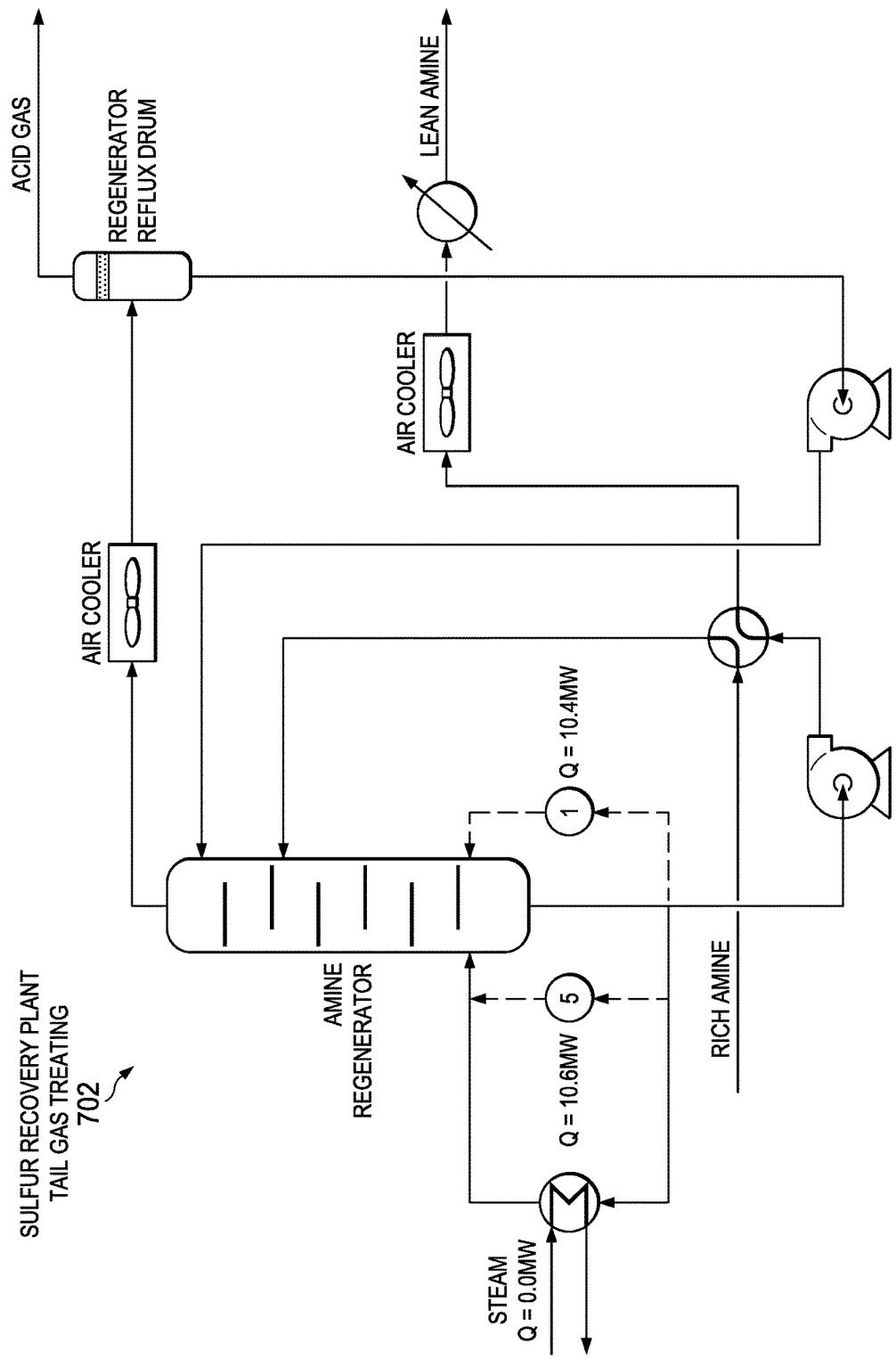
Figure 1C:
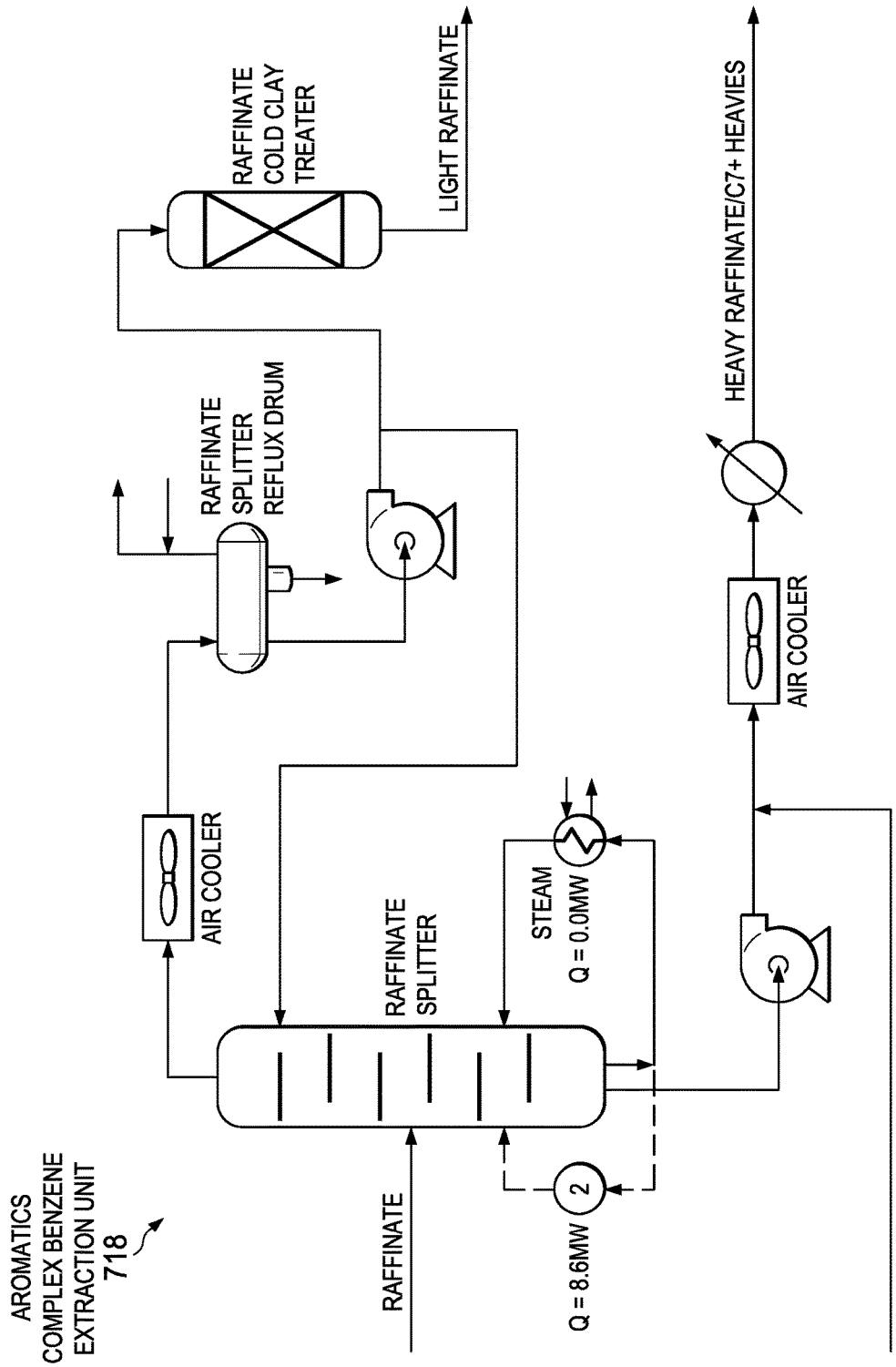
Figure 1C:
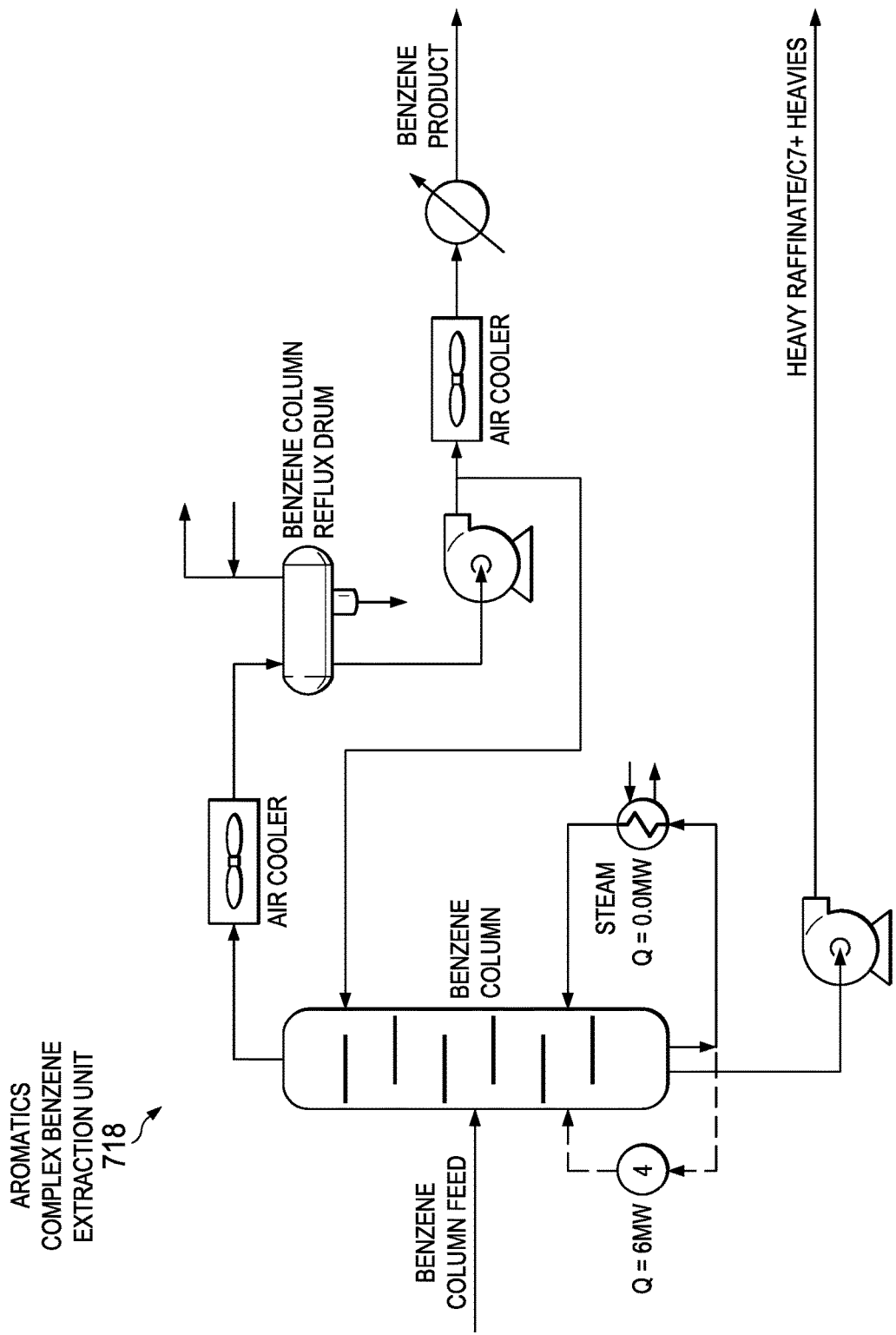
Figure 1C:
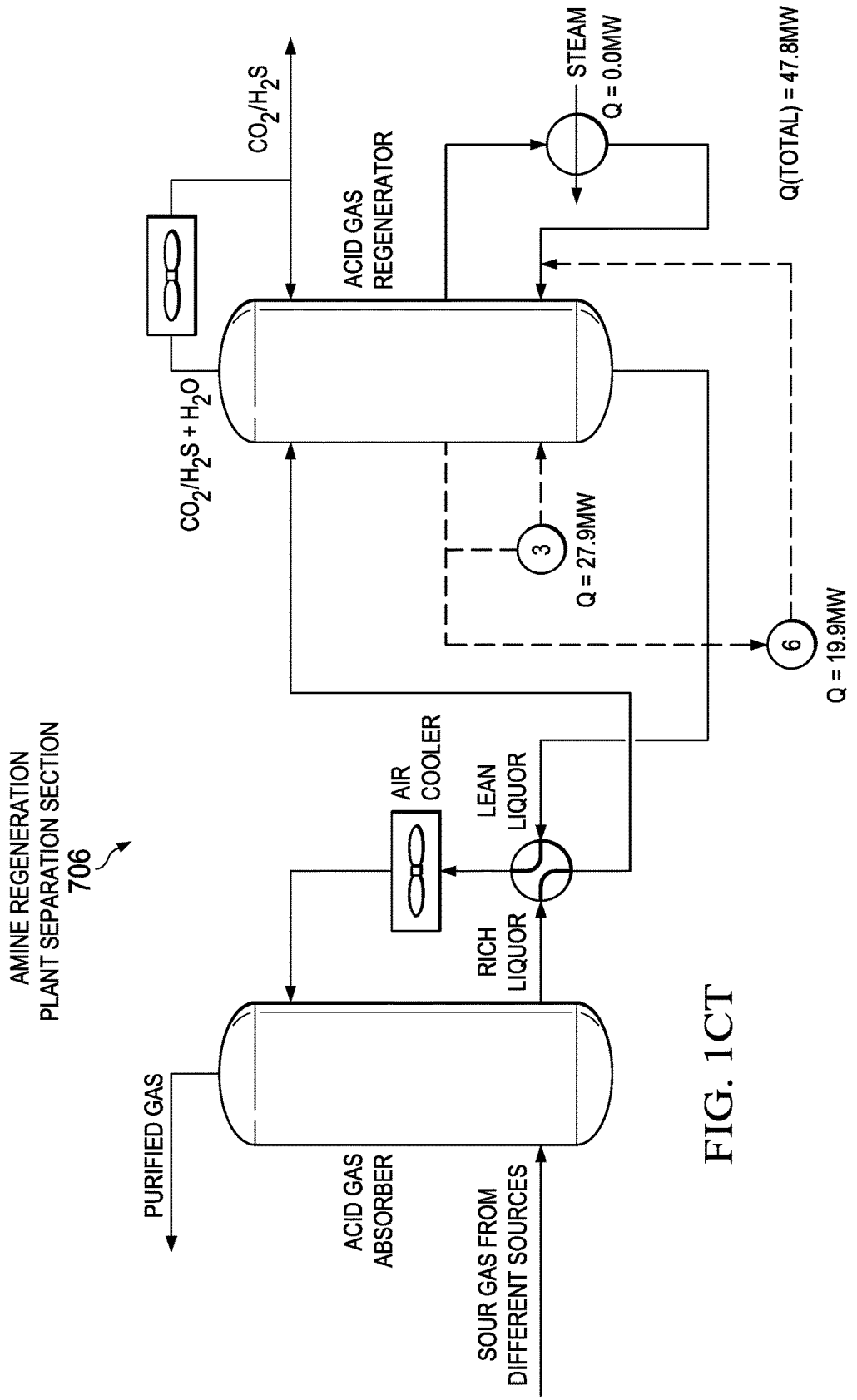
Figure 1C:
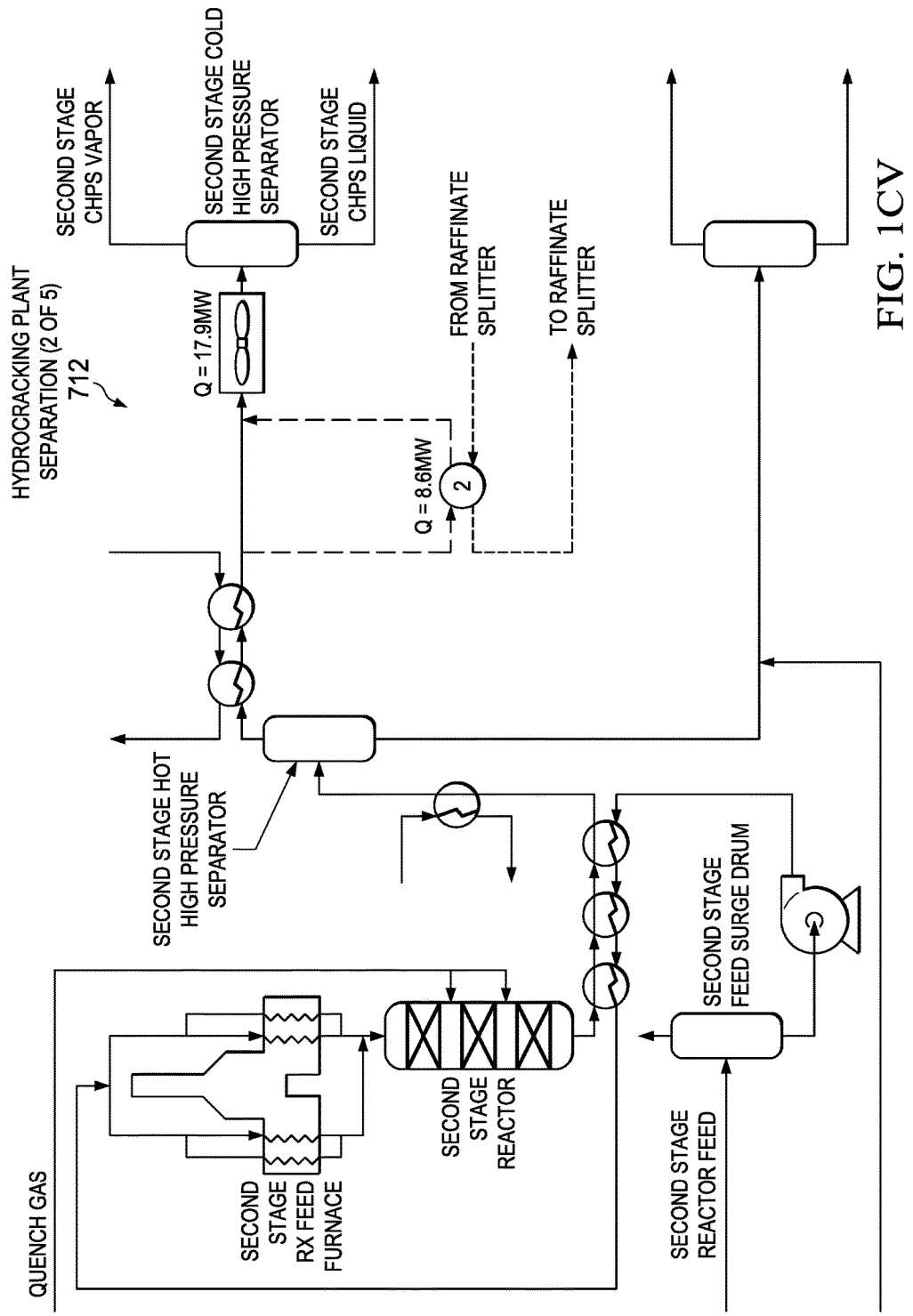
Figure 1C:
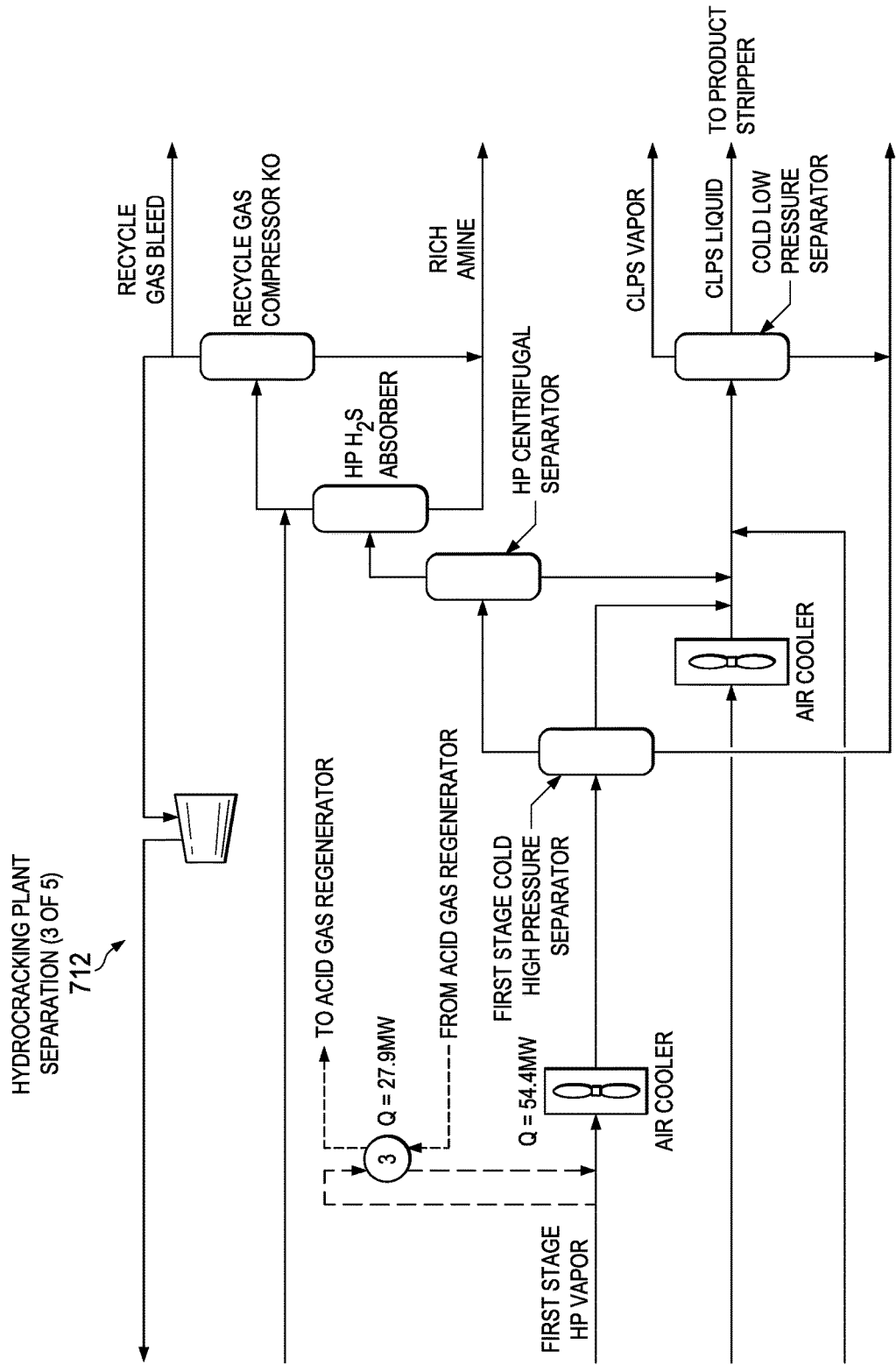
Figure 1C:
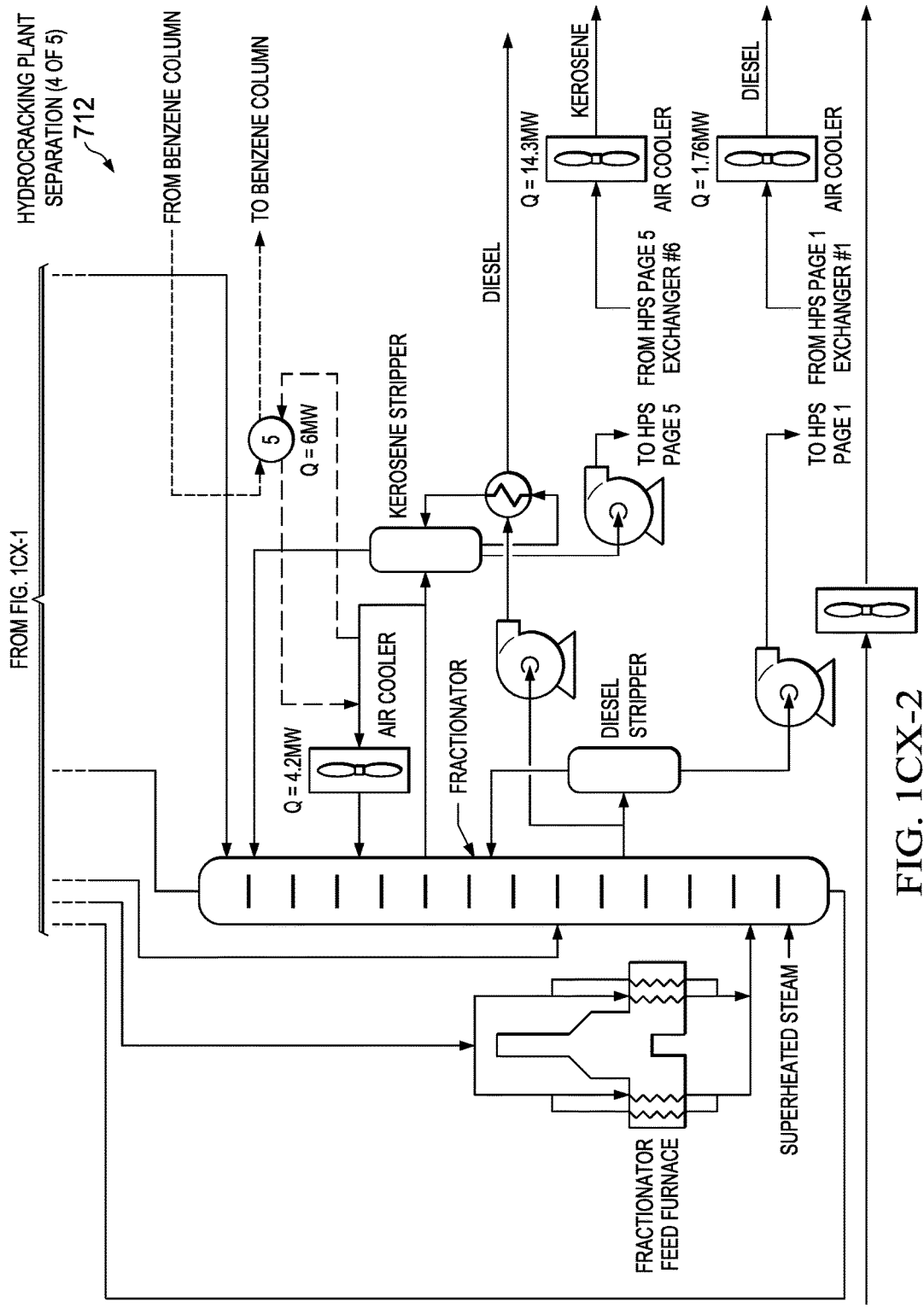
Figure 1C:
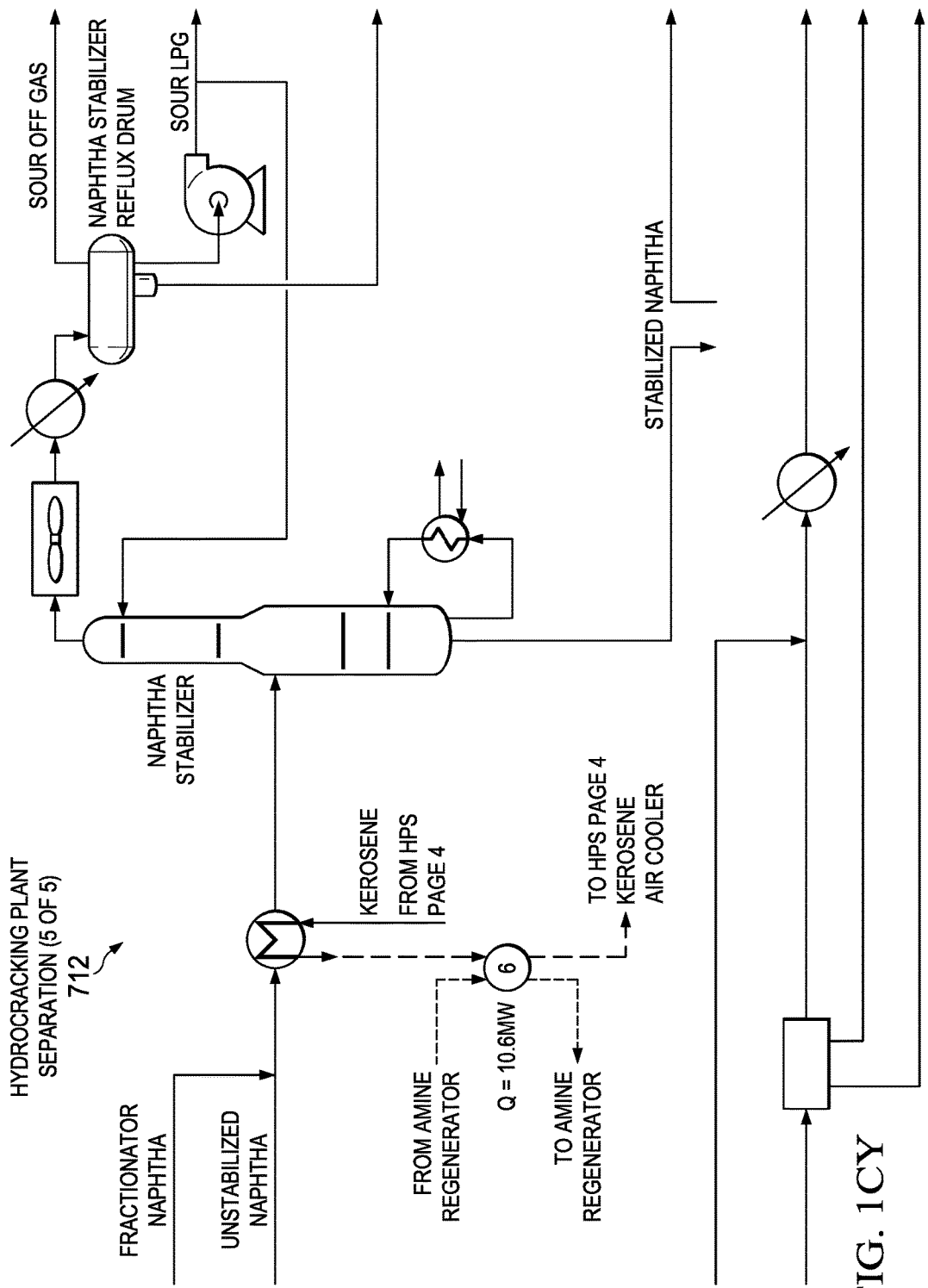
Figure 1C:
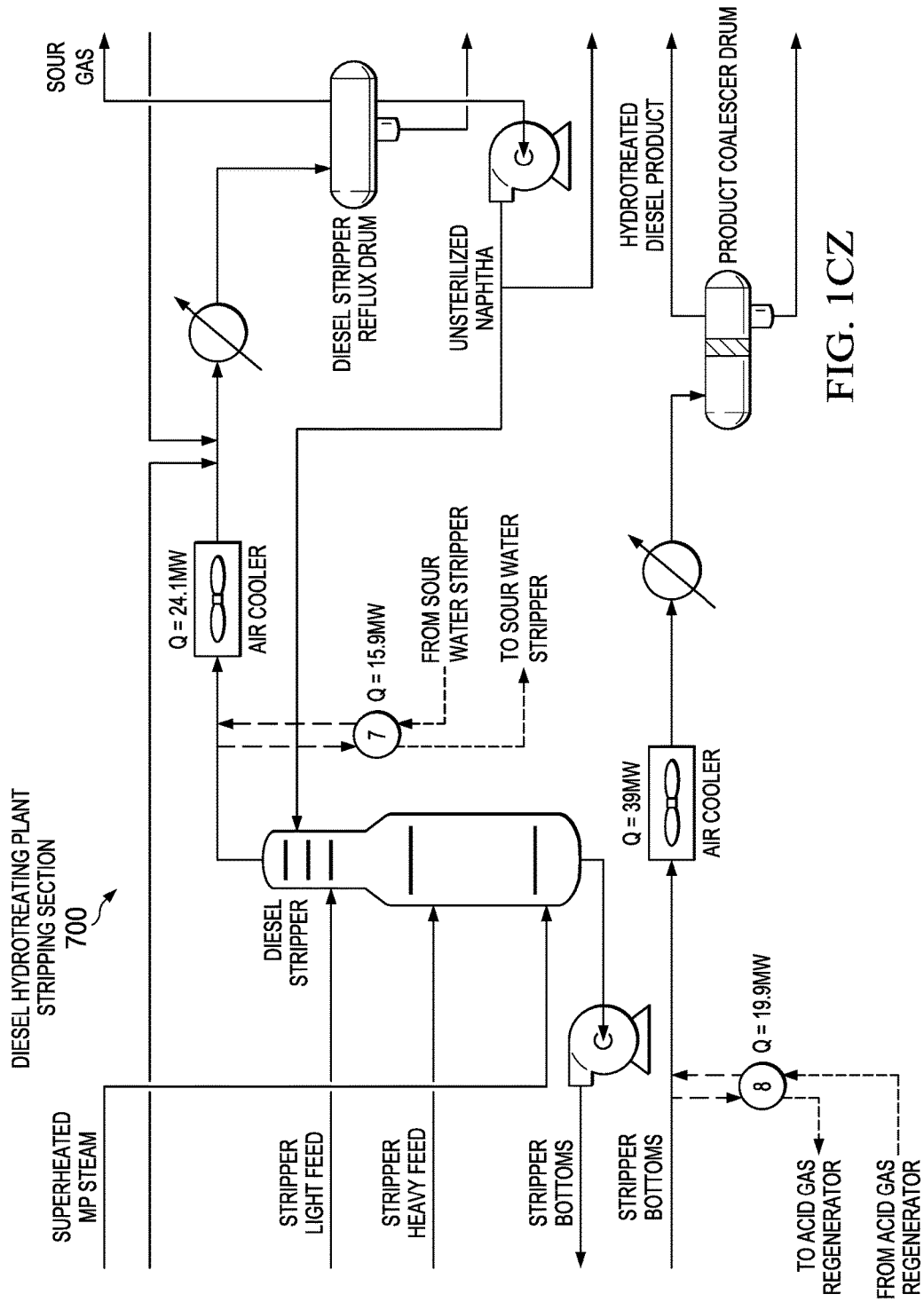
Figure 1D:
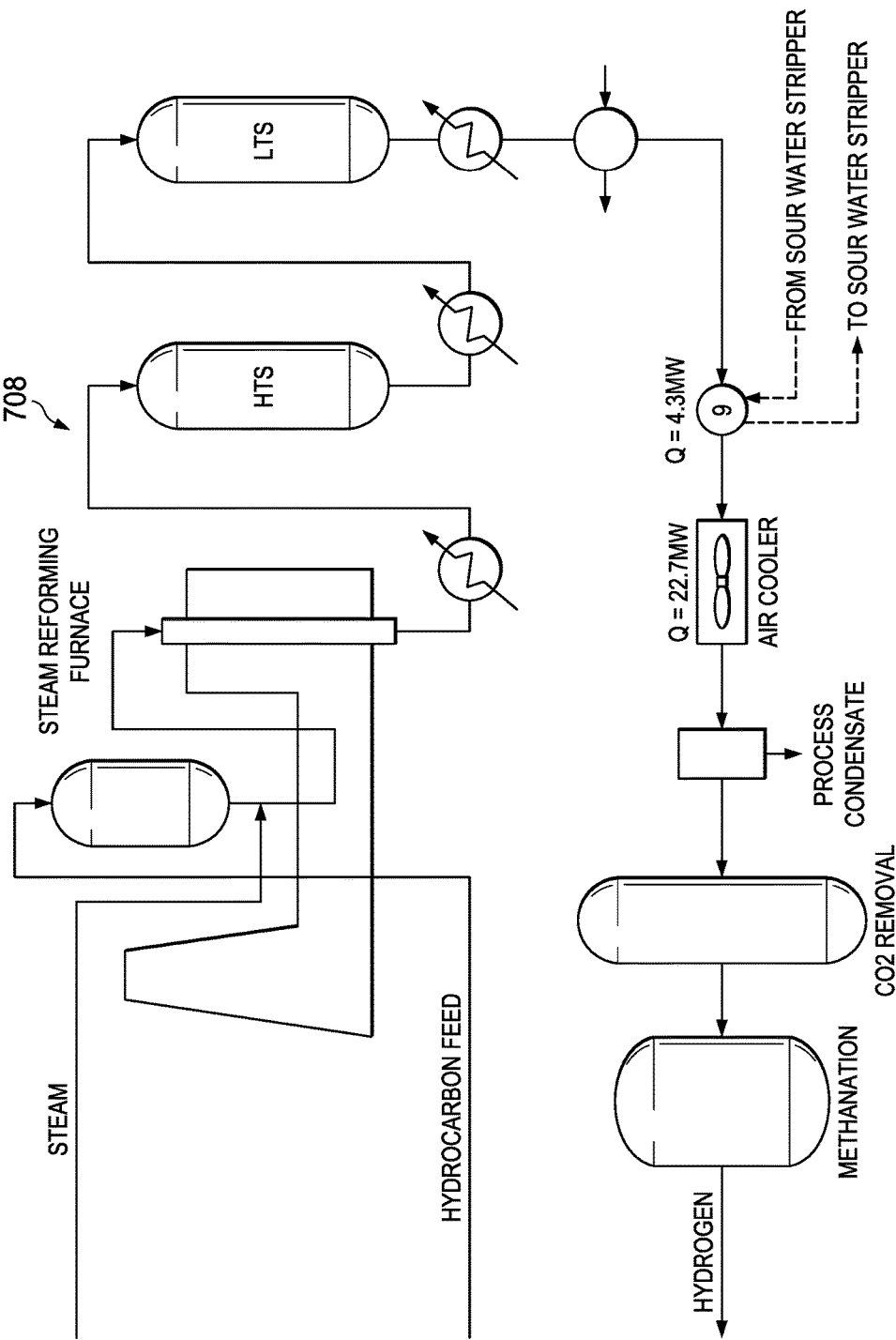
Figure 1D:
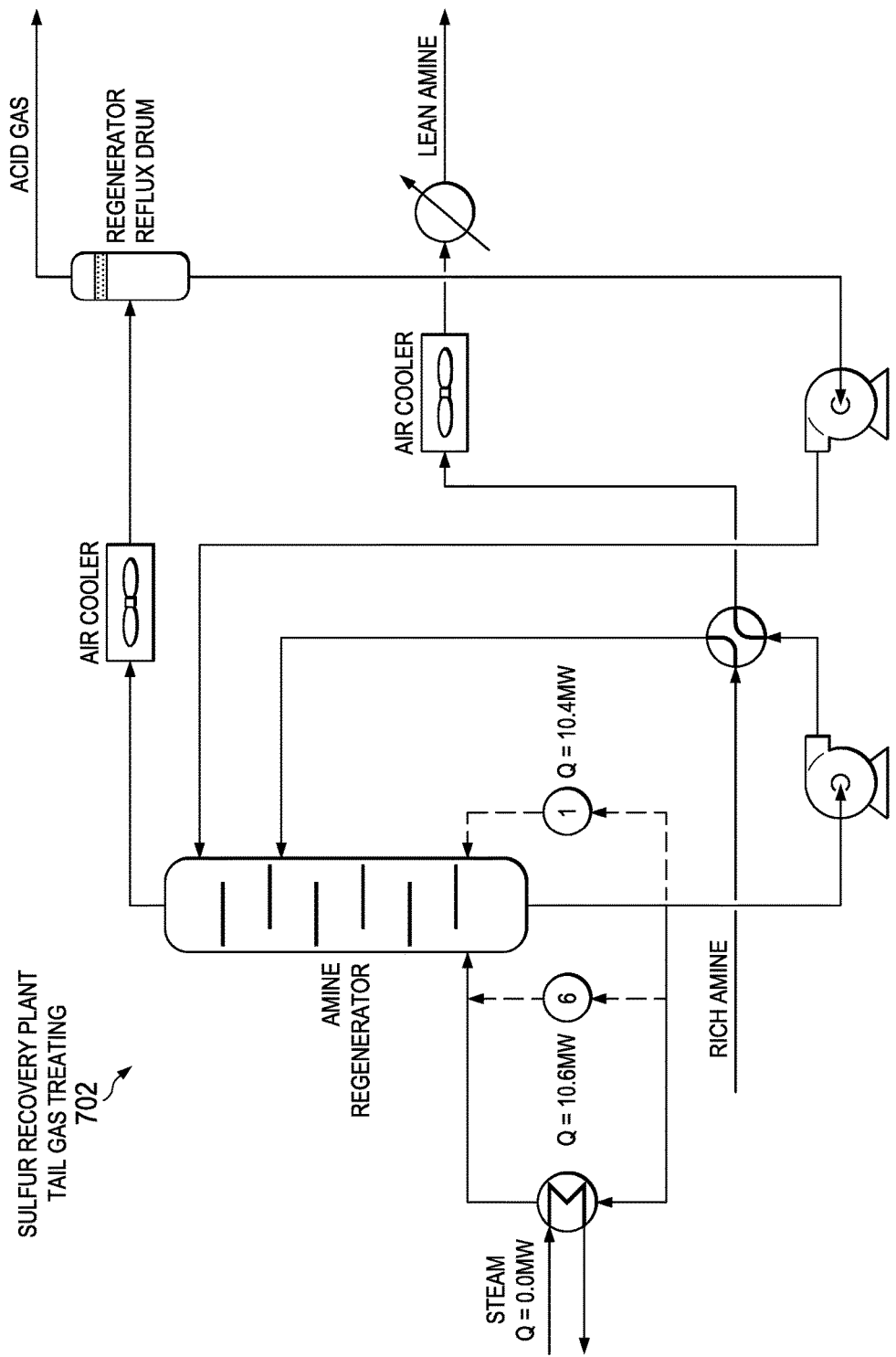
Figure 1D:
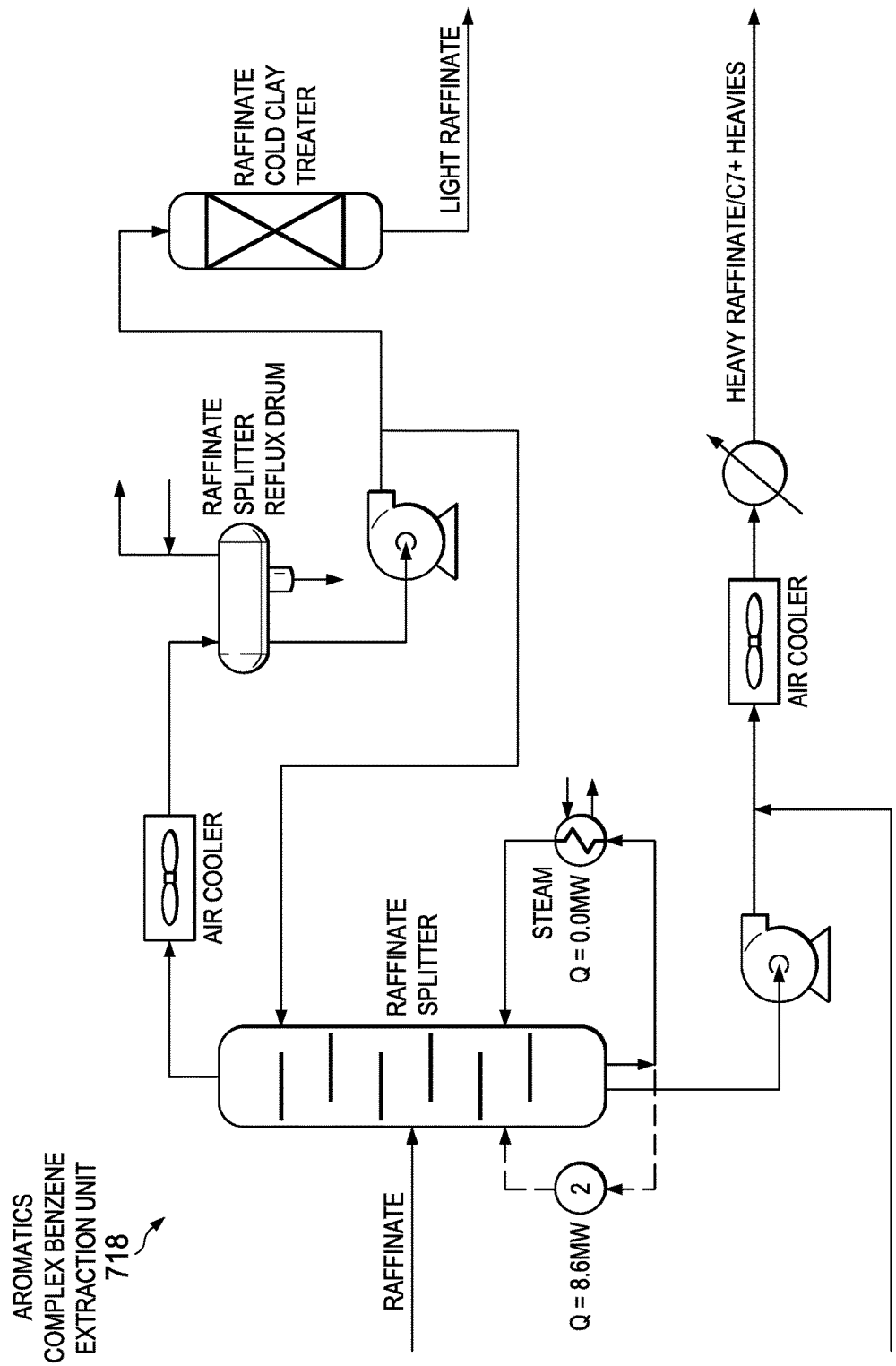
Figure 1D:
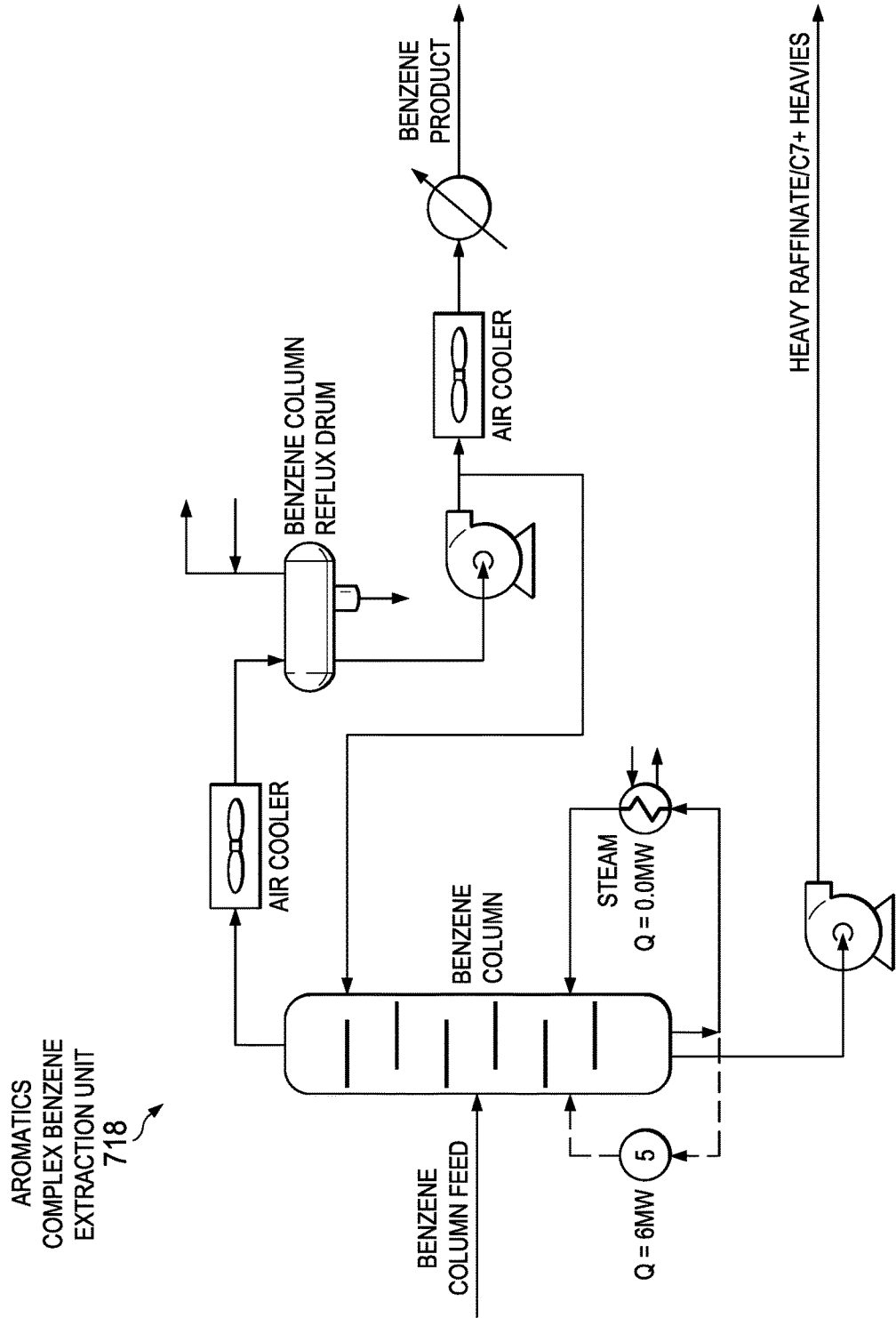
Figure 1D:
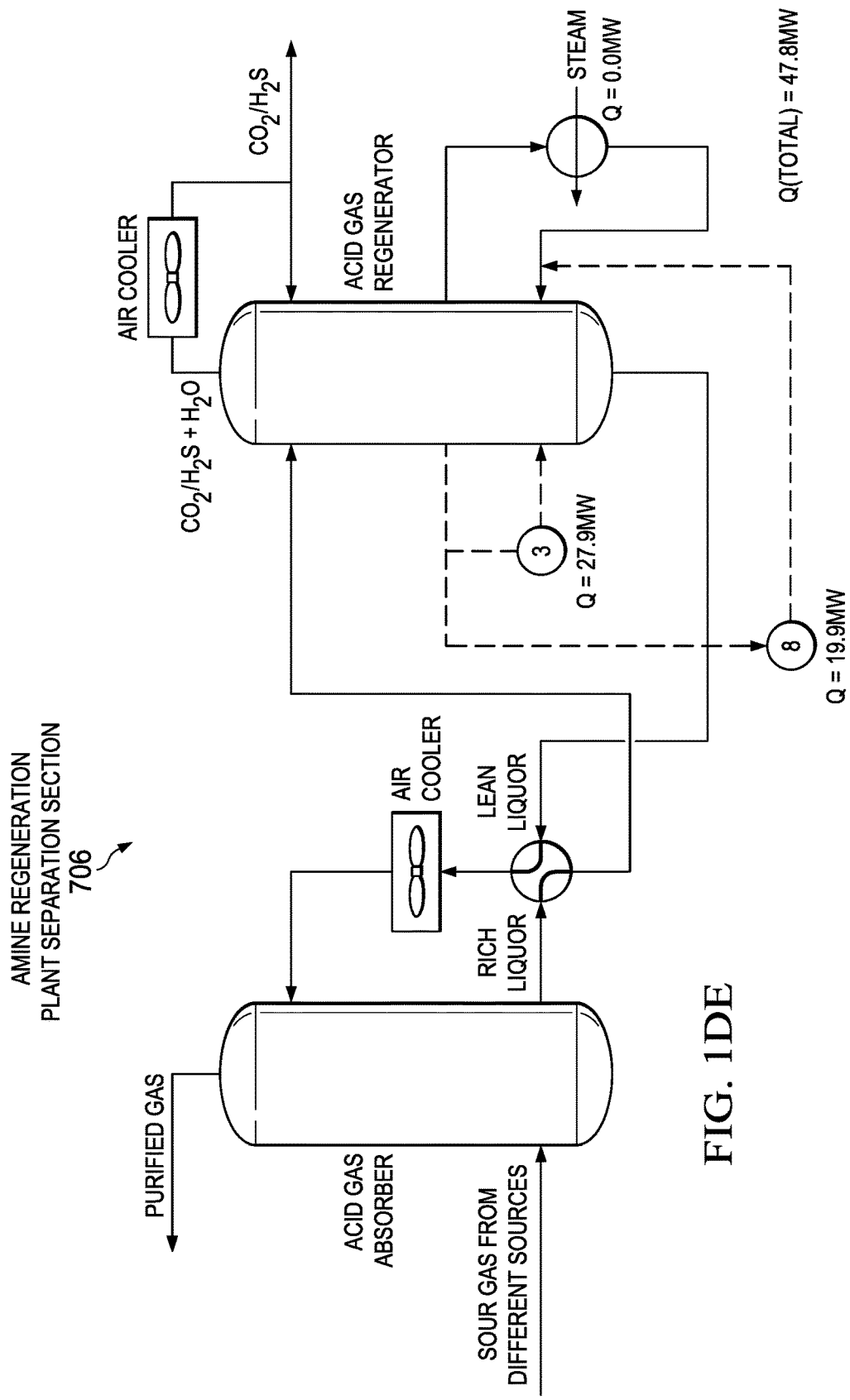
Figure 1D:
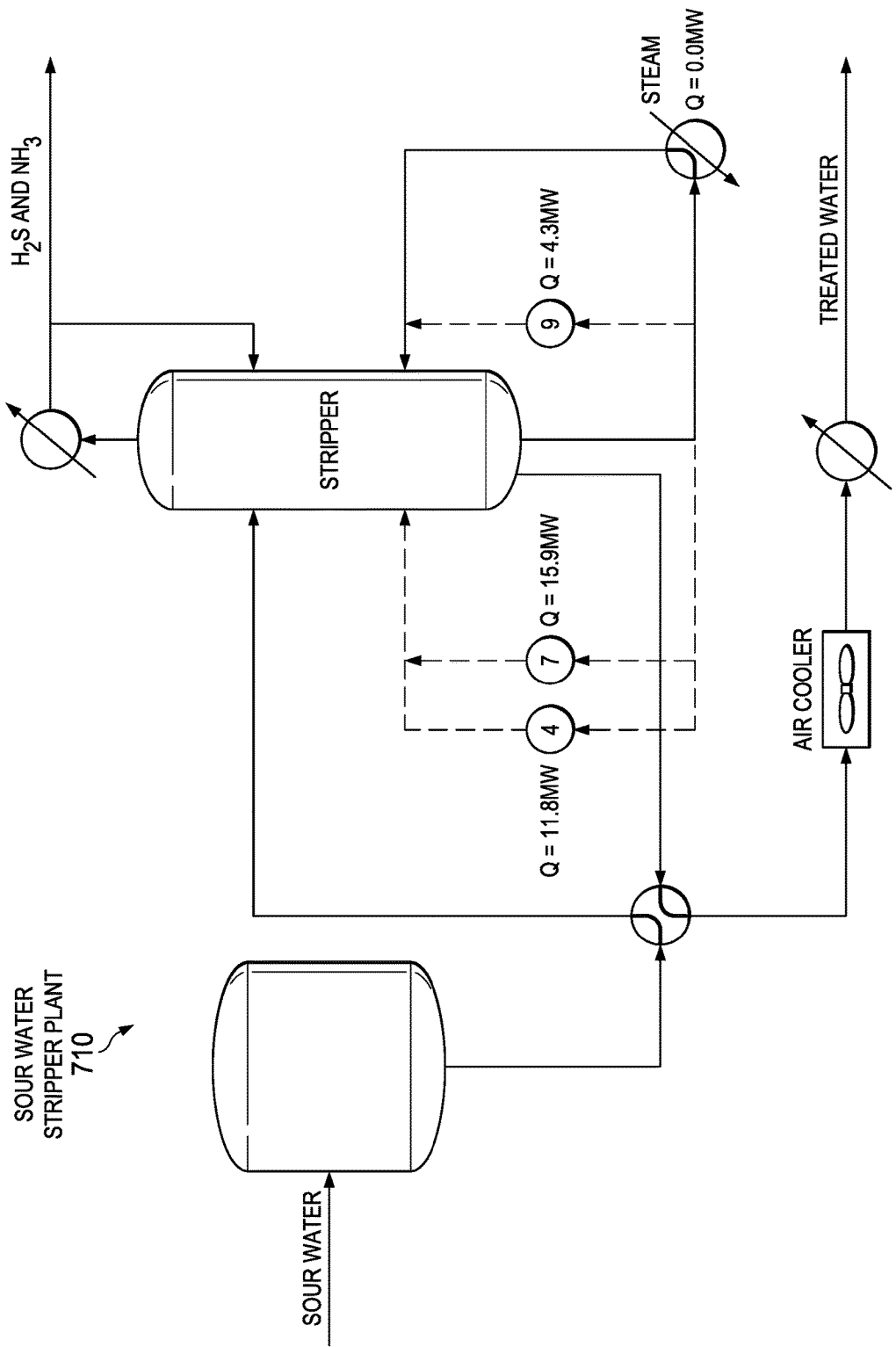
Figure 1D:
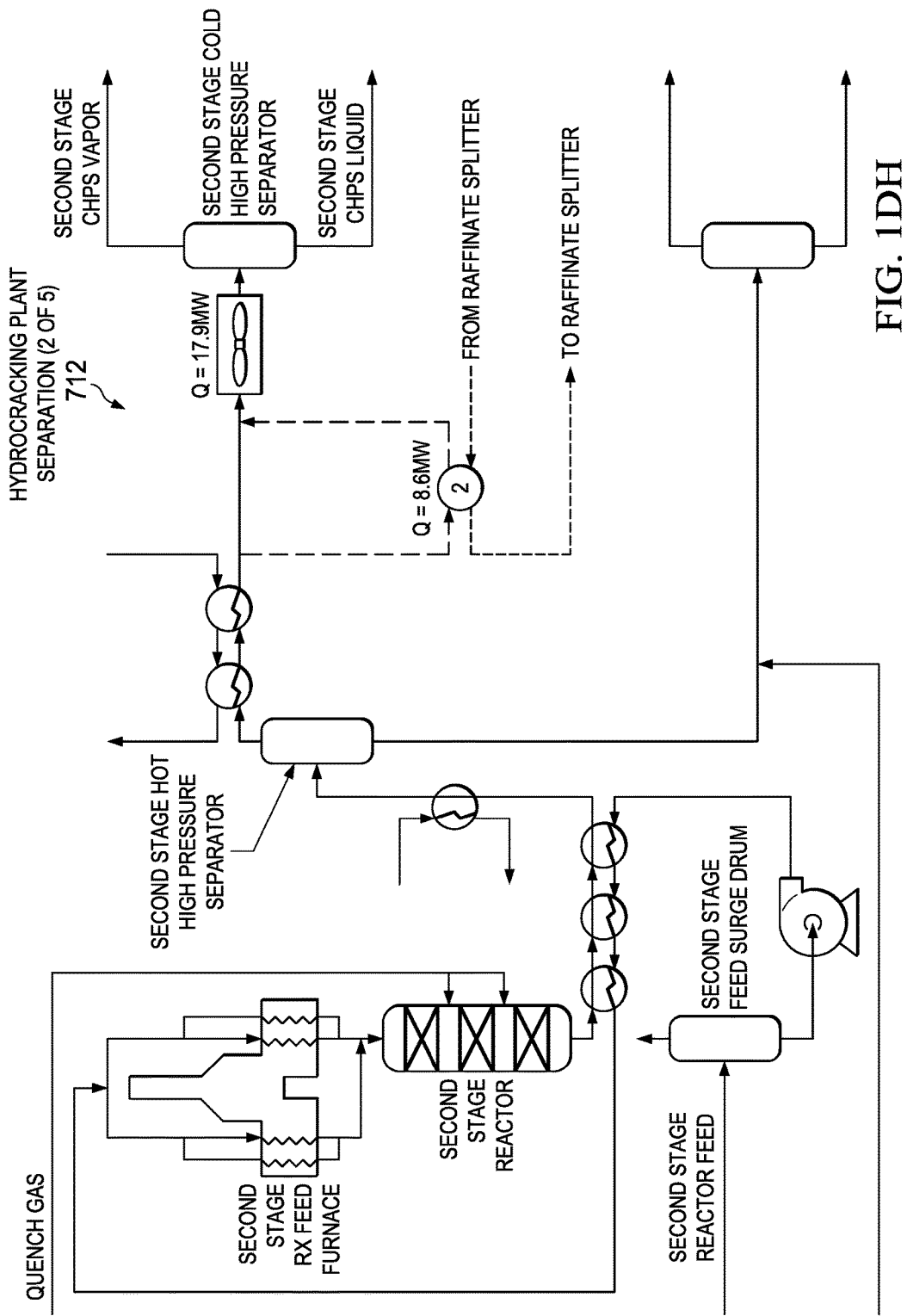
Figure 1D:
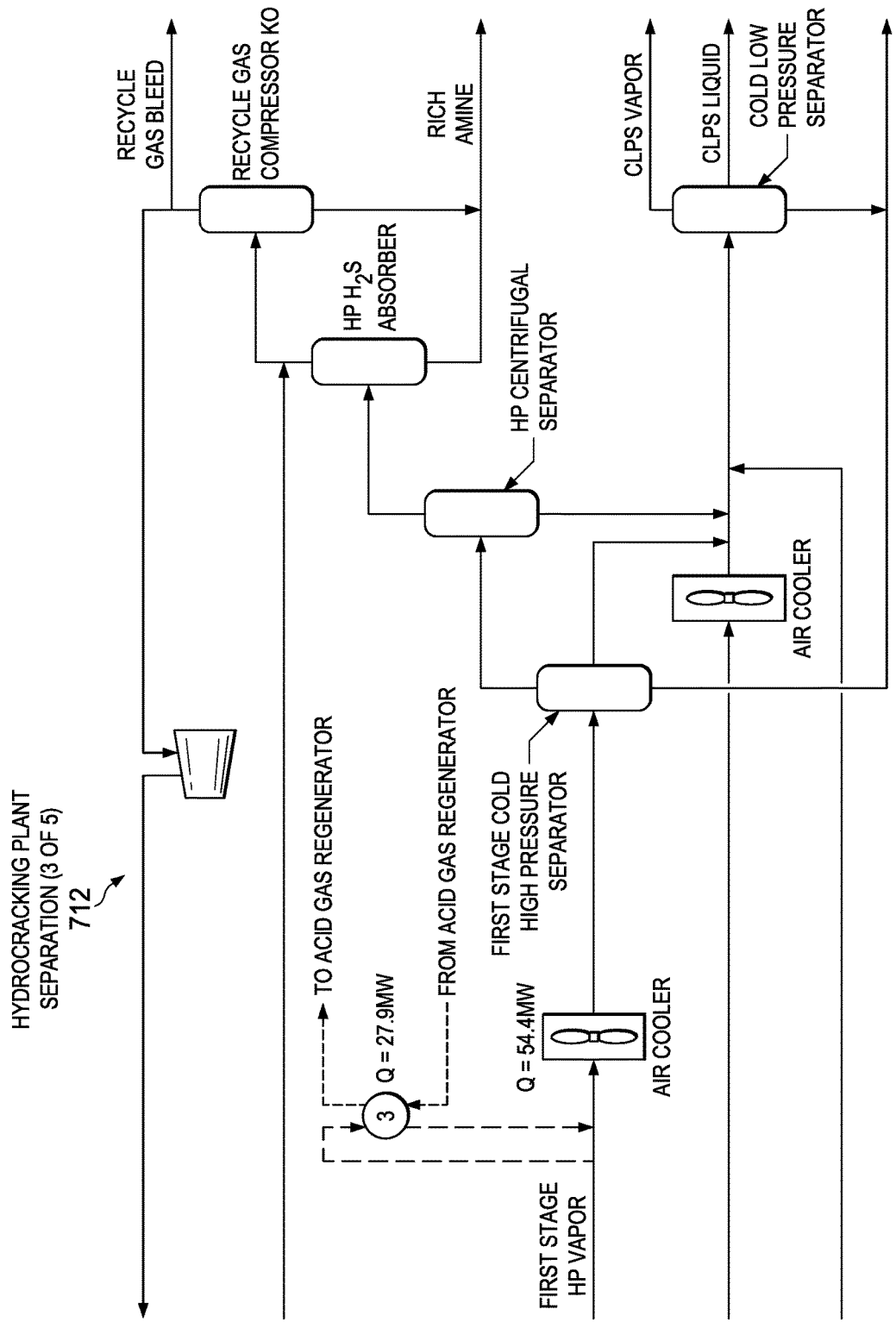
Figure 1D:
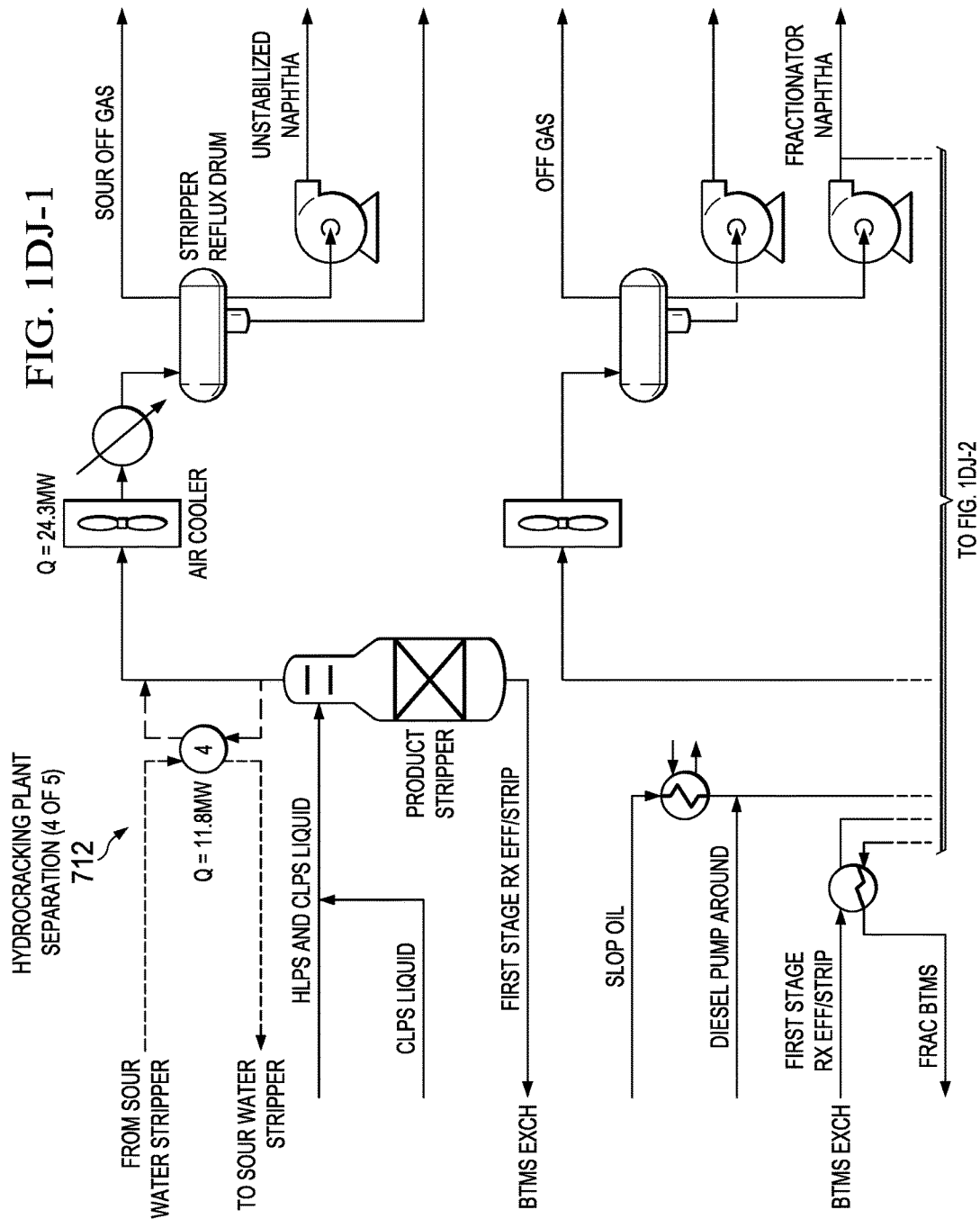
Figure 1D:
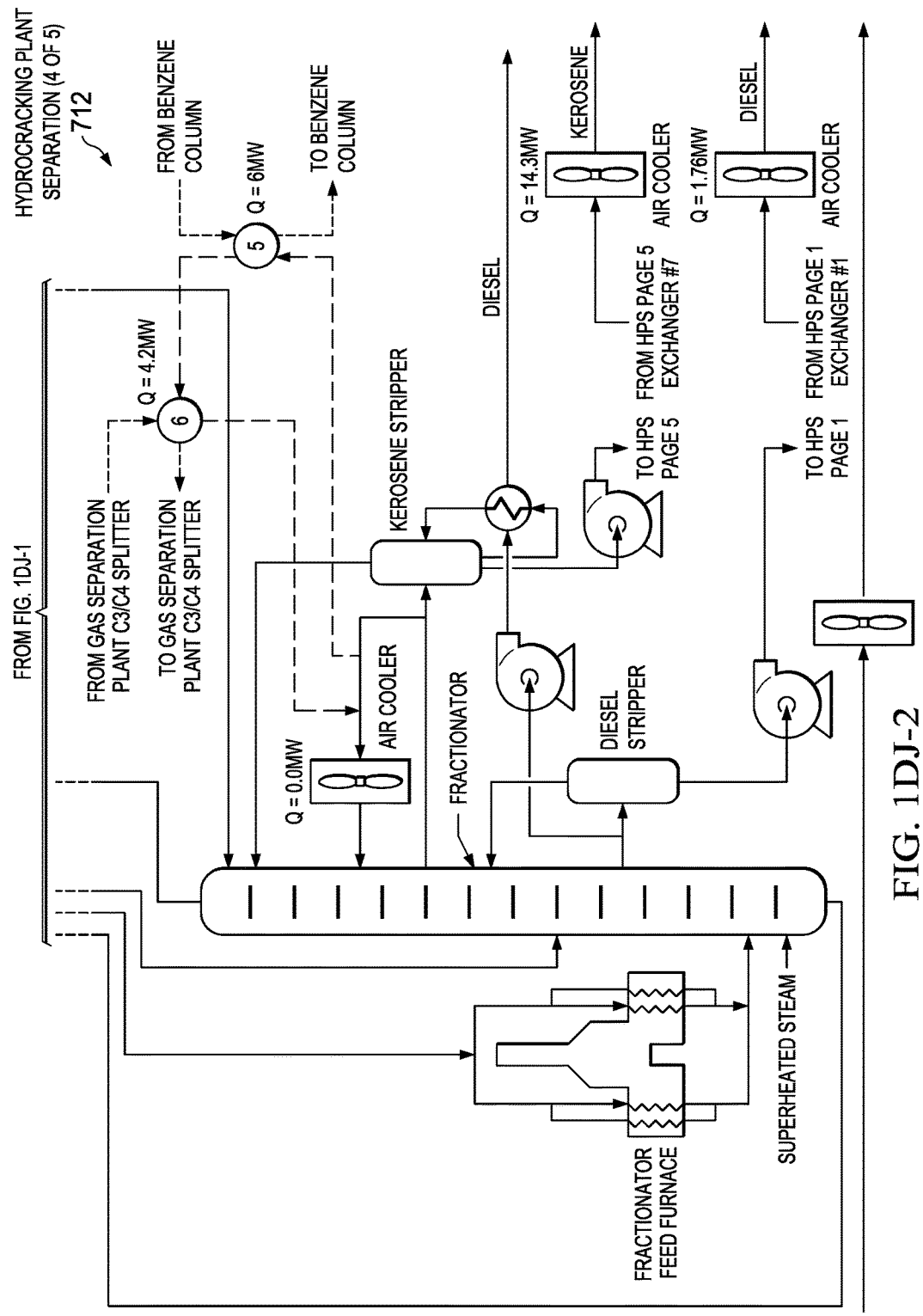
Figure 1D:
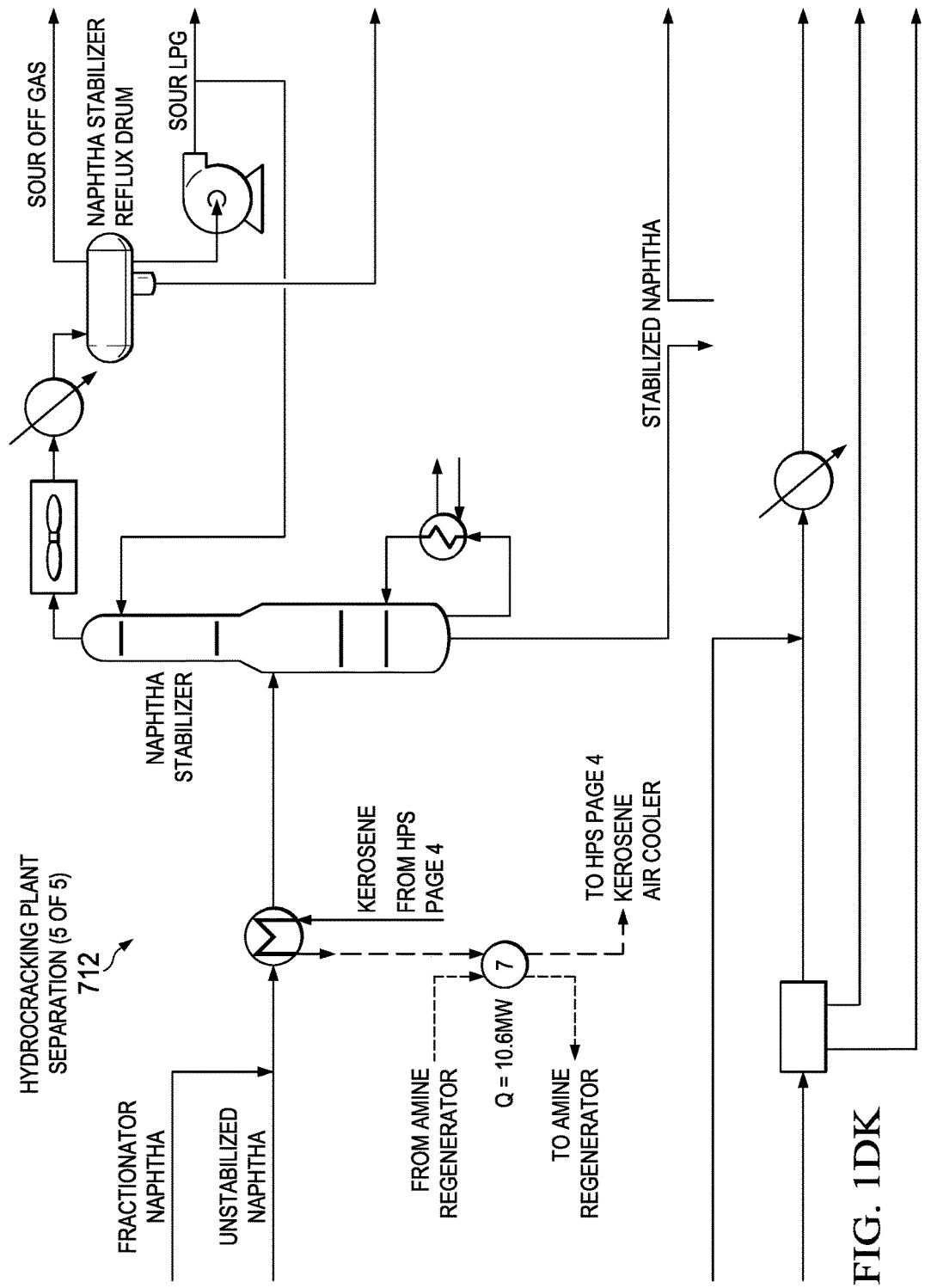
Figure 1D:
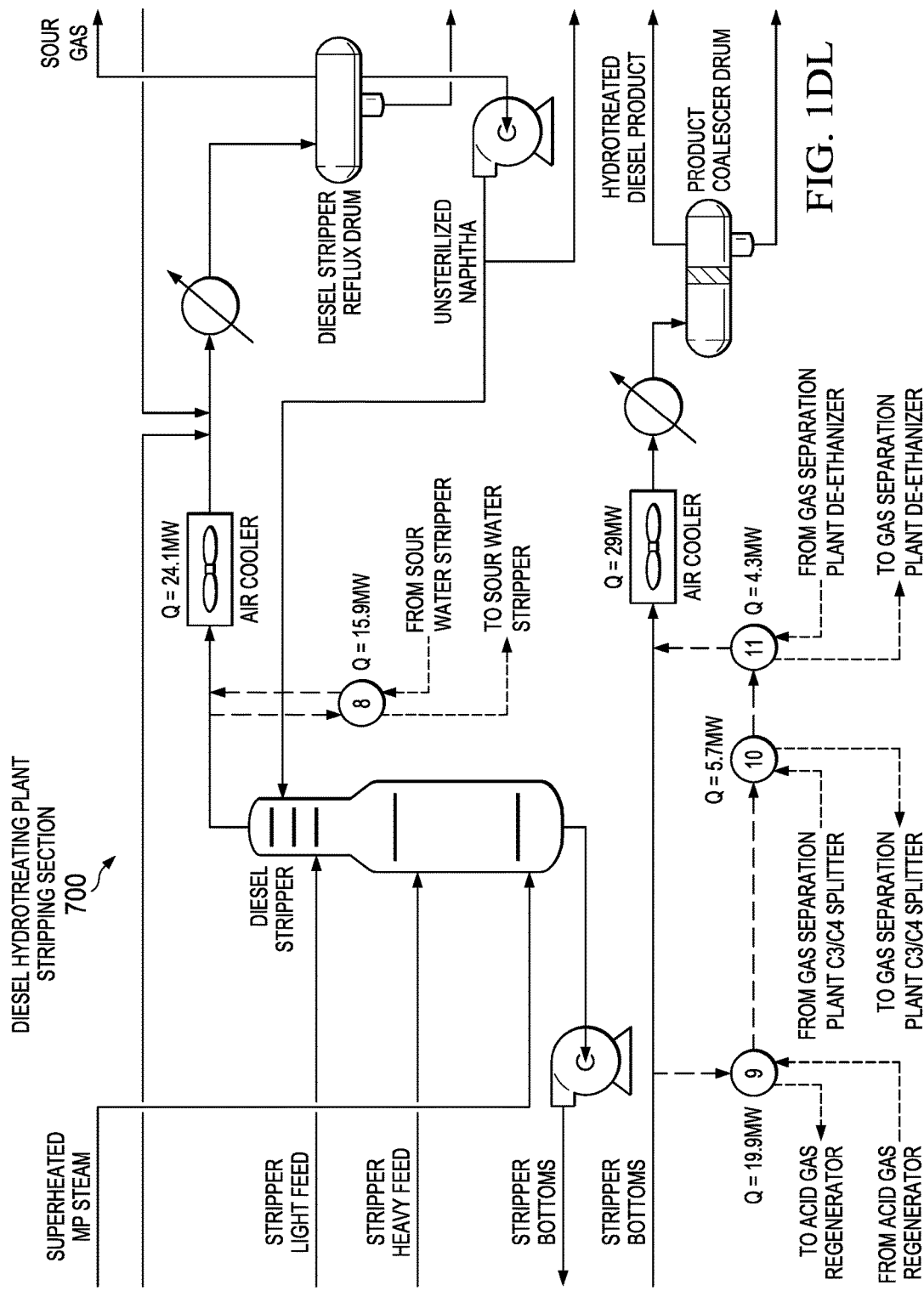
Figure 1D:
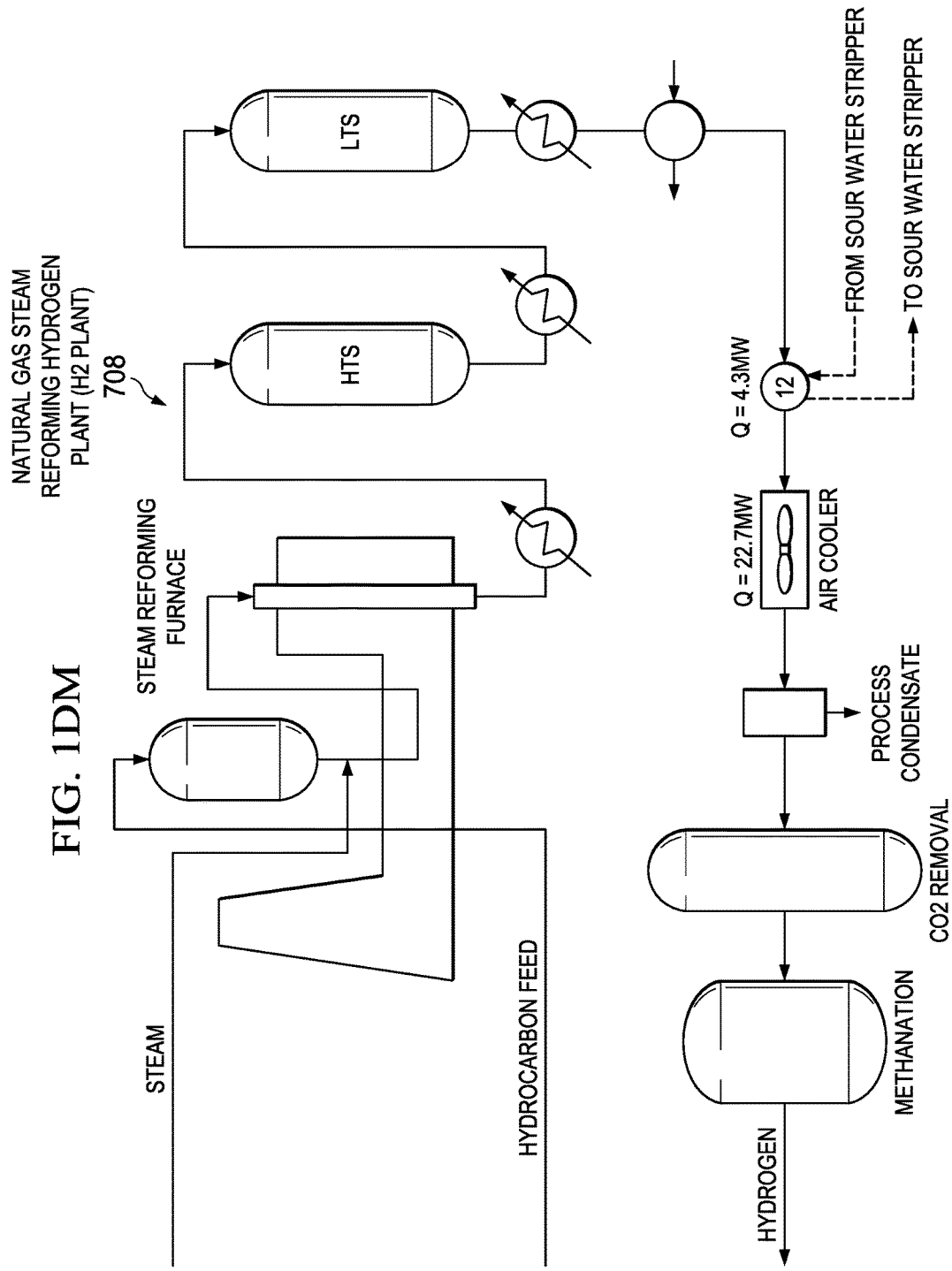
Figure 1D:
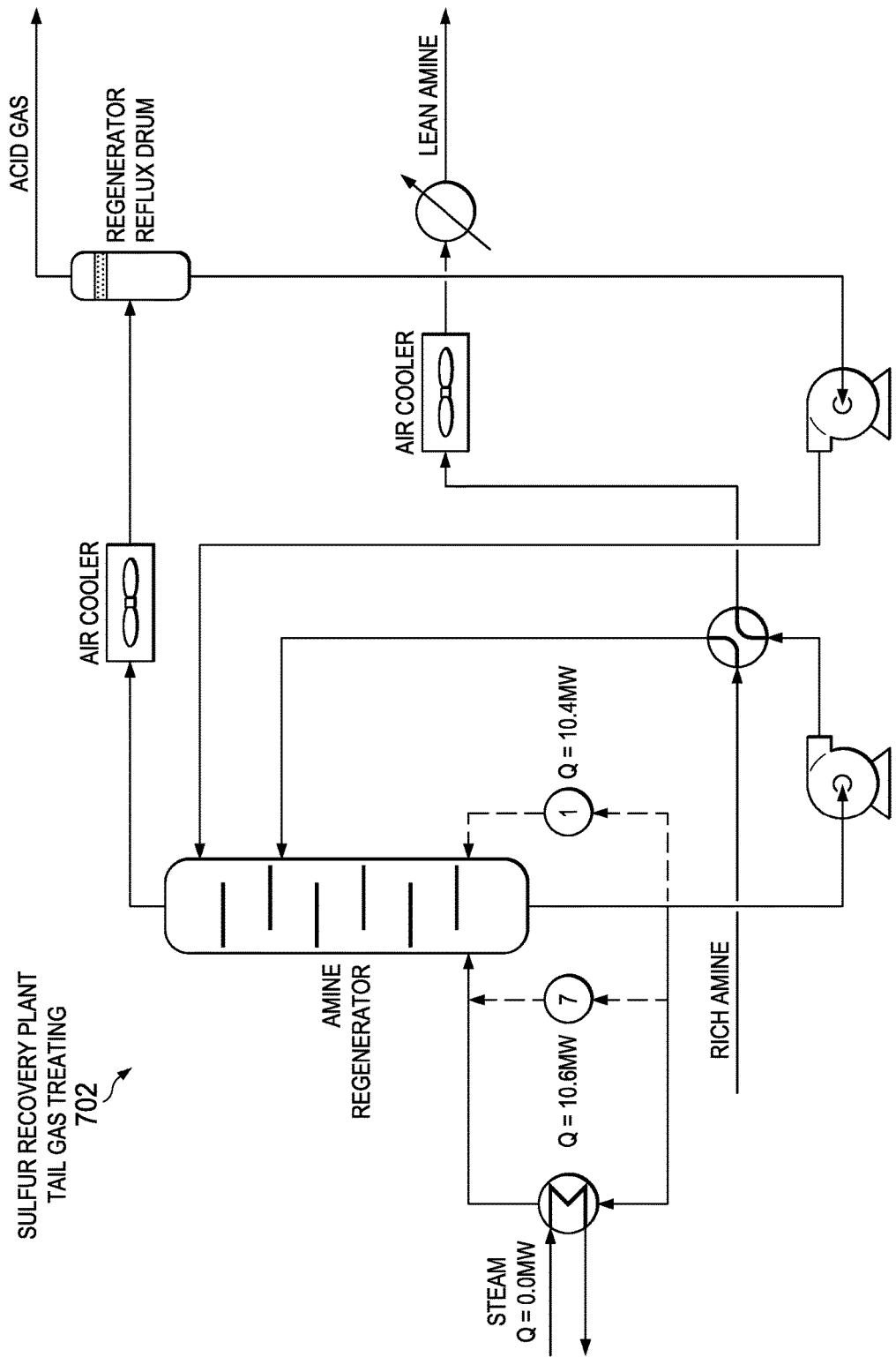
Figure 1D:
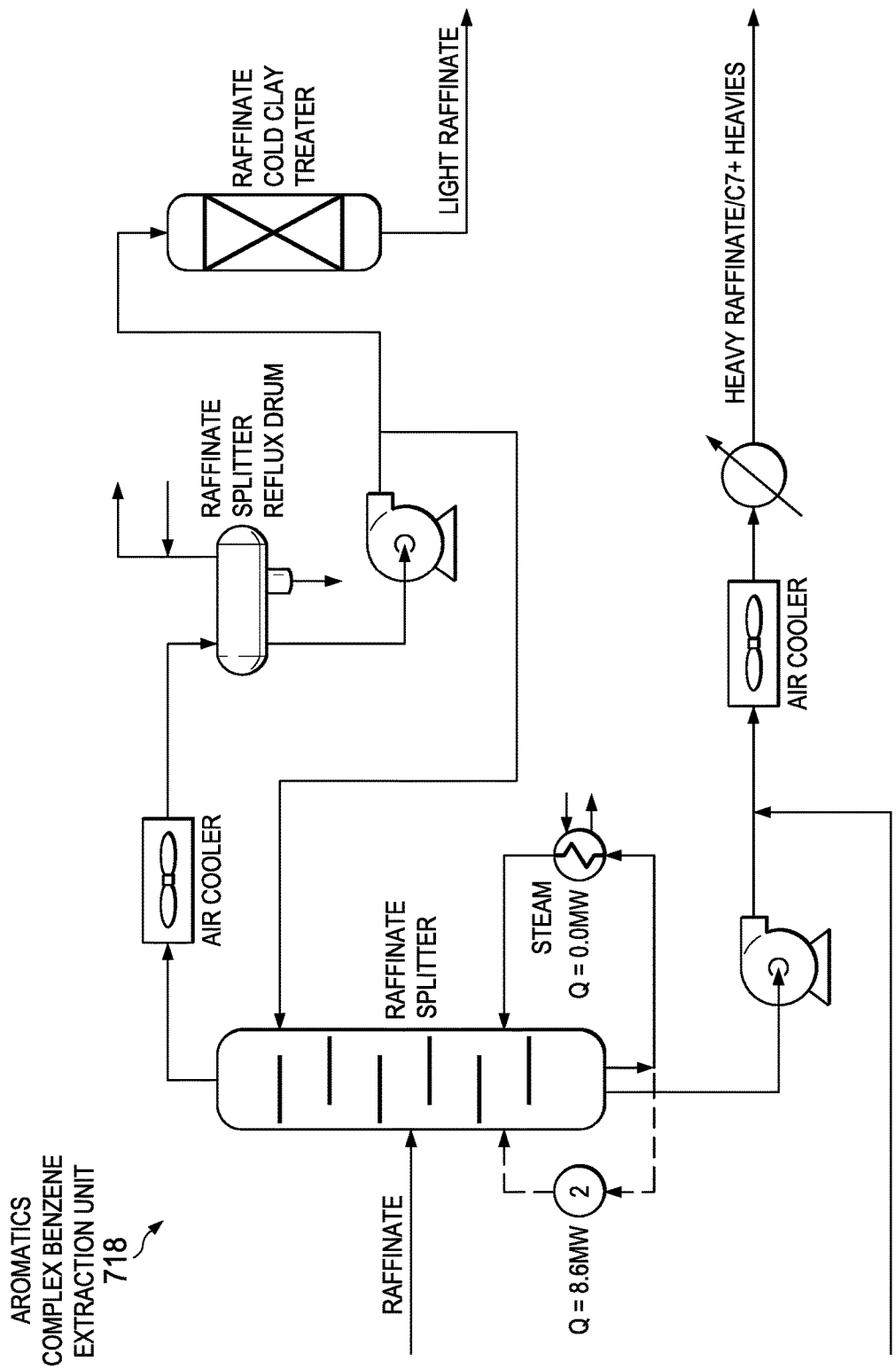
Figure 1D:
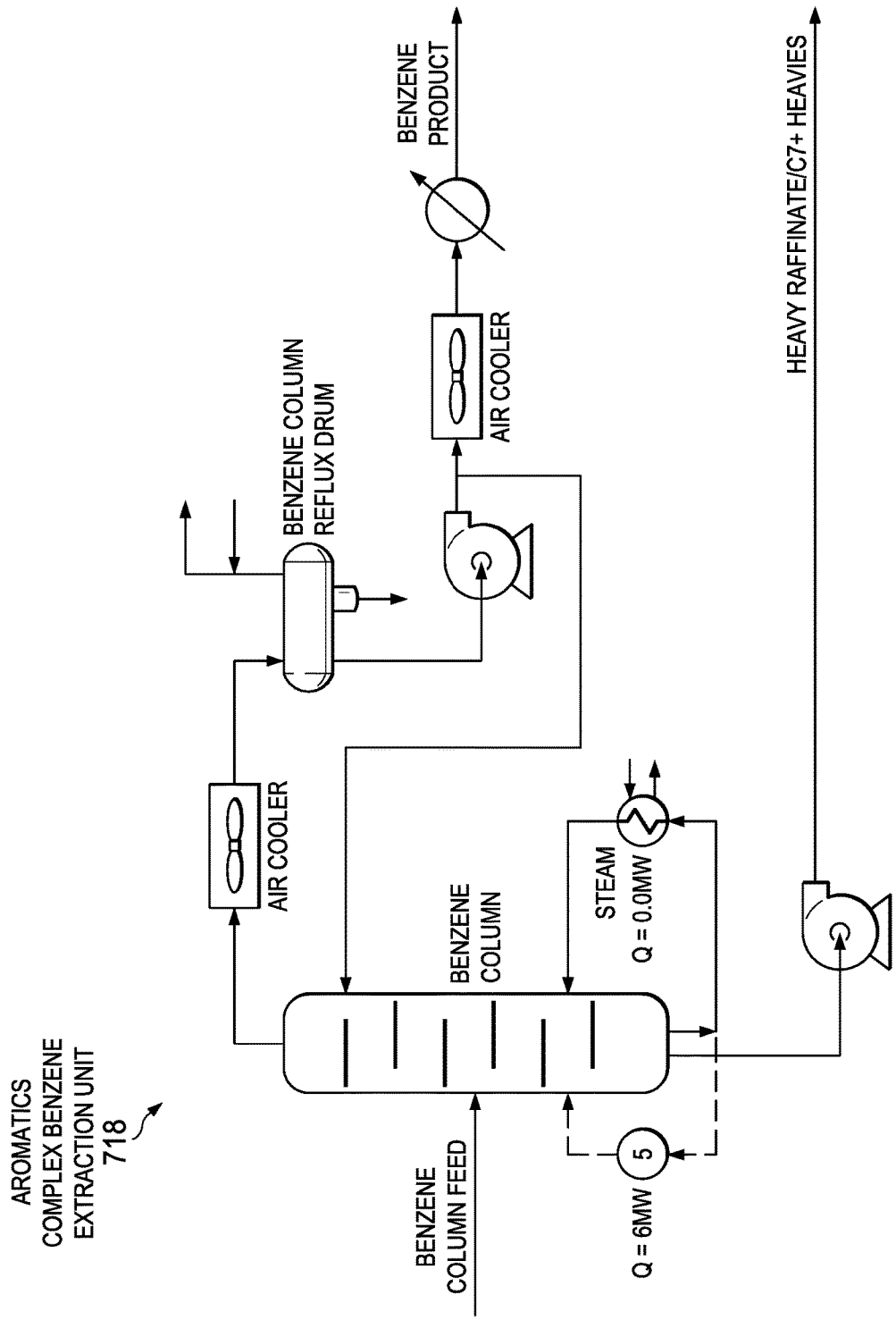
Figure 1D:
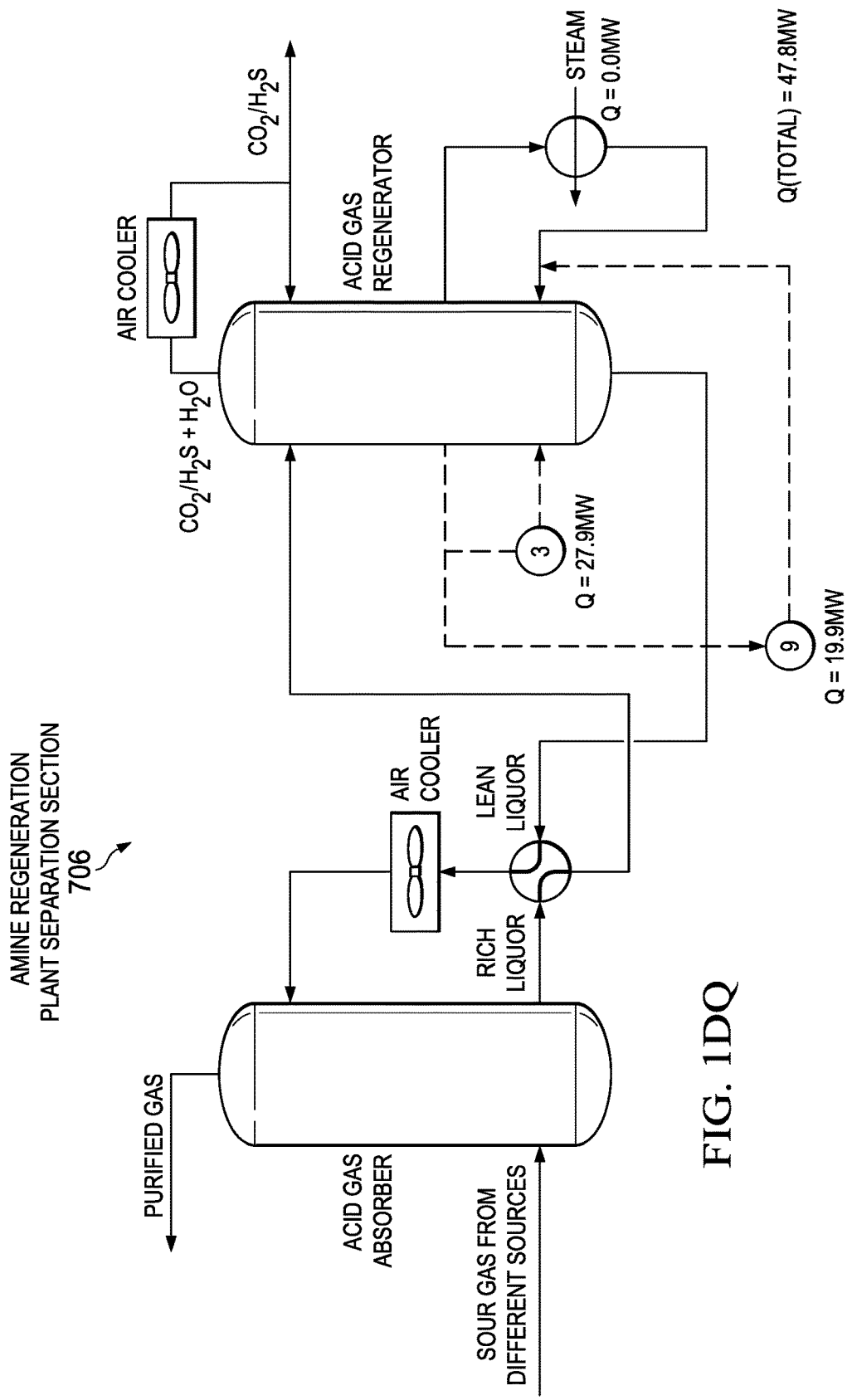
Figure 1D:
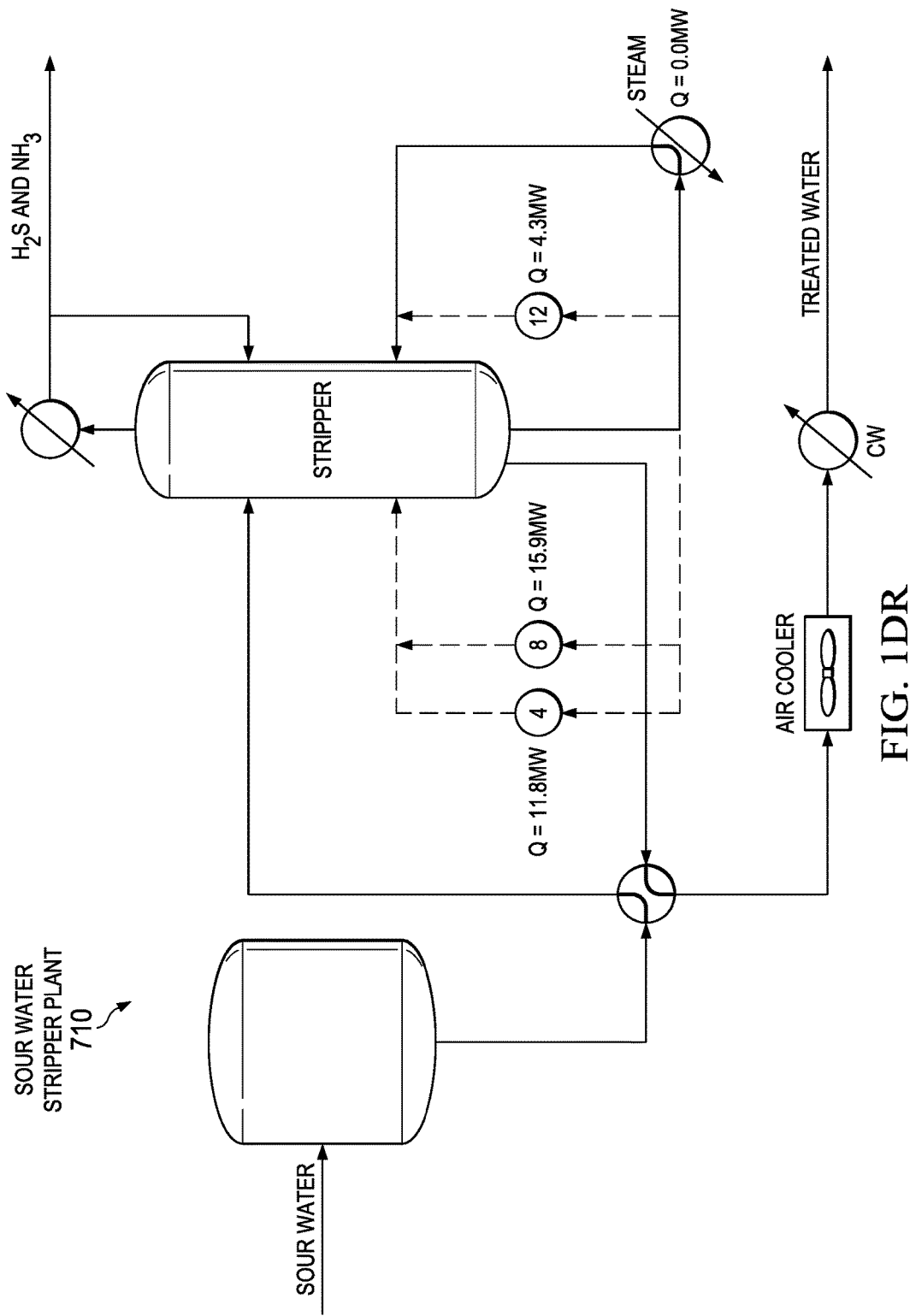
Figure 1D:
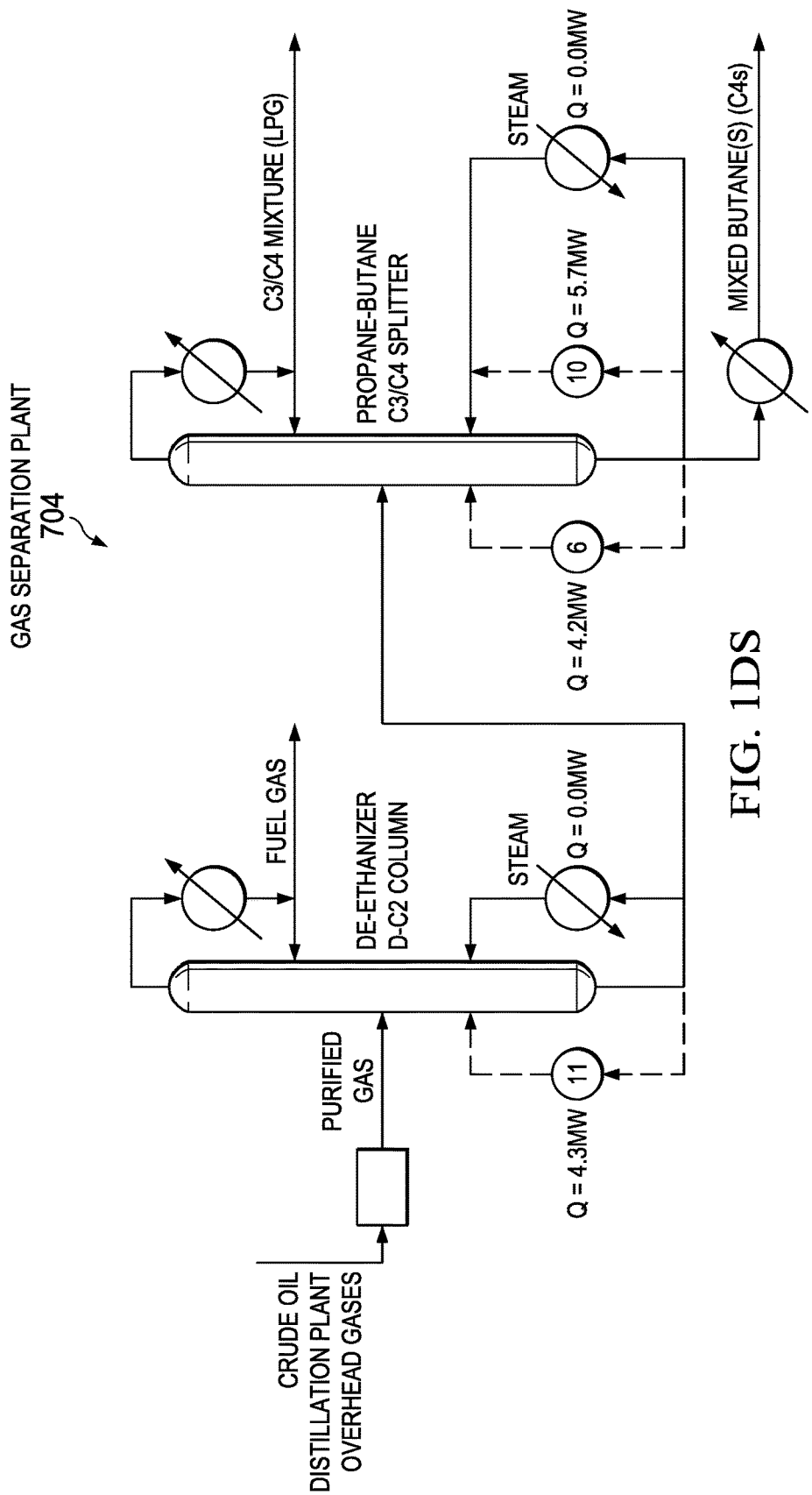

FIGS. 1W-1Z shows a hydrocracking plant 712 in a crude oil refining facility. Specifically, in FIG. 1W, a first buffer fluid stream can be heated using a diesel product stream in a first heat exchanger with a thermal duty that can range between about 5 MW and 15 MW (for example, 9.4 MW). As shown in FIG. 1X, a second buffer fluid stream can be heated using a first stage reaction section feed to a first stage cold high pressure separator in a second heat exchanger with a thermal duty that can range between about 10 MW and 20 MW (for example, 15.6 MW). As shown in FIG. 1Y (represented collectively by FIGS. 1Y-1 and 1Y-2) (specifically FIG. 1Y-1), a third buffer fluid stream can be heated using a product stripper overheads stream in a third heat exchanger with a thermal duty that can range between about 1 MW and 10 MW (for example, 3.95 MW). As shown specifically in FIG. 1Y-2, a fourth buffer fluid branch can be heated using a kerosene pumparound stream in a fourth heat exchanger with a thermal duty that can range between about 5 MW and 15 MW (for example, 8.65 MW). As shown in FIG. 1Z, a fifth buffer fluid stream can be heated using a kerosene product stream in a fifth heat exchanger with a thermal duty that can range between about 5 MW and 15 MW (for example, 9 MW). The diesel product stream, first stage reaction section feed to a first stage cold high pressure separator, product stripper overheads stream, the kerosene pumparound stream and the kerosene product stream are each returned to the hydrocracking plant 712 for further processing. In all instances, the buffer fluid absorbs heat that would have otherwise been discharged to the environment.

The first, second, third, fourth and fifth heated buffer fluid streams are combined into a combined heated buffer fluid in a collection header. In this manner, the first, second, third, fourth and fifth heat exchangers are parallel to one another relative to the flow of the buffer fluid.

The combined heated buffer fluid from the collection header (or in some embodiments, a heated or insulated buffer fluid tank or storage unit that can hold heated collected buffer fluid for a period before use) can be flowed to the sour water stripper plant 710 or aromatics complex benzene extraction unit 718 or combination thereof.

In an instance, the combined heated buffer fluid can be flowed to the benzene extraction unit 718. FIG. 1AA shows an aromatics complex benzene extraction unit 718 in a crude oil refining facility. The benzene column bottoms stream can be heated using the combined heated buffer fluid in a sixth heat exchanger with a thermal duty that can range between about 1 MW and 10 MW (for example, 6 MW). The sixth heat exchanger is coupled to, in series with and is downstream of the set of first, second, third, fourth, and fifth heat exchanger relative to the flow of buffer fluid. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AB also shows the aromatics complex benzene extraction unit 718. A raffinate column bottoms stream can be heated using the combined heated buffer fluid in a seventh heat exchanger with a thermal duty that can range between about 5 MW and 15 MW (for example, 8.6 MW). The seventh heat exchanger is coupled to, in series with and is downstream of the set of first, second, third, fourth, and fifth heat exchanger relative to the flow of buffer fluid. The steam heat input for the raffinate column can be 0 MW because the alternative flow path disclosed in this configuration may satisfy the entire heat load for the operation of the column. In an alternative embodiment, the steam heat input for the raffinate column can be reduced because the alternative flow path disclosed in this configuration may partially satisfy the heat load for the operation of the column.

FIG. 1AC shows the sour water stripper plant 710 in a crude oil refining facility. The combined heated buffer fluid is flowed tot the sour water stripper plant 710. A sour water stripper bottoms stream can be heated using the combined heated buffer fluid in an eighth heat exchanger with a thermal duty that can range between about 25 MW and 35 MW (for example, 32 MW). The eighth heat exchanger is coupled to, in series with and is downstream of the set of first, second, third, fourth, and fifth heat exchanger relative to the flow of buffer fluid. The steam heat input for the sour water stripper can be 0 MW because the alternative flow path disclosed in this configuration may satisfy the entire heat load for the operation of the column. In an alternative embodiment, the steam heat input for the sour water striper can be reduced because the alternative flow path disclosed in this configuration may partially satisfy the heat load for the operation of the column.

The combined heated buffer fluid after passing through the eighth heat exchanger is flowed back to the collection header or the buffer fluid tank for reuse. In this manner, the sixth, the seventh and the eighth heat exchanger are coupled to, in series with each other relative to the flow of buffer fluid.

In some implementations, the heated buffer fluid can be flowed in series through the different plants. For example, the heated buffer fluid can be flowed first to the sour water stripper plant and then to the benzene extraction unit. In another implementation, within the benzene extraction unit the heated buffer fluid stream may flow through the heat exchangers in a different order as presented. The heated buffer fluid exiting the eighth heat exchanger can be flowed to a buffer fluid tank. The buffer fluid from the buffer fluid tank can then be flowed to the different plants to restart the waste heat recovery and reuse cycle.

Such recovery and reuse of waste heat indirectly from the hydrocracking plant can result in decreasing or eliminating the heat energy for heating the sour water stripper plant, the aromatics complex or combinations of them such as by about 41 MW.

Configuration 3

FIGS. 1AD-1AK illustrate configurations and related scheme details for thermally integrating different refining plants in the crude oil refining facility. The thermal integration described in these configurations and illustrated in FIGS. 1AD-1AK can reduce the crude oil refining facility's energy consumption (for example, heating and cooling utilities). For example, a reduction in energy consumption by about 50 MW, for example, 49.8 MW, can translate to at least about 7%, for example, 7.66%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 3—Scheme A

In some implementations, multiple first streams in the multiple first plants can be directly heated using multiple second streams in a second plant. In some implementations, the multiple first plants can include a sulfur recovery plant, a gas separation plant and an aromatics plant sub-unit including an aromatics benzene extraction unit. The second plant can include a hydrocracking plant.

FIGS. 1AD-1AG show a hydrocracking plant 712 in a crude oil refinery facility. As shown in FIG. 1AD, a second stage reaction section feed stream to a second stage cold high pressure separator can directly heat a C3/C4 splitter bottoms stream in a first heat exchanger with a thermal duty that can range between about 5 MW and 15 MW (for example, 9.9 MW). The transfer of heat directly to another process streams captures heat that would have otherwise been discharged to the environment. The second stage reaction section feed is returned to the hydrocracking plant 712 for further processing.

As shown in FIG. 1AE, a first stage reaction feed stream to first stage cold high pressure separator can directly heat an amine regenerator bottoms stream in a second heat exchanger with a thermal duty that can range between about 15 MW and 25 MW (for example, 21 MW). The transfer of heat directly to another process streams captures heat that would have otherwise been discharged to the environment. The first stage reaction feed stream to first stage cold high pressure separator is returned to the hydrocracking plant 712 for further processing.

As shown in FIG. 1AF (represented collectively by FIGS. 1AF-1 and 1AF-2) (specifically FIG. 1AF-2), a kerosene pumparound stream 712 can directly heat a benzene column bottoms stream in a third heat exchanger with a thermal duty that can range between about 1 MW and 10 MW (for example, 6 MW). The transfer of heat directly to another process streams captures heat that would have otherwise been discharged to the environment. The kerosene pumparound stream is returned to the hydrocracking plant 712 for further processing.

As shown in FIG. 1AG, the kerosene product stream can directly heat a raffinate column bottoms stream in a fourth heat exchanger with thermal duty that can range between about 5 MW and 15 MW (for example, 8.6 MW. The transfer of heat directly to another process streams captures heat that would have otherwise been discharged to the environment.

The kerosene product stream can also directly heat a de-ethanizer bottom stream in a fifth heat exchanger with a thermal duty that can range between 1 MW and 10 MW (for example, 4.3 MW). The transfer of heat directly to another process streams captures heat that would have otherwise been discharged to the environment. The kerosene product stream is returned to the hydrocracking plant 712 for further processing.

As shown in FIG. 1AG, the fifth heat exchanger is coupled to, in series with and is downstream of the fourth heat exchanger relative to the flow of kerosene product stream. In some implementations, the kerosene product stream can be flowed in series through the different plants. For example, the kerosene product stream is flowed first through the de-ethanizer heat exchanger and then through the aromatics complex heat exchanger.

FIG. 1AH shows a gas separation plant 704 in a crude oil refining facility. The heated C3/C4 splitter bottoms stream can be flowed to the gas separation plant 704. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

Also in FIG. 1AH, the heated de-ethanizer bottoms stream can also be flowed to the gas separation plant 704. The steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

FIG. 1AI shows a sulfur recovery plant 702 in a crude oil refining facility. The heated amine regenerator bottoms stream can then be flowed to the sulfur recovery plant 702. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

FIG. 1AJ shows an aromatics complex benzene extraction unit 718 in a crude oil refining facility. The heated benzene column bottoms stream can be flowed to the benzene extraction plant 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AK also shows an aromatics complex benzene extraction unit 718. The heated raffinate splitter bottoms stream can be flowed to the benzene extraction plant 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Such recovery and reuse of waste heat directly from the hydrocracking plant can result in decreasing or eliminating the heat energy to heat the gas separation plant, an amine regeneration plant, a sulfur recovery plant, the aromatics complex or a combinations of them such as by about 50 MW.

Configuration 3—Scheme B

In some implementations, the multiple first streams in the crude oil refining facility such as those present in the multiple first plants, such as in the sulfur recovery plant, a gas separation plant and an aromatics plant sub-unit including an aromatics benzene extraction unit, can be indirectly heated using the multiple second streams in a second plant, such as one or more hydrocracking plant, as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712. The buffer fluid can be flowed into the plant as a single stream and split into multiple streams or it can be flowed into the plant as multiple streams.

To do so, one or more buffer fluid streams (for example, oil, water or other buffer fluid) can be heated using streams in the hydrocracking plant using respective heat exchangers. The heated buffer fluids can be collected in a buffer fluid collection header. Streams in the gas separation plant 704, the sulfur recovery plant 702 and the benzene extraction unit 718 can be heated using branches of or the combined heated buffer fluid in respective heat exchangers. The streams of or the combined heated buffer fluid exiting the heat exchangers can be flowed to a buffer fluid tank. The buffer fluid from the buffer fluid tank can then be flowed to the aromatics plant to restart the waste heat recovery and reuse cycle.

Configuration 4

FIGS. 1AL-1AT illustrate configurations and related scheme details for thermally integrating different refining plants in the crude oil refining facility. The thermal integration described in these configurations and illustrated in FIGS. 1AL-1AT can reduce the crude oil refining facility's energy consumption (for example, heating and cooling utilities). For example, a reduction in energy consumption by about 59 MW, for example, 58.9 MW, can translate to at least about 9%, for example, 9%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 4—Scheme A

In some implementations, multiple first streams in the multiple first plants can be directly heated using multiple second streams in the second plant. In some implementations, the multiple first plants can include a sour water stripper plant, a naphtha hydrotreating plant and an aromatics complex sub-unit including an aromatic complex benzene extraction plant. The multiple second plants can include a hydrocracking plant FIG. 1AQ shows a naphtha hydrotreating plant 714 in a crude oil refinery facility. The naphtha splitter bottoms stream can be flowed in the plant as a single stream and split into multiple streams or it can be flowed into the plant as multiple streams to facilitate heat recovery.

FIG. 1AR shows a sour water stripper plant 710 in a crude oil refinery facility. The sour water stripper bottoms stream can be flowed in the plant as a single stream and split into multiple streams or it can be flowed into the plant as multiple streams to facilitate heat recovery.

FIGS. 1AL-1AP show a hydrocracking plant 712 in a crude oil refinery facility. As shown in FIG. 1AL, a diesel product stream can directly heat a first naphtha splitter bottom stream in a first heat exchanger with a thermal duty that can range between about 1 MW and 10 MW (for example, 6.6 MW). The transfer of heat directly to another process streams captures heat that would have otherwise been discharged to the environment. The diesel product stream is returned to the hydrocracking plant 712 for further processing.

As shown in FIG. 1AM, a second stage reaction feed stream to a second stage cold high pressure separator can directly heat a raffinate column bottoms stream in a second heat exchanger with a thermal duty that can range between about 5 MW and 15 MW (for example, 8.6 MW). The transfer of heat directly to another process streams captures heat that would have otherwise been discharged to the environment. The second stage reaction feed is returned to the hydrocracking plant 712 for further processing.

As shown in FIG. 1AN, a first stage reaction feed stream to a first stage cold high pressure separator can directly heat a first sour water stripper bottom stream in a third heat exchanger with a thermal duty that can range between about 15 MW and 25 MW (for example, 20.5 MW). The transfer of heat directly to another process streams captures heat that would have otherwise been discharged to the environment. The first stage reaction feed to a first stage cold high pressure separator is returned to the hydrocracking plant 712 for further processing.

As shown in FIG. 1AO (represented collectively by FIGS. 1AO-1 and 1AO-2) (specifically FIG. 1AO-1), a product stripper overheads stream can directly heat a second sour water stripper bottoms stream in a fourth heat exchanger with a thermal duty that can range between about 5 MW and 15 MW (for example, 11.5 MW). The transfer of heat directly to another process streams captures heat that would have otherwise been discharged to the environment. The product stripper overheads stream is returned to the hydrocracking plant 712 for further processing.

As shown in FIG. 1AO-2, a kerosene pumparound stream can directly heat a second naphtha splitter bottoms stream in a fifth heat exchanger (thermal duty that can range between about 1 MW and 10 MW (for example, 5.7 MW). The transfer of heat directly to another process streams captures heat that would have otherwise been discharged to the environment. The kerosene pumparound stream is returned to the hydrocracking plant 712 for further processing.

As shown in FIG. 1AP, the kerosene product stream can directly heat a raffinate splitter bottom stream in a sixth heat exchanger with a thermal duty that can range between about 1 MW and 10 MW (for example, 6 MW). The transfer of heat directly to another process streams captures heat that would have otherwise been discharged to the environment. The kerosene product stream is returned to the hydrocracking plant 712 for further processing.

As shown in FIG. 1AQ, the two streams of the heated naphtha splitter bottoms streams are recombined and flowed to the naphtha hydrotreating plant 714. In this manner, the first heat exchanger and the fifth heat exchanger can be coupled to each other in parallel relative to the flow of naphtha splitter bottoms. The steam heat input for the naphtha splitter can be 0 MW because the alternative flow path disclosed in this configuration may satisfy the entire heat load for the operation of the column. In an alternative embodiment, the steam heat input for he naphtha splitter can be reduced because the alternative flow path disclosed in this configuration may partially satisfy the heat load for the operation of the column.

As shown in FIG. 1AQ, the two streams of the sour water stripper bottoms streams are recombined and flowed to the sour water stripper plant 710. In this manner, the first heat exchanger and the second heat exchanger can be coupled to each other in parallel relative to the flow of sour water stripper bottoms. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

FIG. 1AT shows an aromatics complex benzene extraction unit 718 in a crude oil refining facility. The heated benzene column bottoms stream can be flowed to the benzene extraction plant 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AS also shows an aromatics complex benzene extraction unit 718. The heated raffinate splitter column bottom stream can be flowed to the benzene extraction plant 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

Such recovery and reuse of waste heat directly from the hydrocracking plant can result in decreasing or eliminating the heat energy to heat the aromatics complex, the sour water stripper plant, the naphtha hydrotreating plant or a combination of them such as by about 59 MW.

Configuration 4—Scheme B

In some implementations, the multiple first streams in the crude oil refining facility such as those present in the multiple first plants, such as in the naphtha hydrotreating plant, the sour water stripper plant, and an aromatics plant sub-unit including a benzene extraction unit, can be indirectly heated using the multiple second streams in a second plant, such as one or more hydrocracking plant, as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712. The buffer fluid can be flowed into the plant as a single stream and split into multiple streams or it can be flowed into the plant as multiple streams.

To do so, one or more buffer fluid streams (for example, oil, water or other buffer fluid) can be heated using streams in the hydrocracking plant 712 using respective heat exchangers. The heated buffer fluids can be collected in a buffer fluid collection header. Streams in the sour water stripper plant 710, the naphtha hydrotreating plant 714 and the aromatic complex benzene extraction plant 718 can be heated using the heated buffer fluid in respective heat exchangers. The heated buffer fluid exiting the heat exchangers can be flowed to a buffer fluid tank. The buffer fluid from the buffer fluid tank can then be flowed to the aromatics plant to restart the waste heat recovery and reuse cycle.

Configuration 5

FIGS. 1AU-1BB illustrate configurations and related scheme details for thermally integrating different refining plants in the crude oil refining facility. The thermal integration described in these configurations and illustrated in FIGS. 1AU-1BB can reduce the crude oil refining facility's energy consumption (for example, heating and cooling utilities). For example, a reduction in energy consumption by about 61 MW, which translates to at least about 9% of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 5—Scheme A

In some implementations, multiple first streams in the multiple first plants can be directly heated using multiple second streams in the second plant. In some implementations, the multiple first plants can include a sour water stripper plant, a gas separation plant and an aromatics complex sub-unit including an aromatic complex benzene extraction unit. The second plant can include a hydrocracking plant.

FIG. 1AY shows a sour water stripper plant 710 in a crude oil refinery facility. The sour water stripper bottoms stream can be flowed in the plant as a single stream and split into multiple streams or it can be flowed into the plant as multiple streams to facilitate heat recovery.

FIGS. 1AU-1AX show a hydrocracking plant 712 in a crude oil refinery facility. As shown in FIG. 1AU, a second stage reaction feed stream to a second stage cold high pressure separator can directly heat a C3/C4 splitter bottoms stream in a third heat exchanger with a thermal duty that can range between about 5 MW and 15 MW (for example, 9.9 MW). The transfer of heat directly to another process streams captures heat that would have otherwise been discharged to the environment. The second stage reaction feed to a second stage cold high pressure separator is returned to the hydrocracking plant 712 for further processing.

As shown in FIG. 1AV, a first stage reaction feed stream to a first stage cold high pressure separator can directly heat a first sour water stripper bottom stream in a second heat exchanger with a thermal duty that can range between about 15 MW and 25 MW (for example, 20.5 MW). The transfer of heat directly to another process streams captures heat that would have otherwise been discharged to the environment. The first stage reaction feed stream to a first stage cold high pressure separator is returned to the hydrocracking plant 712 for further processing.

As shown in FIG. 1AW (represented collectively by FIGS. 1AW-1 and 1AW-2) (specifically FIG. 1AW-1), a product stripper overheads stream can directly heat a second sour water stripper bottoms stream in a first heat exchanger with a thermal duty that can range between about 5 MW and 15 MW (for example, 11.5 MW). The transfer of heat directly to another process streams captures heat that would have otherwise been discharged to the environment. The product stripper overheads stream is returned to the hydrocracking plant 712 for further processing.

As shown specifically in FIG. 1AW-2, a kerosene pump-around stream can heat a benzene column bottoms stream in a sixth heat exchanger with a thermal duty that can range between about 1 MW and 10 MW (for example, 6 MW). The transfer of heat directly to another process streams captures heat that would have otherwise been discharged to the environment. The kerosene pumparound stream is returned to the hydrocracking plant 712 for further processing.

As shown in FIG. 1AX, the kerosene product stream can heat a raffinate splitter bottom in a fourth heat exchanger that has a thermal duty that can range between about 5 MW and 15 MW (for example, 8.6 MW). The kerosene product stream can also heat a de-ethanizer column bottom stream in a fifth heat exchanger having a thermal duty that can range between about 1 MW and 10 MW (for example, 4.3 MW). The transfer of heat directly to another process streams captures heat that would have otherwise been discharged to the environment. The kerosene product stream is returned to the hydrocracking plant 712 for further processing.

As shown in FIG. 1AX, the fifth heat exchanger is coupled to, in series with and is downstream of the fourth heat exchanger relative to the flow of kerosene product stream. In some implementations, the kerosene product stream can be flowed in series through the different plants. For example, the kerosene product stream is flowed first through the de-ethanizer heat exchanger and then through the aromatics complex heat exchanger.

FIG. 1BB shows an aromatics complex benzene extraction unit 718 in a crude oil refining facility. The heated benzene column bottoms stream can be flowed to the benzene extraction unit 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1AZ also shows an aromatics complex benzene extraction unit 718. The heated raffinate splitter column bottom stream can be flowed to the benzene extraction unit 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

FIG. 1BA shows a gas separation plant 704 in a crude oil refining facility. The heated C3/C4 splitter bottoms stream can be flowed to the gas separation plant 704. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

Also shown in FIG. 1BA, the heated de-ethanizer bottoms stream can also be flowed to the gas separation plant 604. The steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

As shown in FIG. 1AQ, the two sour water stripper bottoms streams are recombined and can be flowed to the sour water stripper plant 710. In this manner, the first heat exchanger and the second heat exchanger can be coupled to each other in parallel relative to the flow of sour water stripper bottoms. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Such recovery and reuse of waste heat directly from the hydrocracking plant can result in decreasing or eliminating the heat energy to heat the aromatics complex, the sour water stripper plant, the gas separation plant or a combination of them such as by about 61 MW.

Configuration 5—Scheme B

In some implementations, the multiple streams in the crude oil refining facility such as those present in the multiple first plants, such as in sour water stripper plant, the gas separation plant and the an aromatics complex sub-unit including an aromatic complex benzene extraction unit can be indirectly heated using the multiple second streams in a second plant, such as one or more hydrocracking plant, as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712. The buffer fluid can be flowed into the plant as a single stream and split into multiple streams or it can be flowed into the plant as multiple streams.

To do so, one or more buffer fluid streams (for example, oil, water or other buffer fluid) can be heated using streams in the hydrocracking plant 712 using respective heat exchangers. The heated buffer fluids can be collected in a buffer fluid collection header. Streams in the sour water stripper plant 710, the gas separation plant 704 and the benzene extraction plant 718 can be heated using the heated buffer fluid streams in respective heat exchangers. The heated buffer fluid exiting the heat exchangers can be flowed to a buffer fluid tank. The buffer fluid from the buffer fluid tank can then be flowed to the aromatics plant to restart the waste heat recovery and reuse cycle.

Configuration 6

FIGS. 1BC-1BQ illustrate configurations and related scheme details for thermally integrating different refining plants in the crude oil refining facility. The thermal integration described in these configurations and illustrated in FIGS. 1BC-1BQ can reduce the crude oil refining facility's energy consumption (for example, heating and cooling utilities). For example, a reduction in energy consumption by about 62 MW, for example, 62.4 MW, can translate to at least about 9%, for example, 9.6%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 6—Scheme A

In some implementations, multiple first streams in the multiple first plants can be directly heated using multiple second streams in the second plant. In some implementations, the multiple first plants can include an amine regeneration plant and an aromatics plant sub-unit including an aromatic complex benzene extraction unit. The second plant can include a hydrocracking plant.

FIG. 1BI shows an amine regeneration plant 706 in a crude oil refinery facility. The acid gas regenerator bottoms stream can be flowed in the plant as a single stream and split into multiple streams or it can be flowed into the plant as multiple streams to facilitate heat recovery.

FIGS. 1BC-1BF show a hydrocracking plant 712 in a crude oil refinery facility. As shown in FIG. 1BC, a second stage reaction feed stream to a second stage cold high pressure separator can directly heat a raffinate splitter bottoms stream in a first heat exchanger with a thermal duty that can range between about 5 MW and 15 MW (for example, 8.6 MW). The transfer of heat directly to another process streams captures heat that would have otherwise been discharged to the environment. The second stage reaction feed stream to a second stage cold high pressure separator is returned to the hydrocracking plant 712 for further processing.

As shown in FIG. 1BD, a first stage reaction feed stream to a first stage cold high pressure separator can directly heat a first acid gas regenerator bottom streams in a second heat exchanger with a thermal duty that can range between about 25 MW and 35 MW (for example, 27.8 MW). The transfer of heat directly to another process streams captures heat that would have otherwise been discharged to the environment. The first stage reaction feed stream to a first stage cold high pressure separator is returned to the hydrocracking plant 712 for further processing.

As shown in FIG. 1BE (represented collectively by FIGS. 1BE-1 and 1BE-2) (specifically FIG. 1BE-1), a product stripper overheads stream can directly heat a second acid gas regenerator bottoms stream in a third heat exchanger with a thermal duty that can range between about 10 MW and 20 MW (for example, 14.8 MW). The transfer of heat directly to another process streams captures heat that would have otherwise been discharged to the environment. The product stripper overheads stream is returned to the hydrocracking plant 712 for further processing.

As shown in FIG. 1BF, a kerosene product stream can directly heat a third acid gas regenerator bottoms stream in a fourth heat exchanger (thermal duty that can range between about 1 MW and 10 MW (for example, 5.2 MW)). The transfer of heat directly to another process streams captures heat that would have otherwise been discharged to the environment.

The kerosene product stream can also directly heat a benzene column bottoms stream in a fifth heat exchanger with a thermal duty that can range between about 1 MW and 10 MW (for example, 6 MW). The transfer of heat directly to another process streams captures heat that would have otherwise been discharged to the environment. The kerosene product stream is returned to the hydrocracking plant 712 for further processing.

As shown in FIG. 1BF, the fourth heat exchanger is coupled to, in series with and is downstream of the fifth heat exchanger relative to the flow of kerosene product stream. In some implementations, the kerosene product stream can be flowed in series through the different plants. For example, the kerosene product stream is flowed first through the acid gas regenerator heat exchanger and then through the aromatics complex heat exchanger.

FIG. 1BG shows an aromatics complex benzene extraction unit 718 in a crude oil refining facility. The heated benzene column bottom stream can be flowed to the benzene extraction plant 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1BH also shows an aromatics complex benzene extraction unit 718. The heated raffinate splitter column bottom stream can be flowed to the benzene extraction plant 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

As shown in FIG. 1BI, the three streams of the heated acid gas regenerator bottoms are recombined and flowed to the amine regeneration plant 706. In this manner, the first heat exchanger, the second heat exchanger, and the third heat exchanger can be coupled to each other in parallel relative to the flow of acid gas regenerator bottoms. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

Such recovery and reuse of waste heat directly from the hydrocracking plant can result in decreasing or eliminating the heat energy to heat the aromatics complex, an amine regeneration plant, or a combination of them, such as by about 62 MW.

Configuration 6—Scheme B

In some implementations, the multiple first streams in the crude oil refining facility such as those present in the multiple first plants, such as in the aromatic complex sub-units such as the benzene extraction unit and the amine regeneration plant, can be indirectly heated using the multiple second streams in a second plant, such as one or more hydrocracking plant, as heat energy sources Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712. The buffer fluid can be flowed into the plant as a single stream and split into multiple streams or it can be flowed into the plant as multiple streams.

FIGS. 1BJ-1BN shows a hydrocracking plant 712 in a crude oil refining facility. Specifically, in FIG. 1BJ, a first buffer fluid stream can be heated using a diesel product stream in a first heat exchanger with a thermal duty that can range between about 5 MW and 15 MW (for example, 10.87 MW). In an alternative embodiment, the cooling requirement of the diesel product stream can be 0 MW because the alternative flow path disclosed in this configuration may satisfy the entire cooling requirement for the diesel product stream. As shown in FIG. 1BK, a second buffer fluid stream can be heated using a second reaction stage feed stream to a second stage cold high pressure separator in a second heat exchanger with a thermal duty that can range between about 5 MW and 15 MW (for example, 7.3 MW). As shown in FIG. 1BL, a third buffer fluid stream can be heated using a first reaction section feed stream to a first stage cold high pressure separator stream in a third heat exchanger with a thermal duty that can range between about 20 MW and 30 MW (for example, 23.8 MW). As shown in FIG. 1BM (represented collectively by FIGS. 1BM-1 and 1BM-2) (specifically FIG. 1BM-2), a fourth buffer fluid stream can be heated using a kerosene pumparound stream in a fourth heat exchanger with a thermal duty that can range between about 5 MW and 15 MW (for example, 10.2 MW). In an embodiment, the cooling requirement of the kerosene pumparound stream can be 0 MW because the alternative flow path disclosed in this configuration may satisfy the entire cooling requirement for the kerosene pumparound stream for the operation of the fractionator column. As shown in FIG. 1BN, a fifth buffer fluid stream can be heated using a kerosene product stream in a fifth heat exchanger with a thermal duty that can range between about 5 MW and 15 MW (for example, 11 MW) (FIG. 1BN). The diesel product stream, second reaction stage feed stream to a second stage cold high pressure separator, first stage reaction section feed to a first stage cold high pressure separator, the kerosene pumparound stream and the kerosene product stream are each returned to the hydrocracking plant 712 for further processing. In all instances, the buffer fluid absorbs heat that would have otherwise been discharged to the environment.

The first, second, third, fourth and fifth heated buffer fluid streams are combined into a combined heated buffer fluid in a collection header. In this manner, the first, second, third, fourth and fifth heat exchangers are parallel to one another relative to the flow of the buffer fluid.

The combined heated buffer fluid from the collection header (or in some embodiments, a heated or insulated buffer fluid tank or storage unit that can hold heated collected buffer fluid for a period before use) can be flowed to the amine regeneration plant 706 or aromatics complex benzene extraction unit 718 or combination thereof.

In an instance, the combined heated buffer fluid can be flowed to the benzene extraction unit 718. FIG. 1BO shows an aromatics complex benzene extraction unit 718 in a crude oil refining facility. The benzene column bottoms stream can be heated using the combined heated buffer fluid in a sixth heat exchanger with a thermal duty that can range between about 1 MW and 10 MW (for example, 6 MW). The sixth heat exchanger is coupled to, in series with and is downstream of the set of first, second, third, fourth, and fifth heat exchangers relative to the flow of buffer fluid. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1BP also shows the aromatics complex benzene extraction unit 718. A raffinate column bottoms stream can be heated using the combined heated buffer fluid in a seventh heat exchanger with a thermal duty that can range between about 5 MW and 15 MW (for example, 8.6 MW). The seventh heat exchanger is coupled to, in series with and is downstream of the set of first, second, third, fourth, and fifth heat exchanger relative to the flow of buffer fluid. The steam heat input for the raffinate column can be 0 MW because the alternative flow path disclosed in this configuration may satisfy the entire heat load for the operation of the column. In an alternative embodiment, the steam heat input for the raffinate column can be reduced because the alternative flow path disclosed in this configuration may partially satisfy the heat load for the operation of the column.

FIG. 1BQ shows the amine regeneration plant 706 in a crude oil refining facility. The combined heated buffer fluid is flowed tot the amine regeneration plant 706. As shown in FIG. 1BQ, an acid gas regenerator bottoms stream can be heated using the combined heated buffer fluid in an eighth heat exchanger with a thermal duty that can range between about 45 MW and 55 MW (for example, 47.8 MW). The eighth heat exchanger is coupled to, in series with and is downstream of the set of first, second, third, fourth, and fifth heat exchangers relative to the flow of buffer fluid. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The combined heated buffer fluid branch exiting the eighth heat exchanger is flowed to the collection header or the buffer fluid tank for reuse. In this manner, the sixth, the seventh and the eighth heat exchangers are coupled to, in series with each other relative to the flow of buffer fluid.

In some implementations, the heated buffer fluid can be flowed in series through the different plants. For example, the heated buffer fluid can be flowed first to the sour water stripper plant and then to the benzene extraction unit. In another implementation, within the benzene extraction unit the heated buffer fluid stream may flow through the heat exchangers in a different order as presented. The heated buffer fluid exiting the eighth heat exchanger can be flowed to a buffer fluid tank. The buffer fluid from the buffer fluid tank can then be flowed to the different plants to restart the waste heat recovery and reuse cycle.

Such recovery and reuse of waste heat indirectly from the hydrocracking plant can result in decreasing or eliminating the heat energy for heating the sour water stripper plant, the aromatics complex or combinations of them such as by about 62 MW.

Configuration 7

FIGS. 1BR-1BZ illustrate configurations and related scheme details for thermally integrating different refining plants in the crude oil refining facility. The thermal integration described in these configurations and illustrated in FIGS. 1BR-1BZ can reduce the crude oil refining facility's energy consumption (for example, heating and cooling utilities). For example, a reduction in energy consumption by about 68 MW, for example, 67.6 MW, translate to at least about 10%, for example, 10.4%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 7—Scheme A

In some implementations, multiple first streams in the multiple first plants can be directly heated using multiple second streams in a second plant. In some implementations, the multiple first plants can include a sour water stripper plant, a sulfur recovery plant and an aromatics complex sub-unit including an aromatics complex benzene extraction unit. The second plant can include a hydrocracking plant.

FIG. 1BW shows a sour water stripper plant 710 in a crude oil refinery facility. The sour water stripper bottoms stream can be flowed in the plant as a single stream and split into multiple streams or it can be flowed into the plant as multiple streams to facilitate heat recovery.

FIG. 1BZ shows a sulfur recovery plant 702 in a crude oil refinery facility. The sour water stripper bottoms stream can be flowed in the plant as a single stream and split into multiple streams or it can be flowed into the plant as multiple streams to facilitate heat recovery.

FIGS. 1BR-1BV show a hydrocracking plant 712 in a crude oil refinery facility. As shown in FIG. 1BR, a diesel product stream can directly heat a first amine regenerator bottoms stream in a first heat exchanger with a thermal duty that can range between about 5 MW and 15 MW (for example, 10.4 MW). The transfer of heat directly to another process streams captures heat that would have otherwise been discharged to the environment. The diesel product stream is returned to the hydrocracking plant 712 for further processing.

As shown in FIG. 1BS, a second stage reaction section feed to a second stage cold high pressure separator can directly heat a raffinate splitter bottoms stream in a second heat exchanger with a thermal duty that can range between about 5 MW and 15 MW (for example, 8.6 MW). The transfer of heat directly to another process streams captures heat that would have otherwise been discharged to the environment. The second stage reaction section feed to a second stage cold high pressure separator is returned to the hydrocracking plant 712 for further processing.

As shown in FIG. 1BT, a first stage reaction section first stage cold high pressure separator stream can directly heat a first sour water stripper bottoms in a third heat exchanger with a thermal duty that can range between about 15 MW and 25 MW (for example, 20.5 MW). The transfer of heat directly to another process streams captures heat that would have otherwise been discharged to the environment. The first stage reaction section first stage cold high pressure separator stream is returned to the hydrocracking plant 712 for further processing.

As shown in FIG. 1BU (represented collectively by FIGS. 1BU-1 and 1BU-2) (specifically in FIG. 1BU-1), a product stripper overheads stream can directly heat a second sour water stripper bottoms stream in a fourth heat exchanger with a thermal duty that can range between about 5 MW and 15 MW (for example, 11.5 MW). The transfer of heat directly to another process streams captures heat that would have otherwise been discharged to the environment. The product stripper overheads is returned to the hydrocracking plant 712 for further processing.

As shown specifically in FIG. 1BU-2, a kerosene pumparound stream can directly heat a benzene column bottoms stream in a fifth heat exchanger with a thermal duty that can range between about 1 MW and 10 MW (for example, 6 MW). The transfer of heat directly to another process streams captures heat that would have otherwise been discharged to the environment. The kerosene pumparound stream is returned to the hydrocracking plant 712 for further processing.

As shown in FIG. 1BV an, a kerosene product stream in the hydrocracking plant 712 can directly heat a second amine regenerator bottoms stream in a sixth heat exchanger with a thermal duty that can range between about 5 MW and 15 MW (for example, 10.6 MW). The transfer of heat directly to another process streams captures heat that would have otherwise been discharged to the environment. The kerosene product stream is returned to the hydrocracking plant 712 for further processing.

FIG. 1BY shows an aromatics complex benzene extraction unit 718 in a crude oil refining facility. The heated benzene column bottoms stream can be flowed to the benzene extraction plant 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1BX also shows an aromatics complex benzene extraction unit 718. The heated raffinate splitter column bottom stream can be flowed to the benzene extraction plant 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

As shown in FIG. 1BZ, the two heated amine regenerator bottoms streams are recombined and flowed to the sulfur recovery plant 702. In this manner, the first heat exchanger and the sixth heat exchanger can be coupled to each other in parallel relative to the flow of amine regenerator bottoms. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

As shown in FIG. 1BW, the two heated sour water stripper bottoms streams are recombined and flowed to the sour water stripper plant 710. In this manner, the third heat exchanger and the fourth heat exchanger can be coupled to each other in parallel relative to the flow of sour water stripper bottoms. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Such recovery and reuse of waste heat directly from the hydrocracking plant can result in decreasing or eliminating the heat energy to heat the aromatics complex, the sour water stripper plant, the sulfur recovery plant or a combination of them, such as by about 68 MW.

Configuration 7—Scheme B

In some implementations, the multiple streams in the crude oil refining facility such as those present in the multiple first plants, such as in the aromatics complex, the sour water stripper plant and the sulfur recovery plant, can be indirectly heated using the multiple second streams in a second plant, such as one or more hydrocracking plant, as heat energy sources.

Indirectly heating the streams can include heating the streams through a buffer fluid, for example, oil, water, or other buffer fluid. A buffer fluid (for example, high pressure water) from a buffer fluid tank (for example, hot water tank)

is flowed to the hydrocracking plant 712. The buffer fluid can be flowed into the plant as a single stream and split into multiple streams or it can be flowed into the plant as multiple streams.

To do so, one or more buffer fluid streams (for example, oil, water or other buffer fluid) can be heated using streams in the hydrocracking plant 712 using respective heat exchangers. The heated buffer fluids can be collected in a buffer fluid collection header. Streams in the sour water stripper plant 710, the sulfur recovery plant 702 and the benzene extraction plant 718 can be heated using the heated buffer fluid in respective heat exchangers. The heated buffer fluid exiting the heat exchangers can be flowed to a buffer fluid tank. The buffer fluid from the buffer fluid tank can then be flowed to the aromatics plant to restart the waste heat recovery and reuse cycle.

Configuration 8

FIGS. 1CA-1CJ illustrate configurations and related scheme details for thermally integrating different refining plants in the crude oil refining facility. The thermal integration described in these configurations and illustrated in FIGS. 1CA-1CJ can reduce the crude oil refining facility's energy consumption (for example, heating and cooling utilities). For example, a reduction in energy consumption by about 73 MW, for example, 73.1 MW, can translate to at least about 12%, for example, 11.2%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 8—Scheme A

In some implementations, multiple first streams in the multiple first plants can be directly heated using multiple second streams in the second plant. In some implementations, the multiple first plants can include a naphtha hydrotreating plant, a sour water stripper plant, a gas separation plant and an aromatics complex sub-unit including an aromatic complex benzene extraction unit. The second plant can include a hydrocracking plant 712.

FIG. 1CF shows a naphtha hydrotreating plant 714 in a crude oil refinery facility. The naphtha splitter bottoms stream can be flowed in the plant as a single stream and split into multiple streams or it can be flowed into the plant as multiple streams to facilitate heat recovery.

FIG. 1CG shows a sour water stripper plant 710 in a crude oil refinery facility. The sour water stripper bottoms stream can be flowed in the plant as a single stream and split into multiple streams or it can be flowed into the plant as multiple streams to facilitate heat recovery.

FIG. 1CJ shows a gas separation plant 704 in a crude oil refinery facility. The C3/C4 splitter bottoms stream can be flowed in the plant as a single stream and split into multiple streams or it can be flowed into the plant as multiple streams to facilitate heat recovery.

FIGS. 1CA-1CE show a hydrocracking plant 712 in a crude oil refinery facility. As shown in FIG. 1CA, a diesel product stream can directly heat a first naphtha splitter bottoms stream in a first heat exchanger with a thermal duty that can range between about 5 MW and 10 MW (for example, 6.6 MW). The diesel product stream can also directly heat a first C3/C4 splitter bottoms stream in a second heat exchanger with a thermal duty that can range between about 1 MW and 10 MW (for example, 4.9 MW). For both streams, the transfer of heat directly to another process streams captures heat that would have otherwise been discharged to the environment. In an alternative embodiment, the cooling requirement of the diesel product stream can be 0 MW because the alternative flow path disclosed in this configuration may satisfy the entire cooling requirement for the diesel product stream. The diesel product stream is returned to the hydrocracking plant 712 for further processing.

As shown in FIG. 1CA, the second heat exchanger is coupled to, in series with and is downstream of the first heat exchanger relative to the flow of the diesel product stream. In some implementations, the diesel product stream can be flowed in series through the different plants. For example, the diesel product stream is flowed first through the gas separation plant heat exchanger and then through the naphtha hydrotreating plant heat exchanger.

As shown in FIG. 1CB, a second reaction section feed stream to second stage cold high pressure separator can directly heat a raffinate splitter bottoms stream in a third heat exchanger with a thermal duty that can range between about 5 MW and 15 MW (for example, 8.6 MW). The transfer of heat directly to another process streams captures heat that would have otherwise been discharged to the environment. The second reaction section feed to second stage cold high pressure separator is returned to the hydrocracking plant 712 for further processing.

As shown in FIG. 1CC, a first reaction section feed stream to a first stage cold high pressure separator in the hydrocracking plant 712 can directly heat a first sour water stripper bottoms stream in a fourth heat exchanger with a thermal duty that can range between about 15 MW and 25 MW (for example, 20.5 MW). The transfer of heat directly to another process streams captures heat that would have otherwise been discharged to the environment. The first reaction section feed stream to a first stage cold high pressure separator is returned to the hydrocracking plant 712 for further processing.

As shown in FIG. 1CD (represented collectively by FIGS. 1CD-1 and 1CD-2) (specifically FIG. 1CD-1), a product stripper overheads stream can directly heat a second sour water stripper bottoms stream in a fifth heat exchanger with a thermal duty that can range between about 5 MW and 15 MW (for example, 11.5 MW). The transfer of heat directly to another process streams captures heat that would have otherwise been discharged to the environment. The product stripper overheads stream is returned to the hydrocracking plant 712 for further processing.

As shown specifically in FIG. 1CD-2, the kerosene pumparound stream can directly heat a second naphtha splitter bottoms stream in a sixth heat exchanger with a thermal duty that can range between about 1 MW and 10 MW (for example, 5.7 MW). The kerosene pumparound stream can also directly heat a de-ethanizer bottoms stream in a seventh heat exchanger with a thermal duty that can range between about 1 MW and 10 MW (for example, 4.3 MW). For both streams, the transfer of heat directly to another process streams captures heat that would have otherwise been discharged to the environment. In an alternative embodiment, the cooling requirement of the kerosene pumparound stream can be 0 MW because the alternative flow path disclosed in this configuration may satisfy the entire cooling requirement for the kerosene pumparound stream for the operation of the fractionator column. The kerosene pumparound stream is returned to the hydrocracking plant 712 for further processing.

As shown in FIG. 1CD, the seventh heat exchanger is coupled to, in series with and is downstream of the sixth heat exchanger relative to the flow of kerosene pumparound stream. In some implementations, the kerosene pumparound stream can be flowed in series through the different plants. For example, the kerosene pumparound stream is flowed first through the de-ethanizer heat exchanger and then through the naphtha splitter heat exchanger.

As shown in FIG. 1CE, the kerosene product stream can directly heat a benzene column bottoms stream in an eighth heat exchanger with a thermal duty that can range between about 1 MW and 10 MW (for example, 6 MW). The kerosene product stream can also directly heat a second C3/C4 splitter bottom stream in a ninth heat exchanger with a thermal duty that can range between about 1 MW and 10 MW (for example, 5 MW). For both streams, the transfer of heat directly to another process streams captures heat that would have otherwise been discharged to the environment. The kerosene product stream is returned to the hydrocracking plant 712 for further processing.

As shown in FIG. 1CE, the ninth heat exchanger is coupled to, in series with and is downstream of the eighth heat exchanger relative to the flow of kerosene product stream. In some implementations, the kerosene product stream can be flowed in series through the different plants. For example, the kerosene product stream is flowed first through the C3/C4 splitter heat exchanger and then through the benzene column heat exchanger.

FIG. 1CI shows an aromatics complex benzene extraction unit 718 in a crude oil refining facility. The heated benzene column bottoms stream can be flowed to the benzene extraction unit 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1CH also shows an aromatics complex benzene extraction unit 718. The heated raffinate splitter column bottoms stream can be flowed to the benzene extraction unit 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

As shown in FIG. 1CF, the two naphtha splitter bottoms streams are recombined and can be flowed to the naphtha hydro-treating plant 714. In this manner, the first and the sixth heat exchangers can be coupled to each other in parallel relative to the flow of naphtha splitter bottoms. The steam heat input for the naphtha splitter can be 0 MW because the alternative flow path disclosed in this configuration may satisfy the entire heat load for the operation of the column. In an alternative embodiment, the steam heat input for the naphtha splitter can be reduced because the alternative flow path disclosed in this configuration may partially satisfy the heat load for the operation of the column.

As shown in FIG. 1CG, the two sour water stripper bottoms streams are recombined and can be flowed to the sour water stripper plant 710. In this manner, the fourth heat exchanger and the fifth heat exchanger can be coupled to each other in parallel relative to the flow of sour water stripper bottoms. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

As shown in FIG. 1CJ, the two C3/C4 splitter bottoms streams are recombined and can be flowed to the gas separation plant 704. In this manner, the second heat exchanger and the ninth heat exchanger can be coupled to each other in parallel relative to the flow of C3/C4 splitter bottoms. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

As shown in FIG. 1CJ, the heated de-ethanizer bottoms stream can also be flowed to the gas separation plant 704. The steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

Such recovery and reuse of waste heat directly from the hydrocracking plant can result in decreasing or eliminating the heat energy to heat the gas separation plant, an amine regeneration plant, the aromatics complex or a combinations of them such as by about 73 MW.

Configuration 8—Scheme B

In some implementations, the multiple streams in the crude oil refining facility such as those present in the aromatic complex, the sour water stripper plant, the sulfur recovery plant can be indirectly heated using a buffer fluid, for example, oil, water or other buffer fluid, using the multiple second streams in the hydrocracking plant as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712. The buffer fluid can be flowed into the plant as a single stream and split into multiple streams or it can be flowed into the plant as multiple streams.

To do so, one or more buffer fluid stream (for example, oil, water or other buffer fluid) can be heated using streams in the hydrocracking plant using respective heat exchangers. The heated buffer fluids can be collected in a buffer fluid collection header. Streams in the naphtha hydro-treating plant 714, the sour water stripper plant 710, and the aromatic complex benzene extraction plant 718 can be heated using the heated buffer fluid streamsin respective heat exchangers. The heated buffer fluid exiting the heat exchangers can be flowed to a buffer fluid tank. The buffer fluid from the buffer fluid tank can then be flowed to the aromatics plant to restart the waste heat recovery and reuse cycle.

Configuration 9

FIGS. 1CK-1CT illustrate configurations and related scheme details for thermally integrating different refining plants in the crude oil refining facility. The thermal integration described in these configurations and illustrated in FIGS. 1CK-1CT can reduce the crude oil refining facility's energy consumption (for example, heating and cooling utilities). For example, a reduction in energy consumption by about 83 MW, for example, 83.4 MW, can translate to at least about 12%, for example, 12.8%, of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 9—Scheme A

In some implementations, multiple first streams in the multiple first plants can be directly heated using multiple second streams in the multiple second plants. In some implementations, the multiple first plants can include an amine regeneration plant, a sulfur recovery plant and an aromatic complex sub-unit including an aromatic complex benzene extraction plant. The multiple second plants can include a hydrocracking plant and a diesel hydro-treating plant. In some implementations, one of the first multiple plants is directly heated by all of the multiple second plants and one of the second multiple plants directly heats only one of the first multiple plants. In such an instance, the one first multiple plant is the amine regeneration plant and the one second multiple plant is the diesel hydrotreating plant.

FIG. 1CQ shows sulfur recovery plant 702 in a crude oil refinery facility. The amine regenerator bottoms stream can be flowed in the plant as a single stream and split into multiple streams or it can be flowed into the plant as multiple streams to facilitate heat recovery.

FIG. 1CT shows an amine regeneration plant 706 in a crude oil refinery facility. The acid gas regenerator bottoms stream can be flowed in the plant as a single stream and split into multiple streams or it can be flowed into the plant as multiple streams to facilitate heat recovery.

FIGS. 1BC-1BF show a hydrocracking plant 712 in a crude oil refinery facility. As shown in FIG. 1CK, a diesel product stream can directly heat a first amine regenerator bottoms stream in a first heat exchanger with a thermal duty that can range between about 5 MW and 15 MW (for example, 10.4 MW). The transfer of heat directly to another process streams captures heat that would have otherwise been discharged to the environment. The diesel product stream is returned to the hydrocracking plant 712 for further processing.

As shown in FIG. 1CL, a second reaction section feed stream to second stage cold high pressure separator can directly heat a raffinate splitter bottoms stream in a second heat exchanger with a thermal duty that can range between about 5 MW and 15 MW (for example, 8.6 MW). The transfer of heat directly to another process streams captures heat that would have otherwise been discharged to the environment. The second reaction section feed stream to second stage cold high pressure separator is returned to the hydrocracking plant 712 for further processing.

As shown in FIG. 1CM, a first stage cold high pressure separator feed can directly heat a first acid gas regenerator feed stream in a third heat exchanger with a thermal duty that can range between about 25 MW and 35 MW (for example, 27.9 MW). The transfer of heat directly to another process streams captures heat that would have otherwise been discharged to the environment. The first stage cold high pressure separator feed is returned to the hydrocracking plant 712 for further processing.

As shown in FIG. 1CN (represented collectively by FIGS. 1CN-1 and 1CN-2) (specifically FIG. 1CN-2), a kerosene pumparound stream can directly heat a benzene column bottoms stream in a fourth heat exchanger with a thermal duty that can range between about 1 MW and 10 MW (for example, 6 MW). The transfer of heat directly to another process streams captures heat that would have otherwise been discharged to the environment. The kerosene pumparound stream is returned to the hydrocracking plant 712 for further processing.

As shown in FIG. 1CO, a kerosene product stream can directly heat a second amine regenerator bottoms branch in a fifth heat exchanger with a thermal duty that can range between about 5 MW and 15 MW (for example, 10.6 MW). The transfer of heat directly to another process streams captures heat that would have otherwise been discharged to the environment. The kerosene product stream is returned to the hydrocracking plant 712 for further processing.

FIG. 1CP shows a diesel hydrotreating plant 700 in a crude oil refinery facility. As shown in FIG. 1CP, a diesel stripper bottoms stream in can directly heat a second acid gas regenerator bottoms stream in a sixth heat exchanger with a thermal duty that can range between about 15 MW and 25 MW (for example, 19.9 MW). The diesel stripper bottoms stream is returned to the hydrocracking plant 712 for further processing.

FIG. 1CS shows an aromatics complex benzene extraction unit 718 in a crude oil refining facility. The heated benzene column bottoms stream can be flowed to the benzene extraction plant 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1CR also shows an aromatics complex benzene extraction unit 718. The heated raffinate splitter column bottoms stream can be flowed to the benzene extraction plant 718 in the aromatics complex. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

As shown in FIG. 1CQ, the two amine regenerator bottoms streams are recombined and can be flowed to the sulfur recovery plant 702. In this manner, the first and the fifth heat exchangers can be coupled to each other in parallel relative to the flow of amine regenerator bottoms. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column. In this configuration, only the hydrocracking plant 712 provides energy to the sulfur recovery plant 702.

As shown in FIG. 1CT, the two acid gas regenerator bottoms streams are recombined and can be flowed to the amine regeneration plant 706. In this manner, the third and the sixth heat exchangers can be coupled to each other in parallel relative to the flow of acid gas regenerator bottoms. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column. In this configuration, the hydrocracking plant 712 and the diesel hydrotreating plant 700 provide energy to the amine regeneration plant 706.

Such recovery and reuse of waste heat directly from both the hydrocracking and the diesel hydrotreating plants can result in decreasing or eliminating the heat energy to heat the aromatic complex, sulfur recovery plant, an amine regeneration plant or a combination of them such as by about 83 MW.

Configuration 9—Scheme B

In some implementations, the multiple streams in the crude oil refining facility such as those present in the aromatic complex, sulfur recovery plant, and the amine regeneration plant can be indirectly heated using a buffer fluid, for example, oil, water or other buffer fluid, using the multiple second streams in hydrocracking plant or diesel hydrotreating plant as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712 and the diesel hydrotreating plant 700. The buffer fluid can be flowed into each plant as a single stream and split into multiple streams or it can be flowed into the plant as multiple streams.

To do so, the one or more buffer fluid streams (for example, oil, water or other buffer fluid) can be heated using streams in the hydrocracking plant 712 and the diesel hydro-treating plant 700 using respective heat exchangers. The heated buffer fluids can be collected in a buffer fluid collection header. Streams in the sulfur recovery plant 702, the amine regenerator plant 706, and the aromatic complex benzene extraction plant 718 can be heated using the heated buffer fluid streams in respective heat exchangers. The heated buffer fluid exiting the heat exchangers can be flowed to a buffer fluid tank. The buffer fluid from the buffer fluid tank can then be flowed to the aromatics plant to restart the waste heat recovery and reuse cycle.

Configuration 10

FIGS. 1CU-1DF illustrate configurations and related scheme details for thermally integrating different refining plants in the crude oil refining facility. The thermal integration described in these configurations and illustrated in FIGS. 1CU-1DF can reduce the crude oil refining facility's energy consumption (for example, heating and cooling utilities) by about 115 MW, which translates to at least about 17% of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 10—Scheme A

In some implementations, multiple first streams in the multiple first plants can be directly heated using multiple second streams in the multiple second plants. In some implementations, the multiple first plants can include amine regeneration plant, a sulfur recovery plant, a sour water stripper plant 710, and an aromatics complex sub-unit including an aromatic complex benzene extraction plant. The multiple second plants can include a hydrocracking plant, a natural gas steam reforming hydrogen plant and a diesel hydrotreating plant. In some implementations, one of the first multiple plants is directly heated by all of the multiple second plants and one of the second multiple plants directly heats only one of the first multiple plants. In such an instance, the one first multiple plant is the sour water stripper plant and the one second multiple plants is the natural gas steam reforming hydrogen plant. In some implementations, one of the first multiple plants is directly heated by two of the multiple second plants. In such an instance, the one of the first multiple plants is the amine regeneration plant and the two of the multiple second plants are the hydrocracking plant and the diesel hydrotreating plant.

FIG. 1DB shows sulfur recovery plant 702 in a crude oil refinery facility. The amine regenerator bottoms stream can be flowed in the plant as a single stream and split into multiple streams or it can be flowed into the plant as multiple streams to facilitate heat recovery.

FIG. 1DE shows an amine regeneration plant 706 in a crude oil refinery facility. The acid gas regenerator bottoms stream can be flowed in the plant as a single stream and split into multiple streams or it can be flowed into the plant as multiple streams to facilitate heat recovery.

FIG. 1DF shows a sour water stripper plant 710 in a crude oil refinery facility. The sour water stripper bottoms stream can be flowed in the plant as a single stream and split into multiple streams or it can be flowed into the plant as multiple streams to facilitate heat recovery.

FIGS. 1CU-1CY show a hydrocracking plant 712 in a crude oil refinery facility. As shown in FIG. 1CU, a diesel product stream can directly heat a first amine regenerator bottoms stream in a first heat exchanger with a thermal duty that can range between about 5 MW and 15 MW (for example, 10.4 MW). The transfer of heat directly to another process streams captures heat that would have otherwise been discharged to the environment. The diesel product stream is returned to the hydrocracking plant 712 for further processing.

As shown in FIG. 1CV, a second reaction section feed stream to second stage cold high pressure separator can directly heat a raffinate splitter bottoms stream in a second heat exchanger with a thermal duty that can range between about 5 MW and 15 MW (for example, 8.6 MW). The transfer of heat directly to another process streams captures heat that would have otherwise been discharged to the environment. The second reaction section feed stream to second stage cold high pressure separator is returned to the hydrocracking plant 712 for further processing.

As shown in FIG. 1CW, a first stage cold high pressure separator feed can directly heat a first acid gas regenerator bottom stream in a third heat exchanger with a thermal duty that can range between about 25 MW and 35 MW (for example, 27.9 MW). The transfer of heat directly to another process streams captures heat that would have otherwise been discharged to the environment. The first stage cold high pressure separator feed is returned to the hydrocracking plant 712 for further processing.

As shown in FIG. 1CX (represented collectively by FIGS. 1CX-1 and 1CX-2) (specifically FIG. 1CX-1), a product stripper overhead stream can directly heat a first sour water stripper bottoms branch in a fourth heat exchanger with a thermal duty that can range between about 5 MW and 15 MW (for example, 11.8 MW). The transfer of heat directly to another process streams captures heat that would have otherwise been discharged to the environment. The product stripper overhead stream is returned to the hydrocracking plant 712 for further processing.

As shown specifically in FIG. 1CX-2, a kerosene pumparound stream can directly heat a benzene column bottoms stream in a fifth heat exchanger with a thermal duty that can range between about 1 MW and 10 MW (for example, 6 MW). The transfer of heat directly to another process streams captures heat that would have otherwise been discharged to the environment. The kerosene pumparound stream is returned to the hydrocracking plant 712 for further processing.

As shown in FIG. 1CY, a kerosene product stream can directly heat a second amine regenerator bottoms stream in a sixth heat exchanger with a thermal duty that can range between about 5 MW and 15 MW (for example, 10.6 MW). The transfer of heat directly to another process streams captures heat that would have otherwise been discharged to the environment. The kerosene product stream is returned to the hydrocracking plant 712 for further processing.

FIG. 1CZ shows a diesel hydrotreating plant 700 in a crude oil refinery facility. A diesel stripper overheads stream can directly heat a second sour water stripper bottoms branch in a seventh heat exchanger with a thermal duty that can range between about 10 MW and 20 MW (for example, 15.9 MW). The transfer of heat directly to another process streams captures heat that would have otherwise been discharged to the environment. The diesel stripper overheads is returned to the diesel hydrotreating plant 700 for further processing.

Also shown in FIG. 1CZ, a diesel stripper bottoms stream can directly heat a second acid gas regenerator bottoms stream in an eighth heat exchanger with a thermal duty that can range between about 15 MW and 25 MW (for example, 19.9 MW). The transfer of heat directly to another process streams captures heat that would have otherwise been discharged to the environment. The diesel stripper bottoms stream is returned to the diesel hydro-treating plant 700 for further processing.

FIG. 1DA shows a natural gas steam reforming hydrogen plant 708 in a crude oil refinery facility. A low temperature shift (LTS) converter product steam can directly heat a third sour water stripper bottoms stream in a ninth heat exchanger with a thermal duty that can range between about 1 MW and 10 MW (for example, 4.3 MW). The transfer of heat directly to another process streams captures heat that would have otherwise been discharged to the environment. The LTS converter product steam is returned to the hydrogen plant 708 for further processing.

FIG. 1DD shows an aromatics complex benzene extraction unit 718 in a crude oil refining facility. The heated benzene column bottom stream can be flowed to the benzene extraction unit 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1DC also shows an aromatics complex benzene extraction unit 718. The heated raffinate splitter column bottom stream can be flowed to the benzene extraction unit 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

As shown in FIG. 1DF, the three streams of the sour water stripper bottoms are recombined and flowed to the sour water stripper plant 710. In this manner, the fourth heat exchanger, the seventh heat exchanger and the ninth exchanger can be coupled to each other in parallel relative to the flow of sour water stripper bottoms. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column. In this configuration, the hydrocracking plant 712, the diesel hydrotreating plant 700, and the natural gas steam reforming hydrogen plant 708 provide energy to the sour water stripper plant 710.

As shown in FIG. 1DB, the two streams of the amine regenerator bottoms are recombined and flowed to the sulfur recovery plant 702. In this manner, the first heat exchanger and the sixth heat exchanger can be coupled to each other in parallel relative to the flow of amine regenerator bottoms. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column. In this configuration, only the hydrocracking plant 712 provide energy to the sulfur recovery plant 702.

As shown in FIG. 1DE, the two streams of the acid gas regenerator bottoms are recombined and flowed to the amine regeneration plant 706. In this manner, the third and the eighth heat exchangers can be coupled to each other in parallel relative to the flow of acid gas regenerator bottoms. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column. In this configuration, both the hydrocracking plant 712 and diesel hydrotreating plant 700 provide energy to the amine regeneration plant 706.

Such recovery and reuse of waste heat directly from the hydrocracking, the diesel hydrotreating, and the natural gas steam reforming hydrogen plants can result in decreasing or eliminating the heat energy to heat the aromatics complex, the sour water stripper plant, the sulfur recovery plant, the amine regeneration plant or a combination of them, such as by about 115 MW.

Configuration 10—Scheme B

In some implementations, the multiple streams in the crude oil refining facility such as those present in the aromatic complex, the sour water stripper plant, the sulfur recovery plant, the amine regeneration plant can be indirectly heated using a buffer fluid, for example, oil, water or other buffer fluid, using the multiple second streams in hydrocracking plant, the diesel hydrotreating plant, the natural gas steam reforming hydrogen plant, or combinations thereof, as heat energy sources Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712, the diesel hydrotreating plant 700 and natural gas steam reforming hydrogen plant 708. The buffer fluid can be flowed into each plant as a single stream and split into multiple streams or it can be flowed into the plant as multiple streams.

To do so, the one or more buffer fluid streams (for example, oil, water or other buffer fluid) can be heated using streams in the hydrocracking plant 712, the diesel hydrotreating plant 700, and the hydrogen plant 708 using respective heat exchangers. The heated buffer fluids can be collected in a buffer fluid collection header. Streams in the aromatic complex benzene extraction plant 718, the sour water stripper plant 702, the sulfur recovery plant 702, and the amine regeneration plant 706 can be heated using the heated buffer fluid streams in respective heat exchangers. The heated buffer fluid exiting the heat exchangers can be flowed to a buffer fluid tank. The buffer fluid from the buffer fluid tank can then be flowed to the aromatics plant to restart the waste heat recovery and reuse cycle.

Configuration 11

FIGS. 1DG-1DS illustrate configurations and related scheme details for thermally integrating different refining plants in the crude oil refining facility. The thermal integration described in these configurations and illustrated in FIGS. 1DG-1DS can reduce the crude oil refining facility's energy consumption (for example, heating and cooling utilities). For example, a reduction in energy consumption by about 130 MW can translate to at least about 20% of the energy consumption in the crude oil refining facility. In certain schemes, a process stream (for example, a stream from one refining sub-unit of an aromatics plant or other process streams) can be used to directly heat another process stream (for example, a hydrocracking plant stream or other process stream). In certain configurations, heat exchange between process streams can be implemented using an intermediate buffer fluid, for example, water, oil, or other buffer fluid.

Configuration 11—Scheme A

In some implementations, multiple first streams in the multiple first plants can be directly heated using multiple second streams in the multiple second plants In some implementations, the multiple first plants can include an amine regeneration plant, a sulfur recovery plant, a gas separation plant, a sour water stripper plant, and an aromatics complex including an aromatics benzene extraction unit. The multiple second plants can include a hydrocracking plant, a natural gas steam reforming hydrogen plant and a diesel hydro-treating plant. In some implementations, one of the first multiple plants is directly heated by all of the multiple second plants and one of the second multiple plants directly heats only one of the first multiple plants. In such an instance, the one first multiple plant is the sour water stripper plant and the one second multiple plants is the natural gas steam reforming hydrogen plant. In some implementations, two of the first multiple plants are directly heated by the same two of the multiple second plants. In such an instance, the two of the first multiple plants is the amine regeneration plant and the gas separation plant and the same two of the multiple second plants are the hydrocracking plant and the diesel hydrotreating plant.

FIG. 1DN shows sulfur recovery plant 702 in a crude oil refinery facility. The amine regenerator bottoms stream can be flowed in the plant as a single stream and split into multiple streams or it can be flowed into the plant as multiple streams to facilitate heat recovery.

FIG. 1DQ shows an amine regeneration plant 706 in a crude oil refinery facility. The acid gas regenerator bottoms stream can be flowed in the plant as a single stream and split into multiple streams or it can be flowed into the plant as multiple streams to facilitate heat recovery.

FIG. 1DR shows a sour water stripper plant 710 in a crude oil refinery facility. The sour water stripper bottoms stream can be flowed in the plant as a single stream and split into multiple streams or it can be flowed into the plant as multiple streams to facilitate heat recovery.

FIG. 1DS shows a gas separation plant 704 in a crude oil refinery facility. The C3/C4 splitter bottoms stream can be flowed in the plant as a single stream and split into multiple streams or it can be flowed into the plant as multiple streams to facilitate heat recovery.

As shown in FIG. 1DG, a diesel product stream in can directly heat a first amine regenerator bottoms stream in a first heat exchanger with a thermal duty that can range between about 5 MW and 15 MW (for example, 10.4 MW). The transfer of heat directly to another process streams captures heat that would have otherwise been discharged to the environment. The diesel product stream is returned to the hydrocracking plant 712 for further processing.

As shown in FIG. 1DH, a second reaction section feed stream to second stage cold high pressure separator can directly heat a raffinate splitter bottoms stream in a second heat exchanger with a thermal duty that can range between about 5 MW and 15 MW (for example, 8.6 MW). The transfer of heat directly to another process streams captures heat that would have otherwise been discharged to the environment. The second reaction section feed stream to second stage cold high pressure separator is returned to the hydrocracking plant 712 for further processing.

As shown in FIG. 1DI, a first stage cold high pressure separator stream can directly heat a first acid gas regenerator bottoms stream in a third heat exchanger with a thermal duty that can range between about 25 MW and 35 MW (for example, 27.9 MW). The transfer of heat directly to another process streams captures heat that would have otherwise been discharged to the environment. The first stage cold high pressure separator stream is returned to the hydrocracking plant 712 for further processing.

As shown in FIG. 1DJ (represented collectively by FIGS. 1DJ-1 and 1DJ-2) (specifically FIG. 1DJ-1), a product stripper overheads stream can directly heat a first sour water stripper bottoms stream in a fourth heat exchanger with a thermal duty that can range between about 5 MW and 15 MW (for example, 11.8 MW). The transfer of heat directly to another process streams captures heat that would have otherwise been discharged to the environment. The product stripper overhead stream is returned to the hydrocracking plant 712 for further processing.

As specifically shown in FIG. 1DJ-2, a kerosene pumparound stream in the hydrocracking plant can directly heat a benzene column bottoms stream in a fifth heat exchanger with a thermal duty that can range between about 1 MW and 10 MW (for example, 6 MW). The kerosene pumparound stream can also directly heat a first C3/C4 stripper bottoms stream in a sixth heat exchanger with a thermal duty that can range between about 1 MW and 10 MW (for example, 4.2 MW). For both streams, the transfer of heat directly to another process streams captures heat that would have otherwise been discharged to the environment. In this configuration the cooling requirement of the kerosene pumparound stream can be 0 MW because the alternative flow path disclosed in this configuration may satisfy the entire cooling requirement for the kerosene pumparound stream for the operation of the fractionator column. The kerosene pumparound stream is returned to the hydrocracking plant 712 for further processing.

As shown in FIG. 1DJ-2, the sixth heat exchanger is coupled to, in series with and is downstream of the fifth heat exchanger relative to the flow of the kerosene pumparound stream. In some implementations, the kerosene pumparound stream can be flowed in series through the different plants. For example, the kerosene pumparound stream is flowed first through the gas separation plant heat exchanger and then through the aromatics complex plant heat exchanger.

As shown in FIG. 1DK, a kerosene product stream can directly heat a second amine regenerator bottoms stream in a seventh heat exchanger with a thermal duty that can range between about 5 MW and 15 MW (for example, 10.6 MW). The transfer of heat directly to another process streams captures heat that would have otherwise been discharged to the environment. The kerosene product stream is returned to the hydrocracking plant 712 for further processing.

FIG. 1DL shows a diesel hydrotreating plant 712 in a crude oil refining facility. As shown in FIG. 1DL, a diesel stripper overheads stream can directly heat a second sour water stripper plant bottoms stream in an eighth heat exchanger with a thermal duty that can range between about 10 MW and 20 MW (for example, 15.9 MW). The transfer of heat directly to another process streams captures heat that would have otherwise been discharged to the environment. The diesel stripper overhead stream is returned to the hydrocracking plant 712 for further processing.

Also shown in FIG. 1DL, a diesel stripper bottoms stream can directly heat a second acid gas regenerator bottoms stream in a ninth heat exchanger with a thermal duty that can range between about 15 MW and 25 MW (for example, 19.9 MW). The diesel stripper bottoms stream can also directly heat a second C3/C4 splitter bottoms stream in a tenth heat exchanger with a thermal duty that can range between about 1 MW and 10 MW (for example, 5.7 MW). As well, the diesel stripper bottoms stream can also directly heat a de-ethanizer bottoms stream branch in an eleventh heat exchanger with a thermal duty that can range between about 1 MW and 10 MW (for example, 4.3 MW). For all three streams, the transfer of heat directly to another process streams captures heat that would have otherwise been discharged to the environment. The diesel product stream is returned to the hydrocracking plant 700 for further processing.

As shown in FIG. 1DL, the eleventh heat exchanger is coupled to, in series with and is downstream of the tenth heat exchanger relative to the flow of diesel stripper bottoms stream, and the tenth heat exchanger is coupled to, in series with and is downstream of the ninth heat exchanger relative to the flow of diesel stripper bottoms stream. In some implementations, the diesel stripper bottoms stream can be flowed in series through the different plants. For example, the diesel stripper bottoms stream is flowed first through the two gas separation plant exchangers and then the amine regeneration plant exchanger. As well, the intra-plant series order, specifically the gas separation plant exchangers, may also be different in alternative embodiments.

FIG. 1DM shows a natural gas steam reforming hydrogen plant 708 in a crude oil refining facility. A low temperature shift (LTS) converter product stream can directly heat a third sour water stripper bottoms stream in a twelfth heat exchanger with a thermal duty that can range between about 1 MW and 10 MW (for example, 4.3 MW). The transfer of heat directly to another process streams captures heat that would have otherwise been discharged to the environment. The LTS product stream is returned to the natural gas steam reforming hydrogen plant 708 for further processing.

FIG. 1DP shows an aromatics complex benzene extraction unit 718 in a crude oil refining facility. The heated benzene column bottom stream can be flowed to the benzene extraction unit 718. The steam heat input for the benzene column can be 0 MW because the alternative flow path disclosed in this configuration may satisfy the entire heat load for the operation of the column. In an alternative embodiment, the steam heat input for the benzene column can be reduced because the alternative flow path disclosed in this configuration may partially satisfy the heat load for the operation of the column.

FIG. 1DO also shows an aromatics complex benzene extraction unit 718. The heated raffinate splitter column bottom stream can be flowed to the benzene extraction plant 718. The steam heat input for the raffinate splitter can be 0 MW because the alternative flow path disclosed in this configuration may satisfy the entire heat load for the operation of the column. In an alternative embodiment, the steam heat input for the raffinate splitter can be reduced because the alternative flow path disclosed in this configuration may partially satisfy the heat load for the operation of the column.

As shown in FIG. 1DR, the three sour water stripper bottoms streams are recombined and can be flowed to the sour water stripper plant 710. In this manner, the fourth, eighth and twelfth heat exchangers can be coupled to each other in parallel relative to the flow of sour water stripper bottoms. The steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column. In this configuration, the hydrocracking plant 712, the diesel hydrotreating plant 700, and the natural gas steam reforming hydrogen plant 708 provide energy to the sour water stripper plant 710.

As shown in FIG. 1DN, the two streams of the amine regenerator bottoms are recombined and flowed to the sulfur recovery plant 702. In this manner, the first heat exchanger and the seventh heat exchanger can be coupled to each other in parallel relative to the flow of amine regenerator bottoms. The steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column. In this configuration, only the hydrocracking plant 712 provide energy to the sulfur recovery plant 702.

As shown in FIG. 1DQ, the two streams of the acid gas regenerator bottoms are recombined and flowed to the amine regeneration plant 706. In this manner, the third and the ninth heat exchangers can be coupled to each other in parallel relative to the flow of acid gas regenerator bottoms. The steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column. In this configuration, both the hydrocracking plant 712 and diesel hydrotreating plant 700 provide energy to the amine regeneration plant 706.

As shown in FIG. 1DS, the two C3/C4 splitter bottoms streams are recombined and can be flowed to the gas separation plant 704. In this manner, the sixth heat exchanger and the tenth heat exchanger can be coupled to each other in parallel relative to the flow of C3/C4 splitter bottoms. The steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

As shown in FIG. 1DS, the heated de-ethanizer bottoms stream can also be flowed to the gas separation plant 704. The steam heat input for the de-ethanizer column can be 0 MW because the alternative flow path disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column. In this configuration, both the hydrocracking plant 712 and diesel hydrotreating plant 700 provide energy to the gas separation plant 704.

Such recovery and reuse of waste heat directly from the hydrocracking, the diesel hydrotreating, and the natural gas steam reforming hydrogen plants can result in decreasing or eliminating the heat energy to heat the aromatics complex, sulfur recovery plant, an amine regeneration plant, a gas separation plant or a combination of them, such as by about 130 MW.

Configuration 11—Scheme B

In some implementations, the multiple streams in the crude oil refining facility can be indirectly heated using a buffer fluid, for example, oil, water or other buffer fluid, using the multiple second streams in hydrocracking plant, hydrogen plant, and diesel hydrotreating plant as heat energy sources.

Indirectly heating the streams can include heating the streams through a buffer fluid, for example, oil, water, or other buffer fluid. A buffer fluid (for example, high pressure water) from a buffer fluid tank (for example, hot water tank) is flowed to the hydrocracking plant 712, the diesel hydrotreating plant 700 and natural gas steam reforming hydrogen plant 708. The buffer fluid can be flowed into each plant as a single stream and split into multiple streams or it can be flowed into the plant as multiple streams.

To do so, the one or more buffer fluid streams (for example, oil, water, or other buffer fluid) can be heated using streams in the hydrocracking plant 712, the natural gas steam reforming hydrogen plant 708 and the diesel hydrotreating plant 700 using respective heat exchangers. The heated buffer fluids can be collected in a buffer fluid collection header. Streams in the aromatics complex benzene extraction plant 718, the sour water stripper plant 710, the sulfur recovery plant 702, the gas separation plant 704 and the amine regeneration plant 706 can be heated using heated buffer fluid streams in respective heat exchangers. The heated buffer fluid exiting the heat exchangers can be flowed to a buffer fluid tank. The buffer fluid from the buffer fluid tank can then be flowed to the aromatics plant to restart the waste heat recovery and reuse cycle.

In summary, this disclosure describes configurations and related processing schemes of specific direct or indirect inter-plants integration for energy consumption reduction synthesized for grassroots medium grade crude oil semi-conversion refineries to increase energy efficiency from specific portions of low grade waste heat sources. The disclosure also describes configurations and related processing schemes of specific direct or indirect inter-plants integration for energy consumption reduction synthesized for integrated medium grade crude oil semi-conversion refineries and aromatics complex for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A method implemented in a crude oil refining facility, the method comprising:

in a crude oil refining facility comprising a plurality of oil refining plants, each oil refining plant configured to perform at least one oil refining process, each oil refining plant comprising a plurality of interconnected oil refining sub-systems, wherein a plurality of streams at respective temperatures flow between the plurality of oil refining sub-systems:

flowing a first plurality of streams from a first subset of the plurality of oil refining plants to a plurality of heat exchangers, wherein the first subset comprises two or more of a naphtha hydrotreating plant, a gas separation plant, an amine regeneration plant, a sulfur recovery plant, a sour water stripper plant, and an aromatics plant which comprises an aromatics complex benzene extraction unit, wherein the first plurality of streams comprises two or more of a sulfur recovery plant amine regeneration unit stripper bottom stream in the sulfur recovery plant, a raffinate splitter bottoms stream in the aromatics complex benzene extraction unit, an acid gas regenerator bottoms stream in the amine regeneration plant, a sour water stripper bottoms stream in the sour water stripper plant, a benzene column bottoms stream in the aromatics complex benzene extraction unit, a C3/C4 stripper bottom stream in the gas separation plant, and a de-ethanizer bottoms stream in the gas separation plant;

flowing a second plurality of streams from a second subset of the plurality of oil refining plants to the plurality of heat exchangers, wherein the second subset comprises two or more of a hydrogen plant, a diesel hydrotreating plant, and hydrocracking plant, wherein the second plurality of streams comprises two or more of a kerosene pumparound stream in the hydrocracking plant, a kerosene product stream in the diesel hydrotreating plant, a diesel stripper overheads stream in the diesel hydrotreating plant, a stripper bottom product stream in the diesel hydrotreating plant, a diesel stripper bottoms stream in the diesel hydrotreating plant, and a low temperature shift converter steam in the hydrogen plant, wherein the plurality of heat exchangers transfer heat from the first plurality of streams to the second plurality of streams; and heating the first plurality of streams with the second plurality of streams in one or more oil refining processes at the second subset of the plurality of oil refining plants.

2. The method of claim 1, wherein the plurality of heat exchangers directly transfer heat by:

heating, in a first heat exchanger, a benzene column bottoms stream in the aromatics complex benzene extraction unit using a kerosene product stream in the hydrocracking plant;

heating, in a second heat exchanger, a raffinate splitter bottoms stream in the aromatics complex benzene extraction unit using a second stage reaction section feed to a second stage cold high pressure separator in the hydrocracking plant;

heating, in a third heat exchanger, an amine regenerator bottoms stream in the sulfur recovery plant using a first stage reaction section feed to a first stage cold high pressure separator in the hydrocracking plant;

flowing the heated benzene column bottoms stream and the raffinate splitter bottoms stream to the aromatics complex benzene extraction unit; and flowing the heated amine regenerator bottoms stream to sulfur recovery plant.

3. The method of claim 1, wherein the plurality of heat exchangers directly transfer heat by:

heating, in a first heat exchanger, a branch of a sour water stripper bottoms stream in the sour water stripper plant using a diesel product stream in the hydrocracking plant;

heating, in a second heat exchanger, a branch of the sour water stripper bottoms stream in the sour water stripper plant using a first stage reaction feed to a first stage cold high pressure separator in the hydrocracking plant;

heating, in a third heat exchanger, a branch of the sour water stripper bottoms stream using a kerosene product stream in the hydrocracking plant;

heating, in a fourth heat exchanger, a benzene column bottoms stream in the aromatics complex benzene extraction unit using the kerosene product stream;

heating, in a fifth heat exchanger, a raffinate splitter bottoms stream in the aromatics complex benzene extraction unit using a second stage reaction section feed to a second stage cold high pressure separator in the hydrocracking plant;

flowing the branches of the heated sour water stripper bottoms stream to the sour water stripper plant; and flowing the heated benzene column bottoms stream and the raffinate splitter bottoms stream to the aromatics complex benzene extraction unit.

4. The method of claim 1, wherein the plurality of heat exchangers directly transfer heat by:

heating, in a first heat exchanger, a C3/C4 splitter bottom cold stream in the gas separation plant using a second stage reaction section feed to a second stage cold high pressure separator in the hydrocracking plant;

heating, in a second heat exchanger, an amine regenerator bottoms stream in the sulfur recovery plant using a first stage reaction feed to a first stage cold high pressure separator in the hydrocracking plant;

heating, in a third heat exchanger, a benzene column bottoms stream in the aromatics complex benzene extraction unit using a kerosene product stream in the hydrocracking plant;

heating, in a fourth heat exchanger, a raffinate column bottom stream in the aromatics complex benzene extraction unit using the kerosene product stream;

heating, in a fifth heat exchanger, a de-ethanizer bottoms stream in the gas separation plant using the kerosene product stream;

flowing the heated C3/C4 splitter bottom cold stream and the heated de-ethanizer bottoms stream to the gas separation plant;

flowing the heated amine regenerator bottoms stream to the sulfur recovery plant; and flowing the heated benzene column bottoms stream and the raffinate splitter bottoms stream to the aromatics complex benzene extraction unit.

5. The method of claim 1, wherein the plurality of heat exchangers directly transfer heat by:

heating, in a first heat exchanger, a branch of a naphtha splitter bottoms stream in the naphtha hydrotreating plant using a diesel product stream in the hydrocracking plant;

heating, in a second heat exchanger, a raffinate column bottom stream in the aromatics complex benzene extraction unit using a second stage reaction feed to second stage cold high pressure separator in the hydrocracking plant;

heating, in a third heat exchanger, a branch of a sour water stripper bottoms stream in the sour water stripper unit using a first stage reaction feed to a first stage cold high pressure separator in the hydrocracking plant;

heating, in a fourth heat exchanger, a branch of the sour water stripper bottoms stream using a product stripper overheads stream in the hydrocracking plant;

heating, in a fifth heat exchanger, a branch of the naphtha splitter bottoms stream using a kerosene product stream in the hydrocracking plant;

heating, in a sixth heat exchanger, a raffinate splitter bottoms stream in the aromatics complex benzene extraction unit using the kerosene product stream;

flowing the branches of the heated naphtha splitter bottoms stream to the naphtha hydrotreating plant;

flowing the branches of the heated sour water stripper bottoms stream to the sour water stripper plant; and flowing the heated benzene column bottoms stream and the raffinate splitter bottoms stream to the aromatics complex benzene extraction unit.

6. The method of claim 1, wherein the plurality of heat exchangers directly transfer heat by:

heating, in a first heat exchanger, a branch of the sour water stripper bottoms stream using a product stripper overheads stream in the hydrocracking plant;

heating, in a second heat exchanger, a branch of a sour water stripper bottoms stream using a first stage reaction feed to a first stage cold high pressure separator;

heating, in a third heat exchanger, a C3/C4 splitter bottom stream in the gas separation plant using a second stage reaction feed to second stage cold high pressure separator;

heating, in a fourth heat exchanger, a raffinate splitter bottoms stream in the aromatics complex benzene extraction unit using the kerosene product stream;

heating, in a fifth heat exchanger, a de-ethanizer column bottom stream using the kerosene product stream;

heating, in a sixth heat exchanger, a benzene column bottoms stream in the aromatics complex benzene extraction unit using a kerosene product stream in the hydrocracking plant;

flowing the heated benzene column bottoms stream and the raffinate splitter bottoms stream to the aromatics complex benzene extraction unit;

flowing the heated C3/C4 splitter bottom stream and the heated de-ethanizer stream to the gas separation plant; and flowing the branches of the heated sour water stripper bottoms stream to the sour water stripper plant.

7. The method of claim 1, wherein the plurality of heat exchangers directly transfer heat by:

heating, in a first heat exchanger, a raffinate splitter bottoms stream in the aromatics complex benzene extraction unit using a second stage reaction section feed to a second stage cold high pressure separator in the hydrocracking plant;

heating, in a second heat exchanger, a branch of an acid gas regenerator bottoms stream in the amine regeneration plant using a first stage reaction section feed to a first stage cold high pressure separator stream in the hydrocracking plant;

heating, in a third heat exchanger, a branch of the acid gas regenerator bottoms stream in the amine regeneration plant using a product stripper overheads stream in the hydrocracking plant;

heating, in a fourth heat exchanger, a branch of the acid gas regenerator bottoms stream in the amine regeneration plant using a kerosene product stream in the hydrocracking plant;

heating, in a fifth heat exchanger, a benzene column bottoms stream in the aromatics complex benzene extraction unit using the kerosene product stream;

flowing the heated benzene column bottoms stream and the raffinate splitter bottoms stream to the aromatics complex benzene extraction unit; and flowing the branches of the heated acid gas regenerator bottoms streams to the amine regeneration plant.

8. The method of claim 1, wherein the plurality of heat exchangers directly transfer heat by:

heating, in a first heat exchanger, a branch of a stripper bottom stream in the sulfur recovery plant amine regeneration unit using a diesel product stream in the hydrocracking plant;

heating, in a second heat exchanger, a raffinate splitter bottoms stream in the aromatics complex benzene extraction unit using a second stage reaction section feed to a second stage cold high pressure separator in the hydrocracking plant;

heating, in a third heat exchanger, a branch of a sour water stripper bottoms stream in the sour water stripper plant using a first stage reaction section feed to a first stage cold high pressure separator stream in the hydrocracking plant;

heating, in a fourth heat exchanger, a branch of the sour water stripper bottoms stream using a product stripper overheads stream in the hydrocracking plant;

heating, in a fifth heat exchanger, a benzene column bottoms stream in the aromatics complex benzene extraction unit using a kerosene pumparound stream in the hydrocracking plant;

heating, in a sixth heat exchanger, a branch of the stripper bottom stream in the sulfur recovery plant amine regeneration unit using a kerosene product stream;

flowing the heated benzene column bottoms stream and the raffinate splitter bottoms stream to the aromatics complex benzene extraction unit;

flowing the branches of the heated sour water stripper bottoms stream to the sour water stripper plant; and flowing the branches of the heated stripper bottom stream to the sulfur recovery plant amine regeneration unit.

9. The method of claim 1, wherein the plurality of heat exchangers directly transfer heat by:

heating, in a first heat exchanger, a branch of a naphtha splitter bottoms stream in the naphtha hydrotreating plant using a diesel product stream in the hydrocracking plant;

heating, in a second heat exchanger, a branch of a C3/C4 splitter bottom stream in the gas separation plant using the diesel product stream;

heating, in a third heat exchanger, a raffinate splitter bottoms stream in the aromatics complex benzene extraction unit using a second stage reaction section feed to a second stage cold high pressure separator in the hydrocracking plant;

heating, in a fourth heat exchanger, a branch of the sour water stripper bottoms stream using a first stage reaction section feed to a first stage cold high pressure separator in the hydrocracking plant;

heating, in a fifth heat exchanger, a branch of a sour water stripper bottoms stream in the sour water stripper plant using a product stripper overheads stream in the hydrocracking plant;

heating, in a sixth heat exchanger, a branch of the naphtha splitter bottoms stream using a kerosene pumparound stream in the hydrocracking plant;

heating, in a seventh heat exchanger, a de-ethanizer bottoms stream in the gas separation plant using the kerosene pumparound stream;

heating, in an eighth heat exchanger, a benzene column bottoms stream in the aromatics complex benzene extraction unit using the kerosene product stream;

heating, in a ninth heat exchanger, a branch of the C3/C4 splitter bottom stream using the kerosene product stream;

flowing the heated benzene column bottoms stream and the raffinate splitter bottoms stream to the aromatics complex benzene extraction unit;

flowing the branches of the heated naphtha splitter bottoms stream to the naphtha hydrotreating plant;

flowing the branches of the heated sour water stripper bottoms stream to the sour water stripper plant; and flowing the branches of the heated C3/C4 splitter bottom streams and the heated de-ethanizer stream to the gas separation plant.

10. The method of claim 1, wherein the plurality of heat exchangers directly transfer heat by:

heating, in a first heat exchanger, a branch of a sulfur recovery plant amine regeneration unit stripper bottom stream in the sulfur recovery plant using a diesel product stream in the hydrocracking plant;

heating, in a second heat exchanger, a raffinate splitter bottoms stream in the aromatics complex benzene extraction unit using a second stage reaction section feed to a second stage cold high pressure separator in the hydrocracking plant;

heating, in a third heat exchanger, a branch of an acid gas regenerator bottoms stream in the amine regeneration plant using a first stage reaction section feed to a first stage cold high pressure separator in the hydrocracking plant;

heating, in a fourth heat exchanger, a benzene column bottoms stream in the aromatics complex benzene extraction unit using a kerosene pumparound stream in the hydrocracking plant;

heating, in a fifth heat exchanger, a branch of the sulfur recovery plant amine regeneration unit stripper bottom stream using a kerosene product stream in the hydrocracking plant;

heating, in a sixth heat exchanger, a branch of the acid gas regenerator bottoms stream using a stripper bottom product stream in the diesel hydrotreating plant;

flowing the heated benzene column bottoms stream and the raffinate splitter bottoms stream to the aromatics complex benzene extraction unit;

flowing the branches of the heated sulfur recovery plant amine regeneration unit stripper bottom stream to the sulfur recovery plant; and flowing the branches of the heated acid gas regenerator bottoms streams to the amine regeneration plant.

11. The method of claim 1, wherein the plurality of heat exchangers directly transfer heat by:

heating, in a first heat exchanger, a branch of a sulfur recovery plant amine regeneration unit stripper bottom stream in the sulfur recovery plant using a diesel product stream in the hydrocracking plant;

heating, in a second heat exchanger, a raffinate splitter bottoms stream in the aromatics complex benzene extraction unit using a second stage reaction section feed to a second stage cold high pressure separator in the hydrocracking plant;

heating, in a third heat exchanger, a branch of an acid gas regenerator bottoms stream in the amine regeneration plant using a first stage reaction section feed to a first stage cold high pressure separator in the hydrocracking plant;

heating, in a fourth heat exchanger, a branch of a sour water stripper bottoms stream in the sour water stripper plant using a stripper overhead stream in the hydrocracking plant;

heating, in a fifth heat exchanger, a benzene column bottoms stream in the aromatics complex benzene extraction unit using a kerosene pumparound stream in the hydrocracking plant;

heating, in a sixth heat exchanger, a branch of the sulfur recovery plant amine regeneration unit stripper bottom stream using a kerosene product stream in the hydrocracking plant;

heating, in a seventh heat exchanger, a branch of the sour water stripper bottoms stream using a diesel stripper overheads stream in the diesel hydrotreating plant;

heating, in an eighth heat exchanger, an acid gas regenerator bottoms stream in the amine regeneration plant using a stripper bottom product stream in the diesel hydrotreating plant;

heating, in a ninth heat exchanger, a branch of the sour water stripper bottoms stream using a low temperature shift converter steam in the hydrogen plant;

flowing the heated benzene column bottoms stream and the raffinate splitter bottoms stream to the aromatics complex benzene extraction unit;

flowing the branches of the heated sour water stripper streams to the sour water stripper plant;

flowing the branches of the heated sulfur recovery plant amine regeneration unit stripper bottom stream to the sulfur recovery plant; and flowing the branches of the heated acid gas regenerator bottoms streams to the amine regeneration plant.

12. The method of claim 1, wherein heating the first plurality of streams comprises indirectly heating the first plurality of streams using the second plurality of streams through a buffer fluid by:

heating, in a first heat exchanger, a first branch of the buffer fluid using a diesel product stream in the hydrocracking plant;

heating, in a second heat exchanger, a second branch of the buffer fluid using a first stage reaction section feed to a first stage cold high pressure separator in the hydrocracking plant;

heating, in a third heat exchanger, a third branch of the buffer fluid using a kerosene product stream in the hydrocracking plant;

collecting the heated first branch, the heated second branch and the heated third branch in a buffer fluid collection header;

flowing heated buffer fluid to the aromatics complex benzene extraction unit and the sulfur recovery plant;

heating, in a fourth heat exchanger, a benzene column bottoms stream in the aromatics complex benzene extraction unit using the heated buffer fluid;

heating, in a fifth heat exchanger, a raffinate column bottom stream in the aromatics complex benzene extraction unit using the heated buffer fluid;

heating, in a sixth heat exchanger, a sulfur recovery column bottom stream in the sulfur recovery plant using the heated buffer fluid.

13. The method of claim 12, wherein the heated buffer fluid is first flowed to the fourth heat exchanger, wherein the heated buffer fluid is flowed to the fifth heat exchanger and the sixth heat exchanger either in series or in parallel, wherein the method further comprises flowing the heated buffer fluid exiting the fifth heat exchanger or the sixth heat exchanger to a buffer fluid tank.

14. The method of claim 1, wherein heating the first plurality of streams comprises indirectly heating the first plurality of streams using the second plurality of streams through a buffer fluid by:

heating, in a first heat exchanger, a first branch of the buffer fluid using a diesel product stream in the hydrocracking plant;

heating, in a second heat exchanger, a second branch of the buffer fluid using a first stage reaction section feed to a first stage cold high pressure separator in the hydrocracking plant;

heating, in a third heat exchanger, a third branch of the buffer fluid using a product stripper overheads stream in the hydrocracking plant;

heating, in a fourth heat exchanger, a fourth branch of the buffer fluid using a kerosene pumparound stream in the hydrocracking plant;

heating, in a fifth heat exchanger, a fifth branch of the buffer fluid using a kerosene product stream in the hydrocracking plant;

collecting the heated first branch, the heated second branch, the heated third branch, the heated fourth branch and the heated fifth branch in a buffer fluid collection header;

flowing heated buffer fluid to the aromatics complex benzene extraction unit and the sour water stripper plant;

heating, in a sixth heat exchanger, a benzene column bottoms stream in the aromatics complex benzene extraction unit using the heated buffer fluid;

heating, in a seventh heat exchanger, a raffinate column bottom stream in the aromatics complex benzene extraction unit using the heated buffer fluid;

heating, in an eighth heat exchanger, a sour water stripper bottoms stream in the sour water stripper plant using the heated buffer fluid.

15. The method of claim 14, wherein the heated buffer fluid is first flowed to the sixth heat exchanger, wherein the heated buffer fluid is flowed to the seventh heat exchanger and the eighth heat exchanger either in series or in parallel, and wherein the method further comprises flowing the heated buffer fluid exiting the seventh heat exchanger or the eighth heat exchanger to a buffer fluid tank.

16. The method of claim 1, wherein heating the first plurality of streams comprises indirectly heating the first plurality of streams using the second plurality of streams through a buffer fluid by:

heating, in a first heat exchanger, a first branch of the buffer fluid using a diesel product stream in the hydrocracking plant;

heating, in a second heat exchanger, a second branch of the buffer fluid using a second stage reaction stage feed to second stage cold high pressure separator stream in the hydrocracking plant;

heating, in a third heat exchanger, a third branch of the buffer fluid using a first stage reaction section feed to a first stage cold high pressure separator stream in the hydrocracking plant;

heating, in a fourth heat exchanger, a fourth branch of the buffer fluid using a kerosene pumparound stream in the hydrocracking plant;

heating, in a fifth heat exchanger, a fifth branch of the buffer fluid using a kerosene product stream in the hydrocracking plant;

collecting the heated first branch, the heated second branch, the heated third branch, the heated fourth branch, the heated fifth branch and the heated sixth branch in a buffer fluid collection header;

flowing heated buffer fluid to the aromatics complex benzene extraction unit and the amine regeneration plant;

heating, in a sixth heat exchanger, a benzene column bottoms stream in the aromatics complex benzene extraction unit using the heated buffer fluid;

heating, in a seventh heat exchanger, a raffinate splitter bottoms stream in the aromatics complex benzene extraction unit using the heated buffer fluid;

heating, in an eighth heat exchanger, an amine regenerator bottoms stream using the heated buffer fluid.

17. The method of claim 16, wherein the heated buffer fluid is first flowed to the sixth heat exchanger, then to the seventh heat exchanger from the sixth heat exchanger, and then to the eighth heat exchanger from the seventh heat exchanger, and wherein the method further comprises flowing the heated buffer fluid exiting the eighth heat exchanger to a buffer fluid tank.

* * * * *